(12) United States Patent
Kamen et al.

(10) Patent No.: US 8,968,232 B2
(45) Date of Patent: *Mar. 3, 2015

(54) HEAT EXCHANGE SYSTEMS, DEVICES AND METHODS

(75) Inventors: Dean Kamen, Bedford, NH (US); Jason A. Demers, Manchester, NH (US); David E. Altobelli, Hollis, NH (US); Larry B. Gray, Merrimack, NH (US); N. Christopher Perry, Manchester, NH (US); Brian Tracey, Litchfield, NH (US); James D. Dale, Nashua, NH (US); Dirk A. van der Merwe, Manchester, NH (US); Kingston Owens, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 909 days.

This patent is subject to a terminal disclaimer.

(21) Appl. No.: 13/018,054

(22) Filed: Jan. 31, 2011

(65) Prior Publication Data

US 2011/0218600 A1    Sep. 8, 2011

Related U.S. Application Data

(63) Continuation of application No. 11/787,213, filed on Apr. 13, 2007, now abandoned.

(60) Provisional application No. 60/792,073, filed on Apr. 14, 2006, provisional application No. 60/835,490, filed on Aug. 4, 2006, provisional application No. 60/904,024, filed on Feb. 27, 2007, provisional application No. 60/921,314, filed on Apr. 2, 2007.

(51) Int. Cl.
*A61M 37/00* (2006.01)
*C02F 1/44* (2006.01)

(Continued)

(52) U.S. Cl.
CPC ............. *A61M 1/106* (2013.01); *A61M 1/1037* (2013.01); *A61M 1/369* (2013.01); *F04B 43/06* (2013.01);

(Continued)

(58) Field of Classification Search
USPC ............. 604/4.01, 5.01, 6.09, 6.1, 6.11, 6.13, 604/246; 422/44, 46, 48; 417/477.2, 437; 210/645, 252, 257.2, 258, 175
See application file for complete search history.

(56) References Cited

U.S. PATENT DOCUMENTS 2,529,028 A    11/1950 Landon
3,656,873 A *    4/1972 Schiff .......................... 417/395

(Continued)

FOREIGN PATENT DOCUMENTS

DE    33 28 744 A1    2/1995
EP    0 687 474 A1    12/1995

(Continued)

OTHER PUBLICATIONS

International Search Report and Written Opinion mailed Aug. 1, 2008 for Application No. PCT/US2008/055000

(Continued)

*Primary Examiner* — Leslie Deak
(74) *Attorney, Agent, or Firm* — Wolf, Greenfield & Sacks, P.C.

(57) ABSTRACT

Embodiments of the present invention relate generally to heat-exchanger systems that can be used to heat or cool a fluid such as blood. Pod pumps that provide low shear and low turbulence may be used in such systems, particularly for systems that pump blood. A certain heat-exchanger system used to heat blood or other fluids may be used to provide whole-body hyperthermic treatments or regional hyperthermic chemotherapy treatments. A disposable unit may be used to separate the fluid path from the fluid control systems. The disposable unit typically includes a heat-exchanger component that is received by a corresponding heat exchanger in a base unit. Fluid pumped through the heat-exchanger component is heated by the heat exchanger.

36 Claims, 107 Drawing Sheets

(51) Int. Cl.
*A61M 1/00* (2006.01)
*A61M 1/10* (2006.01)
*A61M 1/36* (2006.01)
*F04B 43/06* (2006.01)
*F04B 43/073* (2006.01)
*G01K 1/08* (2006.01)
*G01K 1/16* (2006.01)
*G01M 3/18* (2006.01)
*A61F 7/12* (2006.01)

(52) U.S. Cl.
CPC .............. *F04B 43/0736* (2013.01); *G01K 1/08* (2013.01); *G01K 1/16* (2013.01); *G01M 3/188* (2013.01); *A61M 1/1086* (2013.01); *A61F 2007/126* (2013.01); *A61M 1/3626* (2013.01); *A61M 2205/27* (2013.01); *A61M 2205/3368* (2013.01); *A61M 2205/3606* (2013.01); *A61M 2205/3653* (2013.01); *A61M 2205/502* (2013.01); *A61M 2205/12* (2013.01)
USPC ........... 604/6.11; 604/4.01; 604/246; 422/44; 417/437; 417/37; 210/645

(56) References Cited

U.S. PATENT DOCUMENTS

| | | |
|---|---|---|
| RE27,849 E | 12/1973 | Wortman |
| 4,096,211 A | 6/1978 | Rameau |
| 4,161,264 A | 7/1979 | Malmgren et al. |
| 4,309,592 A | 1/1982 | Le Boeuf |
| 4,479,760 A | 10/1984 | Bilstad et al. |
| 4,479,761 A * | 10/1984 | Bilstad et al. .................. 417/395 |
| 4,574,876 A | 3/1986 | Aid |
| 4,623,450 A | 11/1986 | Vantard et al. |
| 4,680,445 A | 7/1987 | Ogawa |
| 4,731,072 A | 3/1988 | Aid |
| 4,808,161 A | 2/1989 | Kamen et al. |
| 4,826,482 A | 5/1989 | Kamen |
| 4,863,461 A | 9/1989 | Jarvik |
| 4,906,816 A | 3/1990 | van Leerdam |
| 4,927,411 A | 5/1990 | Pastrone et al. |
| 4,976,162 A | 12/1990 | Kamen |
| 4,976,729 A | 12/1990 | Holfert et al. |
| 5,062,774 A | 11/1991 | Kramer et al. |
| 5,074,838 A | 12/1991 | Kroyer |
| 5,088,515 A | 2/1992 | Kamen |
| 5,088,901 A | 2/1992 | Brauer |
| 5,125,069 A | 6/1992 | O'Boyle |
| 5,245,693 A | 9/1993 | Ford et al. |
| 5,247,434 A | 9/1993 | Peterson et al. |
| 5,306,242 A | 4/1994 | Joyce et al. |
| 5,324,422 A | 6/1994 | Colleran et al. |
| 5,349,896 A | 9/1994 | Delaney, III et al. |
| 5,350,357 A | 9/1994 | Kamen et al. |
| 5,420,962 A | 5/1995 | Bakke |
| 5,421,823 A | 6/1995 | Kamen et al. |
| 5,429,485 A | 7/1995 | Dodge |
| 5,431,626 A | 7/1995 | Bryant et al. |
| 5,438,510 A | 8/1995 | Bryant et al. |
| 5,441,343 A | 8/1995 | Pylkki et al. |
| 5,472,614 A | 12/1995 | Rossi |
| 5,474,683 A | 12/1995 | Bryant et al. |
| 5,476,444 A | 12/1995 | Keeling et al. |
| 5,486,286 A | 1/1996 | Peterson et al. |
| 5,496,273 A | 3/1996 | Pastrone et al. |
| 5,516,429 A * | 5/1996 | Snodgrass et al. ............ 210/767 |
| 5,542,919 A | 8/1996 | Simon et al. |
| 5,586,438 A * | 12/1996 | Fahy .................. 62/78 |
| 5,593,290 A | 1/1997 | Greisch et al. |
| 5,628,908 A | 5/1997 | Kamen et al. |
| 5,634,896 A | 6/1997 | Bryant et al. |
| 5,645,531 A * | 7/1997 | Thompson et al. ............. 604/67 |
| 5,690,831 A | 11/1997 | Kenley et al. |
| 5,729,653 A | 3/1998 | Magliochetti et al. |
| 5,730,720 A | 3/1998 | Sites et al. |
| 5,875,282 A | 2/1999 | Jordan et al. |
| 5,899,873 A | 5/1999 | Jones et al. |
| 5,947,931 A | 9/1999 | Bierman et al. |
| 5,989,423 A | 11/1999 | Kamen et al. |
| 6,042,784 A | 3/2000 | Wamsiedler et al. |
| 6,047,108 A | 4/2000 | Sword et al. |
| 6,070,761 A | 6/2000 | Bloom et al. |
| 6,109,881 A | 8/2000 | Snodgrass et al. |
| 6,210,361 B1 | 4/2001 | Kamen et al. |
| 6,223,130 B1 | 4/2001 | Gray et al. |
| 6,274,303 B1 | 8/2001 | Wowk et al. |
| 6,277,272 B1 | 8/2001 | Nikaido et al. |
| 6,302,653 B1 | 10/2001 | Bryant et al. |
| 6,321,597 B1 | 11/2001 | Demers et al. |
| 6,336,003 B1 | 1/2002 | Mitsunaga et al. |
| 6,347,633 B1 | 2/2002 | Groth et al. |
| 6,382,923 B1 | 5/2002 | Gray |
| 6,406,426 B1 | 6/2002 | Reuss et al. |
| 6,413,233 B1 | 7/2002 | Sites et al. |
| 6,415,797 B1 | 7/2002 | Groth et al. |
| 6,464,666 B1 | 10/2002 | Augustine et al. |
| 6,480,257 B2 | 11/2002 | Cassidy et al. |
| 6,485,263 B1 | 11/2002 | Bryant et al. |
| 6,497,676 B1 | 12/2002 | Childers et al. |
| 6,517,510 B1 | 2/2003 | Stewart et al. |
| 6,520,747 B2 | 2/2003 | Gray et al. |
| 6,529,775 B2 | 3/2003 | Whitebook et al. |
| 6,535,689 B2 | 3/2003 | Augustine et al. |
| 6,539,172 B2 | 3/2003 | Akahane |
| 6,579,253 B1 | 6/2003 | Burbank et al. |
| 6,579,496 B1 | 6/2003 | Fausset et al. |
| RE38,203 E | 7/2003 | Kelly |
| 6,608,968 B2 | 8/2003 | Bakke |
| 6,660,974 B2 | 12/2003 | Faries, Jr. et al. |
| 6,709,417 B1 | 3/2004 | Houle et al. |
| 6,726,656 B2 | 4/2004 | Kamen et al. |
| 6,749,403 B2 | 6/2004 | Spencer et al. |
| 6,768,085 B2 | 7/2004 | Faries et al. |
| 6,775,473 B2 | 8/2004 | Augustine et al. |
| 6,788,885 B2 | 9/2004 | Mitsunaga et al. |
| 6,808,369 B2 | 10/2004 | Gray et al. |
| 6,814,547 B2 | 11/2004 | Childers et al. |
| 6,868,309 B1 | 3/2005 | Begelman |
| 6,877,713 B1 | 4/2005 | Gray et al. |
| 6,929,751 B2 | 8/2005 | Bowman et al. |
| 6,939,471 B2 | 9/2005 | Gross et al. |
| 6,949,079 B1 | 9/2005 | Westberg et al. |
| 7,029,245 B2 | 4/2006 | Maianti et al. |
| 7,083,719 B2 | 8/2006 | Bowman et al. |
| 7,169,303 B2 | 1/2007 | Sullivan et al. |
| 7,175,606 B2 | 2/2007 | Bowman et al. |
| 7,273,465 B2 | 9/2007 | Ash |
| 7,300,413 B2 | 11/2007 | Burbank et al. |
| 7,318,892 B2 | 1/2008 | Connell et al. |
| 7,794,141 B2 | 9/2010 | Perry et al. |
| 7,967,022 B2 | 6/2011 | Grant et al. |
| 8,042,563 B2 | 10/2011 | Grant et al. |
| 8,246,826 B2 | 8/2012 | Wilt et al. |
| 8,273,049 B2 | 9/2012 | Demers et al. |
| 8,292,594 B2 * | 10/2012 | Tracey et al. ................... 417/43 |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,459,292 B2 | 6/2013 | Wilt et al. |
| 8,491,184 B2 | 7/2013 | Kamen et al. |
| 8,499,780 B2 | 8/2013 | Wilt et al. |
| 8,545,698 B2 | 10/2013 | Wilt et al. |
| 8,562,834 B2 | 10/2013 | Kamen et al. |
| 8,721,879 B2 | 5/2014 | Van der Merwe et al. |
| 8,721,884 B2 | 5/2014 | Wilt et al. |
| 2002/0056672 A1 | 5/2002 | Lyle et al. |
| 2002/0103453 A1 | 8/2002 | Burbank et al. |
| 2002/0179505 A1 | 12/2002 | Rovatti et al. |
| 2002/0182090 A1 | 12/2002 | Gray |
| 2003/0194328 A1 | 10/2003 | Bryant et al. |
| 2003/0220605 A1 | 11/2003 | Bowman, Jr. et al. |

(56) References Cited

U.S. PATENT DOCUMENTS

| | | |
|---|---|---|
| 2003/0230191 A1 | 12/2003 | Ohrle et al. |
| 2004/0001766 A1 | 1/2004 | Maianti et al. |
| 2004/0091374 A1 | 5/2004 | Gray |
| 2004/0136843 A1 | 7/2004 | Jahn et al. |
| 2004/0138607 A1 | 7/2004 | Burbank et al. |
| 2005/0020958 A1 | 1/2005 | Paolini et al. |
| 2005/0069425 A1 | 3/2005 | Gray et al. |
| 2005/0095154 A1 | 5/2005 | Tracey et al. |
| 2005/0145010 A1 | 7/2005 | Vanderveen et al. |
| 2005/0230292 A1 | 10/2005 | Beden et al. |
| 2006/0093531 A1 | 5/2006 | Tremoulet et al. |
| 2006/0184084 A1 | 8/2006 | Ware et al. |
| 2006/0195064 A1 | 8/2006 | Plahey et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0253463 A1 | 11/2007 | Perry et al. |
| 2008/0015493 A1 | 1/2008 | Childers et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Gavin et al. |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0208103 A1 | 8/2008 | Demers et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Knelp et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Shah et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0024070 A1 | 1/2009 | Gelfand et al. |
| 2009/0043239 A1 | 2/2009 | Gagel et al. |
| 2009/0076434 A1 | 3/2009 | Mischelevich et al. |
| 2009/0095679 A1 | 4/2009 | Demers et al. |
| 2009/0101549 A1 | 4/2009 | Kamen et al. |
| 2009/0101550 A1 | 4/2009 | Muller et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2010/0051529 A1 | 3/2010 | Grant et al. |
| 2010/0051551 A1 | 3/2010 | Grant et al. |
| 2010/0056975 A1 | 3/2010 | Dale et al. |
| 2010/0057016 A1 | 3/2010 | Dale et al. |
| 2010/0192686 A1 | 8/2010 | Kamen et al. |
| 2011/0105877 A1 | 5/2011 | Wilt et al. |
| 2011/0299358 A1 | 12/2011 | Wilt et al. |
| 2012/0106289 A1 | 5/2012 | Wilt et al. |
| 2012/0207627 A1 | 8/2012 | Demers et al. |
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0126413 A1 | 5/2013 | Van der Merwe et al. |
| 2013/0177457 A1 | 7/2013 | Demers et al. |
| 2013/0284648 A1 | 10/2013 | Grant et al. |
| 2013/0304020 A1 | 11/2013 | Wilt et al. |
| 2013/0317454 A1 | 11/2013 | Grant et al. |
| 2014/0102299 A1 | 4/2014 | Wilt et al. |
| 2014/0102958 A1 | 4/2014 | Kamen et al. |
| 2014/0102970 A1 | 4/2014 | Wilt et al. |
| 2014/0112828 A1 | 4/2014 | Grant et al. |
| 2014/0153356 A1 | 6/2014 | Grant et al. |

FOREIGN PATENT DOCUMENTS

| | | |
|---|---|---|
| EP | 0 992 255 A2 | 4/2000 |
| JP | S60-077782 U | 5/1985 |
| JP | H09-099060 | 4/1997 |
| JP | H11-210633 A | 8/1999 |
| JP | 2006-204343 A | 8/2006 |
| WO | WO 98/39058 A1 | 9/1998 |
| WO | WO 99/10028 A1 | 3/1999 |
| WO | WO 01/37895 A2 | 5/2001 |
| WO | WO 02/03879 A1 | 1/2002 |
| WO | WO 02/30267 A2 | 4/2002 |
| WO | WO 2004/041081 A1 | 5/2004 |
| WO | WO 2005/044339 A1 | 5/2005 |
| WO | WO 2005/044435 A2 | 5/2005 |
| WO | WO 2006/120415 A1 | 11/2006 |
| WO | WO 2007/120812 A2 | 10/2007 |
| WO | WO 2007/126360 A1 | 11/2007 |
| WO | WO 2008/106191 A2 | 9/2008 |
| WO | WO 2008/106440 A1 | 9/2008 |
| WO | WO 2008/106538 A2 | 9/2008 |
| WO | WO 2009/051669 A1 | 4/2009 |
| WO | WO 2010/027435 A1 | 3/2010 |
| WO | WO 2010/027437 A2 | 3/2010 |

OTHER PUBLICATIONS

International Preliminary Report on Patentability mailed Sep. 11, 2009 for Application No. PCT/US2008/055000.

Invitation to Pay Additional Fees mailed Aug. 5, 2008 for Application No. PCT/US2008/055168.

International Search Report and Written Opinion mailed Nov. 10, 2008 for Application No. PCT/US2008/055168.

International Preliminary Report on Patentability mailed Sep. 11, 2009 for Application No. PCT/US2008/055168.

Invitation to Pay Additional Fees mailed Nov. 27, 2009 for Application No. PCT/US2009/004866.

International Search Report and Written Opinion mailed Jan. 27, 2010 for Application No. PCT/US2009/004866.

Invitation to Pay Additional Fees mailed Dec. 8, 2009 for Application No. PCT/US/2009/004877.

International Search Report and Written Opinion mailed Feb. 12, 2010 for Application No. PCT/US/2009/004877.

International Preliminary Report on Patentability mailed Oct. 23, 2008 for Application No. PCT/US2007/009107.

International Search Report and Written Opinion mailed Feb. 20, 2009 for Application No. PCT/US2008/011663.

International Preliminary Report on Patentability mailed Apr. 22, 2010 for Application No. PCT/US2008/011663.

Office Action for U.S. Appl. No. 11/871,712, filed Oct. 12, 2007, published as US 2009/0004033 on Jan. 1, 2009, which Office Action is dated Feb. 4, 2010, and claims as pending for U.S. Appl. No. 11/871,712 as of Feb. 4, 2010.

Office Action for U.S. Appl. No. 11/787,112, filed Apr. 13, 2007, published as US 2007-253463 on Nov. 1, 2007, which Office Action is dated Nov. 21, 2008, and claims as pending for U.S. Appl. No. 11/787,112 as of Nov. 21, 2008.

(56) References Cited

OTHER PUBLICATIONS

Bengtsson et al., Haemo dialysis software architecture design experiences. Proceedings of the 1999 International Conference on Software Engineering. ACM New York, NY. 1999:516-525.

Choppy et al., Architectural patterns for problem frames. IEE Proceedings: Software. Aug. 2005;152(4):198-208.

Gentilini et al., Multitasked closed-loop control in anesthesia. *IEEE Eng Med Biol Mag.* Jan.-Feb. 2001;20(1):39-53.

Harel, Statecharts: A visual formalism for complex systems. Science of Computer Programming 1987;8:231-274.

Krasner et al., A cookbook for using the model-view-controller user interface paradigm in smalltalk-80. JOOP. Aug. 1988;1(3):26-49.

\* cited by examiner

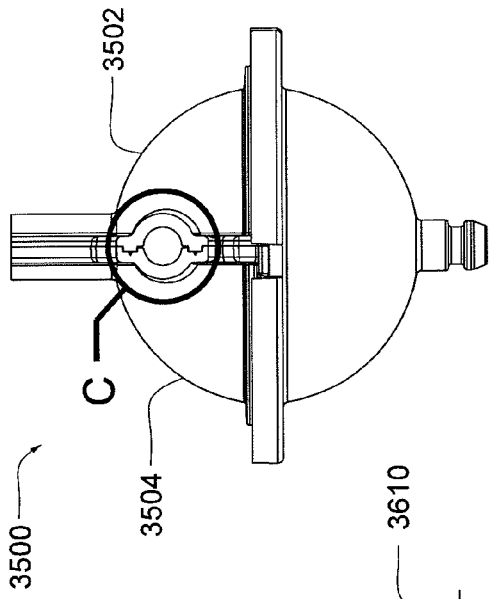
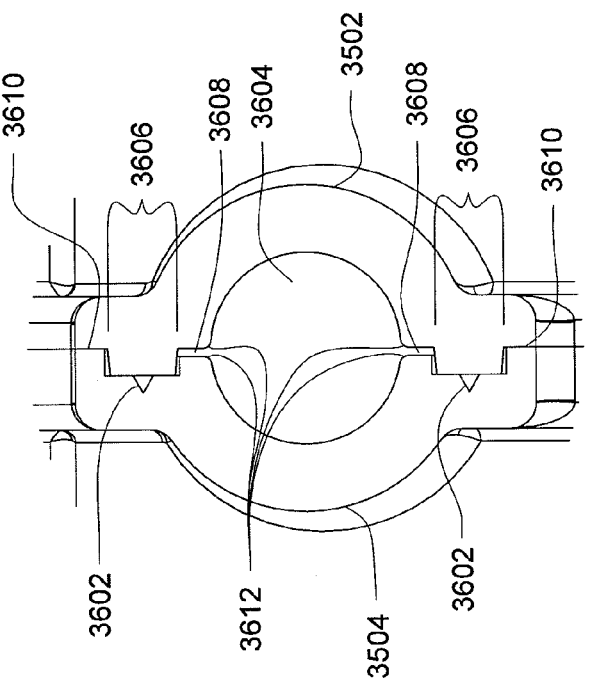
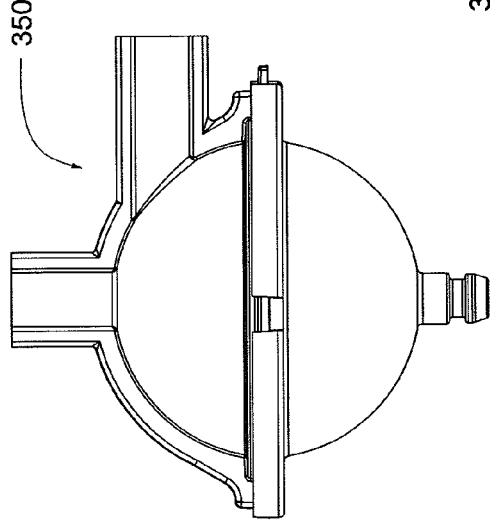

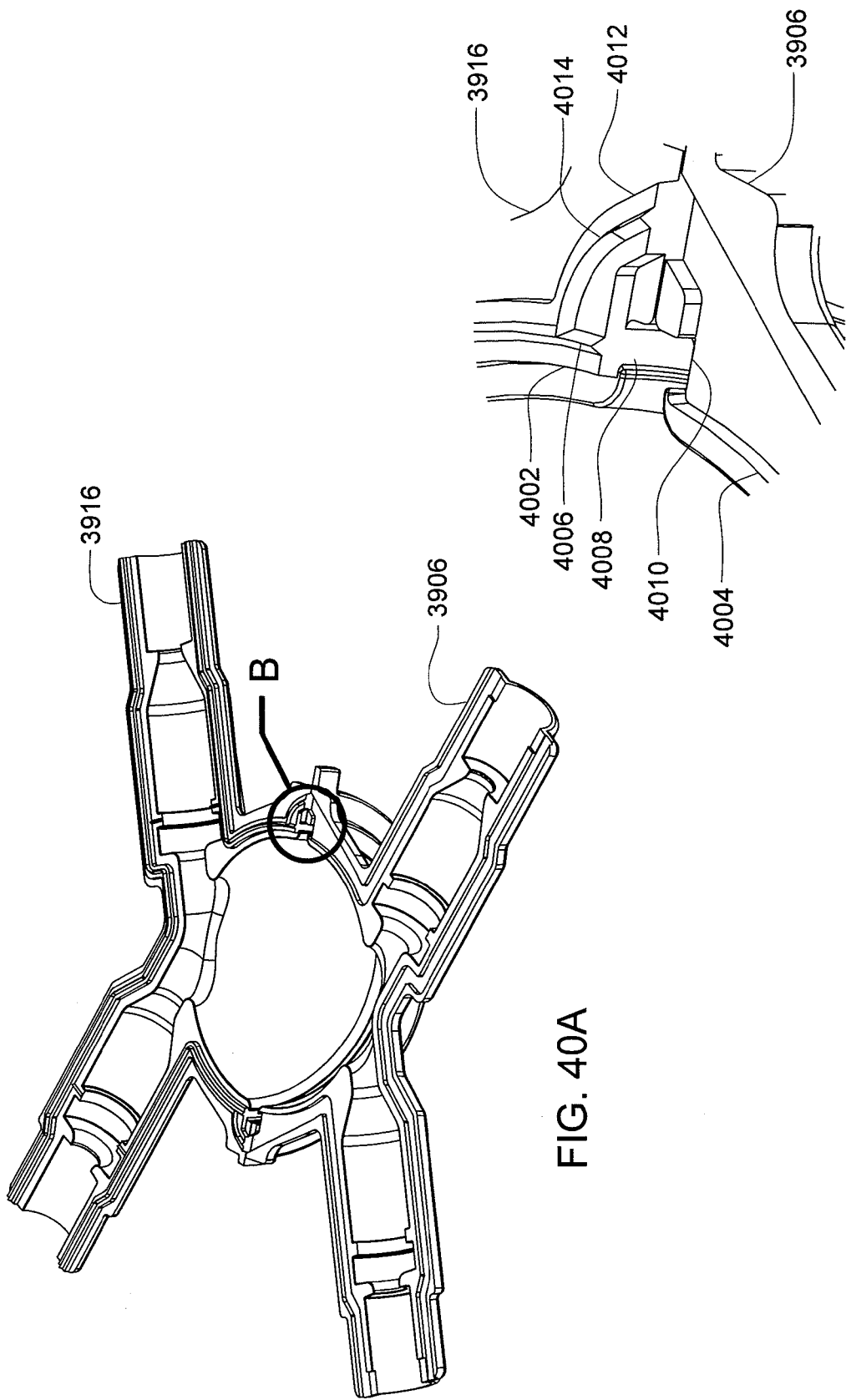

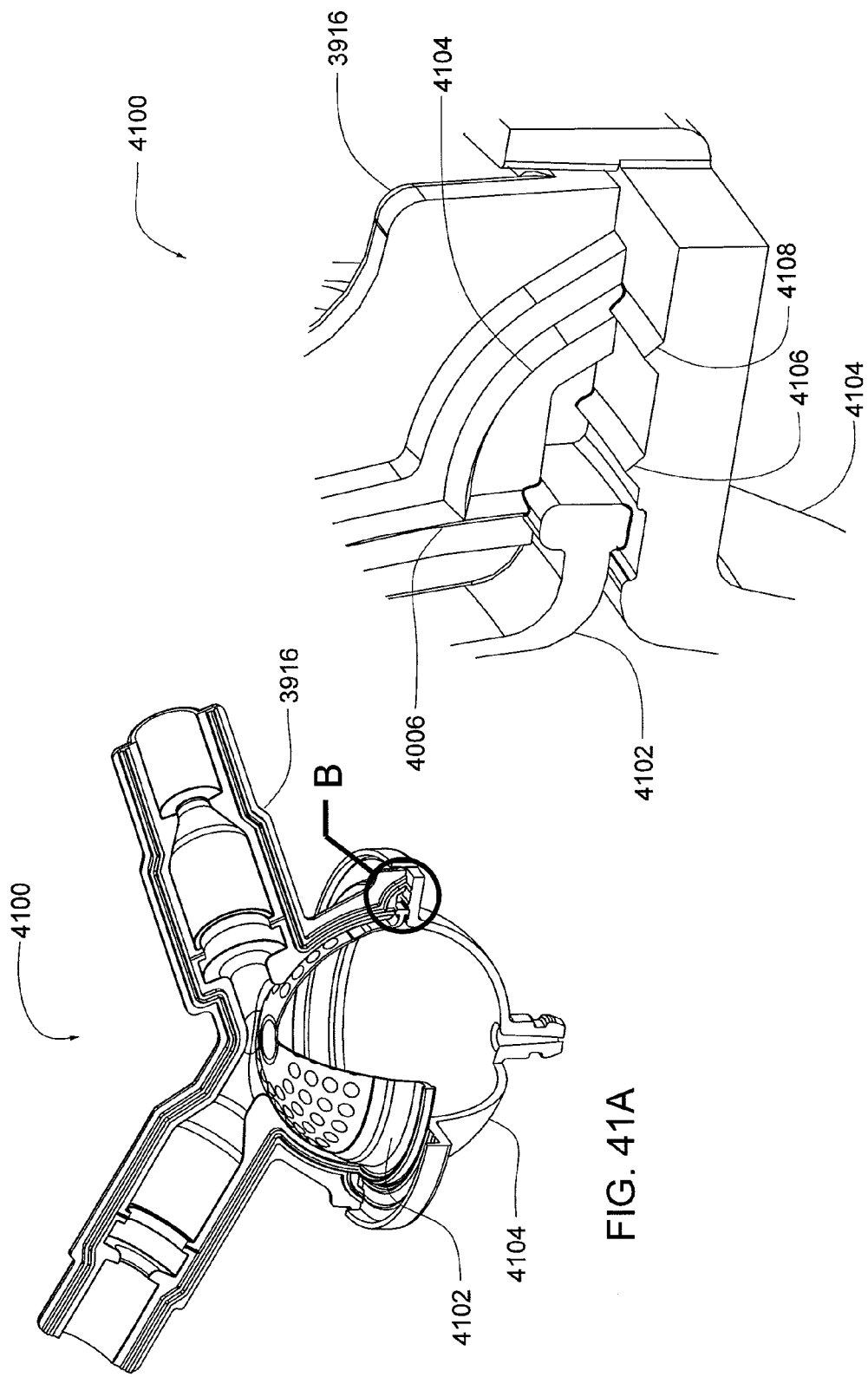

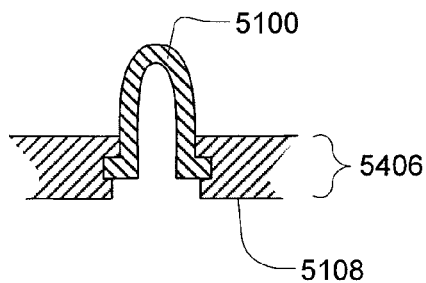
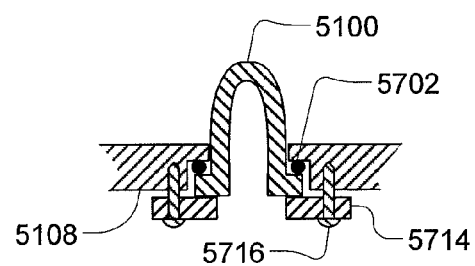
FIG. 56M          FIG. 56N
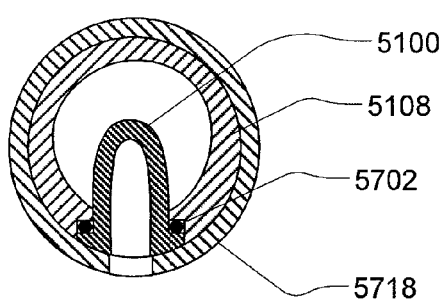
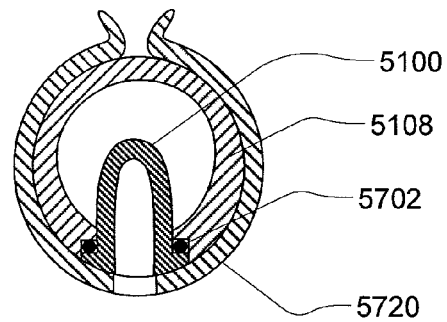
FIG. 56O          FIG. 56P

HEAT EXCHANGE SYSTEMS, DEVICES AND METHODS

CROSS-REFERENCE TO RELATED APPLICATIONS

This application is a continuation of U.S. patent application Ser. No. 11/787,213, entitled "Heat Exchange Systems, Devices and Methods," by Dean Kamen et al., filed on Apr. 13, 2007, which is incorporated herein by reference in its entirety.

U.S. patent application Ser. No. 11/787,213 claims priority from the following United States Provisional Patent Applications, all of which are hereby incorporated herein by reference in their entireties:

U.S. Provisional Patent Application No. 60/792,073 entitled Extracorporeal Thermal Therapy Systems and Methods filed on Apr. 14, 2006;

U.S. Provisional Patent Application No. 60/835,490 entitled Extracorporeal Thermal Therapy Systems and Methods filed on Aug. 4, 2006;

U.S. Provisional Patent Application No. 60/904,024 entitled Hemodialysis System and Methods filed on Feb. 27, 2007; and U.S. Provisional Patent Application No. 60/921,314 entitled Sensor Apparatus filed on Apr. 2, 2007.

This application is also related to the following United States Patent Applications, all of which are hereby incorporated herein by reference in their entireties:

U.S. patent application Ser. No. 11/787,212 entitled FLUID PUMPING SYSTEMS, DEVICES AND METHODS filed on Apr. 13, 2007 and published as Publication No. US-2008-0175719; and U.S. patent application Ser. No. 11/787,112 entitled THERMAL AND CONDUCTIVITY SENSING SYSTEMS, DEVICES, AND METHODS filed on Apr. 13, 2007 and published as Publication No. US-2007-0253463.

This application is also related to U.S. patent application Ser. No. 10/697,450 entitled BEZEL ASSEMBLY FOR PNEUMATIC CONTROL filed on Oct. 30, 2003 and now issued as U.S. Pat. No. 7,632,080 (DEKA Docket No. D75) and related PCT Application No. PCT/US2004/035952 entitled BEZEL ASSEMBLY FOR PNEUMATIC CONTROL filed on Oct. 29, 2004 and published as Publication No. WO 2005/044435 (DEKA Docket No. D71WO), both of which are hereby incorporated herein by reference in their entireties.

TECHNICAL FIELD

The present invention relates heat exchange systems

BACKGROUND ART

It is known in the prior art that altering the body temperature of a patient by means of extracorporeal heating can treat a variety of diseases, such as Hepatitis C and possibly some types of cancer, HIV/AIDS, rheumatoid arthritis and psoriasis. In order to heat the blood in a reasonable amount of time, high flow rates are necessary from the patient's body to a heater and back to the patient.

Centrifugal pumps have been used in prior art systems in order to achieve relatively large flow rates of blood to and from the patient's body. Although the centrifugal pumps can achieve the necessary high flow rates, the centrifugal pumps create relatively large shear forces on the blood resulting in an undesirable amount of hemolysis. Heated blood is even more prone to hemolysis.

Because of the large flow rates of blood to and from the patient, a leak in the system could quickly result in the death of the patient.

The prior art systems also typically involve bulky equipment and are relatively clumsy, resulting in time lags when switching the system from one patient to the next, and increasing the risk of the system being improperly set up.

SUMMARY OF THE INVENTION

In accordance with one aspect of the invention there is provided a method for heating or cooling a fluid, the method comprising:

providing at least one reciprocating positive-displacement pump, each pump having:
  a curved rigid chamber wall;
  a flexible membrane attached to the rigid chamber wall, so that the flexible membrane and rigid chamber wall define a pumping chamber;
  an inlet for directing fluid through the rigid chamber wall into the pumping chamber in at least one of (a) a direction that is substantially tangential to the rigid chamber wall and (b) a direction that provides low-shear flow into the pumping chamber; and
  an outlet for directing fluid through the rigid chamber wall out of the pumping chamber in at least one of (a) a direction that is substantially tangential to the rigid chamber wall and (b) a direction that provides low-shear flow out of the pumping chamber;
providing a heat exchanger; and
pumping the fluid from a source using the at least one reciprocating positive-displacement pump so as to cause the fluid to pass through the heat exchanger.

In accordance with another aspect of the invention there is provided a disposable unit for use in a heat exchanger system, the disposable unit comprising:

at least one reciprocating positive-displacement pump, each pump having
  a curved rigid chamber wall;
  a flexible membrane attached to the rigid chamber wall, so that the flexible membrane and rigid chamber wall define a pumping chamber;
  an inlet for directing fluid through the rigid chamber wall into the pumping chamber in at least one of (a) a direction that is substantially tangential to the rigid chamber wall and (b) a direction that provides low-shear flow into the pumping chamber; and
  an outlet for directing fluid through the rigid chamber wall out of the pumping chamber in at least one of (a) a direction that is substantially tangential to the rigid chamber wall and (b) a direction that provides low-shear flow out of the pumping chamber; and
a heat-exchanger component, in fluid communication with the at least one pump and adapted to be received by a heat exchanger.

In accordance with another aspect of the invention there is provided a heat-exchanger system comprising:

a heat exchanger for receiving a heat-exchanger component of a disposable unit;
a pneumatic actuation system for operating at least one pump of the disposable unit for pumping fluid through the heat-exchanger component; and
a controller for controlling the pneumatic actuation system.

In some embodiments, the disposable unit may be considered to be part of the heat-exchanger system.

In accordance with another aspect of the invention there is provided a method of moving blood between a patient-access device and a heat exchanger for heating the blood, the method comprising:

providing a reciprocating positive-displacement pump;

providing a flow line having a first portion between the patient-access device and the pump and having a second portion between the pump and the heat exchanger;

providing for each of the first and second portions of the flow line a valve for permitting flow in only one direction of the flow line; and actuating the pump to cause the flow of blood between the patient-access device and the heat exchanger.

In accordance with another aspect of the invention there is provided a system for extracorporeal thermal therapy, the system comprising:

a heat exchanger for heating the blood;

a reciprocating positive-displacement pump for moving blood between a patient-access device and the heat exchanger, the pump having an inlet line and an outlet line;

a first valve, located in the inlet line, for preventing flow of blood out of the pump; and a second valve, located in the outlet line, for preventing flow of blood into the pump.

In accordance with another aspect of the invention there is provided a heat exchanger for heating extracorporeal blood for hyperthermia treatment, the heat exchanger comprising a pump according to one of above claims, and further including a heat-exchange flow path having an inlet for unheated blood an outlet for heated blood;

an electricity-to-heat converter that turns electrical power into heat for absorption by the blood;

a first temperature sensor located at the inlet for measuring the temperature of the blood entering the heat exchanger;

a second temperature sensor located at the outlet for measuring the temperature of the blood exiting the heat exchanger;

a metering system that measures the flow rate of blood passing through the heat exchanger; and a controller in communication with the converter, the first and second temperature sensors, and the metering system, the controller receiving information regarding the amount of power being used by the converter, receiving temperature information from the first and second temperature sensors, receiving flow-rate information from the metering system, analyzing the received information in order to determine whether a fault condition exists, and generating a signal if a fault condition is detected.

In accordance with another aspect of the invention there is provided a heat exchanger for heating extracorporeal blood for hyperthermia treatment, the heat exchanger comprising:

an inlet for unheated blood;

an outlet for heated blood;

a flow path from the inlet to the outlet;

a set of heating elements overlapping the flow path, including at least first and second heating elements, the second heating element being located adjacent the flow path near the outlet, and the first heating element being located adjacent the flow path at a point upstream of the second heating element;

a first temperature sensor located adjacent the flow path upstream of the first heating element;

a second temperature sensor located adjacent the flow path between the first and second heating elements; and a controller for receiving temperature information from the first and second temperature sensors and for generating a signal if a temperature difference being measured by the first and second sensors exceeds a limit.

In accordance with another aspect of the invention there is provided a heat exchanger for heating extracorporeal blood for hyperthermia treatment, the heat exchanger comprising:

an inlet for unheated blood;

an outlet for heated blood;

a flow path from the inlet to the outlet;

a set of heating elements overlapping the flow path, including at least first, second and third heating elements, the third heating element being located adjacent the flow path near the outlet, the second heating element being located adjacent the flow path at a point prior to the third heating element, and the first heating element being located adjacent the flow path at a point prior to the second heating element;

a first temperature sensor located adjacent the flow path between the first and second heating elements;

a second temperature sensor located adjacent the flow path between the second and third heating elements; and a controller for receiving temperature information from the first and second temperature sensors and for generating a signal if a temperature difference being measured by the first and second sensors exceeds a limit.

In accordance with another aspect of the invention there is provided a heat exchanger for heating extracorporeal blood for hyperthermia treatment, the heat exchanger comprising:

an inlet for unheated blood;

an outlet for heated blood;

an electricity-to-heat converter that turns electrical power into heat for absorption by the blood;

a first temperature sensor located at the inlet for measuring the temperature of the blood entering the heat exchanger;

a second temperature sensor located at the outlet for measuring the temperature of the blood exiting the heat exchanger;

a metering system that measures the flow rate of blood passing through the heat exchanger; and a controller in communication with the converter, the first and second temperature sensors, and the metering system, the controller receiving information regarding the amount of power being used by the converter, receiving temperature information from the first and second temperature sensors, receiving flow-rate information from the metering system, analyzing the received information in order to determine whether a fault condition exists, and generating a signal if a fault condition is detected.

In accordance with another aspect of the invention there is provided a heat exchanger for heating extracorporeal blood for hyperthermia treatment, the heat exchanger comprising:

an inlet for unheated blood;

an outlet for heated blood;

an electricity-to-heat converter that turns electrical power into heat for absorption by the blood;

a disposable unit containing a flow path of the blood from the inlet to the outlet, the disposable unit being made primarily of a thermoplastic material;

an electrical-conductivity sensor for measuring the resistance between the blood in the flow path a thermowell and the converter; and a controller in communication with the electrical-conductivity sensor and generating a signal if the measured resistance does not satisfy a safety parameter.

In accordance with another aspect of the invention there is provided a heat exchanger for heating extracorporeal blood for hyperthermia treatment, the heat exchanger comprising:

a disposable unit having an inlet for unheated blood, an outlet for heated blood, and
a flow path of the blood from the inlet to the outlet; and
a base unit having
a heater for heating blood in the flow path, the heater including a first thermally conductive plate for conducting heat to a first side of the disposable unit, and a second thermally conductive plate for conducting heat to a second side of the disposable unit opposite the first plate, the first and second plates being adapted to squeeze together, upon actuation by a controller, in order to urge blood out of the disposable.

In accordance with another aspect of the invention there is provided a method of locating temperature probes for monitoring a patient's temperature, the method comprising:
taking temperature readings from a first temperature probe to be located at a first location in the patient's body;
taking temperature readings from a second temperature probe to be located at a second location in the patient's body;
comparing the temperature readings from the first and second probes;
positioning the first and second temperature probes in the patient's body;
determining if the temperature reading from the first or second location is above a pre-set limit; and
generating a placement signal, if the temperature reading from the first probe is within a pre-set range from the temperature reading from the second probe, and if the reading from the first or second location is above a pre-set limit.

In accordance with another aspect of the invention there is provided a method of providing a hyperthermic treatment to a patient, the method comprising:
providing a heat-exchanger system for heating blood from the patient and pumping heated blood to the patient;
connecting a first temperature probe from the patient to the heat-exchanger system, the heat-exchanger system controlling the blood heating and pumping based on temperature information received from the first temperature probe and displaying the temperature information received from the first temperature probe to an operator;
monitoring patient temperature by the operator using an independent second temperature probe; and
terminating the treatment if either of the temperature probes conveys an unacceptable temperature reading.

In some embodiments of the invention there is provided a pump-pod geometry that reduces shear on the fluid being pumped and, when used to pump blood (especially heated blood), reduces hemolysis.

In one embodiment of the invention, a reciprocating positive-displacement pump is provided with a hemispherical rigid chamber wall; a flexible membrane attached to the rigid chamber wall, so that the flexible membrane and rigid chamber wall define a pumping chamber; an inlet for directing flow through the rigid chamber wall into the pumping chamber in a direction that provides low-shear flow into the pumping chamber; and an outlet for directing flow through the rigid chamber wall out of the pumping chamber in a direction that provides low-shear flow out of the pumping chamber.

In one embodiment of the invention, a reciprocating positive-displacement pump is provided comprising a rigid hemispherical chamber wall; a flexible membrane attached to the rigid chamber wall, so that the flexible membrane and rigid chamber wall define a pumping chamber; an inlet for directing flow through the rigid chamber wall into the pumping chamber in a direction that is substantially tangential to the rigid chamber wall; and an outlet for directing flow through the rigid chamber wall out of the pumping chamber in a direction that is substantially tangential to the rigid chamber wall. In some embodiments, the reciprocating positive-displacement pump also includes a rigid limit structure for limiting movement of the membrane and limiting the maximum volume of the pumping chamber, the flexible membrane and the rigid limit structure defining an actuation chamber. The rigid limit structure may be adapted to limit movement of the flexible membrane such that, when the pumping chamber is at maximum volume, the rigid chamber and the flexible membrane (which will be urged against the rigid limit structure) define the pumping chamber as a spherical volume. The rigid limit structure may be a hemispherical limit wall that, together with the flexible membrane, defines a spherical actuation chamber when the pumping chamber is at minimum volume.

In certain embodiments, the reciprocating positive-displacement pump is provided with a pneumatic actuation system that intermittently provides either a positive or a negative pressure to the actuation chamber. The pneumatic actuation system in some embodiments include a reservoir containing a gas at either a positive or a negative pressure, and a valving mechanism for controlling the flow of gas between the actuation chamber and the gas reservoir. The reciprocating positive-displacement pump may be provided with an actuation-chamber pressure transducer for measuring the pressure of the actuation chamber, and a controller that receives pressure information from the actuation-chamber pressure transducer and controls the valving mechanism. In certain embodiments, a reservoir pressure transducer for measuring the pressure of the pressure of gas in the reservoir is provided, and the controller receives pressure information from the reservoir pressure transducer. The controller in some embodiments compares the pressure information from the actuation-chamber and reservoir pressure transducers to determine whether either of the pressure transducers is malfunctioning.

In certain embodiments, the pneumatic actuation system alternately provides positive and negative pressure to the actuation chamber. In one arrangement, the pneumatic actuation system includes a positive-pressure gas reservoir, a negative-pressure gas reservoir, and a valving mechanism for controlling the flow of gas between the actuation chamber and each of the gas reservoirs. In such embodiments, an actuation-chamber pressure transducer is also provided for measuring the pressure of the actuation chamber, and a controller that receives pressure information from the actuation-chamber pressure transducer and controls the valving mechanism. In addition, such embodiments may include a positive-pressure-reservoir pressure transducer for measuring the pressure of the positive-pressure gas reservoir, and a negative-pressure-reservoir pressure transducer for measuring the pressure of the negative-pressure gas reservoir. The controller receives pressure information from these transducers and analyzes the pressure information to determine whether any of the pressure transducers are malfunctioning. The controller also controls the pressure of the reservoir or reservoirs to ensure it does not exceed a pre-set limit.

In certain embodiments, the controller causes dithering of the valving mechanism and determines when a stroke ends from pressure information from the actuation-chamber pressure transducer. In further embodiments, the controller controls the valving mechanism to cause the flexible membrane to reach either the rigid chamber wall or the rigid limit structure at each of a stroke's beginning and end. In this embodiment, the controller can determine the amount of flow through the pump based on a number of strokes. In addition, the controller may integrate pressure information from the actuation-chamber pressure transducer over time during a stroke (or otherwise determines the work done during a stroke) as a way of detecting an aberrant flow condition.

In some embodiments of the invention, the reciprocating positive-displacement pump includes an inlet valve for preventing flow out of the pump and an outlet valve for preventing flow into the pump. In some embodiments, these valves are simply passive check valves, and in other embodiments, these valves are active valves that are controlled to cause fluid to flow in the desired direction. In certain embodiments, the pump is adapted for pumping a liquid, and in further embodiments, the pump is adapted for pumping a biological liquid, such as blood. As noted above, some embodiments of the inventions are well adapted for pumping heated blood.

In certain embodiments, the pumps are paired—or otherwise ganged—together so that an inlet line leads to both pumps' inlets and wherein an outlet line leads from both pumps' outlets. In such embodiments, the pumps may be operated out of phase such that when one pump's pumping chamber is substantially full the other pump's pumping chamber is substantially empty.

Embodiments of the invention also provide methods for heating blood extracorporeally. One method includes the steps of providing a reciprocating positive-displacement pump; providing a flow line having a first portion between the patient-access device and the pump and having a second portion between the pump and a heat exchanger; providing for each of the first and second portions of the flow line a valve for permitting flow in only one direction of the flow line; and actuating the pump to cause the flow of blood between the patient-access device and the heat exchanger. The pump may be provided with a flexible membrane as a reciprocating member. A pneumatic actuation system may be provided for alternately providing positive and negative pressure to the membrane. A pump having one of the various structures described herein may be used in such methods.

Certain methods for heating blood extracorporeally include the steps of providing a reciprocating positive-displacement pump having a curved rigid chamber wall, a flexible membrane attached to the rigid chamber wall so that the flexible membrane and rigid chamber wall define a pumping chamber, an inlet for directing flow through the rigid chamber wall into the pumping chamber in a direction that is substantially tangential to the rigid chamber wall, and an outlet for directing flow through the rigid chamber wall out of the pumping chamber in a direction that is substantially tangential to the rigid chamber wall; providing a heater; providing blood from a source; and pumping the blood using the reciprocating positive-displacement pump so as to cause the blood to flow through the heater and be heated. The reciprocating positive-displacement pump is, in certain embodiments, provided with the structural features discussed herein.

Certain embodiments of these methods include the step of monitoring the patient's temperature. Monitoring the patient's temperature may include the steps of taking a temperature reading from a first location in the patient's body; taking a temperature reading from a second location in the patient's body; comparing the temperature readings from the first and second locations; generating a first alarm signal indicating faulty temperature readings, if the temperature reading at the first location is not within a pre-set range from the temperature reading at the second location; determining if the temperature reading from the first location is above a pre-set upper limit; and generating a second alarm signal indicating an overheated condition, if a reading is above the pre-set upper limit.

The methods described herein may use a disposable unit for use in a system for heating blood extracorporeally. Such disposable units may include a reciprocating positive-displacement pump having a curved rigid chamber wall, a flexible membrane attached to the rigid chamber wall so that the flexible membrane and rigid chamber wall define a pumping chamber, an inlet for directing flow through the rigid chamber wall into the pumping chamber in a direction that is substantially tangential to the rigid chamber wall, and an outlet for directing flow through the rigid chamber wall out of the pumping chamber in a direction that is substantially tangential to the rigid chamber wall; and a heat-exchanger component, in fluid communication with the pump, and adapted to be received by a heater. The heat-exchanger component may include a flexible bag that defines a flow path therethrough. The reciprocating positive-displacement pump may have a structure as described herein.

The disposable unit preferably attaches, in an easily removable manner, to a base unit, which preferably includes means for attaching to a pneumatic actuation system that intermittently provides either a positive or a negative pressure to the pump's actuation chamber, and preferably includes the controller for controlling the pneumatic actuation system. The controller preferably controls the system so as to perform methods described herein. The base unit is preferably capable of receiving and holding disposable units having pod pumps with different stroke volumes In one embodiment of a system for extracorporeal thermal therapy, a heat exchanger is provided for heating the blood; a reciprocating positive-displacement pump is provided for moving blood between a patient-access device (e.g., a cannula, needle or shunt) and the heat exchanger, the pump having an inlet line and an outlet line; a first valve, located in the inlet line, is provided for preventing flow of blood out of the pump; and a second valve, located in the outlet line, is provided for preventing flow of blood into the pump. The pump may have a structure as described herein.

In a particular embodiment, the reciprocating positive-displacement pump uses a flexible membrane made from a material that reduces hard snapping of the membrane as the membrane reciprocates. The central portion may include bumps that space the central portion away from the rigid chamber wall when the membrane is in a minimum-pumping-chamber-volume position. Such bumps prevent liquid from being trapped between the membrane and the wall.

The controller, in a particular embodiment, receives temperature information from a first temperature sensor located at the inlet for measuring the temperature of the blood entering the heat exchanger and from a second temperature sensor located at the outlet for measuring the temperature of the blood exiting the heat exchanger, while also receiving flow-rate information from a metering system that measures the flow rate of blood passing through the heat exchanger. These temperature sensors may be located in a base unit of the system, while thermally conductive thermowells in the disposable unit provide thermal communication between the flow path and the base unit's sensors. The controller is also in communication with an electricity-to-heat converter and receives information regarding the amount of power being used by the converter. The controller, in this embodiment, analyzes the received information from the temperature probes, the metering system and the converter in order to determine whether a fault condition exists, and generates a signal if a fault condition is detected.

The controller may also receive temperature information from temperature sensors mounted near heating elements adjacent the heat exchanger's heating plates, wherein electrical current causes the heating elements to heat the heating plates, which in turn heat the blood passing through the heat exchanger. A set of heating elements may overlap the flow path through the heat exchanger. The set of heating elements includes at least first and second heating elements, the second heating element being located adjacent the flow path near the outlet, and the first heating element being located adjacent the flow path at a point upstream of the second heating element. A first temperature sensor is located adjacent the flow path upstream of the first heating element, and a second temperature sensor is located adjacent the flow path between the first and second heating elements. In this embodiment, the controller receives temperature information from the first and second temperature sensors, and generates a signal if a temperature difference being measured by the first and second sensors exceeds a limit. Of course, the heat exchanger may use additional heating elements beyond the two referred to here. The flow path may course through a substantially planar disposable unit. This disposable unit, as noted above, may be a flexible bag.

A first heating plate, which in one embodiment is simply a thermally conductive plate, may be located between the heating elements and the disposable unit. A second heating plate may be located adjacent the disposable unit opposite the first heating plate, and a second set of heating elements may be located on a side of the second plate opposite the disposable unit and overlapping the flow path, including at least fourth, fifth and sixth heating elements, the sixth heating element being located adjacent the flow path near the outlet, the fifth heating element being located adjacent the flow path at a point prior to the sixth heating element, and the fourth heating element being located adjacent the flow path at a point prior to the fifth heating element. In this embodiment, a third temperature sensor may be located adjacent the flow path between the fourth and fifth heating elements, and a fourth temperature sensor is located adjacent the flow path between the fifth and sixth heating elements. The controller also receives temperature information from the third and fourth temperature sensors and generates a signal if a temperature difference being measured by the third and fourth sensors exceeds a limit. In one embodiment, the first and second plates may be adapted to squeeze together, upon actuation by the controller, in order to urge blood out of the disposable.

In a certain embodiment, the thermowells referred to previously may also be electrically conductive and be used to detect leaks or air in the system. The disposable unit adapted to be received by the heat exchanger and containing a flow path of the blood may be made primarily of a thermoplastic material. The thermowells located at each of the inlet and outlet are preferably metal to improve thermal and electrical conductivity between the first temperature sensor and the blood in the inlet and between the second temperature sensor and the blood in the outlet. The heating plates each typically include an electrical-conductivity sensor for measuring the resistance between a thermowell and a plate. The controller is in communication with the electrical-conductivity sensor and generates a signal if the measured resistance is too low (indicating a leak in the disposable unit) and/or too high (indicating air in the disposable unit).

In a certain embodiment, a valving system is provided. The valving system includes a valve cassette and a control cassette. The valve cassette contains a plurality of valves, each valve including a valving chamber and an actuation chamber, each valve being actuatable by a control fluid in the actuation chamber. The control cassette has a plurality of fluid-interface ports for providing fluid communication with a control fluid from a base unit. A plurality of tubes extends between the valve cassette and the control cassette. Each tube provides fluid communication between a fluid-interface port and at least one actuation chamber, such that the base unit can actuate a valve by pressurizing control fluid in a fluid interface port.

These aspects of the invention are not meant to be exclusive or comprehensive and other features, aspects, and advantages of the present invention are possible and will be readily apparent to those of ordinary skill in the art when read in conjunction with the following description, the appended claims, and the accompanying drawings.

BRIEF DESCRIPTION OF THE DRAWINGS

The foregoing features of the invention will be more readily understood by reference to the following detailed description, taken with reference to the accompanying drawings, wherein:

FIGS. 36A and 36B are side and end views of an assembled pod pump with a multi part housing;

FIG. 36C is a close up view of a port on a pod pump with a multi part housing;

FIG. 40A is a pictorial view of two parts of a multi part pod pump housing;

FIG. 40B is a pictorial closeup view of aligning features on parts of a multi part pump housing;

FIG. 41A is a pictorial section view of a pod pump assembly with some portions removed;

FIG. 41B is a close up pictorial view of aligning and joining features on a pod pump housing;

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Definitions

Figure 1:
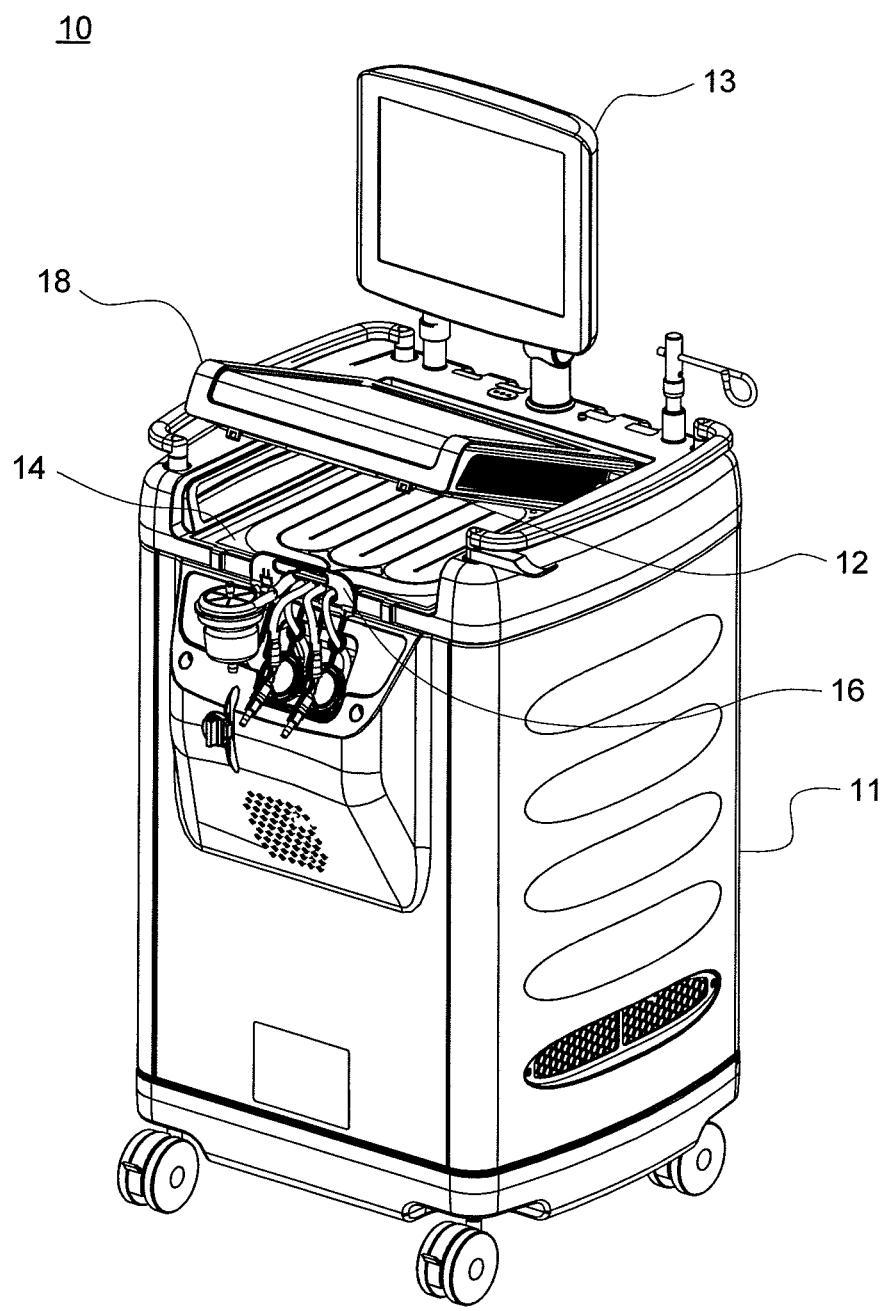
FIG. 1 is a perspective view of an extracorporeal-blood-heating system having a base unit with a disposable unit according to one embodiment of the invention.

As used in this description and the accompanying claims, the following terms shall have the meanings indicated, unless the context otherwise requires:

"Spheroid" means any three-dimensional shape that generally corresponds to a oval rotated about one of its principal axes, major or minor, and includes three-dimensional egg shapes, oblate and prolate spheroids, spheres, and substantially equivalent shapes.

"Hemispheroid" means any three-dimensional shape that generally corresponds to approximately half a spheroid.

"Spherical" means generally spherical.

"Hemispherical" means generally hemispherical.

"Dithering" a valve means rapidly opening and closing the valve.

"Pneumatic" means using air or other gas to move a flexible membrane or other member.

"Substantially tangential" means at an angle less than 75° to a tangent, or in the case of a flat wall, at an angle of less than 75° to the wall.

"Fluid" shall mean a substance, a liquid for example, that is capable of being pumped through a flow line. Blood is a specific example of a fluid.

"Impedance" shall mean the opposition to the flow of fluid.

A "patient" includes a person or animal from whom, or to whom, fluid is pumped, whether as part of a medical treatment or otherwise.

"Subject media" is any material, including any fluid, solid, liquid or gas, that is in contact with either a sensing probe or a thermal well.

Various aspects of the present invention are described below with reference to various exemplary embodiments. It should be noted that headings are included for convenience and do not limit the present invention in any way.

1. EXEMPLARY RECIPROCATING POSITIVE-DISPLACEMENT PUMPS

Embodiments of the present invention relate generally to certain types of reciprocating positive-displacement pumps (which may be referred to hereinafter as "pods," "pump pods," or "pod pumps") used to pump fluids, such as a biological fluid (e.g., blood or peritoneal fluid), a therapeutic fluid (e.g., a medication solution), or a surfactant fluid. Certain embodiments are configured specifically to impart low shear forces and low turbulence on the fluid as the fluid is pumped from an inlet to an outlet. Such embodiments may be particularly useful in pumping fluids that may be damaged by such shear forces (e.g., blood, and particularly heated blood, which is prone to hemolysis) or turbulence (e.g., surfactants or other fluids that may foam or otherwise be damaged or become unstable in the presence of turbulence).

Generally speaking, the pod pump is a modular pump apparatus. The pod pump can be connected to any subject fluid (i.e., liquid, gas or variations thereof) source, which includes but is not limited to a path, line or fluid container, in order to provide movement of said subject fluid. In some embodiments, multiple pod pumps are used, however, in other embodiments, one pod pump is used. The pod pump can additionally be connected to at least one actuation source, which in some embodiments, is at least one air chamber.

In some embodiments, the pod pump is modularly connected to any device or machine. However, in other embodiments, the pod pump is part of a device, machine or container that is attached to another device, machine or container. Although the pod pump is modular, the pod pump may also be part of another modular structure that interacts with any machine, device, container or otherwise.

In one embodiment, the pod pump includes a housing having a diaphragm or movable impermeable membrane attached to the interior of the housing. The diaphragm creates two chambers. One chamber does not come into contact with subject fluid; this chamber is referred to as the actuation chamber. The second chamber comes into contact with the subject fluid. This chamber is referred to as the pump or pumping chamber.

The pod pump, in some embodiments, includes an inlet fluid path and an outlet fluid path. Thus, in these embodiments, a subject fluid is pumped into the pump chamber, then out of the pump chamber. In some embodiments, valving mechanisms are used to ensure that the fluid moves in the intended direction. In other embodiments, the inlet fluid path and the outlet fluid path are one in the same.

The actuation of the diaphragm is provided for by a change in pressure. This change in pressure can be created through use of positive and negative air pressures. In one embodiment, a pneumatic mechanism is used to fill the actuation chamber with air (creating a positive pressure) and then to suck the air out of the actuation chamber (creating a negative pressure). In some embodiments, the air flows through a port in the actuation chamber. The port can be, but is not limited to, an opening or aperture in the actuation chamber. In other embodiments, any fluid (i.e., liquid, gas or variations thereof) can be used as an actuation fluid.

For purposes of this description, exemplary embodiments are shown and described. However, other embodiments are contemplated, thus, the description provided are meant to bring an understanding of the pod pump embodiments, other variations will be apparent.

1.1. Exemplary Pump Pod Configurations

Figure 3:
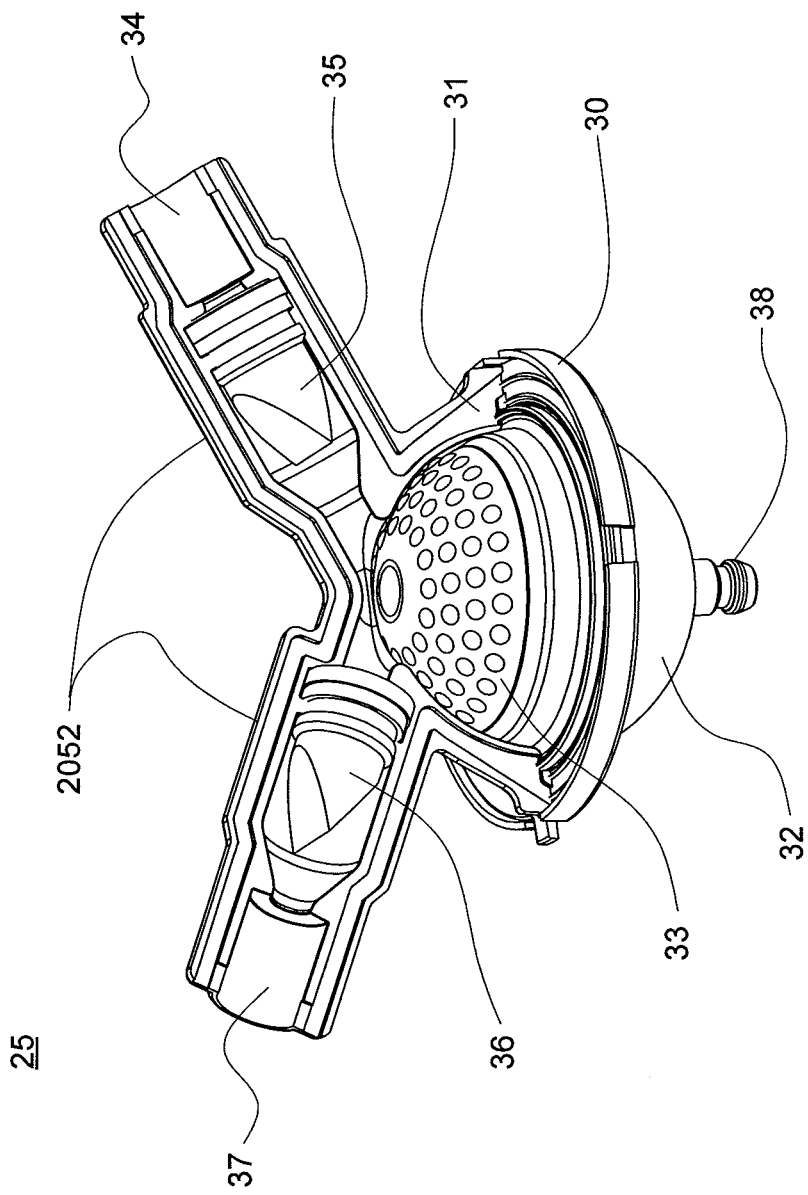
FIG. 3 is a perspective view of a pump pod of the disposable unit shown in FIG. 2.

FIG. 3 shows a reciprocating positive-displacement pump 25 in accordance with an exemplary embodiment of the present invention. In this embodiment, the reciprocating positive-displacement pump 25 is essentially a self-contained unit (which may be referred to hereinafter as a "pod") that may be used as a component of a larger pumping system. The reciprocating positive-displacement pump 25 includes a "top" portion (also referred to as the "pumping chamber wall") 31 and a "bottom" portion (also referred to as the "actuation chamber wall") 32 that are coupled together at pod wall 30, for example, by ultrasonic welding or other technique. It should be noted that the terms "top" and "bottom" are relative and are used here for convenience with reference to the orientation shown in FIG. 3. Each of the portions 31 and 32 has a rigid interior surface that is preferably (although not necessarily) hemispherical, such that the pod has an interior cavity that is preferably (although not necessarily) spherical.

Figure 37:
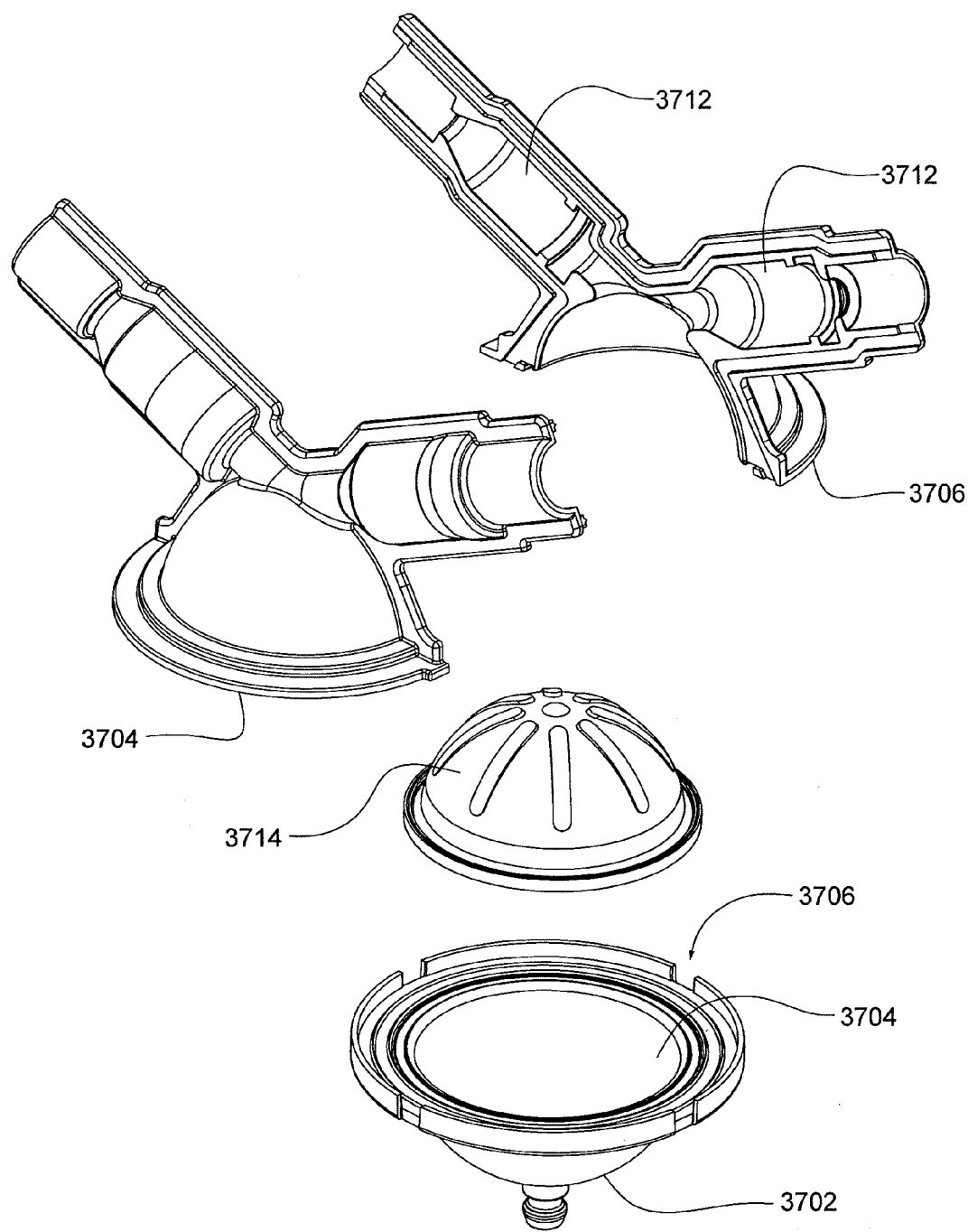
FIG. 37 is an exploded pictorial view of a multi part pod pump housing.
Figure 38A:
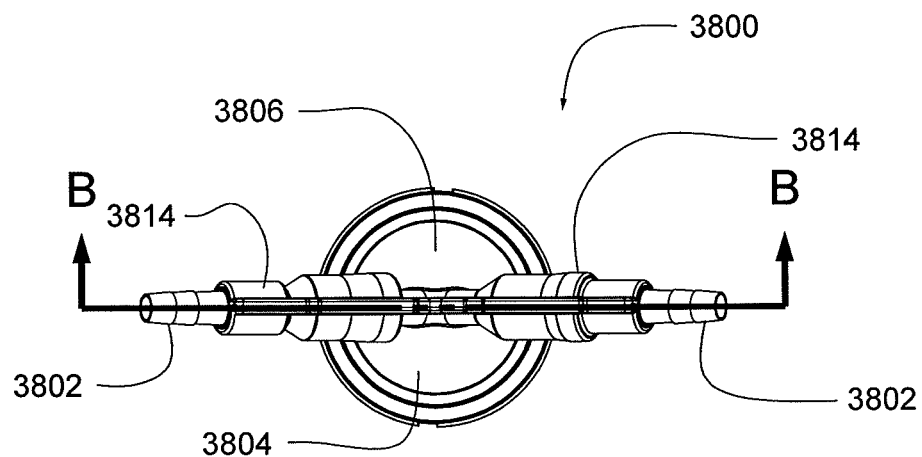
FIGS. 38A and 38B are top and section views of a pod pump assembly with integral valves.
Figure 38B:
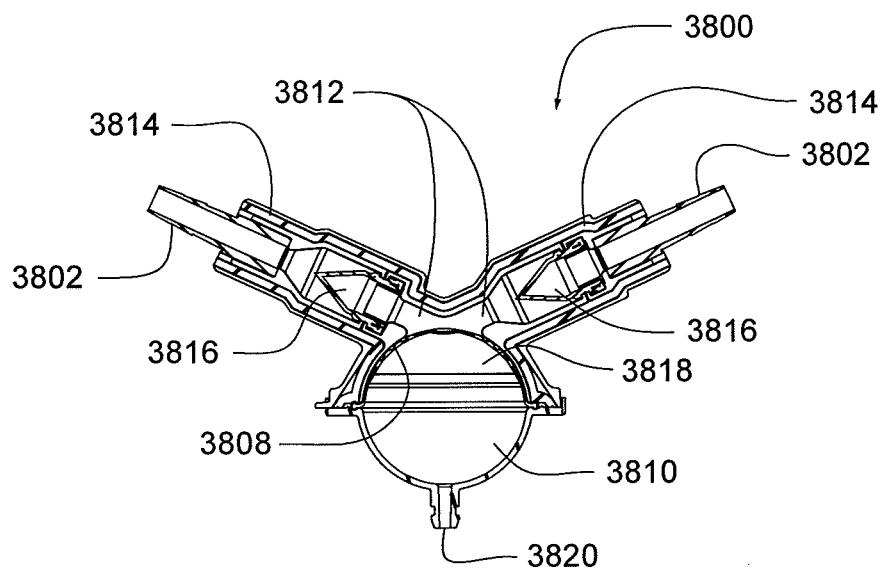
Figure 39:
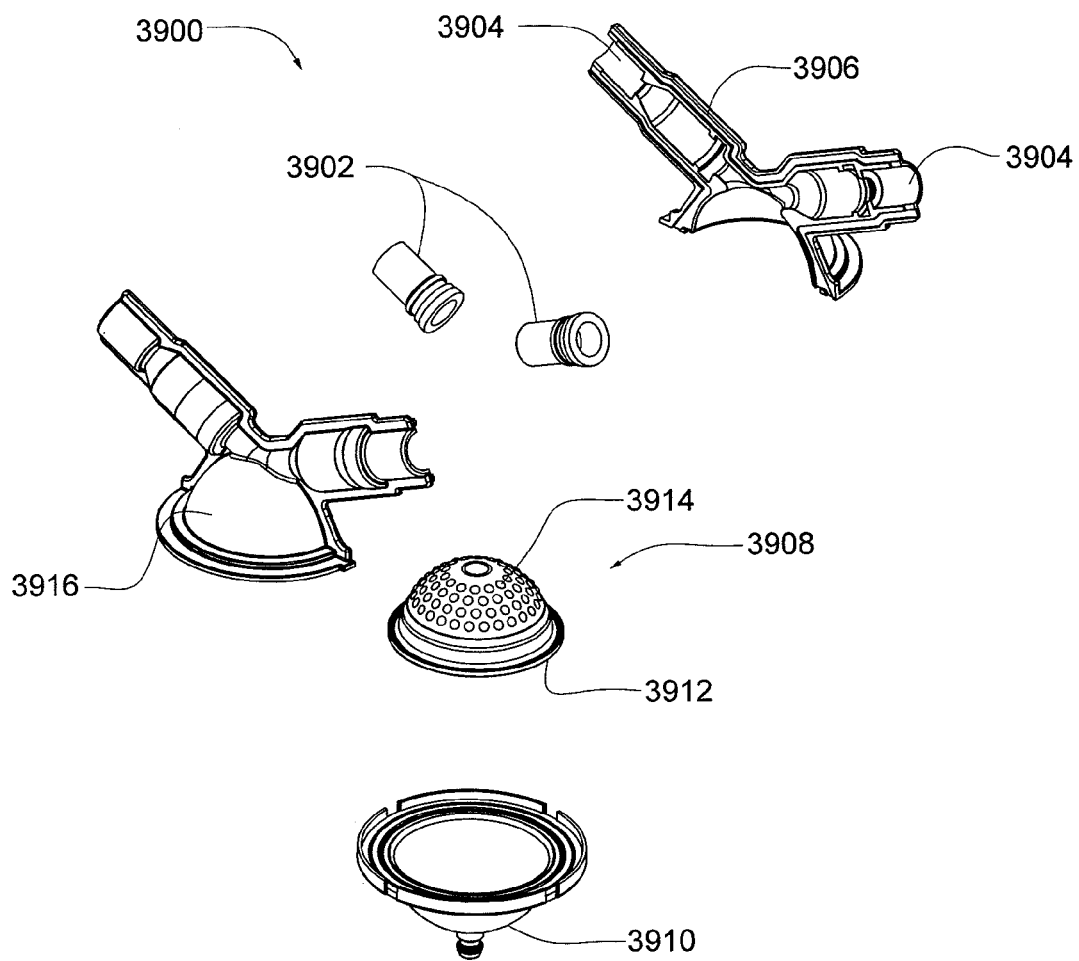
FIG. 39 is an exploded pictorial view of a pod pump assembly.

In the embodiment shown in FIG. 3, the actuation chamber wall 32 is a unitary structure while the pumping chamber wall 31 is formed from two halves that are coupled together along perimeter 2052, for example, by ultrasonic welding or other technique (which facilitates assembly of the integral valves, discussed below). FIG. 37 shows an exploded view of the three pump pod wall sections in accordance with an exemplary embodiment of the present invention. FIG. 38A shows a top view of the assembled three-piece pump pod. FIG. 38B shows a side cross-sectional view of the assembled three-piece pump pod. FIG. 39 shows an exploded view of the pump pod components. FIGS. 37-39 are discussed in greater detail below. Of course, the present invention is in no way limited to the way in which the pumping chamber wall 31 and the actuation chamber wall 32 are constructed or assembled, although ultrasonic welding of the pumping chamber wall 31 and the actuation chamber wall 32 is considered a preferred embodiment.

Within the reciprocating positive-displacement pump 25, a flexible membrane 33 (also referred to as the "pump diaphragm") is mounted where the pumping-chamber wall 31 and the actuation-chamber wall 32 meet (i.e., at the pod wall 30). The pump diaphragm 33 effectively divides that interior cavity into a variable-volume pumping chamber (defined by the rigid interior surface of the pumping chamber wall 31 and a top surface of the membrane 33) and a complementary variable-volume actuation chamber (defined by the rigid interior surface of the actuation chamber wall 32 and a bottom side of the membrane 33). The top portion 31 includes a fluid inlet 34 and a fluid outlet 37, both of which are in fluid communication with the pumping chamber. The bottom portion 32 includes a pneumatic interface 38 in fluid communication with the actuation chamber. As discussed in greater detail below, the membrane 33 can be urged to move back and forth within the cavity by alternately applying negative and positive pneumatic pressure at the pneumatic interface 38. As the membrane 33 reciprocates back and forth in the embodiment shown in FIG. 3, the sum of the volumes of the pumping and actuation chambers remains constant.

During typical fluid pumping operations, the application of negative pneumatic pressure to the pneumatic interface 38 tends to withdraw the membrane 33 toward the actuation chamber wall 32 so as to expand the pumping chamber and draw fluid into the pumping chamber through the inlet 34, while the application of positive pneumatic pressure tends to push the membrane 33 toward the pumping chamber wall 31 so as to collapse the pumping chamber and expel fluid in the pumping chamber through the outlet 37. During such pumping operations, the interior surfaces of the pumping chamber wall 31 and the actuation chamber wall 32 limit movement of the membrane 33 as it reciprocates back and forth. In the embodiment shown in FIG. 3, the interior surfaces of the pumping chamber wall 31 and the actuation chamber wall 32 are rigid, smooth, and hemispherical. In lieu of a rigid actuation-chamber wall 32, an alternative rigid limit structure—for example, a portion of a bezel used for providing pneumatic pressure and/or a set of ribs—may be used to limit the movement of the membrane as the pumping chamber approaches maximum value. Bezels and rib structures are described generally in U.S. patent application Ser. No. 10/697,450 entitled BEZEL ASSEMBLY FOR PNEUMATIC CONTROL filed on Oct. 30, 2003 and published as Publication No. US 2005/0095154 and related PCT Application No. PCT/US2004/035952 entitled BEZEL ASSEMBLY FOR PNEUMATIC CONTROL filed on Oct. 29, 2004 and published as Publication No. WO 2005/044435, both of which are hereby incorporated herein by reference in their entireties. Thus, the rigid limit structure—such as the rigid actuation chamber wall 32, a bezel, or a set of ribs—defines the shape of the membrane 33 when the pumping chamber is at its maximum value. In a preferred embodiment, the membrane 33 (when urged against the rigid limit structure) and the rigid interior surface of the pumping chamber wall 31 define a spherical pumping-chamber volume when the pumping chamber volume is at a maximum.

Thus, in the embodiment shown in FIG. 3, movement of the membrane 33 is limited by the pumping-chamber wall 31 and the actuation-chamber wall 32. As long as the positive and negative pressurizations provided through the pneumatic port 38 are strong enough, the membrane 33 will move from a position limited by the actuation-chamber wall 32 to a position limited by the pumping-chamber wall 31. When the membrane is forced against the actuation-chamber wall 32, the membrane and the pumping-chamber wall 31 define the maximum volume of the pumping chamber. When the membrane is forced against the pumping-chamber wall 31, the pumping chamber is at its minimum volume.

In a preferred embodiment, the pumping-chamber wall 31 and the actuation-chamber wall 32 both have a hemispheroid shape so that the pumping chamber will have a spheroid shape when it is at its maximum volume. More preferably, the pumping-chamber wall 31 and the actuation-chamber wall 32 both have a hemispherical shape so that the pumping chamber will have a spherical shape when it is at its maximum volume. By using a pumping chamber that attains a spheroid shape— and particularly a spherical shape—at maximum volume, circulating flow may be attained throughout the pumping chamber. Such shapes accordingly tend to avoid stagnant pockets of fluid in the pumping chamber. As discussed further below, the orientations of the inlet 34 and outlet 37—with each being substantially tangential to the interior surface of the pumping chamber wall 31—also tend to improve circulation of fluid through the pumping chamber and reduce the likelihood of stagnant pockets of fluid forming. Additionally, compared to other volumetric shapes, the spherical shape (and spheroid shapes in general) tends to create less shear and turbulence as the fluid circulates into, through, and out of the pumping chamber.

1.2. Exemplary Inlet/Outlet Valves

Generally speaking, reciprocating positive-displacement pumps of the types just described may include, or may be used in conjunction with, various valves to control fluid flow through the pump. Thus, for example, the reciprocating positive-displacement pump may include, or be used in conjunction with, an inlet valve and/or an outlet valve. The valves may be passive or active. In the exemplary embodiment shown in FIG. 3, the reciprocating positive-displacement pump 25 includes a passive one-way inlet check valve 35 and a passive one-way outlet check valve 36. The inlet check valve 35 allows fluid to be drawn into the pumping chamber through the inlet 34 but substantially prevents backflow through the inlet 34. The outlet check valve 36 allows fluid to be pumped out of the pumping chamber through the outlet 37 but substantially prevents backflow through the outlet 37.

Thus, in an exemplary embodiment using the reciprocating positive-displacement pump 25, the membrane 33 is urged back and forth by positive and negative pressurizations of a gas provided through the pneumatic port 38, which connects the actuation chamber to a pressure-actuation system. The resulting reciprocating action of the membrane 33 pulls liquid into the pumping chamber from the inlet 34 (the outlet check valve 36 prevents liquid from being sucked back into the pumping chamber from the outlet 37) and then pushes the liquid out of pumping chamber through the outlet 37 (the inlet check valve 35 prevents liquid being forced back into the inlet 34).

In alternative embodiments, active valves may be used in lieu of the passive check valves 35 and 36. The active valves may be actuated by a controller in such a manner as to direct flow in a desired direction. Such an arrangement would generally permit the controller to cause flow in either direction through the pump pod 25. In a typical system, the flow would normally be in a first direction, e.g., from the inlet to the outlet. At certain other times, the flow may be directed in the opposite direction, e.g., from the outlet to the inlet. Such reversal of flow may be employed, for example, during priming of the pump, to check for an aberrant line condition (e.g., a line occlusion, blockage, disconnect, or leak), or to clear an aberrant line condition (e.g., to try to dislodge a blockage).

1.3. Exemplary Pump Inlet/Outlet Orientations

In the embodiment shown in FIG. 3, the inlet 34 and the outlet 37 are oriented so as to direct fluid into and out of the pumping chamber at angles that are substantially tangential to the interior surface of the pumping chamber wall 31. Thus, the fluid flow through the inlet 34 into the pumping chamber avoids being perpendicular to the membrane 33, even as the membrane approaches a position where the pumping chamber is at its minimum volume. This orientation of the inlet 34 and the outlet 37 tends to reduce the shear forces on the liquid being pumped, particularly when compared to centrifugal pumps, which generally apply a great deal of stress on the fluid being pumped.

The orientation of the inlet 34 and outlet 37 with respect to each other also tends to reduce shear flow and turbulence. When the pumping chamber reaches its maximum volume, the fluid continues circulating through the pumping chamber even as fluid stops flowing through the inlet 34. The direction of this circulating flow is a result of the direction of the inlet 34 and the internal flow geometry. Generally speaking, after a very short pause, the membrane 33 will be actuated to start moving to reduce the volume of the pumping chamber and fluid will start flowing through the outlet 37. When the fluid enters the pumping chamber, it moves in a rotating current and stays rotating until exiting the pumping chamber. The exiting fluid peels off from the outer layer of the rotating current in the same direction in which it was rotating. The spherical shape of the pump pods is particularly advantageous to achieve the desired flow circulation. The orientation of the outlet 37 with respect to circulating flow within the pumping chamber at the moment of maximum pumping chamber volume is such that flow does not have to change direction sharply when it begins to be urged through the outlet 37. By avoiding sharp changes in flow direction, shear and turbulence is reduced. Thus, the orientation of the inlet 34 and outlet 37 with respect to each other and the internal flow geometry reduces shear and turbulence on the liquid being pumped. For example, in FIG. 3, there is only a small change in direction in a path extending from the inlet 34 directly to the outlet 37, but other arrangements will also reduce sharp changes in direction as the pump pod transitions from a fill stroke to an expel stroke.

Thus, when the fluid being pumped is whole blood, centrifugal pumps (which apply a great deal of stress on the red blood cells) can cause a large amount of hemolysis and therefore can reduce a patient's hematocrit to the detriment of the patient, whereas pump pods of the types described above (which apply low shear forces and turbulence) tend to produce substantially lower hemolysis. Similarly, when the fluid being pumped is a surfactant or other fluid prone to foaming, the reduced shear forces and reduced turbulence of the pod pumps tends to reduce foaming.

Figure 29:
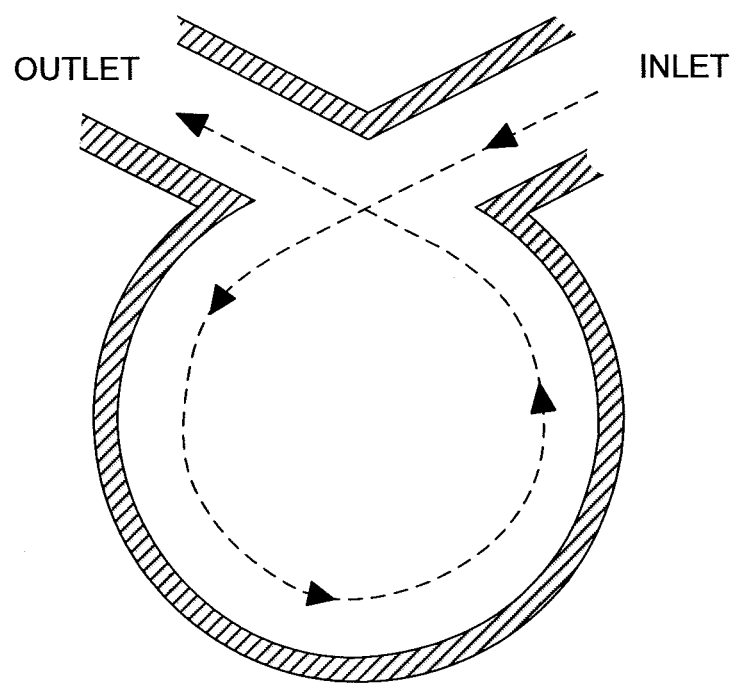
FIG. 29 is a schematic representation of circulatory fluid flow in the pump pod shown in FIG. 3, in accordance with an exemplary embodiment of the present invention.

FIG. 29 is a schematic representation of circulatory fluid flow in the pump pod 25 shown in FIG. 3, in accordance with an exemplary embodiment of the present invention. As fluid enters the pumping chamber through the inlet, the orientation of the inlet directs fluid tangentially to the inside surface of the pumping chamber wall so as to create a circulatory flow. As fluid approaches the outlet, the fluid is already flowing substantially in the direction of the outlet so that the fluid is not required to make any drastic changes in direction when being pumped from the outlet. The fluid therefore tends to peel off of the circulatory flow in a laminar fashion to provide reduced shear forces on the fluid.

Generally speaking, for low shear and/or low turbulence applications, it is desirable for the inlet and outlet to be configured so as to avoid sharp or abrupt changes of fluid direction. It is also generally desirable for the inlet and outlet (and the pump chamber itself) to be free of flash or burrs. The inlet and/or outlet may include rounded edges to help smooth out fluid flow.

1.4. Alternative Pump Configurations

Figure 20:
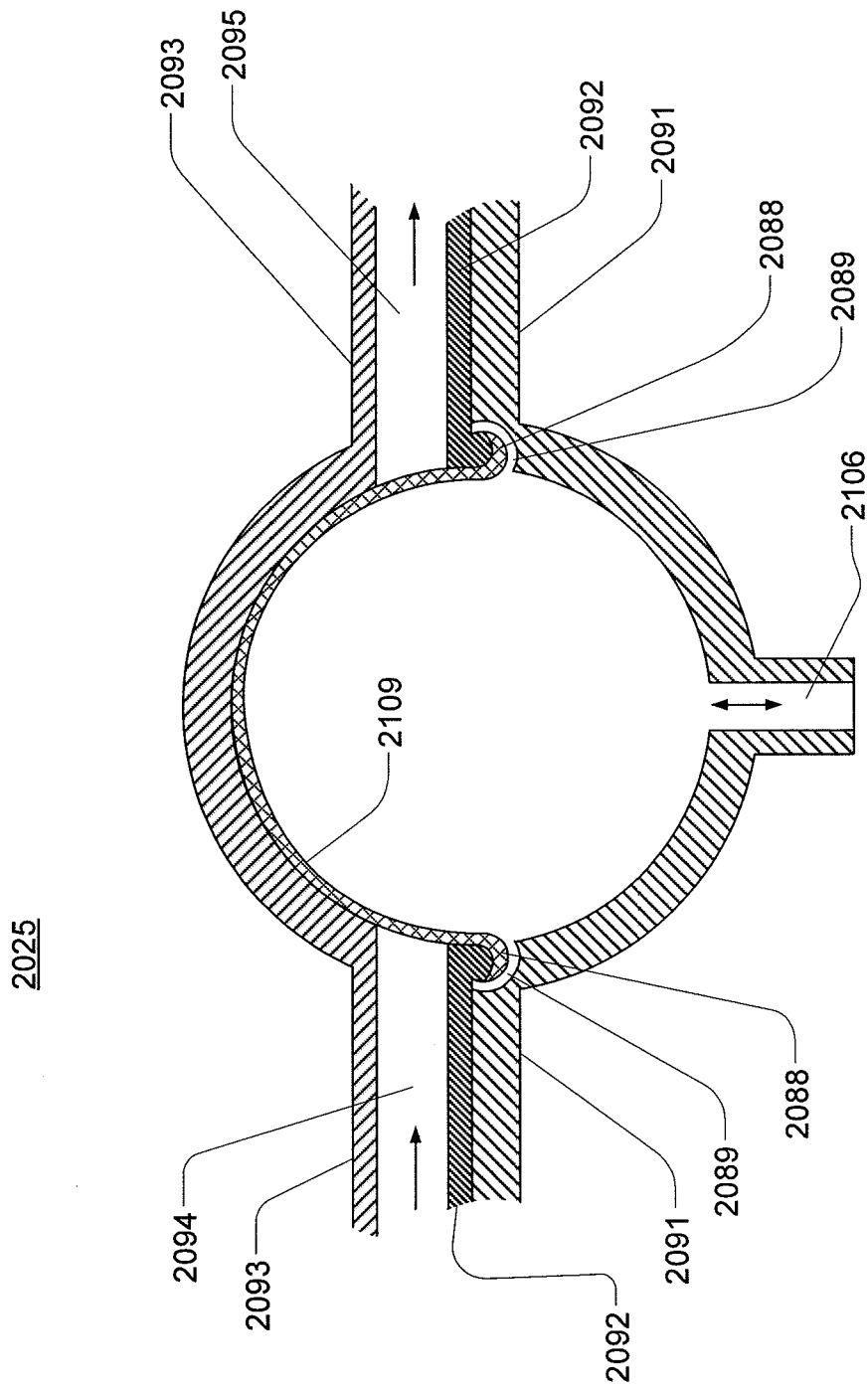
FIG. 20 is a sectional view of a pod-pump that may be incorporated into embodiments of fluid-control cassettes.

FIG. 20 is a sectional view of an alternative pump pod 2025 such as may be incorporated into a larger fluid-control cassette, in accordance with an alternative embodiment of the present invention. In this embodiment, the pump pod is formed from three rigid pieces, namely a "top" plate 2091, a middle plate 2092, and a "bottom" plate 2093 (it should be noted that the terms "top" and "bottom" are relative and are used here for convenience with reference to the orientation shown in FIG. 20). The top and bottom plates 2091 and 2093 may be flat on both sides, while the middle plate 2092 is provided with channels, indentations and holes to define the various fluid paths, chambers, and ports. To form the pump pod 2025, the top and bottom plates 2091 and 2093 may include generally hemispheroid portions that together define a hemispheroid chamber.

A membrane 2109 separates the central cavity of the pump pod into a chamber (the pumping chamber) that receives the fluid to be pumped and another chamber (the actuation chamber) for receiving the control gas that pneumatically actuates the pump. An inlet 2094 allows fluid to enter the pumping chamber, and an outlet 2095 allows fluid to exit the pumping chamber. The inlet 2094 and the outlet 2095 may be formed between middle plate 2092 and the bottom plate 2093. Pneumatic pressure is provided through a pneumatic port 2106 to either force, with positive gas pressure, the membrane 2109 against one wall of pump pod's cavity to minimize the pumping chamber's volume (as shown in FIG. 20), or to draw, with negative gas pressure, the membrane towards the other wall of the pump pod's cavity to maximize the pumping chamber's volume.

The membrane 2109 is provided with a thickened rim 2088, which is held tightly in a groove 2089 in the middle plate 2092. Thus, the membrane 2109 can be placed in and held by the groove 2089 before the top plate 2091 is ultrasonically welded to the middle plate 2092, so the membrane will not interfere with the ultrasonic welding of the two plates together, and so that the membrane does not depend on the two plates being ultrasonically welded together in just the right way to be held in place. Thus, this pump pod should be able to be manufactured easily without relying on ultrasonic welding to be done to very tight tolerances.

Figure 21:
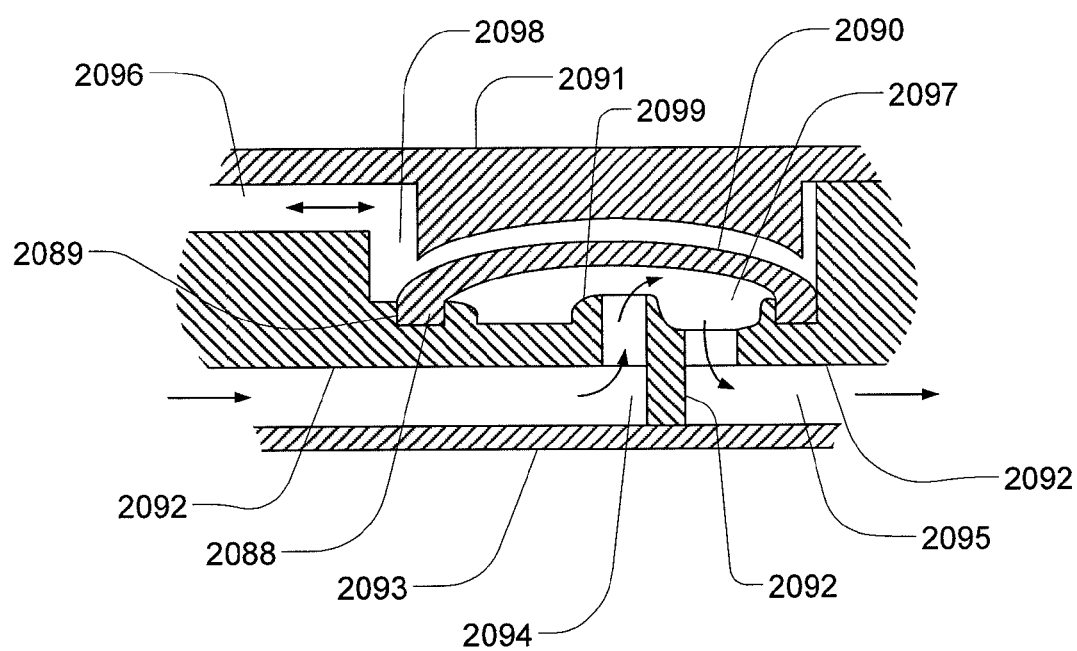
FIG. 21 is a sectional view of a valve that may be incorporated into embodiments of fluid-control cassettes.

One or more pump pods 2025 may be incorporated into a single cassette, which may also include one or more valves 2000. FIG. 21 is a sectional view of a pneumatically controlled valve 2000 that may be used in embodiments of the above-mentioned cassette. A membrane 2090, along with the middle plate 2092, defines a valving chamber 2097. Pneumatic pressure is provided through a pneumatic port 2096 to either force, with positive gas pressure, the membrane 2090 against a valve seat 2099 to close the valve, or to draw, with negative gas pressure, the membrane away from the valve seat to open the valve. A control gas chamber 2098 is defined by the membrane 2090, the top plate 2091, and the middle plate 2092. The middle plate 2092 has an indentation formed on it, into which the membrane 2090 is placed so as to form the control gas chamber 2098 on one side of the membrane and the valving chamber 2097 on the other side.

The pneumatic port 2096 is defined by a channel formed on the "top" surface of the middle plate 2092, along with the top plate 2091. By providing fluid communication between several valving chambers in a cassette, valves can be ganged together so that all the valves ganged together can be opened or closed at the same time by a single source of pneumatic pressure. Channels formed on the "bottom" surface of the middle plate 2092, along with the bottom plate, define the valve inlet 2094 and the valve outlet 2095. Holes formed through the middle plate 2092 provide communication between the inlet 2094 and the valving chamber 2097 (through the valve seat 2099) and between the valving chamber and the outlet 2095.

The membrane 2090 is provided with a thickened rim 2088, which fits tightly in a groove 2089 in the middle plate 2092. Thus, the membrane 2090 can be placed in and held by the groove 2088 before the top plate 2091 is ultrasonically welded to the middle plate 2092, so the membrane will not interfere with the ultrasonic welding of the two plates together, and so that the membrane does not depend on the two plates being ultrasonically welded together in just the right way to be held in place. Thus, this valve should be easy to manufacture without relying on ultrasonic welding to be done to very tight tolerances. As shown in FIG. 21, the top plate 2091 may include additional material extending into control gas chamber 2098 so as to prevent the membrane 2090 from being urged too much in a direction away from the groove 2089, so as to prevent the membrane's thickened rim 2088 from popping out of the groove 2089.

Figure 30A:
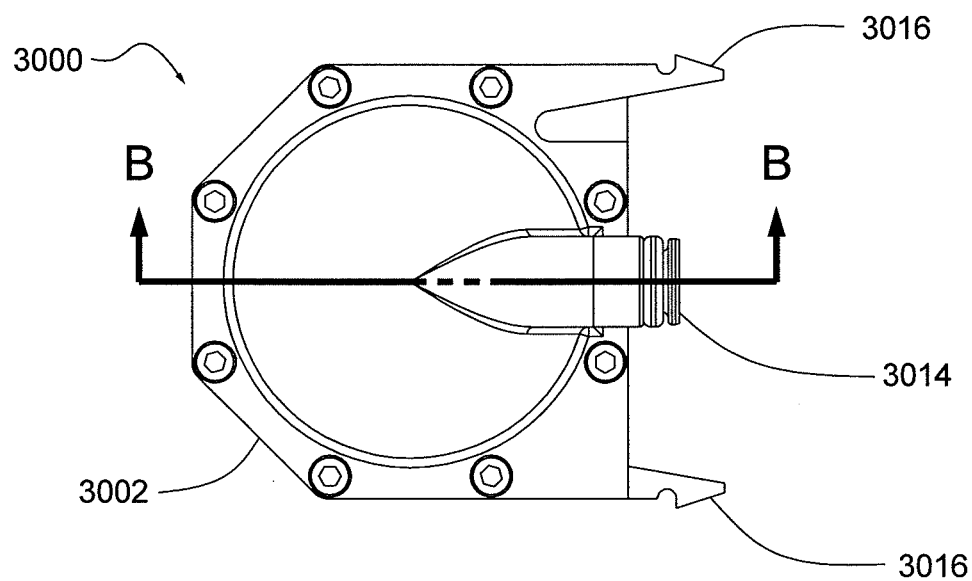
FIGS. 30A and 30B are top and section views of a modular pod pump.
Figure 30B:
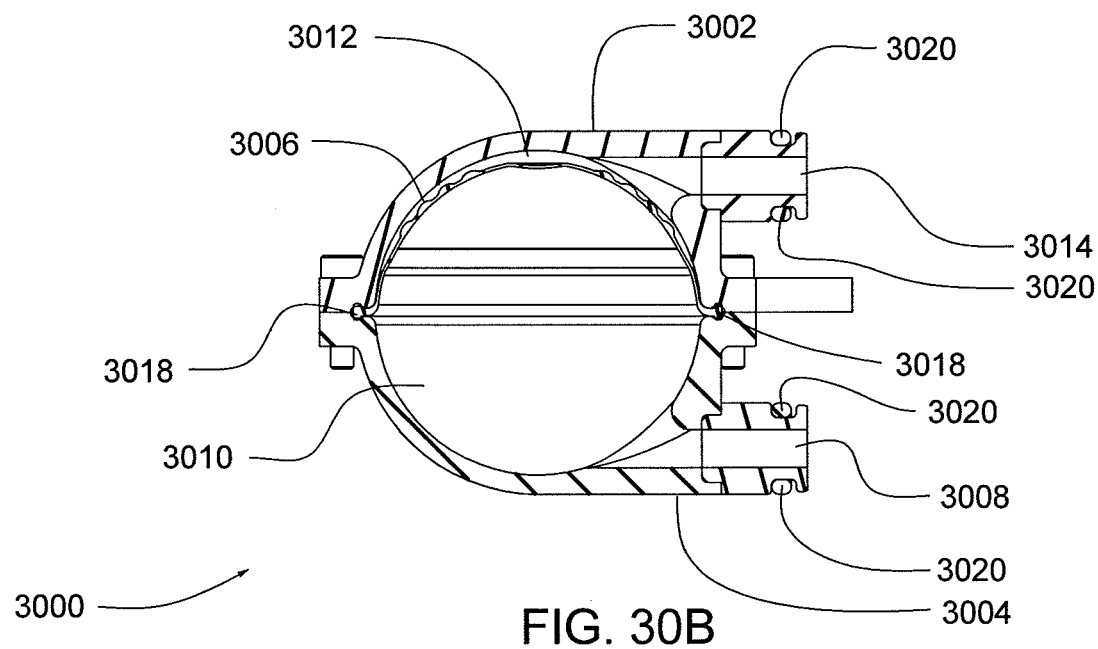

Referring now to FIGS. 30A and 30B, one embodiment of the pod pump 3000 is shown. In this embodiment, the pod pump 3000 includes a housing. Referring now to FIG. 30B, the housing includes two portions 3002, 3004. The portions 3002, 3004 are joined and retain a diaphragm 3006. Referring to FIG. 30A, as shown in this embodiment, the housing portions 3002, 3004 are joined by screws. However, in alternate embodiments, any fasteners or fastening method can be used, which include, but are not limited to: snap together tabs, ultrasonic welding, laser welding or other assembly means known in the art.

Although as shown in the embodiments in FIGS. 30A and 30B, the housing is formed by two portions 3002, 3004, in other embodiments (some described below) the housing is formed from more than two portions. In still other embodiments, the housing is a single portion.

In various embodiments, the size of the housing may vary. The size may vary depending on the volume of subject fluid intended to be pumped by each stroke of the pod pump. Another factor that may influence the size is the desired aspect ratio of the pod pump.

Figure 42A:
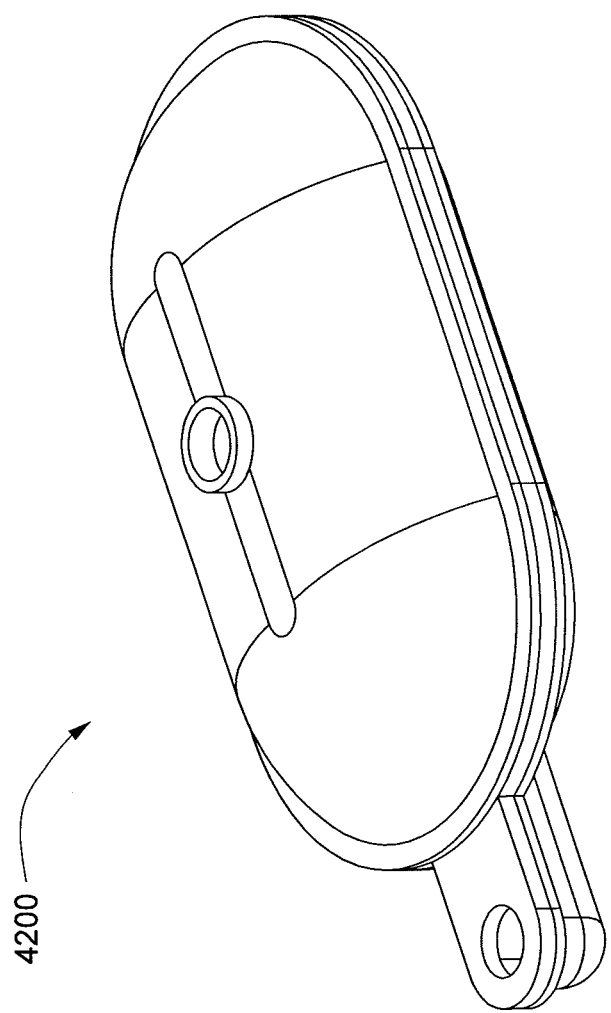
FIG. 42A is a pictorial view of a pod pump.
Figure 42B:
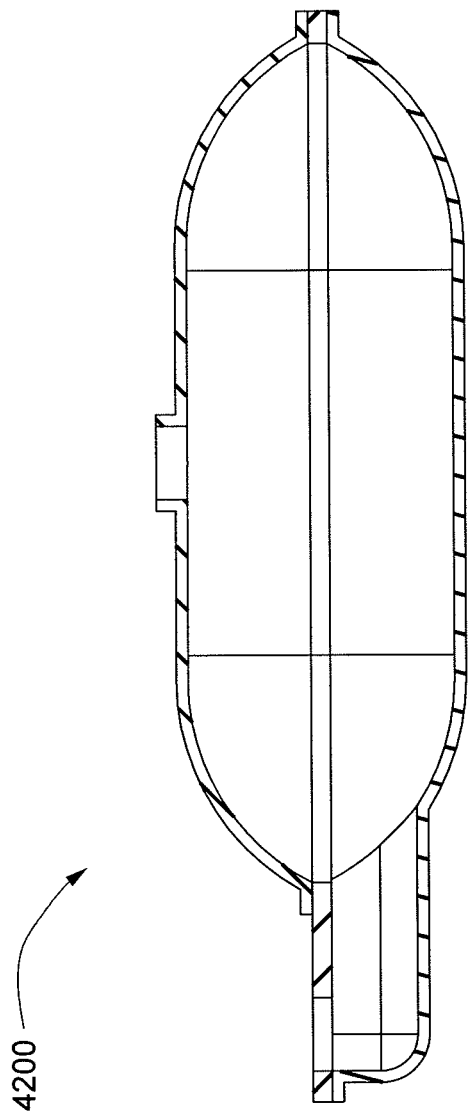
FIG. 42B is a sectional view of the pod pump shown in FIG. 42A.
Figure 42C:
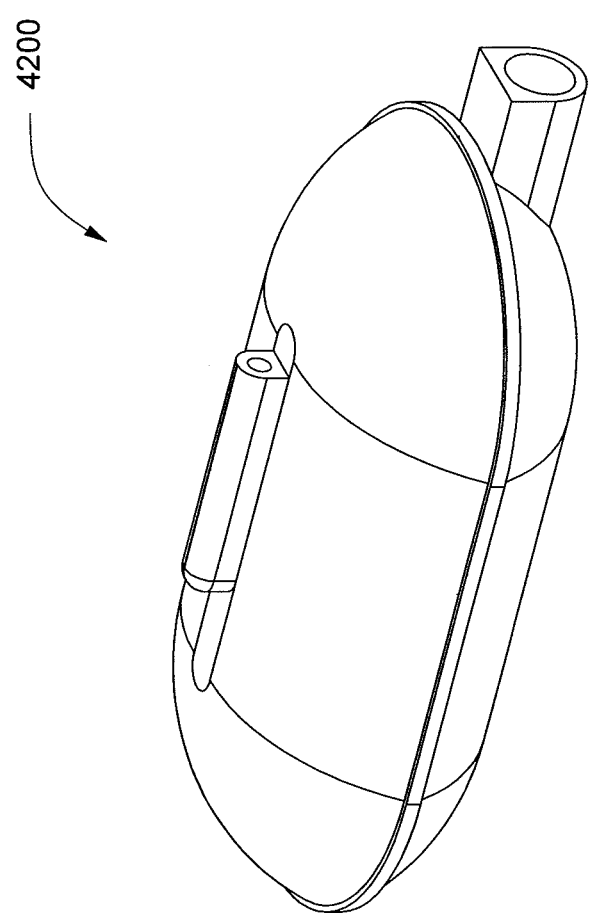
FIG. 42C is a pictorial view of a pod pump.
Figure 42D:
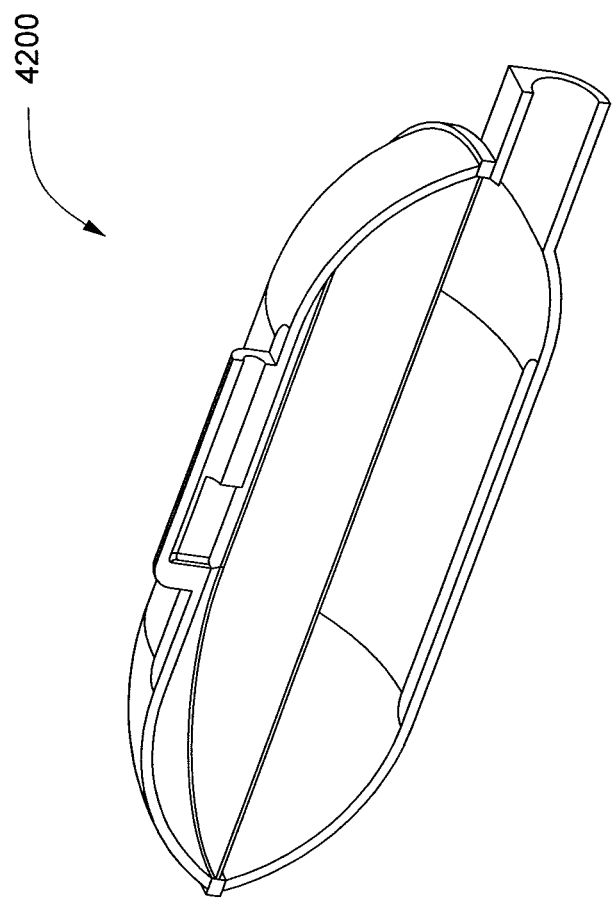
FIG. 42D is a sectional view of the pod pump shown in FIG. 42C.

Also, in various embodiments, the shape of the housing chamber may vary. Thus, although FIGS. 30A and 30B, as well as many of the additional figures in this description describe and show substantially spherical pod pump housing, the pod pump housing is by no means limited to a spherical shape. Referring now to FIGS. 42A and 42B, an alternate pod pump 4200 shape is shown. Thus, although only two shapes are shown herein, in alternate embodiments, the pod pump housing can be any shape desired.

Referring now to FIGS. 42A and 42B, an alternate embodiment of the pod pump is shown. Although in this embodiment, the pod pump is oval shaped, in still other embodiments, the pod pump can be any shape desired. Many of the embodiments of the pod pumps will include a pump chamber, an actuation chamber, a diaphragm (or movable member), at least one actuation port and at least one inlet/outlet port. In some embodiments, the pod pump includes an inlet and an outlet port. Various embodiments are described herein and features described with respect to one embodiment should be understood to be available for any embodiment, thus the embodiment features can be mixed and matched, and any embodiment can include one or more of the features described herein.

Referring again to FIGS. 30A and 30B the pod pump shown in this embodiment, is substantially spherical. As shown in this embodiment, the pump housing (which includes the pump chamber and the actuation chamber) is substantially spherical; however, the lip or façade around the pump housing is not entirely spherical. Thus, the exterior of the housing can be any shape, and in some embodiments, the exterior of the housing is a different shape from the pump housing. However, in some embodiments, the exterior housing is the same shape or substantially the same shape as the pump housing.

The housing portions 3002, 3004, when joined, form a hollow chamber. In embodiments where the housing is a single portion, the interior of the housing is a hollow chamber. Where a diaphragm 3006 is connected or attached to the interior of the housing, the diaphragm 3006 divides the interior of the housing into two chambers, an actuation chamber 3010 and a pump chamber 3012. In some embodiments, the interior of the housing is divided into equal volume chambers, however, in other embodiments, the chambers are varying volume chambers.

The diaphragm 3006 may be made of any flexible material having a desired durability and compatibility with the subject fluid. The diaphragm 3006 can be made from any material that may flex in response to liquid or gas pressure or vacuum applied to the actuation chamber 3010. The diaphragm material may also be chosen for particular bio-compatibility, temperature compatibility or compatibility with various subject fluids that may be pumped by the diaphragm 3006 or introduced to the chambers to facilitate movement of the diaphragm 3006. In the exemplary embodiment, the diaphragm 3006 is made from high elongation silicone. However, in other embodiments, the diaphragm 3006 is made from any elastomer or rubber, including, but not limited to, silicone, urethane, nitrile, EPDM or any other rubber or elastomer.

The shape of the diaphragm 3006 is dependent on multiple variables. These variables include, but are not limited to: the shape of the chamber; the size of the chamber; the subject fluid characteristics; the volume of subject fluid pumped per stroke; and the means or mode of attachment of the diaphragm 3006 to the housing. The size of the diaphragm 3006 is dependent on multiple variables. These variables include, but are not limited to: the shape of the chamber; the size of the chamber; the subject fluid characteristics; the volume of subject fluid pumped per stroke; and the means or mode of attachment of the diaphragm 3006 to the housing. Thus, depending on these or other variables, the shape and size of the diaphragm 3006 may vary in various embodiments.

The diaphragm 3006 can have any thickness. However, in some embodiments, the range of thickness is between 0.002 inches to 0.125 inches. Depending on the material used for the diaphragm, the desired thickness may vary. In one embodiment, high elongation silicone is used in a thickness ranging from 0.015 inches to 0.050 inches.

Figure 35A:
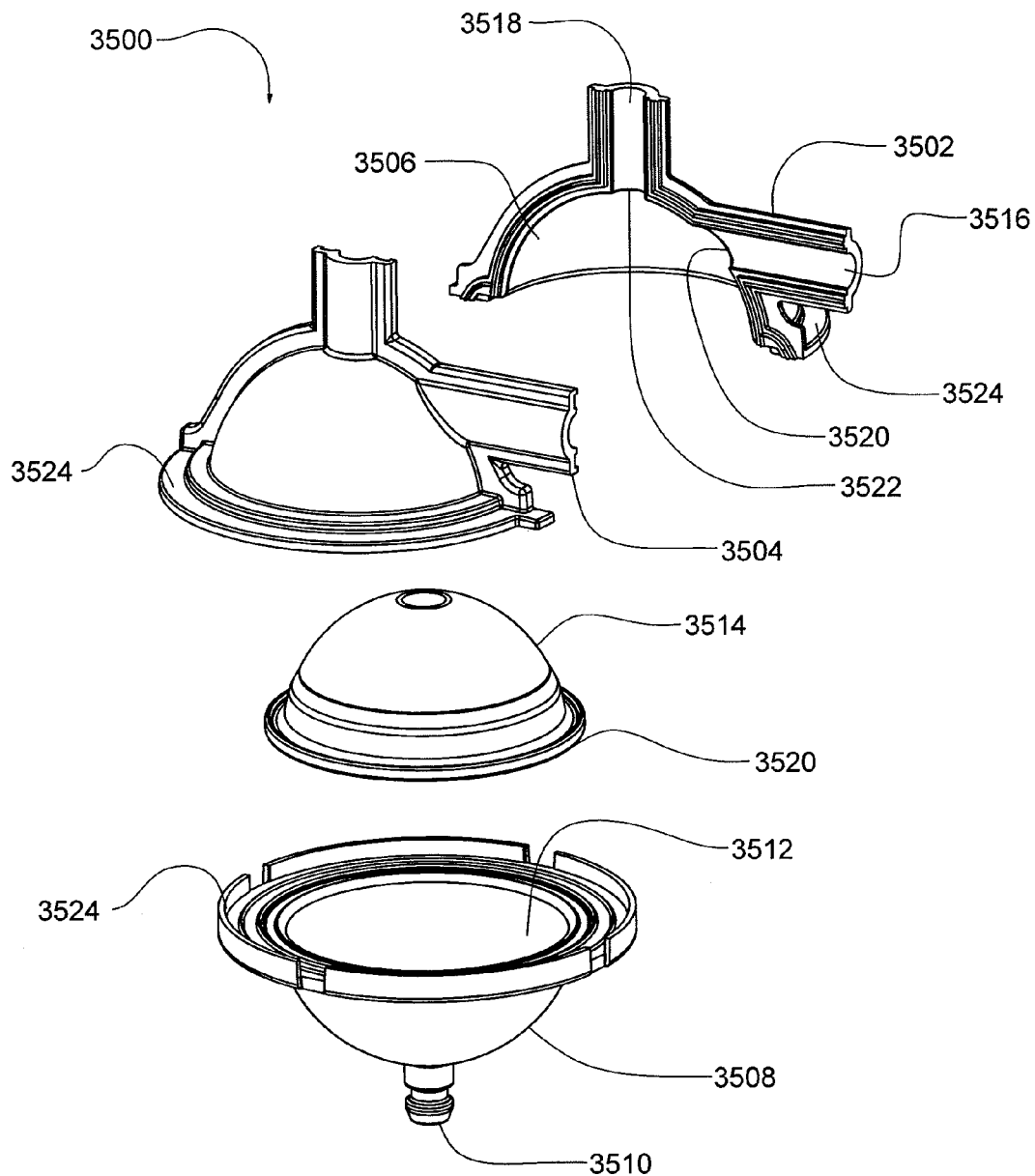
FIG. 35A is an exploded pictorial view of a pod pump with a multi part housing.
Figure 35B:
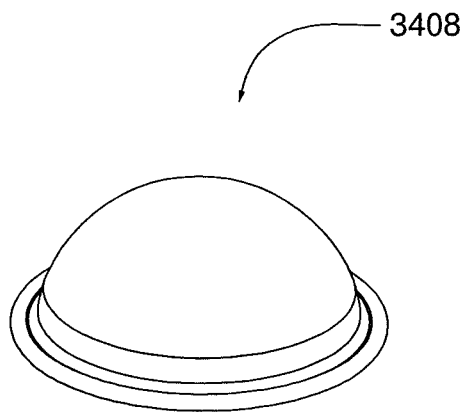
FIGS. 35B-E are pictorial views of various embodiments of diaphragms.
Figure 35C:
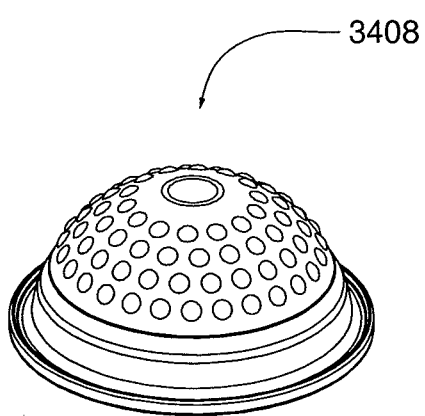
Figure 35D:
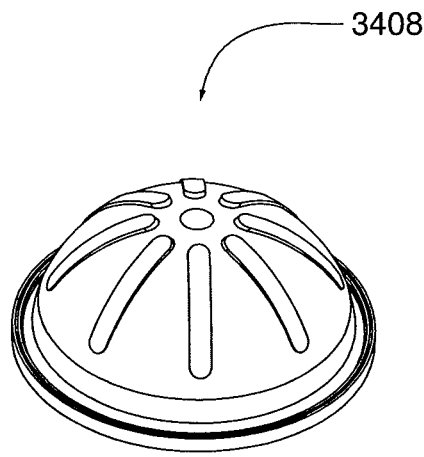
Figure 35E:
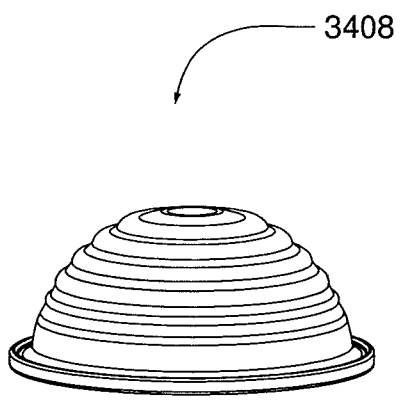

In the exemplary embodiment, the diaphragm 3006 is preformed to include a substantially dome-shape in at least part of the area of the diaphragm 3006. One embodiment of the dome-shaped diaphragm 3006 is shown in FIG. 35A as 3514. Again, the dimensions of the dome may vary based on some or more of the variables described above. However, in other embodiments, the diaphragm 3006 may not include a preformed dome shape.

In the exemplary embodiment, the diaphragm 3006 dome is formed using compression molding. However, in other embodiments, the dome may be formed by using injection molding.

In alternate embodiments, the diaphragm 3006 is substantially flat until actuated. In other embodiments, the dome size, width or height may vary.

In various embodiments, the diaphragm 3006 may be held in place by various means and methods. In one embodiment, the diaphragm 3006 is clamped between the portions of the housing, and in some of these embodiments, the rim of the housing may include features to grab the diaphragm 3006. In others of this embodiment, the diaphragm 3006 is clamped to the housing at least one bolt or another device. In another embodiment, the diaphragm 3006 is over-molded with a piece of plastic and then the plastic is welded or otherwise attached to the housing. In another embodiment, the diaphragm 3006 is bonded to a mid-body portion (not shown, described below with respect to FIGS. 33A-34B) and the actuation housing portion. Although some embodiments for attachment of the diaphragm 3006 to the housing are described, any method or means for attaching the diaphragm 3006 to the housing can be used. The diaphragm 3006, in one alternate embodiment, is attached directly to one portion of the housing at the attachment points 3018.

In the embodiment shown in FIG. 30B, the diaphragm 3006 is held in place in the interior of the housing at attachment points 3018 using one of the above described embodiments or another method for attachment. The attachment points 3018 are areas where the diaphragm 3006 is held between the two portions 3002, 3004 of the housing at the two portions' 3002, 3004 meeting point. In some embodiments, the diaphragm 3006 is thicker at the attachment points 3018 than in other areas of the diaphragm 3006. In some embodiments, this thicker area is a gasket, in some embodiments an O-ring, ring or any other shaped gasket. Referring now to FIG. 35A, an embodiment of the diaphragm 3514 is shown with a gasket 3520. In these embodiments, the gasket 3520 is the point that connects to the housing.

In some embodiments of the gasket 3520, the gasket 3520 is contiguous with the diaphragm 3514. However, in other embodiments, the gasket 3520 is a separate part of the diaphragm 3514. In some embodiments, the gasket 3520 is made from the same material as the diaphragm 3514. However, in other embodiments, the gasket 3520 is made of a material different from the diaphragm 3514. In some embodiments, the gasket 3520 is formed by over-molding a ring around the diaphragm 3514. The gasket 3520 can be any shape ring or seal desired so as to complement the pod pump housing embodiment. In some embodiments, the gasket 3520 is a compression type gasket.

The interior of the housing includes at least one port for subject fluid (pump port) and at least one port for actuation fluid (actuation port). Referring to FIG. 30B, the actuation port 3008 and pump port 3014 are shown. Although the embodiment shown in FIG. 30B includes one pump port 3014 and one actuation port 3008, in other embodiments (some of which are described below) the pod pump includes more than one pump port and/or more than one actuation port.

Still referring to FIG. 30B, the location of the pump port 3014 and the actuation port 3008 may also vary in the different embodiments. In the embodiment shown, the pump port 3014 and the actuation port 3008 are located on one side of the pod pump 3000. In other embodiments, some which are shown and described herein, the pump port and the actuation port may be in various locations on the pod pump, sometimes the same side, sometimes different side, and in embodiments having more than one pump port and/or more than one actuation port, the locations of all of these ports can vary. In most embodiments, however, the actuation port (or, in some embodiments, at least one actuation port) 3008 is in fluid communication with the actuation chamber 3010 and the pump port (or, in some embodiments, at least one actuation port) 3014 is in fluid communication with the pump chamber 3012.

The actuation port 3008 communicates liquid or gas pressure with a liquid or gas source to add or remove liquid or gas from the actuation chamber 3010. Upon addition or removal of liquid or gas from the actuation chamber 3010 the diaphragm 3006 flexes to increase or decrease the volume of the pumping chamber 3012. The action of the diaphragm 3006 flexing causes the movement of the subject fluid either into or out of a pump port 3014. In the embodiments shown in FIG. 30B, both the actuation port 3008 and pumping port 3014 are aligned for attachment to or removal from other equipment. However, as discussed above, the ports may be oriented in any manner desired.

Still referring to FIG. 30B, in the embodiment shown, O-rings 3020 are located at the actuation port 3008 and pumping port 3014. However, in other embodiments, other means for connecting the pod pump 3000 to other equipment such as barbed connectors, quick connects, glue, clamps and other fastening means may be used. Referring to FIG. 30A, in one embodiment, flex tabs 3016 are provided to facilitate the fastening of the pod pump 3000 to other equipment, however, in alternate embodiments, additional or alternative locating and fastening features or means may be used. In still other embodiments, fastening features may not be present on the pod pump 3000.

Movement of the diaphragm 3006 causes the volume of the pump chamber 3012 and the volume of the actuation chamber 3010 to change. When the volume of the actuation chamber 3010 decreases, the volume of the pump chamber 3012 increases. This in turn creates a negative pressure in the pump chamber 3012. The negative pressure causes the subject fluid to enter the pump chamber 3012.

When a positive pressure is present in the actuation chamber 3010, either through air or liquid entering the actuation chamber 3010 through one or more actuation ports 3008, the volume of the pump chamber 3012 decreases, creating a positive pressure in the pump chamber 3012. The positive pressure urges the subject fluid out of the pump chamber 3012 through one or more pump ports 3014. Although one pump port 3014 is shown, in other embodiments, more than one pump port is included. In some of these embodiments, one pump port is an inlet port and one pump port is an outlet port. The location, position and configurations of the pump ports vary and in may vary accordingly to a particular intended purpose.

Figure 31A:
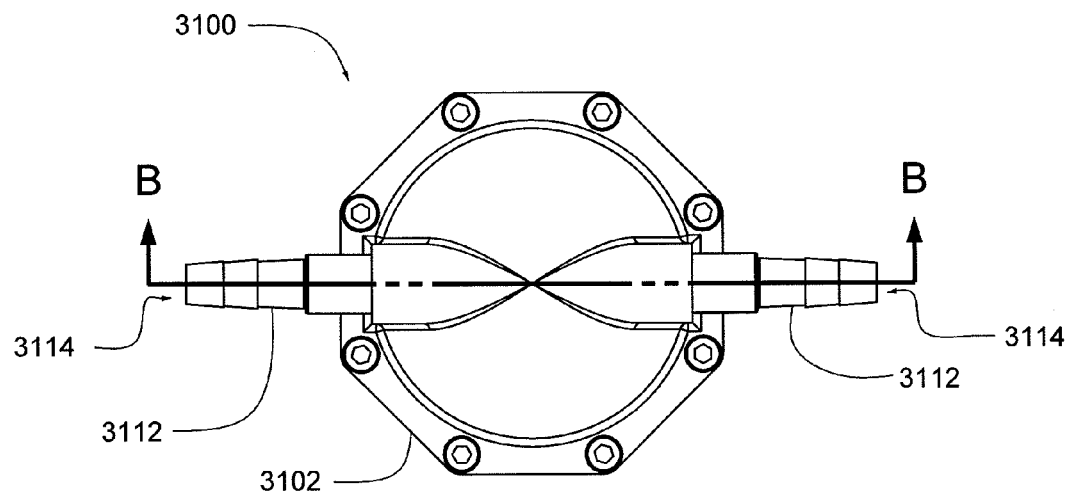
FIGS. 31A and 31B are top and section views of a pod pump with separate inlet and outlet ports, FIG. 31A showing a section line to indicate the view in FIG. 31B.
Figure 31B:
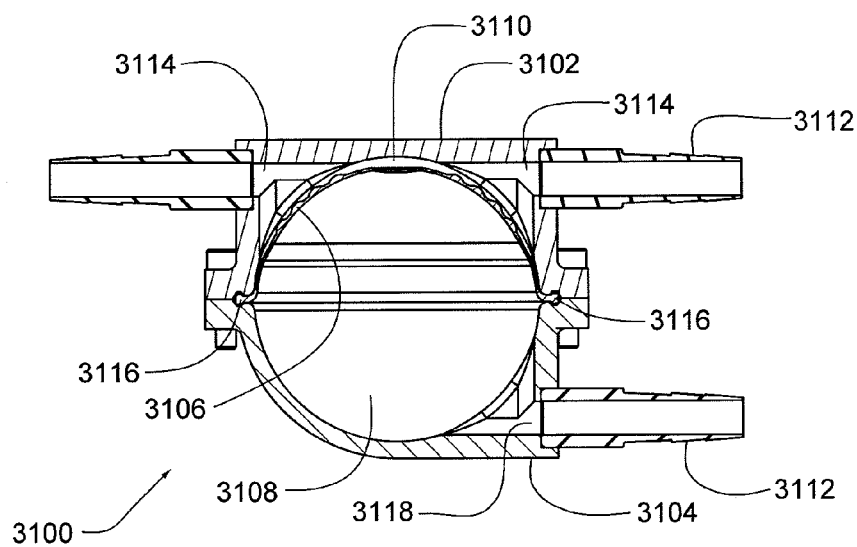

Referring now to FIGS. 31A and 31B, another embodiment of the pod pump 3100 is shown. In this embodiment, the housing includes two portions 3102, 3104. Referring now to FIG. 31B, a diaphragm 3106 is connected to the interior chamber of the housing at points 3116. In this embodiment, the diaphragm 3106 is connected to the housing at a position where the two portions 3102, 3104 meet. This sandwiches the diaphragm 3106 holding the diaphragm 3106.

The diaphragm 3106 divides the interior of the pod pump 3100 housing into two chambers; an actuation chamber 3108 and a pump chamber 3110. In this embodiment the pump chamber 3110 includes with two pump ports 3114, either of which may be an inlet or outlet port when the pump is actuated. Referring again to both FIGS. 31A and 31B, the pod pump 3100 includes barbed connectors 3112, which may be used for the attachment of tubing to the pump ports 3114 and actuation port 3118. The duty of each port is determined by the configuration of other equipment the port is attached to. In this embodiment barbed connectors 3112 are provided for the attachment of tubing but other attachment methods are possible.

Figure 32A:
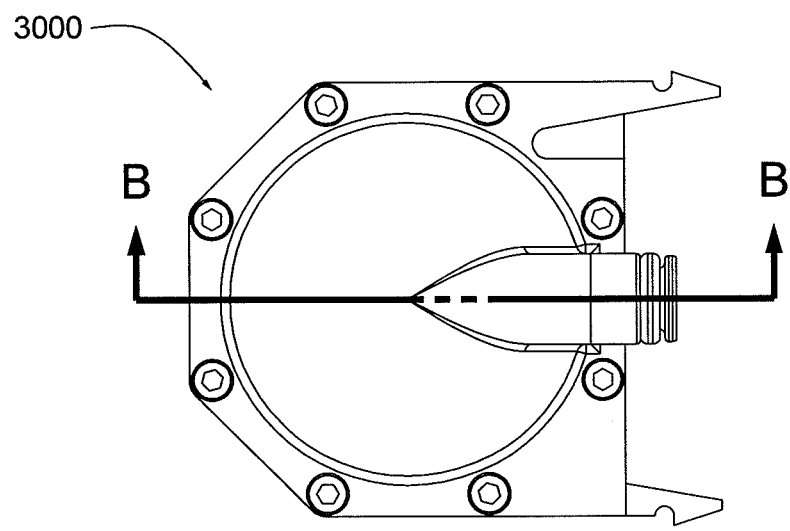
FIGS. 32A and 32B are top and section views of a pod pump with an insert in the actuation chamber.
Figure 32B:
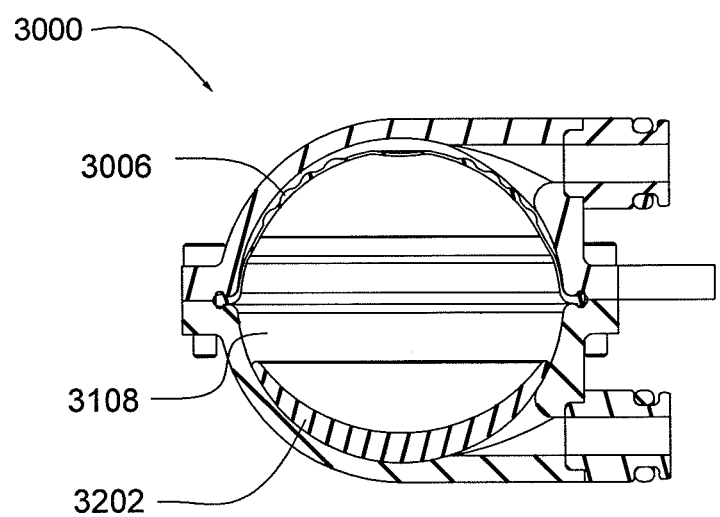

Referring now to FIGS. 32A and 32B, an alternate embodiment of the pod pump 3000 similar to the pod pump shown in FIGS. 30A and 30B is shown. However, in this embodiment, an additional component 3202 is included in the actuating chamber 3108. In some embodiments, an additional component 3202 can also be included in the pump chamber 3110, and in other embodiments, an additional component 3202 can be included in just the pump chamber. The additional component 3202 may serve to limit the motion of the diaphragm 3006, dampen the diaphragm's 3006 travel, filter air or gas entering or leaving the actuation chamber 3108 or dampen sound or vibration in the pod pump 3000. In some embodiments, e.g., where the pod pump 3000 is used in a fluid management system, an additional component 3202 may be present in both chambers to quicken the time for equalizing temperature within the chambers. In some of these embodiments, the additional component(s) 3202 may include a mesh plastic, a woven type material, a copper wool, a foam material, or other material, and may create a greater surface area to equilibrate air or other gas. In some embodiments, the additional component(s) 3202 may be part of a fluid management system (FMS) and may be used to perform certain fluid management system measurements, such as, for example, measuring the volume of subject fluid pumped through the pump chamber during a stroke of the diaphragm 3006 or detecting air in the pumping chamber, e.g., using techniques described in U.S. Pat. Nos. 4,808,161; 4,826,482; 4,976,162; 5,088,515; and 5,350,357, which are hereby incorporated herein by reference in their entireties. The additional component 3202 may completely or partially cover the actuation chamber port or may be completely free of the actuation chamber port.

In the preceding figures, various embodiments, characteristics and features of the pod pump are described and shown. The various characteristics can be "mixed-and-matched", i.e, any one characteristic can be added to any embodiment of the pod pump. The configurations shown are for example only, and the location of the ports, number of ports, attachment means, size of the housing, sizes of the chamber, etc., may vary in the different embodiments. The figures and embodiments described below additionally include various embodiments, characteristics and features, all of which also can be "mixed-and-matched" with any of the characteristics and features described in any of the embodiments in this description.

Figure 33A:
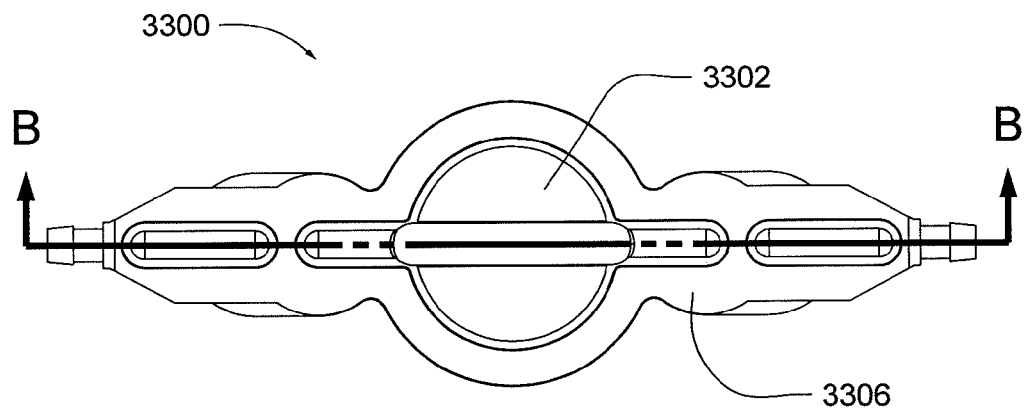
FIGS. 33A and 33B are top and section views of a pod pump with a laminated construction.
Figure 33B:
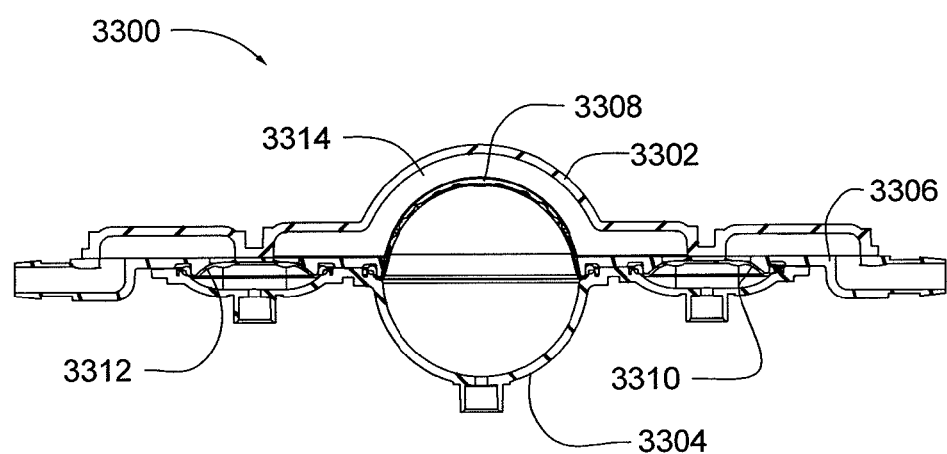

Referring to FIGS. 33A and 33B, an alternate embodiment of a pod pump 3300 is shown with a pump chamber cover 3302, an actuation chamber cover 3304 and a mid plate portion 3306. In this embodiment the mid plate 3306 and the actuation chamber cover 3304 retain the diaphragm 3308 and one or more secondary diaphragms 3310 or 3312. The secondary diaphragms may act passively or may be actuated by gas, liquid or mechanical forces to serve as active valves to control the flow of fluid through the pump chamber cover fluid path 3314. In this embodiment of the pod pump 3300, a fluid path 3314 is formed in the pump chamber cover 3302 such that fluid may flow through the flow path 3314 regardless of the position of the diaphragm 3308. In this embodiment as in other embodiments the pump chamber cover 3302, actuation chamber cover 3304 and mid plate 3306, in one embodiment, are made of plastic but in other embodiments, may be made from other materials including but not limited to metal or glass. In this embodiment the pump chamber cover 3302, actuation chamber cover 3304 and mid plate 3306 may be joined by laser welding or may be joined by various other methods as deemed appropriate for the chosen component materials and the desired pod pump use. Other joining possibilities include but are not limited to snap together tabs, press fit, snap fit, solvent bonding, heat welding, electromagnetic welding, resistance welding, RF welding, screws, bolts, ultrasonic welding, adhesive, clamping by components that neighbor the pump when in use or other joining methods commonly used in the art.

Figure 34A:
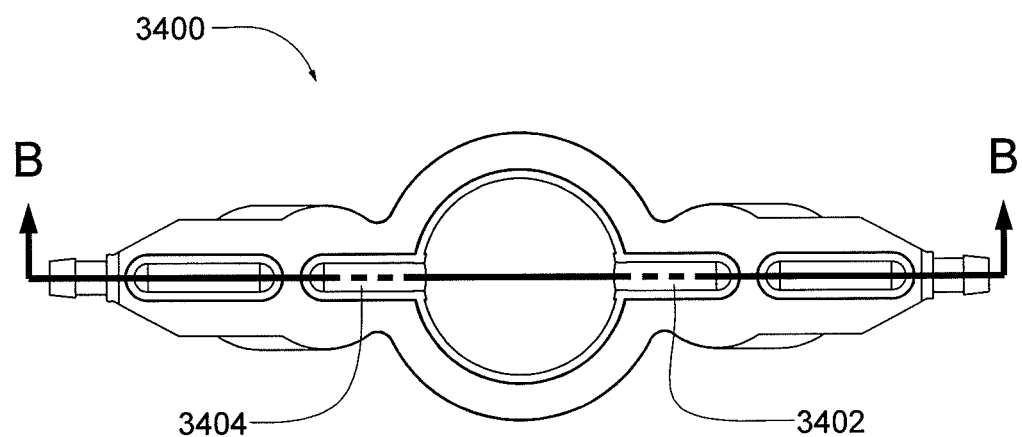
FIGS. 34A and 34B are top and section views of a pod pump with a laminated construction.
Figure 34B:
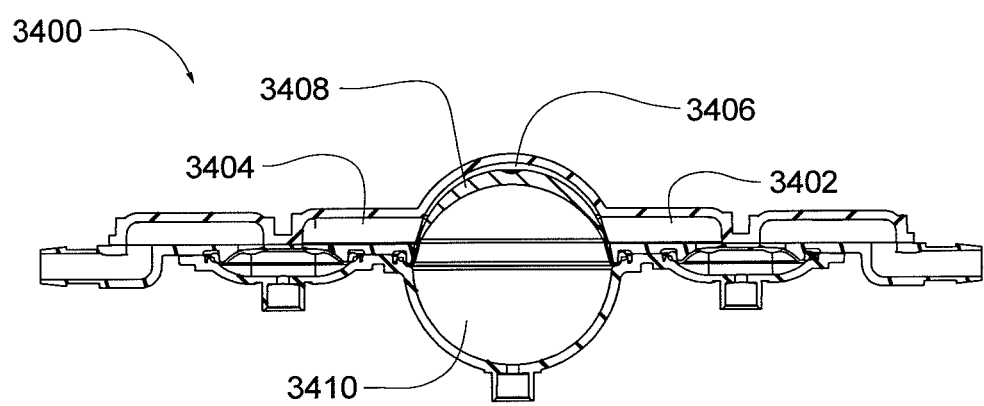

Referring now to FIGS. 34A and 34B one embodiment of a pod pump 3400 is shown. In this embodiment inlet and outlet ports are located at opposite ends of the pump chamber 3406 and are interchangeable depending on the configuration of the pump or its intended use. The diaphragm 3408 is shown nearly fully extended into the pump chamber 3406. In this embodiment the inlet and outlet ports 3402 and 3404 may be partially or fully obscured by the diaphragm 3408 when fully actuated by fluid pressure in the actuation chamber 3410. Blocking of the inlet or outlet ports may serve to limit or switch the flow of subject fluid through the pump chamber 3406 as may be desired in certain applications. In this embodiment the pumping side of the diaphragm 3408, i.e., the side of the diaphragm 3408 that contacts the subject fluid, is smooth, which may provide different flow characteristics with some subject fluids or provide different contact between the diaphragm 3408 and pump chamber 3406 when reduction of flow through the inlet or outlet ports 3402 and 3404 is desired when the diaphragm is fully extended into the pump chamber 3406.

In some embodiments, the diaphragm has a variable cross-sectional thickness, as shown in FIG. 34B. Thinner, thicker or variable thickness diaphragms may be used to accommodate the strength, flexural and other properties of the chosen diaphragm materials. Thinner, thicker or variable diaphragm wall thickness may also be used to manage the diaphragm thereby encouraging it to flex more easily in some areas than in other areas, thereby aiding in the management of pumping action and flow of subject fluid in the pump chamber 3406. This embodiment the diaphragm 3408 is shown having its thickest cross-sectional area closest to its center. However in other embodiments having a diaphragm 3408 with a varying cross-sectional, the thickest and thinnest areas may be in any location on the diaphragm 3408. Thus, for example, the thinner cross-section may be located near the center and the thicker cross-sections located closer to the perimeter of the diaphragm 3408. Still other configurations are possible. Referring to FIGS. 35B-E, one embodiment of a diaphragm is shown having various surface embodiments, these include smooth (FIG. 35), rings (FIG. 35E), ribs (FIG. 35D), dimples or dots (FIG. 35C) of variable thickness and or geometry located at various locations on the actuation and or pumping side of the diaphragm 3408. In one embodiment of the diaphragm, the diaphragm has a tangential slope in at least one section, but in other embodiments, the diaphragm is completely smooth or substantially smooth.

Referring now to FIG. 35A a pictorial exploded view of an exemplary embodiment of a pod pump 3500 is shown. This figure shows one embodiment of the ports, however, an exemplary embodiment is described below with respect to FIG. 37.

In this embodiment the housing is made of three sections. Two of the portions 3502, 3504 may be joined to form a pump chamber 3506 (portions 3502, 3504 referred to as "pump chamber portions") and the third portion 3508 (referred to as the actuation chamber portion) includes an actuation chamber 3512 and an actuation port 3510 to communicate fluid pressure to the actuation chamber 3512. The pump chamber portions 3502, 3504 may be joined together to form a pump chamber assembly. This assembly may then be joined with the actuation chamber portion 3508 to form the housing.

The diaphragm 3514 is connected to the interior of the housing. In the exemplary embodiment, the diaphragm 3514 is sandwiched between the pump chamber 3506 and the actuation chamber 3512. The diaphragm 3514 segregates the actuation chamber 3512 from the pump chamber 3506.

In this exemplary embodiment, where the pump chamber 3506 is composed of two portions 3502, 3504, where the portions are molded, this design may allow for minimum flash or burrs. Thus, in this embodiment, the pump chamber will not have flash in the fluid path thus, presents a gentle pumping environment. This embodiment may be advantageous for use with those subject fluids vulnerable to shearing, and/or where delicate subject fluids are pumped, thus flash or burrs should be avoided.

In the exemplary embodiment shown in FIG. 35A, the pump 3500 is shown having two ports 3518, 3516. For ease of description, these ports 3518, 3516 are called "inlet" and "outlet" ports. However, either port 3518, 3516 can serve as an inlet port, likewise, either port can serve as an outlet port. The pump inlet and outlet ports 3516, 3518 connect to the pump chamber 3506 at edges 3520 and 3522. In one embodiment, the edges 3520, 3522 are left sharp and are subject to flash when they are molded with retractable cores. However, in the exemplary embodiment, the pump may be manufactured without retractable cores and therefore may have radii on the edges 3520, 3522 thereby eliminating flash or burrs from the flow path that may damage delicate or sensitive subject fluids.

Still referring to FIG. 35A, as shown in this exemplary embodiment, the pod pump 3500 includes three housing portions 3502, 3504, 3508 and a diaphragm 3514. Two housing portions 3502, 3504 form a pump chamber 3506 portion as well as two ports 3516, 3518. A third portion 3508 forms the actuation chamber 3512. The diaphragm 3514 is attached between the pump chamber 3506 and actuation chamber 3512 by sandwiching the diaphragm lip 3520, which in one embodiment, is an integral O-ring, however, in other embodiments, can be any other shaped gasket, between the rims 3524 of the housing portions. In the embodiment shown in FIG. 35A, the diaphragm 3514 includes tangent edges. The tangent edges are present where the shape of the diaphragm 3514 is not a continuous dome, thus, in one section; the diaphragm is conical shaped as indicated by the tangent edges. Although tangent edges are depicted in this embodiment, in alternate embodiments, the diaphragm can include various surfaces, which may include, but are not limited to one or more of the following: dimples, rings, ridges, ribs, smooth, or another variable surface.

As discussed above, the pump chamber 3506 and the ports 3516, 3518 are formed by two housing portions 3502, 3504. These portions 3502, 3504 fit together as described below with respect to FIGS. 36A-36C.

Referring now to FIGS. 36A and 36B, assembled side and end views of the pump 3500 of FIG. 35 are shown. Here the pump chamber portions 3502 and 3504 and the actuation chamber portion 3508 have been joined to conceal the diaphragm 3514, not shown. The components of the pod pump housing may be joined by various methods including but not limited to snap together tabs, press fit, snap fit, solvent bonding, heat welding, electromagnetic welding, resistance welding, RF welding, screws, bolts, ultrasonic welding, adhesive, clamping by components that neighbor the pump when in use or other joining methods commonly used in the art.

In the exemplary embodiment as shown in FIGS. 35A-41B, the pod pump 3500 housing includes three portions having features, some specific for the portions to be ultrasonically welded. The design of these three portions includes features that allows for the portions to be joined by ultrasonic welding, but the resultant pod pump is can pump delicate subject fluids with minimal, if any, resultant damage to the subject fluid following ultrasonic welding. A description of the three portions of the housing and the features for assembly is below. Although these embodiments are described with respect to ultrasonic welding, it should be understood that these embodiments alternatively may be laser welded or joined using snap together tabs, press fit, snap fit, solvent bonding, heat welding, electromagnetic welding, resistance welding, RF welding, screws, bolts, adhesive, clamping by components that neighbor the pump when in use or other joining methods commonly used in the art.

Referring now to FIG. 36C an enlarged view of one port is shown. This can be either the inlet or outlet port as shown in FIG. 35A. In this embodiment the inlet and outlet ports are interchangeable and both have similar interior and exterior geometry. However, their locations may vary.

In this embodiment, portions of the housing 3502, 3504 are joined to form a port 3604. In this embodiment the pump chamber portions 3502, 3504 are depicted as being joined by ultrasonic welds at the energy director 3602. However, in alternate embodiments, other joining methods, as described above, can be used. The zone 3606 where housing portions 3502, 3504 are joined is at least partially isolated from the fluid path of the port 3604 by an area 3608. The area 3608 is formed after joining the housing portions 3502, 3504 together. The area 3608, in one embodiment, increases resistance to flow, thus, the area 3608 creates a path of more resistance than the main flow through the chamber. Thus, the area 3608 is a flow inhibiting area. Thus, the flow of fluid to the zone 3606 where the housing portions meet is decreased. This flow inhibiting area 3608 can be any size desired, however, in the embodiment shown, the flow inhibiting area 3608 is created where the distance between the two portions may range from 0.001 inch-0.005 inch and in some embodiments a range of 0.015 inch-0.020 inch. However, the area 3608 can be any size desired and may vary depending on a number of variables including but not limited to: fluid volume, chamber volume and pumping rate. In many embodiments, the distance between the two portions 3502, 3504 creating the area 3608 is a fraction of the size or volume of the main flow path. In other embodiments, the area 3608 is any size or volume desired to present desired resistance to the flow of fluid to the area 3606.

In alternate embodiments, and in some of these embodiments, depending on the overall volume of the pod pump, the area 3608 may have a larger or smaller range. The flow inhibiting area 3608 provides a means where if fluid does flow across the flow inhibiting area 3608 it will experience much greater resistance than fluid flowing through the larger area of the port 3604. By virtue of less fluid flowing in the flow inhibiting area 3608 and reaching the zone 3606 where the housing components are joined, less fluid will tend to contact any burrs, flash, surface irregularities or impurities that may be present in area 3606 where the housing components are joined. This isolation from flash, burrs, surface irregularities or other effects of various joining methods may provide for more gentle and safer transport of delicate of sensitive subject fluids as may be desired for certain applications.

Rounded edges 3612 on the pump housing portions 3502, 3504 provide, amongst other things, a delicate environment for the subject fluid, liquid or gas flowing through the pump 3500. Although the flow inhibiting area 3608 and rounded edges 3612 are shown in specific locations in FIG. 36C, these features can be present in any area of the pump desired.

Referring now to FIG. 37 an exemplary embodiment of the pod pump is shown. In this figure, the ports are shown having valves 3712 within. Again, as shown in this figure, the pod pump housing has three portions 3702, 3704, 3706. Portion 3702 includes the actuation chamber 3704 and alignment features 3706 for assembly with the other two pump housing portions 3704, 3706. In this embodiment the pump housing portions 3704, 3706 include areas where one way valves may be installed 3712. The housing portions 3702, 3704, 3706 may be joined by ultrasonic welding, laser welding, snap together features, screws, bolts, adhesive or other joining methods commonly used in the art.

The diaphragm 3714 is shown with ribs in this embodiment. However, in alternate embodiments, the diaphragm 3714 may include one or more of the variable surfaces as described above, or alternatively, may be a smooth surface. Although each of the various figures herein show one embodiment of the diaphragm, any embodiment of the diaphragm may be used in conjunction with any embodiment of the pod pump.

Referring now to FIGS. 38A and 38B, an alternate embodiment of the pod pump 3800 is shown. In various embodiments, the pod pump 3800 is connected to a system, container or otherwise, where fluid is pumped from and/or into. In some embodiments, the fluid is pumped to/from a system, container or otherwise via a line or tubing. In one embodiment, the fluid is pumped through flexible tubing. In any case, in these embodiments, the line or tubing is connected to the inlet and outlet ports 3814 of the pod pump. However, in alternate embodiments, the fluid can be pumped through a molded fluid line, or the ports can be directly connected to the fluid source, or where the fluid is being pumped.

Still referring to FIGS. 38A and 38B, the housing is a multi portion design, similar to the design shown in FIG. 37, including a two portion pump chamber housing 3704, 3706. However, in this embodiment, barbed hose connectors 3802 are shown for the connection of flexible tubing (not shown). Other means of connection to a system may be used in other embodiments. These means include, but are not limited to, quick connects, press fit or gluing of tubing directly into the inlet or outlet ports or other means and methods commonly used in the art.

Referring now to FIG. 38B a section view of the embodiment shown in FIG. 38A is shown. In this embodiment valves 3816 are installed in the interior of the port 3814 portion of the housing portions (as shown as 3806, 3804 in FIG. 38A). The valves 3816 control the flow of subject fluid in and out of the pump chamber 3818 as the diaphragm 3808 is actuated by variations in liquid or gas pressure in the actuation chamber 3810. As shown in this embodiment, the valves 3816 are duck bill valves, however, in other embodiments, the valves 3816 can be any passive or active valves, including but not limited to, ball check valves, flapper valves, volcano valves, umbrella valves, a poppet, a controlled valve or other types of valves used in the art. In this embodiment the fluid path 3812 is located near the top of the pump chamber 3818 and has a portion not inhibited by the diaphragm 3808 even when the diaphragm is fully extended into the pump chamber 3806 by liquid or gas pressure applied to the actuating chamber 3810 via the actuation port 3820.

As shown in this embodiment, the diaphragm 3808 includes rings, however, as described above, the diaphragm 3808 can include dimples, rings, and/or ribs, or any other variation on the surface, or, in some embodiments, no variation on the surface. The varying embodiments of the diaphragm can be used in any of the embodiments of the pod pumps.

Referring now to FIG. 39, an exploded pictorial view of one embodiment of a pod pump 3900 is shown. Valves 3902, in some embodiments, may be installed in the inlet and or outlet ports 3904 of the pump housing portions 3906 and 3916. The valves 3902 may any passive or active valve, including but not limited to, duck bill valves, ball check valves, flapper valves, volcano valves, umbrella valves, a poppet, a controlled valve or other types of valves used in the art to control the flow of fluid. A diaphragm 3908 is attached between the pump chamber housing portions 3906 and 3916 and the actuation housing portion 3910. The diaphragm 3908 is made of any sufficiently flexible and durable material that it may flex in response to fluid pressure or vacuum applied to the actuation chamber 3910. The diaphragm 3908 material may also be chosen for particular bio-compatible, temperature compatibility or compatibility with various gases or liquids that may be introduced to the pump or actuation chambers.

The diaphragm 3908 may have a ring of thick material 3912 near its outer diameter to be located or fastened in mating features of the pod pump housing components 3906, 3916 and 3910. The moveable portion of the diaphragm 3908 includes two surfaces, for purposes of description; these will be referred to an exterior surface and an interior surface. The exterior surface is the pump chamber surface and the interior surface is the actuation chamber surface. Either surface of the movable portion of the diaphragm may be of uniform or variable thickness, and both surfaces do not have to be the same. Various embodiments of the surface are shown in FIGS. 35B-E.

Either or both surfaces may be smooth or include one or more features including but not limited to dimples, dots, rings, ribs, grooves or bars that stand above or below surrounding surfaces. In this embodiment, an arrangement of dots 3914 are shown on the exterior surface of the diaphragm.

The surface features, or lack thereof, may serve a number of various functions. One of these may be to provide space for fluid to pass through the pump chamber. Another may be to aid in the diaphragm sealing against the pump chamber housing for applications where it is desirable to prevent the flow of fluid through the pump chamber when the diaphragm is pressed against the pump chamber housing by liquid or gas pressure in the actuation chamber. Some diaphragm surfaces may provide one or more of these features, or provide another function or feature.

Geometry on the exterior or interior surface of the diaphragm may also serve to cushion the movement of the diaphragm at either end of the diaphragm stroke. When geometry on the diaphragm contacts the pump or actuation chamber walls those features will stop moving but the diaphragm material between the features may continue to move to allow the fluid that is being pumped to be gently accelerated or decelerated as it enters or leaves the pump chamber.

Referring now to FIG. 40A, a pictorial view of portions 3906 and 3916 of the multi portion pump shown in FIG. 39 is shown. For illustration purposes only, the pump housing portions 3906 and 3916 are shown oriented base to base to illustrate the relationship of the alignment and joining features that may be used in the pump portion of a multi-part pod pump housing. The portions 3906 and 3916 align and join together in two locations in this exemplary embodiment. However, in other embodiments, these features may vary, and the location of the joining of the two portions may vary. For purposes of description, one of the alignment and joining features will be described with respect to FIG. 40B, however, it should be understood, that although one is described, the details can apply to both.

Referring now to FIG. 40B, a close up pictorial view of one area of FIG. 40A is shown. Pump housing portion 3916 has an alignment feature 4002 that may align with a complimentary alignment groove 4004 on housing portion 3906. In this embodiment the aligning feature 4002 includes an energy director 4006 so the housing portions 3906 and 3916 may be joined by ultrasonic welding. In this embodiment the energy director is located in line with a relieved area 4008 in the base of the pump housing 3916. The relieved area 4008 may accommodate the outer ring of a diaphragm (not shown), in embodiments where the diaphragm includes an outer ring.

The relieved area 4008 is continued in pump housing portion 3906 but is only visible as the edge 4010. In this embodiment where ultrasonic welding is used, flash from the energy director 4006 may attempt to flow beyond the edge 4010 upon assembly. By virtue of the energy director 4006 being in line with the outer ring of the diaphragm (not shown) any flash will be adjacent the outer ring of the diaphragm which flexes to seal despite the presence of flash on the diaphragm outer ring sealing surface. When alternate joining methods such as, but not limited to, laser welding, adhesives, screws or other fasteners are used, the energy director 4006 may be excluded and the geometry of the alignment features 4002 and 4004 may vary form the embodiment shown.

In the embodiment an additional aligning feature 4012 and energy director 4014 are present to orient the pump housing components 3906 and 3916 such that they are joined down to their base where they will be joined to an actuation housing (not shown) as shown in earlier and subsequent figures.

Referring now to FIG. 41A, a pictorial view of a partially assembled pod pump 4100 is shown. For illustration purposes, only one portion of the pump housing 3916, a portion of a possible embodiment of a diaphragm 4102 and a portion of an actuator housing 4104 are shown.

Referring now to FIG. 41B, a close up pictorial view of one area of FIG. 41A is shown. In this embodiment of the actuator housing 4104, two energy directors 4106 and 4108 are shown for joining by ultrasonic welding although other joining methods are possible. In this embodiment energy director 4108 is in line with energy director 4014 on pump housing portion 3916. Aligning the energy directors as shown in this embodiment ensures that flash from one weld is consumed by the other ultrasonic weld thereby creating a reliable seal between all three housing portions, one housing portion is excluded from this figure for clarity.

Still referring to FIGS. 41A and 41B, the alignment of energy director 4006 with the outer portion of the diaphragm 4102 is shown. Aligning energy director 4006 with the diaphragm 4102 in this way allows any flash resulting from an ultrasonic weld in the area of energy director 4006 to be sealed by the flexible material of the diaphragm 4102.

The pod pump housing can be made from any material including any plastic, metal, wood or a combination thereof. In one exemplary embodiment, the pod pump housing is made from medical grade polycarbonate. In another exemplary embodiment, the pod pump housing is made from polysulfone. As described in more detail in the description, the compatibility of the materials selected to the subject fluid may be one factor in some embodiments.

Referring now to FIGS. 42A-42D, an alternate shape embodiment of the pod pump 4200 is shown. The shape embodiments shown herein are meant for illustration and description purposes only. In alternate embodiments, it should be understood that the pod pump can be any shape desired.

The pod pump housing can be manufactured using any one of a number of methods of manufacturing, including but not limited to injection molding, compression molding, casting, thermoforming or machining. In some embodiments, for example, where the housing is machined, the housing can be fused together using mechanical fasteners or heat fused.

The wall thickness of the pod pump housing may vary between embodiments. A myriad of variables may contribute to wall thickness selection. These include, but are not limited to, the housing material used, pressure at which the fluid will be pumped; size of the chambers; overall size of the pod pump, strength needed in response to the materials using, durability, assembly method, the device in which the pod pump may be working in conjunction with, cost and manufacturing time. In some embodiments, the pod pump wall thickness is variable.

The wall thickness, in the various embodiments, can range from 0.005 to any thickness. The term "any thickness" is used because in some embodiments, the pod pump can be integrated into a device or machine. Thus, the wall of the pod pump may be the same thickness as the overall machine. Thus, in some cases, the wall thickness is quite large. In the exemplary embodiment described herein, the wall thickness ranges from 0.04 inch to 0.1 inch. In another embodiment, the wall thickness ranges from 0.06 inch to 0.08 inch.

The material selection and method of manufacture of the various embodiments of the pod pump may depend on a number of variables. Some include durability, cost, pressure from the fluid, performance, and many others. In some embodiments, the pod pump housing and diaphragm is intended to last months or years. In other embodiments, the pod pump is intended to be a one-use disposable. In still other embodiments, the pod pump is intended to last any number of hours, days, weeks or years. In some embodiments, even where the pod pump is a one-use disposable, the pod pump is designed to pump for a much longer period of time, for example, days, weeks, months or years.

In one embodiment of the disposable, the housing is made from a thin film made of a material which includes, but is not limited to PETE, PETG, and PET. In these embodiments, the housing may be thermoformed, for example, vacuum or pressure formed, and the diaphragm is formed from a thin plastic film that can be heat sealed to the housing. In some embodiments, the housing is a multi-layer film. This embodiment is conducive to bonding the housing to another component.

The pod pump can be incorporated and/or integrated into another device, machine, container, or other, or act in conjunction with another device, machine, container or other. In some embodiments, a single pod pump is used. However, in other embodiments, two or more pod pumps are used. In some embodiments, the pod pump is incorporated into a device which is then integrated or attached to a machine, device, container or other. One example of this embodiment is a cassette having integrated pod pumps, fluid paths, fluid ports, actuation ports and actuation fluid paths. Two embodiments of a cassette are described with respect to FIGS. 43A-43C and 44A-44B. Many additional embodiments will be understood. For purposes of description, an exemplary embodiment and an alternate embodiment will be described. However, these are only exemplary and other embodiments, with greater or less than two pod pumps, using different valves, various flow paths and incorporating additional containers or other devices, are understood.

Figure 43A:
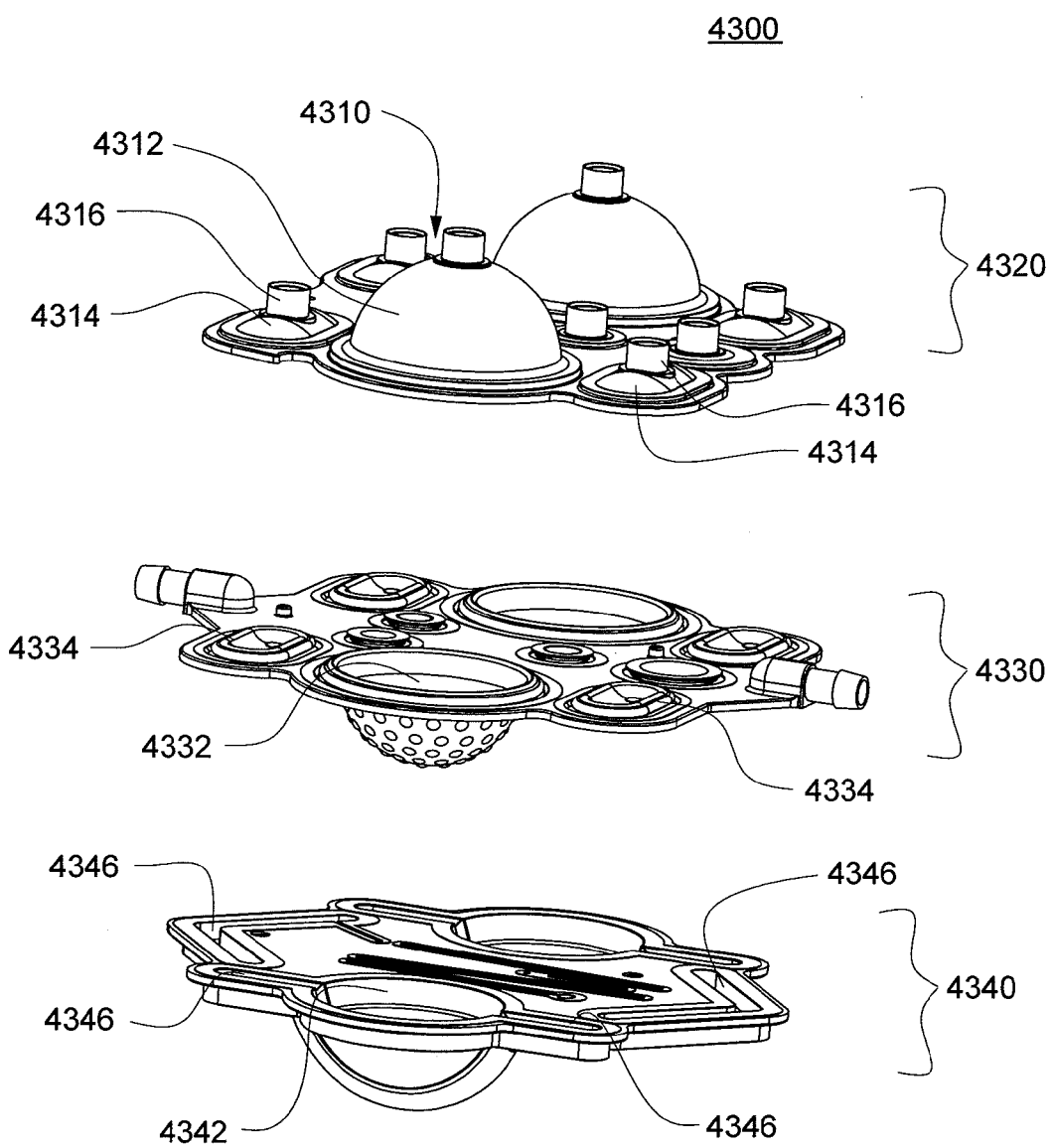
FIGS. 43A-43C are exploded and section views of one embodiment of a pod pump cassette.
Figure 43B:
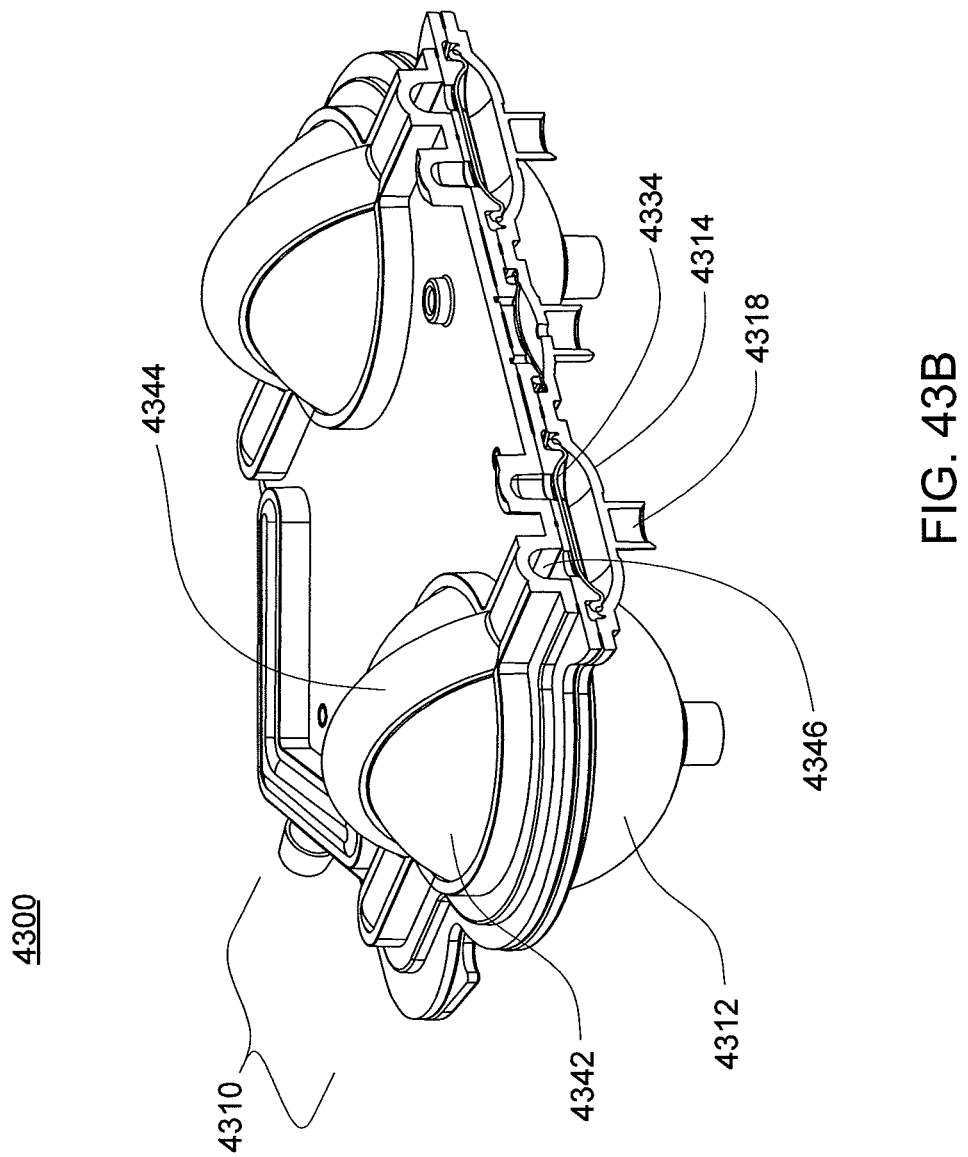
Figure 43C:
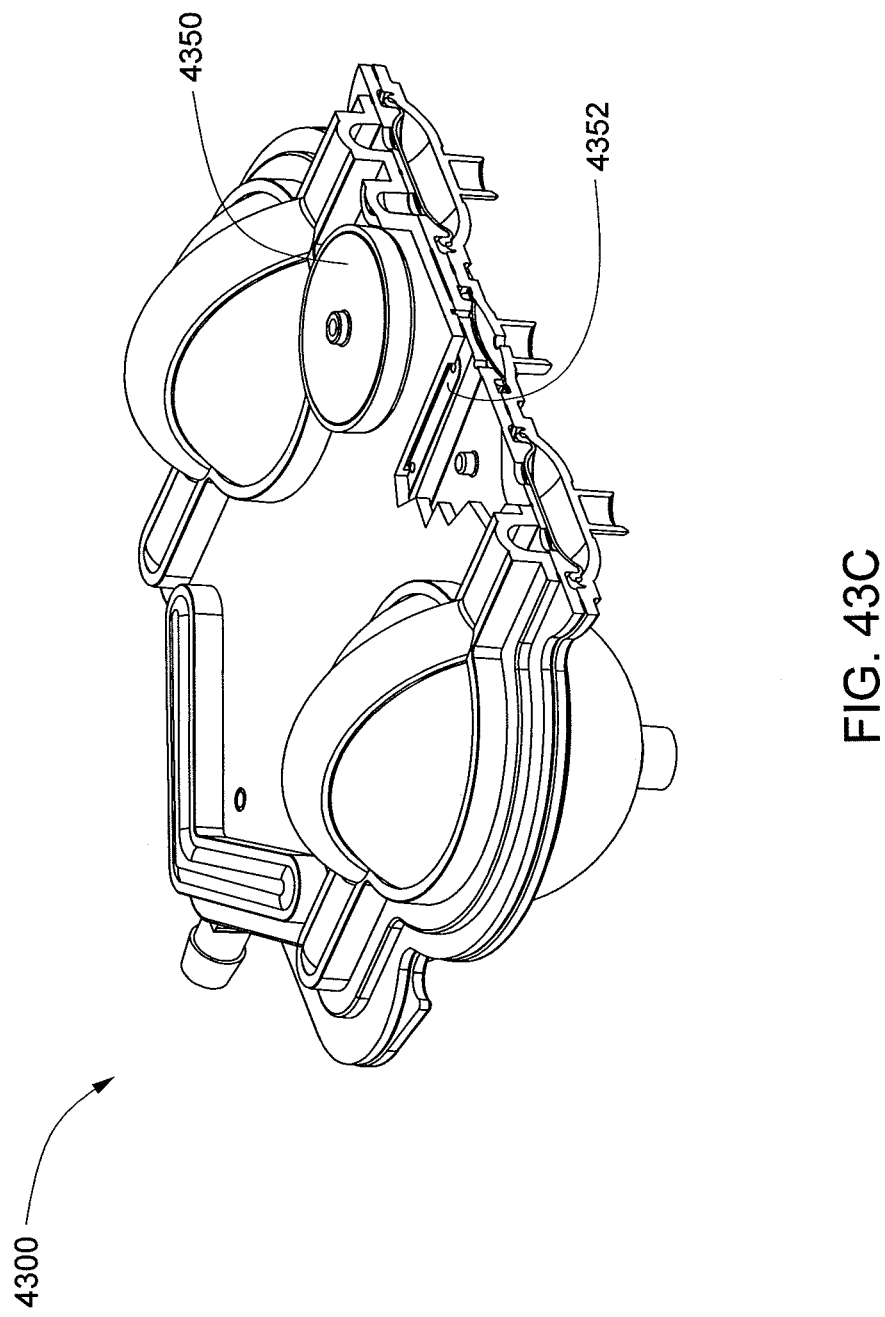

Referring now to FIGS. 43A-43C, one embodiment of a pod pump cassette 4300 is shown. Referring now to FIG. 43A, this embodiment of the pod pump cassette includes two pod pumps 4310. The pod pumps 4310 can be any pod pump embodiment, but in this exemplary embodiment, the pod pumps 4310 are similar to the pod pump shown in FIGS. 33A-33B. The cassette 4300 includes three plates, an actuation plate 4320, a mid plate 4330 and a pump chamber plate 4340.

The actuation plate 4320 includes, for each pod pump 4310, a pod pump actuation chamber housing 4312 portion and two valves actuation housing 4314 portions. The valve actuation housing 4314 includes a valve actuation port 4316. In addition to pod pumps, the cassette 4300, in some embodiments, may contain additional ports and/or containers for various fluids to be pumped to and from.

The mid plate 4330 includes, for each pod pump, a pump diaphragm 4332 and two valve diaphragms 4334. In the embodiment shown, the valves are volcano or active valves actuated by a diaphragm 4334 which is actuated by a fluid, which in this embodiment is pneumatic air. Also shown on this embodiment of the cassette 4300 are additional diaphragms in the mid plate 4330. These are for embodiments that may contain additional container for various fluids to be pumped to and from.

Referring now to the pump plate 4340, each pod pump 4310 includes a pump chamber housing 4342 which includes an integral fluid path 4344. The pump chamber housing 4342 is in fluid connection with an exterior fluid path 4346. In this exemplary embodiment, the three plates 4320, 4330, 4340 are laser welded together. However, in other embodiments, various modes of attachment, some of which are described above, may be used.

Referring now to FIG. 43B, a cross sectional view of the cassette 4300 is shown. The volcano valves are shown including the valve diaphragms 4334, the valves actuation housing 4314 portions and the exterior fluid line 4346. The valves are actuated by pneumatic air through actuation ports 4318.

Referring now to FIG. 43C, in some embodiments, an air filter 4350 and an additional fluid line 4352 may be included in the cassette.

Figure 44A:
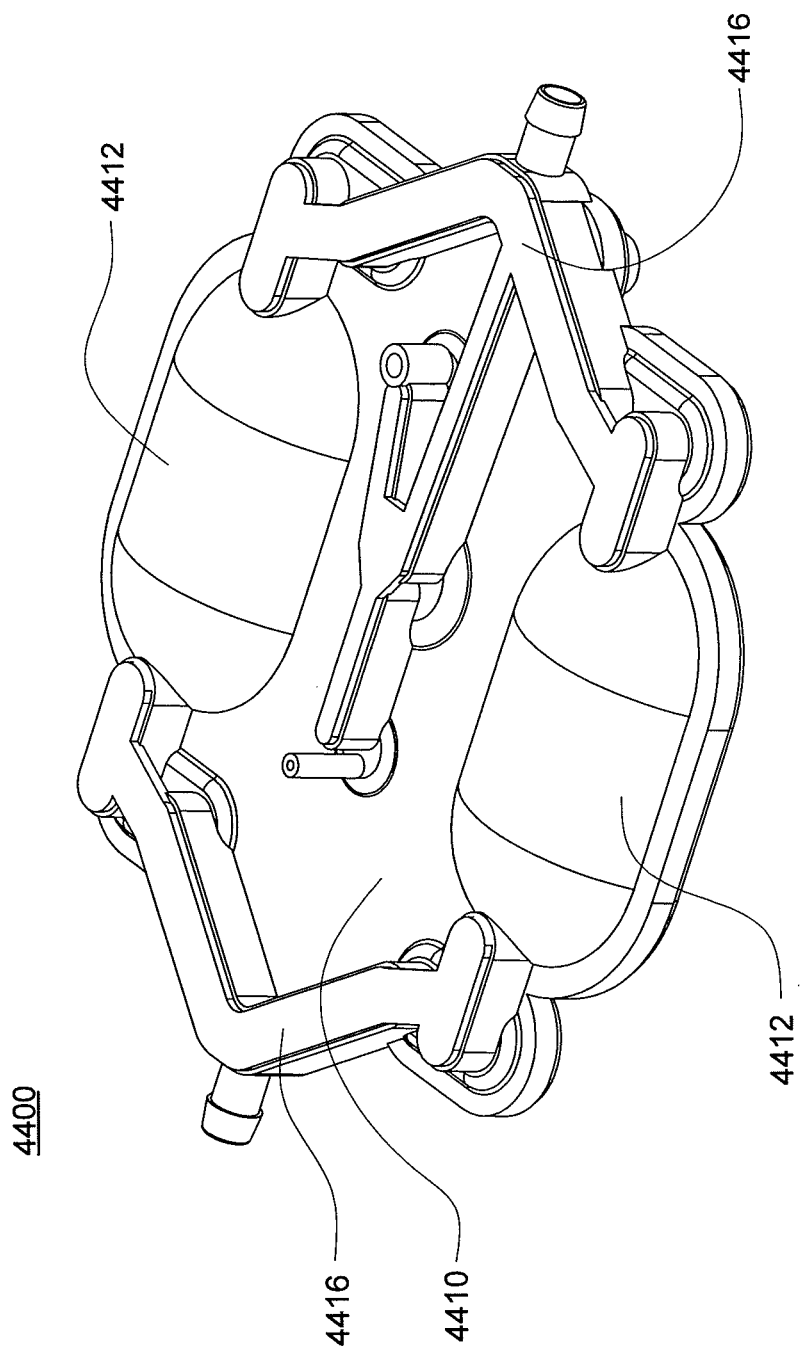
FIGS. 44A-44B are pictorial views of one embodiment of a pod pump cassette.
Figure 44B:
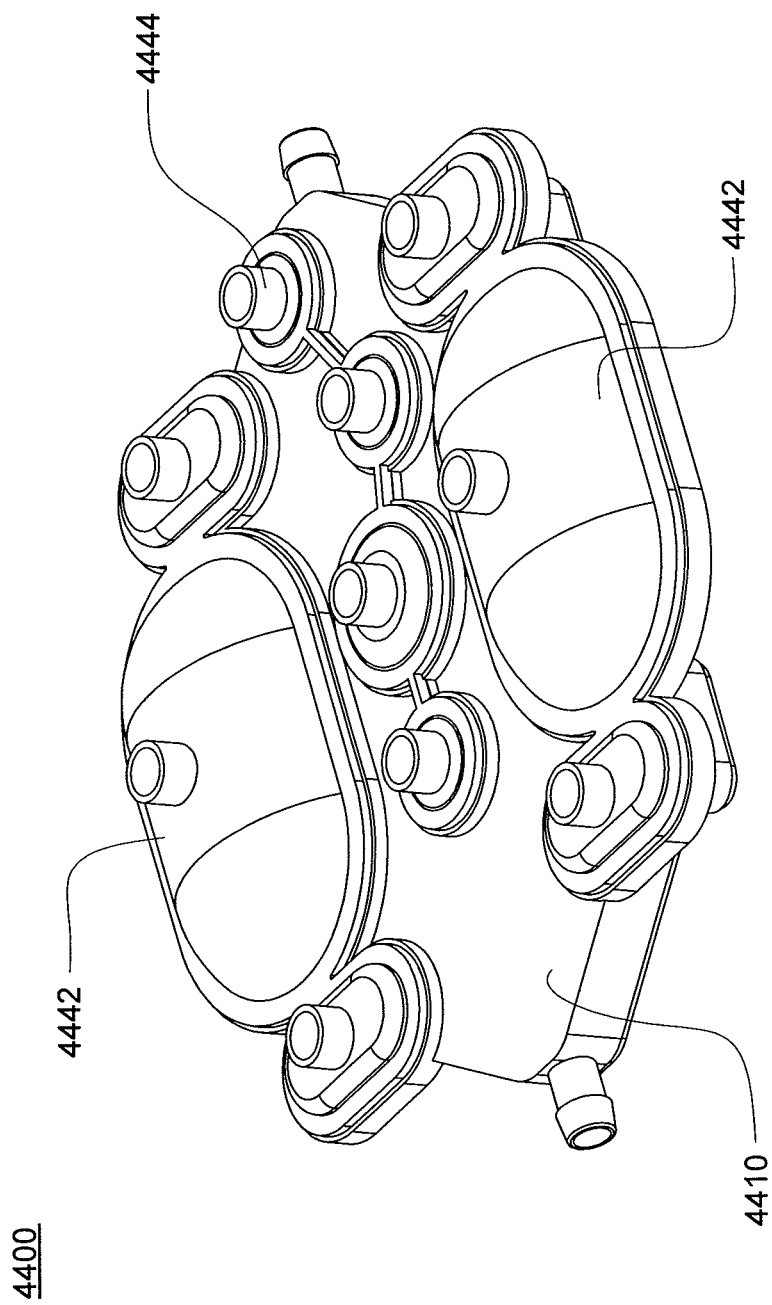

An alternate embodiment of the cassette is shown in FIGS. 44A and 44B. Referring now to FIG. 44A, the cassette 4400 includes greater than three portions. The portions include a mid plate 4410 with multiple covers 4412-4416 laser welded onto the mid plate. These multiple covers 4412-4416 are used rather than the pump plate shown in FIG. 43A as 4340. Referring now to FIG. 44B, the mid plate 4410 again is shown. However, in this embodiment, multiple covers 4442-4444 are used rather than an single actuation plate as shown in FIG. 43A as 4320. As shown in FIGS. 44A-44C, this is one embodiment, however, in other embodiments, the number of multiple covers may vary.

1.5. Exemplary Embodiments Incorporating Multiple Pump Pods

It should also be noted that pumping systems may employ multiple pump pods for pumping fluid. Pump pods may be employed individually, in which case the pump pods may be individually controlled, or pump pods may be interconnected in various ways, such as, for example, interconnecting the inlets of multiple pump pods in order to draw fluid from a common source, interconnecting the outlets of multiple pump pods in order to pump fluid to a common destination, and/or interconnecting the pneumatic ports of multiple pump pods in order to control the pump pods through a common pneumatic interface. In various embodiments, multiple pump pods may be operated out-of-phase (i.e., one pumping chamber is emptying while the other is filling) in order to provide a substantially continuous flow, in-phase in order to provide a pulsatile flow, or in other ways. For in-phase operation, a single pneumatic interface may be provided for multiple pump pods so that the base station can operate the pump pods simultaneously. Similarly, a single pneumatic interface may be provided for multiple valves so that the base station can operate the valves simultaneously.

Figure 2:
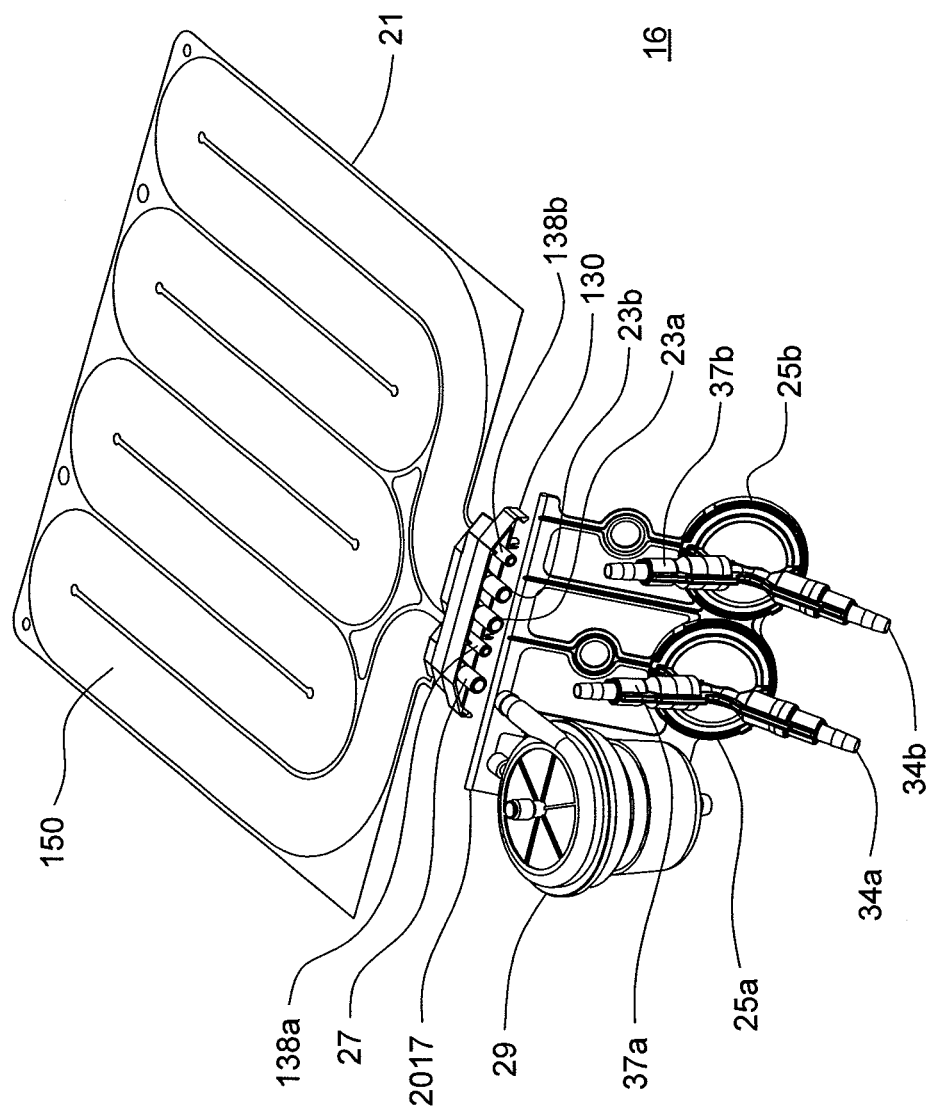
FIG. 2 is a perspective view of components of the disposable unit shown in FIG. 1.
Figure 48:
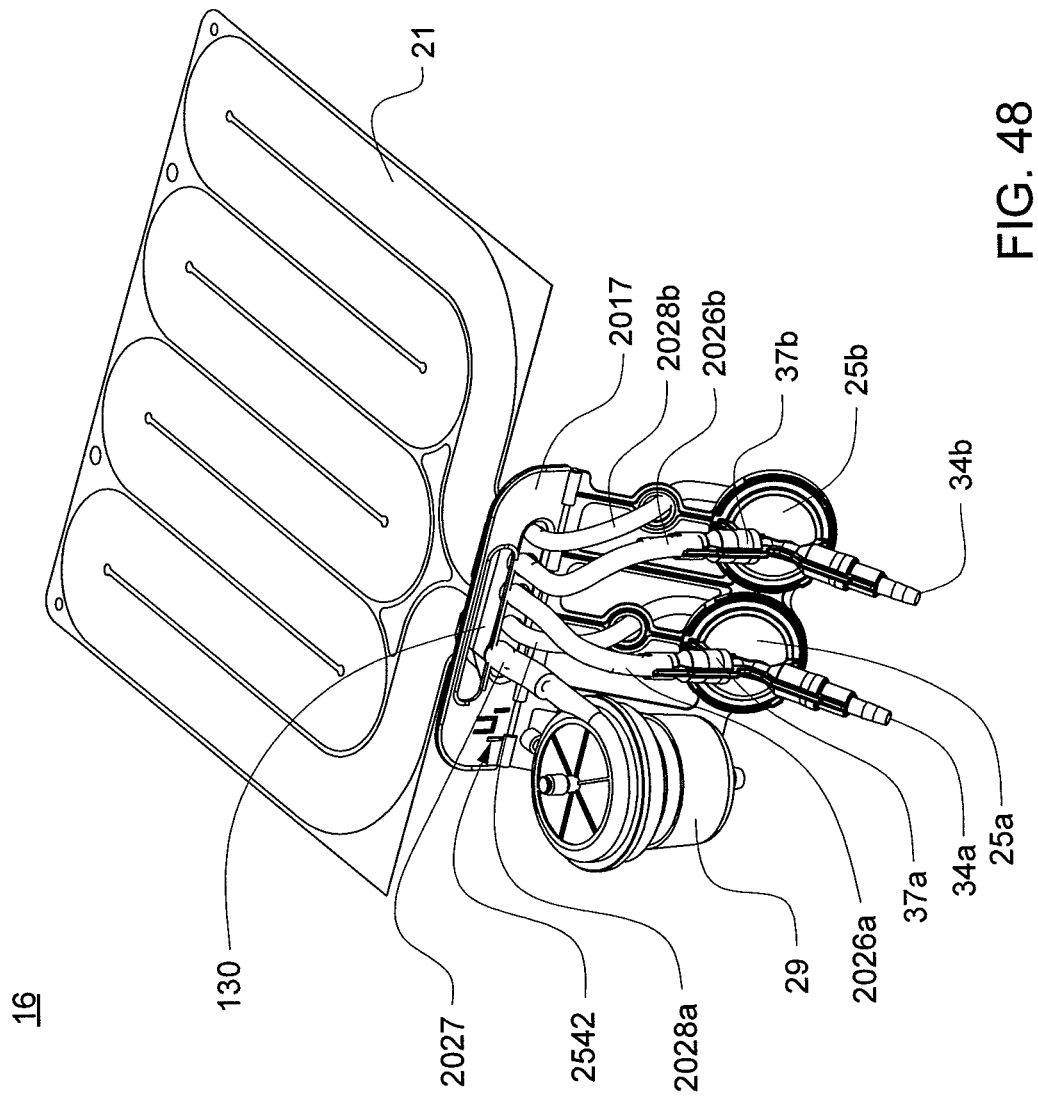
FIG. 48 shows an exemplary disposable unit in accordance with an exemplary embodiment of the present invention.

In the embodiments shown in FIGS. 2 and 48, two individual self-contained pump pods 25a and 25b of the type shown in FIG. 3 are included in a disposable system. In this embodiment, each of the pump pods 25a and 25b has its own pneumatic port 38, so the pump pods 25a and 25b can be controlled separately.

Figure 5A:
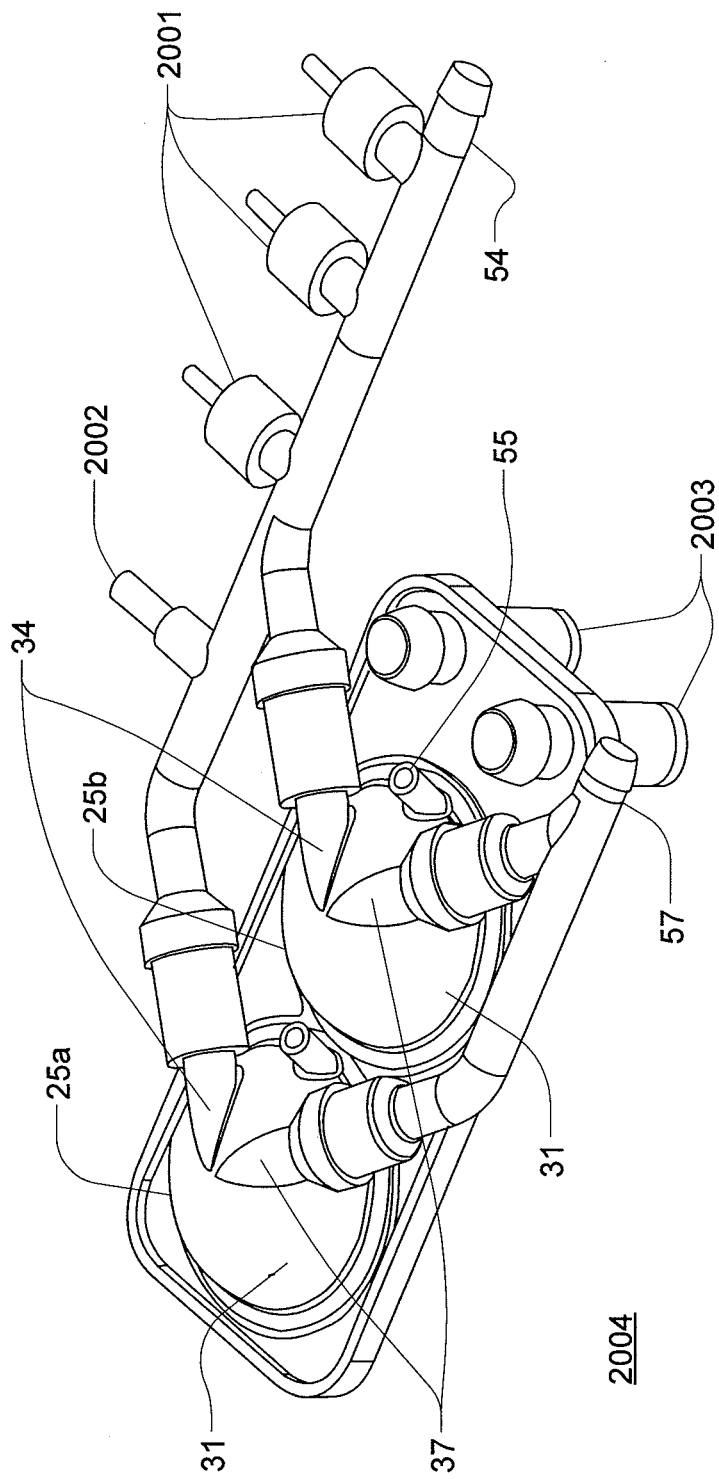
FIGS. 5A and 5B are respectively upper and lower perspective views of an alternative embodiment of a pump pod arrangement.
Figure 5B:
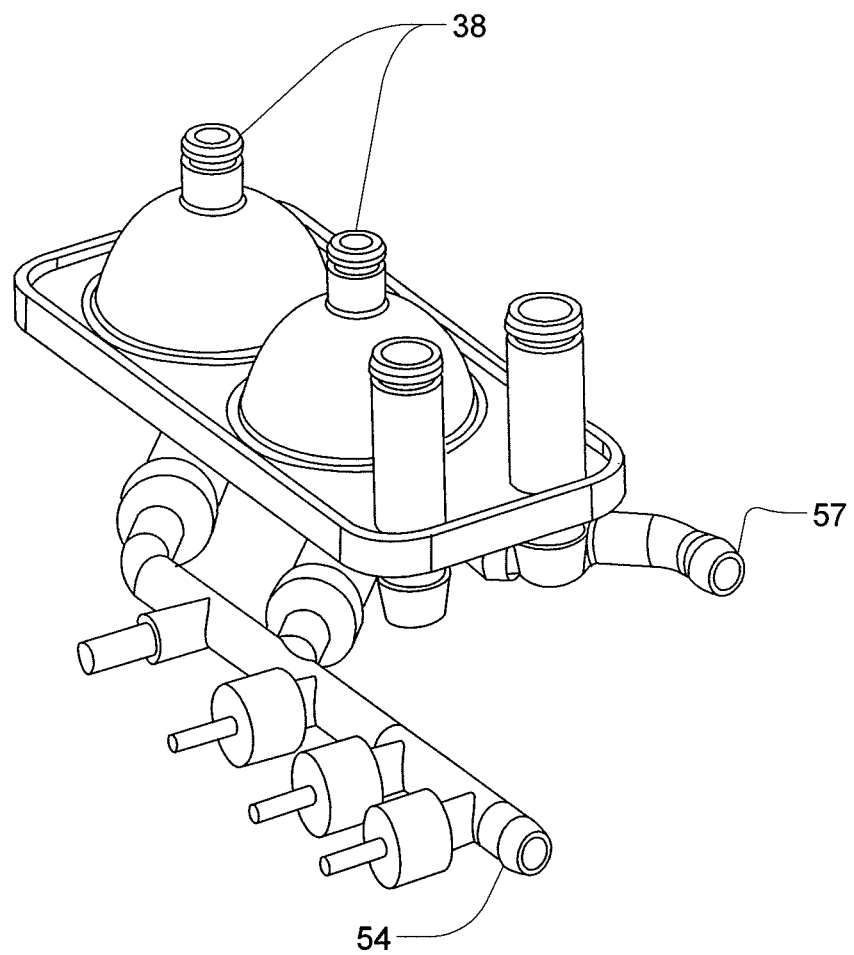

In the embodiment shown in FIGS. 5A and 5B, two pump pods 25a and 25b are incorporated into larger assembly 2004 such that the inlets of two pump pods 25a and 25b are connected to a common inlet line 54 and the outlets of both pump pods 25a and 25b are connected to a common outlet line 57. FIG. 5B shows the pneumatic ports 38 of the pump pods 25a and 25b. The inlets 34 and outlets 37 of the pump pods 25a and 25b are arranged to direct the flows into and out of the pumping chambers at angles that are substantially tangential with the rigid pumping-chamber walls 31 of each pump pod, in order to—as discussed above—reduce shear force and turbulence on the fluid and to improve circulation through the pumping chambers. In this embodiment, the pump pods 25a and 25b have purge ports 55, which allow air to be purged from the system, for example, during priming. Also in this embodiment, the common inlet line 54 is fitted with a number of luer ports 2001 (e.g., to permit attachment of additional fluid sources, such as medical solutions, chemical solutions, dilutants, etc.) and is also fitted with a thermocouple 2002 (e.g., to allow for monitoring the temperature of the fluid entering the pump pods 25a and 25b). Also in this embodiment, the assembly 2004 includes two flow-through ports 2003 having tube connections on the top side (shown in FIG. 5A) and o-ring connections on the bottom side (shown in FIG. 5B). The flow-through ports 2003 can be used to facilitate installation or use of the assembly 2004 with a base station, for example, by allowing all pneumatic and fluidic connections to be made from the bottom of the assembly 2004, in which case the inlet line 54 may be pre-connected via tubing to one of the flow-through ports 2003 and the outlet line 57 may be pre-connected via tubing to the other flow-through port 2003.

Figure 22A:
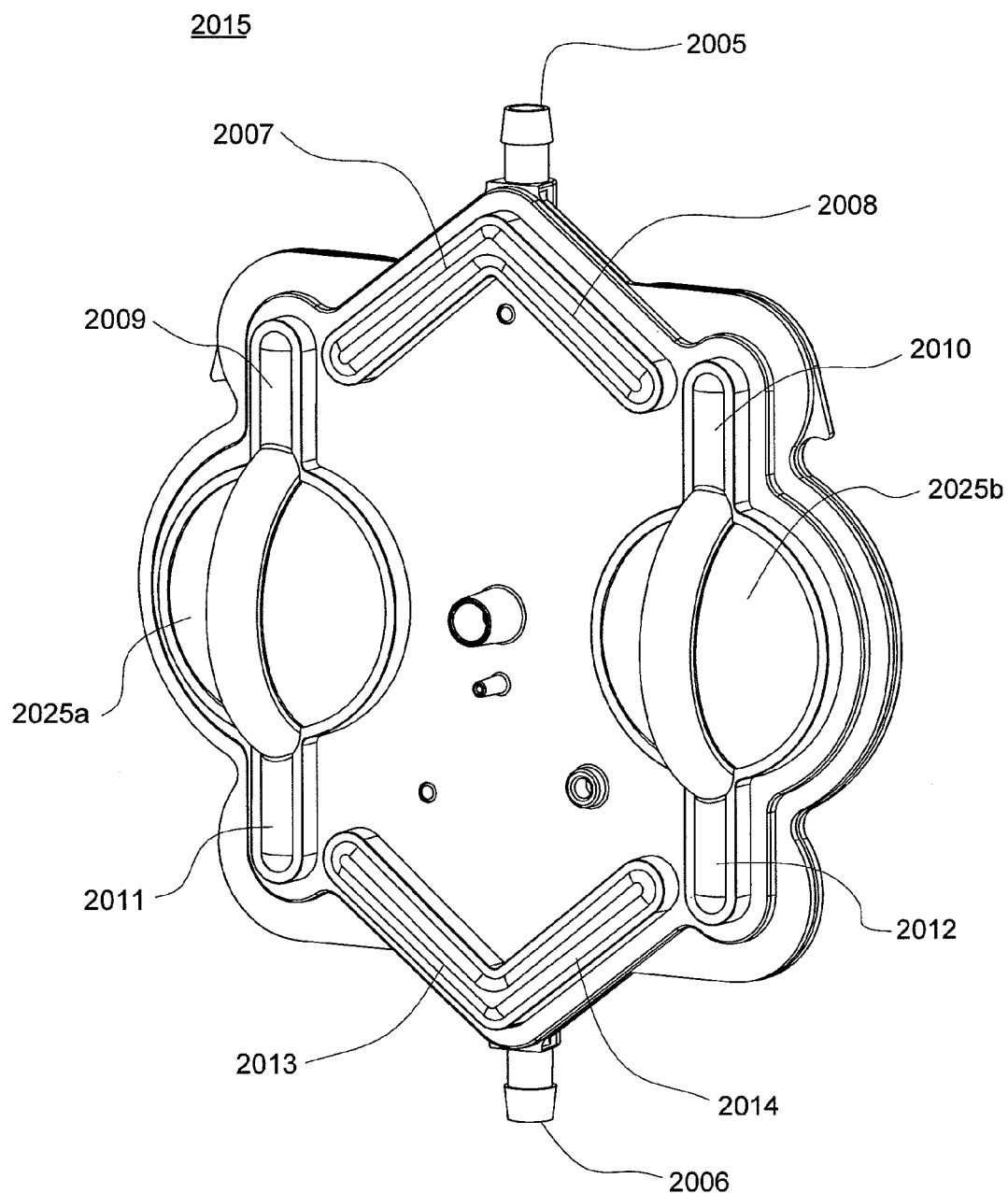
FIGS. 22A and 22B shows a pump cassette incorporating two pump pods of the type shown in FIG. 20 and a number of valves of the type shown in FIG. 21 along with various fluid paths and other components, in accordance with an exemplary embodiment of the present invention.
Figure 22B:
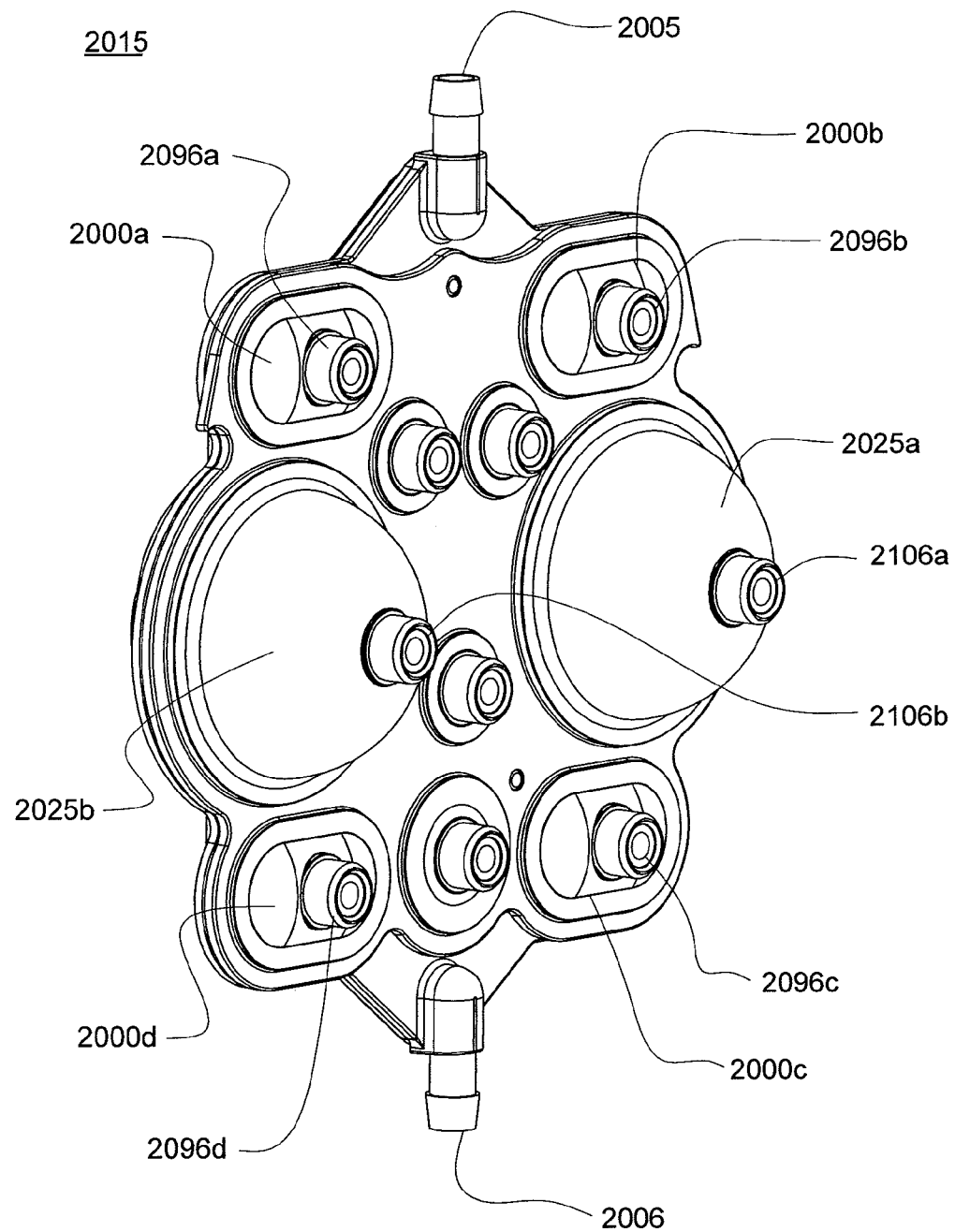

In the embodiment shown in FIGS. 22A and 22B, two pump pods 2025a and 2025b of the type shown in FIG. 20 and a number of valves 2000a-2000d of the type shown in FIG. 21 are incorporated in a pump cassette 2015 along with various fluid paths and other components. The pump cassette 2015 includes a common inlet 2005 in fluid communication with pump pod 2025a via fluid paths 2007 and 2009 and with pump pod 2025b via fluid paths 2008 and 2010. The pump cassette 2015 also includes a common outlet 2006 in fluid communication with pump pod 2025a via fluid paths 2011 and 2013 and with pump pod 2025b via fluid paths 2012 and 2014. Thus, pump pods 2025a and 2025b draw fluid from the common inlet 2005 and pump fluid to the common outlet 2006. That being said, valve 2000a is used to control fluid flow at the intersection of fluid paths 2008 and 2010 (i.e., at the inlet to pump pod 2025b); valve 2000b is used to control fluid flow at the intersection of fluid paths 2007 and 2009 (i.e., at the inlet to pump pod 2025a); valve 2000c is used to control fluid flow at the intersection of fluid paths 2011 and 2013 (i.e., at the outlet of pump pod 2025a); and valve 2000d is used to control fluid flow at the intersection of fluid paths 2012 and 2014 (i.e., at the outlet of pump pod 2025b). Each of the pump pods 2025a and 2025b has its own pneumatic interface 2106a and 2106b, respectively. Also, each of the valves 2000a-2000d has its own pneumatic interface 2096a-2096d, respectively. Thus, each of pump pods and each of the valves can be independently controlled by a base station.

Figure 23:
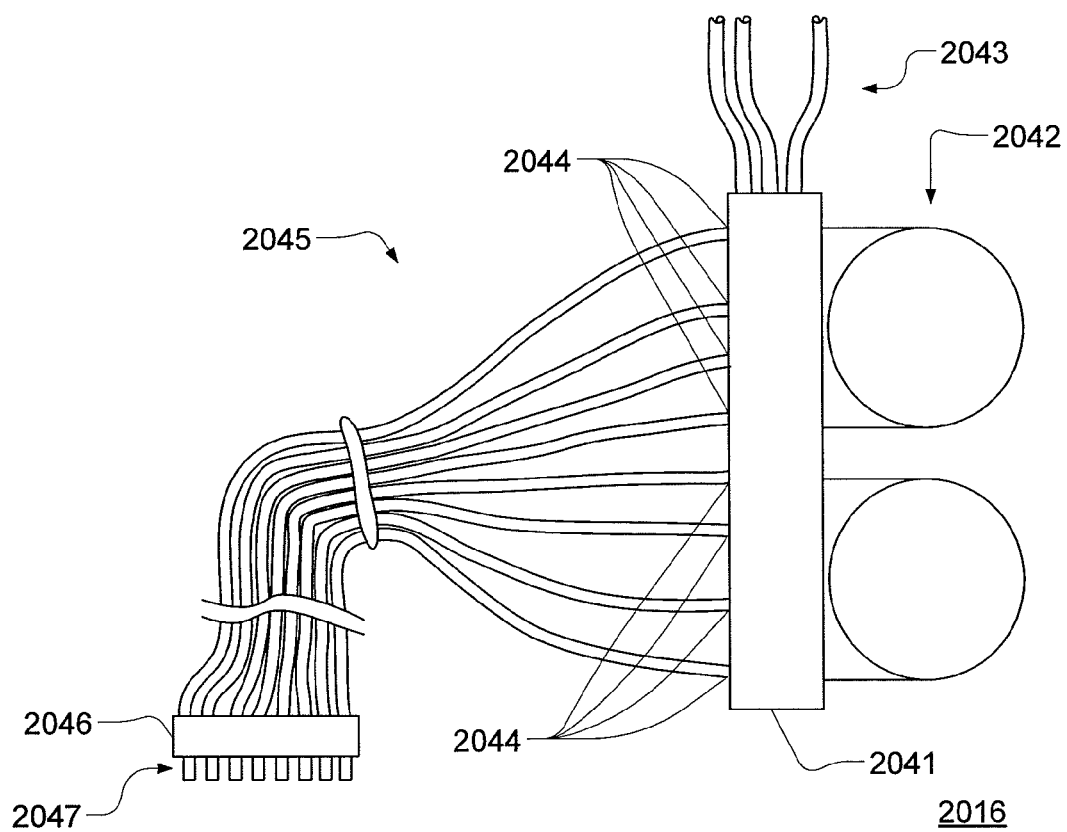
FIG. 23 is a schematic representation of dual-housing cassette arrangement according to one embodiment.

FIG. 23 is a schematic representation of dual-housing arrangement 2016 according to another embodiment of the invention. This arrangement may be advantageously used with disposable cassettes that include many pneumatically actuated pumps and/or valves. If the number of pneumatically actuated pumps and/or valves in a cassette is large enough, the cassette containing these pumps and valves can become so large—and the pressures involved can become so great—that it may become difficult to properly seal and position all of the pumps and valves. This difficulty may be alleviated by using two different housings. The valves and pumps (such as pump pods 2042) are placed in a main housing 2041, from which connecting tubes 2045 lead from pneumatic ports 2044. The main housing 2041 also has inlet and outlet tubes 2043, which allow liquid to flow into and out of the main housing. The connecting tubes 2045 provide pneumatic communication between valves and pumps in the main housing 2041 and a smaller, secondary tube-support housing 2046, which is provided with a pneumatic interface 2047 for each of the tubes. The proper positioning and sealing of all the pneumatic interfaces 2047 against receptacles in the base unit can be accomplished more easily with the smaller tube-support housing 2046 than it would be if the pneumatic actuation was applied to the larger main housing directly.

1.6. Alternative Chamber Configurations and Stroke Sizes

It should be noted that pump pods of the types described above can be configured with different chamber configurations and/or different stroke sizes. Thus, for example, pump pods having different pump volumes may be provided. Furthermore, pump pods having different pump volumes may be provided with a standardized pneumatic port configuration (and perhaps standardized actuation chamber wall configuration) so that pump pods having different volumes may be easily swapped into and out of a common pumping system or apparatus (e.g., a base unit) having a corresponding standardized pneumatic port interface. For example, the base unit may be able to receive lower-volume pump pods for pediatric use and receive higher-volume pump pods for adult use. The pneumatic ports are preferably adapted to be quickly and easily connected to—and disconnected from—the pneumatic actuation system of the base unit. In certain embodiments, the pump pods may be considered to be disposable and may be provided individually or as part of a larger disposable system.

Thus, for example, in the embodiments shown in FIGS. 2 and 48, disposable systems (specifically for use in a heat-exchange system, as discussed more fully below) include two self-contained pump pods 25a and 25b. Different versions of such disposable systems having pump pods of different pump volumes could be provided for different applications (e.g., one version with smaller pump volumes for children, another version with larger pump volumes for adults). Similarly, in the embodiment shown in FIGS. 5A and 5B, different versions of the assembly 2004 having pump pods of different pump volumes could be provided, and in the embodiment shown in FIGS. 22A and 22B, different versions of the cassette 2015 having pump pods of different pump volumes could be provided. Similarly, in the embodiment shown in FIG. 23, different versions of the main housing 2041 having pump pods of different pump volumes could be provided for use with a common secondary tube-support housing 2046.

It should be noted that the pumping chamber wall may be molded, formed, produced, or otherwise configured with various features facilitate intake, circulation, and/or delivery of the fluid. For example, the inside wall of the pumping chamber may include certain features or materials to help induce circulatory flow, induce smooth/laminar flow, reduce boundary layer effects, or even produce turbulence (e.g., to facilitate mixing of materials or prevent coagulation within the pumping chamber).

1.7. Exemplary Diaphragm Configurations

Figure 46A:
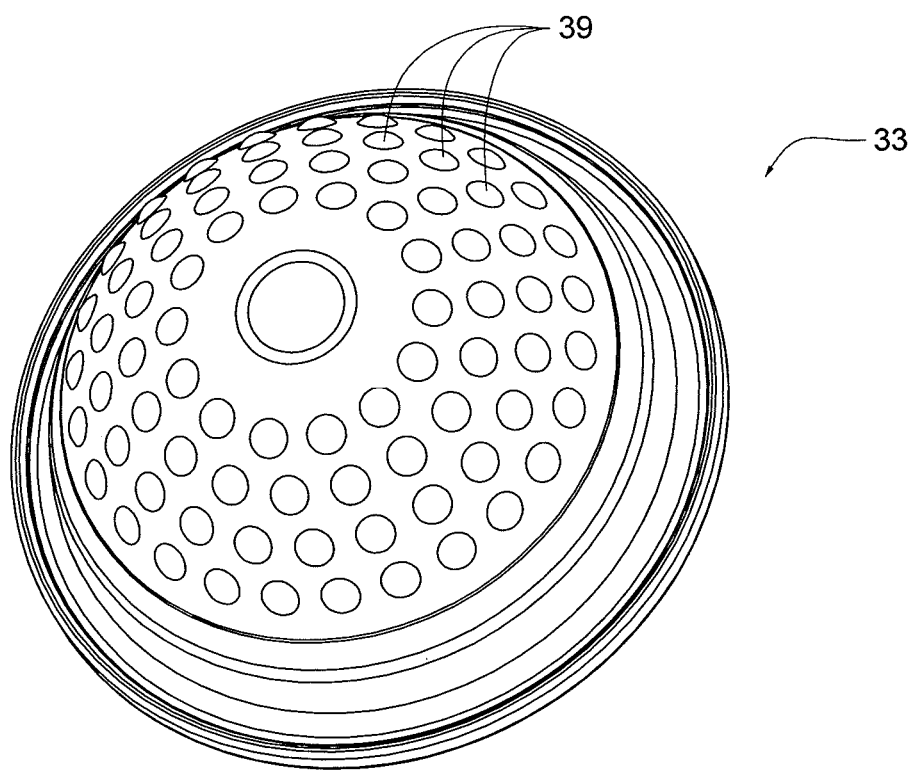
FIGS. 46A and 46B respectively show upper and lower perspective views of a flexible membrane having a configuration of raised bumps, such as may be used in pump pods such as the in the pump pod of FIG. 4, in accordance with an exemplary embodiment of the present invention.
Figure 46B:
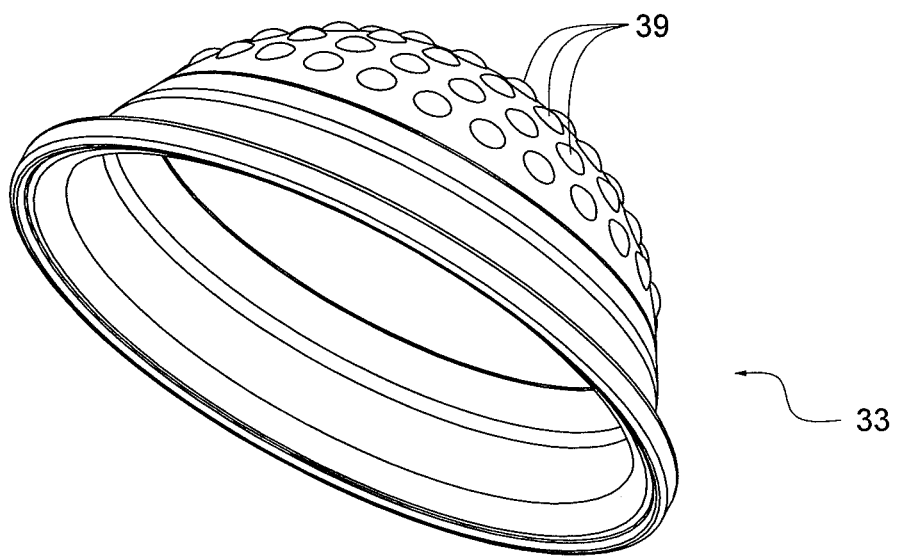

In certain embodiments, the pump pod diaphragm may be provided with small raised bumps, grooves, or other structures, particularly on the side of the membrane facing the pumping chamber. FIGS. 46A and 46B show an exemplary membrane 33 having raised bumps 39, in accordance with an exemplary embodiment of the present invention. Such raised bumps 39 or other raised structures prevent pockets of fluid from being caught away from the inlet and outlet, specifically by keeping the membrane spaced away from the rigid pumping chamber wall even when the pumping chamber volume is at a minimum. This spacing keeps flow passages open for blood to flow from the periphery of the pumping chamber to the outlets. In the exemplary embodiment shown in FIGS. 46A and 46B, the bumps 39 are located on a portion of the membrane spaced away from the edge of the membrane such that the membrane lacks bumps in the area near the edge of the membrane. Generally speaking, such a configuration allows the portion of the membrane around the edge to contact the pumping chamber wall, which tends to force fluid from the edge toward the outlet.

In addition to, or in lieu of, bumps or other raised structures on the membrane, the pump chamber wall may include spacers or conduits to allow for fluid flow as the pumping chamber approaches and reaches its minimum volume.

The membrane may be made from any of a wide variety of flexible materials, but is preferably made of a high-elongation silicone or similar material in order to maintain smooth pumping of the membrane and to reduce the tendency of membrane to "snap hard" into its minimum-pumping-chamber-volume position. By reducing hard snapping, sharp localized spikes of force on the fluid are reduced. Such hard snapping could cause disruptions in the fluid rotation in the chamber and could result in excessive shear forces and turbulence, which, the case of blood pumping, could cause hemolysis, and in the case of surfactant pumping, could result in foaming. Alternatively, the membrane may be made of a variety of thermoplastic elastomers or rubbers. Also, the membrane may be provided with dimples or grooves to make the membrane more flexible.

It should be noted that the membrane may be molded, formed, produced, or otherwise configured so as to bias reciprocation of the membrane in a predetermined pattern or manner. For example, the membrane may be formed with portions of having different thickness or stiffness so that certain portions move more freely than others (e.g., a portion of the membrane proximate to the pump inlet may be configured to be more flexible than a portion of the membrane proximate to the pump outlet so that the inlet side of membrane retreats more quickly during the draw stroke and collapses more quickly during the delivery stroke, which could facilitate filling and emptying of the pumping chamber in some embodiments).

2. EXEMPLARY PUMP CONTROL SYSTEMS

2.1. Pressure Actuation System

Figure 4:
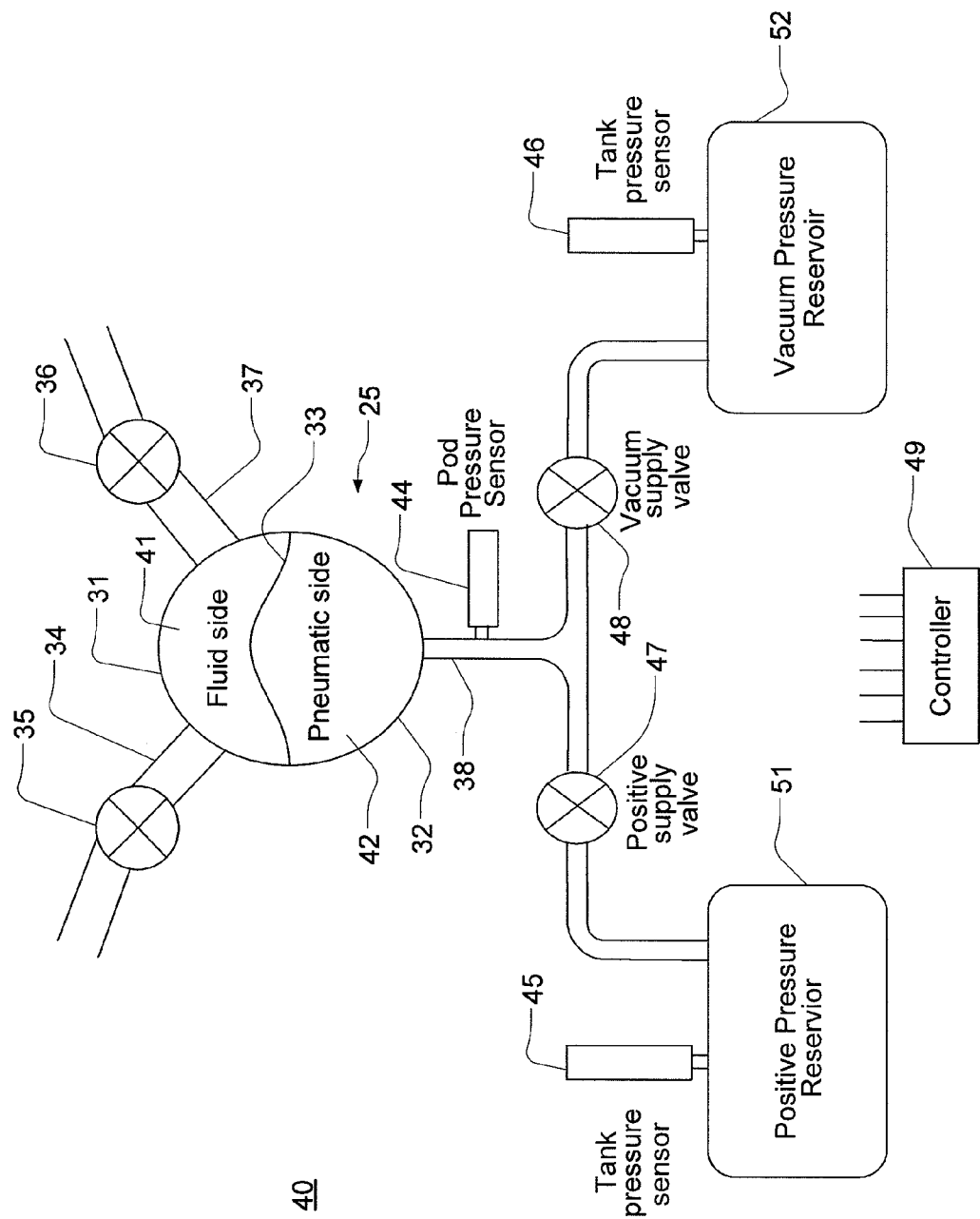
FIG. 4 is a schematic showing a pressure actuation system that may be used to actuate the pump pod shown in FIG. 3.

FIG. 4 is a schematic showing an embodiment of a pressure actuation system 40 that may be used to actuate a pump pod, such as the pump pod 25 shown in FIG. 3, in accordance with an exemplary embodiment of the present invention. The pressure actuation system 40 is capable of intermittently or alternately providing positive and negative pressurizations to the gas in the actuation chamber 42 of the pump pod 25. The pump pod 25—including the flexible membrane 33, the inlet 34, the outlet 37, the pneumatic port 38, the pumping chamber 41, the actuation chamber 42, and possibly including an inlet check valve 35 and an outlet check valve 36 or other valves—may be part of a larger disposable system. The pneumatic actuation system 40—including an actuation-chamber pressure transducer 44, a positive-supply valve 47, a negative-supply valve 48, a positive-pressure gas reservoir 51, a negative-pressure gas reservoir 52, a positive-pressure-reservoir pressure transducer 45, a negative-pressure-reservoir pressure transducer 46, as well as an electronic controller 49 including a user interface console (such as a touch-panel screen)—may be part of a base unit.

The positive-pressure reservoir 51 provides to the actuation chamber 42 the positive pressurization of a control gas to urge the membrane 33 towards a position where the pumping chamber 41 is at its minimum volume (i.e., the position where the membrane is against the rigid pumping-chamber wall 31). The negative-pressure reservoir 52 provides to the actuation chamber 42 the negative pressurization of the control gas to urge the membrane 33 in the opposite direction, towards a position where the pumping chamber 41 is at its maximum volume (i.e., the position where the membrane is against the rigid actuation-chamber wall 32).

A valving mechanism is used to control fluid communication between each of these reservoirs 51, 52 and the actuation chamber 42. In FIG. 4, a separate valve is used for each of the reservoirs; a positive-supply valve 47 controls fluid communication between the positive-pressure reservoir 51 and the actuation chamber 42, and a negative-supply valve 48 controls fluid communication between the negative-pressure reservoir 52 and the actuation chamber 42. These two valves 47, 48 are controlled by the controller 49. Alternatively, a single three-way valve may be used in lieu of the two separate valves 47, 48. The valves 47, 48 may be binary on-off valves or variable-restriction valves.

The controller 49 also receives pressure information from the three pressure transducers shown in FIG. 4: an actuation-chamber pressure transducer 44, a positive-pressure-reservoir pressure transducer 45, and a negative-pressure-reservoir pressure transducer 46. As their names suggest, these transducers respectively measure the pressure in the actuation chamber 42, the positive-pressure reservoir 51, and the negative-pressure reservoir 52. The actuation-chamber-pressure transducer is located in the base unit but is in fluid communication with the actuation chamber 42 through the pump pod's pneumatic port 38. The controller 49 monitors the pressure in the two reservoirs 51, 52 to ensure they are properly pressurized (either positively or negatively). In one exemplary embodiment, the positive-pressure reservoir 51 may be maintained at around 750 mmHG, while the negative-pressure reservoir 52 may be maintained at around −450 mmHG.

A compressor-type pump or pumps (not shown) may be used to maintain the desired pressures in these reservoirs 51, 52. For example, two independent compressors may be used to respectively service the reservoirs 51, 52. Pressure in the reservoirs 51, 52 may be managed using a simple bang-bang control technique in which the compressor servicing the positive-pressure reservoir 51 is turned on if the pressure in the reservoir 51 falls below a predetermined threshold and the compressor servicing the negative-pressure reservoir 52 is turned on if the pressure in the reservoir 52 is above a predetermined threshold. The amount of hysteresis may be the same for both reservoirs or may be different. Tighter control of the pressure in the reservoirs can be achieved by reducing the size of the hysteresis band, although this will generally result in higher cycling frequencies of the compressors. If very tight control of the reservoir pressures is required or otherwise desirable for a particular application, the bang-bang technique could be replaced with a PID control technique and could use PWM signals on the compressors.

The pressure provided by the positive-pressure reservoir 51 is preferably strong enough—under normal conditions—to urge the membrane 33 all the way against the rigid pumping-chamber wall 31. Similarly, the negative pressure (i.e., the vacuum) provided by the negative-pressure reservoir 52 is preferably strong enough—under normal conditions—to urge the membrane all the way against the actuation-chamber wall 32. In a further preferred embodiment, however, these positive and negative pressures provided by the reservoirs 51, 52 are within safe enough limits that even with either the positive-supply valve 47 or the negative-supply valve 48 open all the way, the positive or negative pressure applied against the membrane 33 is not so strong as to damage the pump pod or create unsafe fluid pressures (e.g., that may harm a patient receiving pumped blood or other fluid).

It will be appreciated that other types of actuation systems may be used to move the membrane back and forth instead of the two-reservoir pneumatic actuation system shown in FIG. 4, although a two-reservoir pneumatic actuation system is generally preferred. For example, alternative pneumatic actuation systems may include either a single positive-pressure reservoir or a single negative-pressure reservoir along with a single supply valve and a single tank pressure sensor, particularly in combination with a resilient diaphragm. Such pneumatic actuation systems may intermittently provide either a positive gas pressure or a negative gas pressure to the actuation chamber of the pump pod. In embodiments having a single positive-pressure reservoir, the pump may be operated by intermittently providing positive gas pressure to the actuation chamber, causing the diaphragm to move toward the pumping chamber wall and expel the contents of the pumping chamber, and releasing the gas pressure, causing the diaphragm to return to its relaxed position and draw fluid into the pumping chamber. In embodiments having a single negative-pressure reservoir, the pump may be operated by intermittently providing negative gas pressure to the actuation chamber, causing the diaphragm to move toward the actuation chamber wall and draw fluid into the pumping chamber, and releasing the gas pressure, causing the diaphragm to return to its relaxed position and expel fluid from the pumping chamber.

2.2. Alternative Embodiments Using Active Inlet/Outlet Valves

As discussed above, active valves may be used instead of passive check valves at the pump pod inlet and output. Active valves would allow for greater control and flexibility (generally at the expense of added complexity and cost). Among other things, active valves would allow for reversal of fluid flow, which could be used, for example, to facilitate priming, air purging, and/or detection and mitigation of certain conditions (e.g., occlusion, blockage, leakage, line disconnect). With regard to detection of a line disconnect, a reversal of flow may cause air to be drawn into the pumping chamber through the outlet if the outlet line is disconnected. Such air flow could be detected using any of a variety of techniques, including the amount of work needed to move the pump diaphragm. If the line is safely connected, some amount of work would normally be necessary to reverse flow and draw fluid in through the outlet, whereas if the return line has been disconnected, much less work would generally be necessary to reverse flow, since the pump would be drawing air into the return line. If upon reversing flow, the controller detects an aberrant flow condition, the controller would preferably cause the system to stop pumping blood from the patient.

During normal pump operations, the active valves generally would be operated as follows. During a fill stroke, when fluid is drawn into the pumping chamber, the controller 49 would typically open the inlet valve and close the outlet valve so as to allow fluid to enter the pumping chamber through the inlet but prevent fluid from being drawn back in from the outlet. During a delivery stroke when fluid is pumped out of the pumping chamber (e.g., after the pumping chamber is full or at other appropriate times), the controller 49 would generally close the inlet valve and open the outlet valve so as to allow fluid to be pumped out of the outlet but prevent fluid from being pumped back through the inlet. Between strokes, the controller 49 may cause both the inlet valve and the outlet valve to be closed for some time interval.

It should be noted that for embodiments in which pneumatically actuated inlet and outlet valves (e.g., binary on-off valves either integral to the pump pod or external to the pump pod) are used in place of passive inlet and outlet check valves, such valves may be coupled to the positive and/or negative pressure reservoirs 51, 52 through appropriate supply valves actuated by the controller 49.

The use of active inlet and outlet valves can facilitate detection of air in the pumping chamber. For example, following a full draw stroke to bring the pumping chamber to its maximum volume, positive pressure can be applied to the actuation chamber and the rate at which the pressure in the actuation chamber (or the pumping chamber) increases can be monitored. If the pumping chamber is full of air, then the pressure should increase more gradually, as the air in the pumping chamber will allow the diaphragm to move more readily. If, however, the pumping chamber is full of liquid, then the pressure should increase more rapidly because the pump diaphragm will be held more firmly by the uncompressible liquid.

2.3. Pump Operation

During normal pumping operations, the controller 49 typically monitors the pressure information from the actuation-chamber-pressure transducer 44 and, based on this information, controls the valving mechanism (valves 47, 48) to urge the membrane 33 all the way to its minimum-pumping-chamber-volume position and then after this position is reached to pull the membrane 33 all the way back to its maximum-pumping-chamber-volume position. In this embodiment, volume may be measured by counting full strokes of fluid delivery (e.g., volume=number of full strokes×pumping chamber volume).

In typical embodiments of the invention, the controller may be able to detect the end of a stroke, i.e., when the membrane reaches one of the rigid pumping-chamber or actuation-chamber walls. Referring to FIG. 4, an expel stroke is started by opening positive-supply valve 47, thereby resulting in positive pressure being exerted against the membrane 33. Preferably, the positive-supply valve 47 is cycled on and off (dithered) to create a ripple in the actuation chamber's pressure as long as the membrane 33 is moving. When the membrane 33 reaches the pumping-chamber wall 31 the pressure ripple stops. The controller 49, receiving pressure information from actuation-chamber-pressure transducer 44, monitors this pressure ripple and detects the end of stroke when this pressure ripple stops.

When the controller 49 detects the end of the expel stroke, the controller closes positive-supply valve 47 and dithers the negative-supply valve 48, thereby causing a vacuum to be applied to the membrane 33. The same process followed in the expel stroke is repeated for the fill stroke. The controller determines the time to complete each stroke and uses that information to calculate flow rate. The flow rate information is then used to set the commands for pressure and valving for the next stroke.

The controller 49 sets the flow rate using a timed sequence of alternately applying positive pressure and vacuum to the membrane 33. A positive pressure will be applied for a determined time interval to achieve a desired delivery (i.e., expelling) flow rate. When this time interval has expired, a vacuum is applied to achieve a fill flow rate. This control of time intervals can be an open-loop system without feedback on flow rate; thus, there can be delays between the end of one stroke and the start of another. Such an open-loop time-based system may be used when closed-loop systems based on flow-rate will not operate properly, such as during priming when there is a mixture of liquid and air in the pump pods.

As mentioned above, a stroke is preferably effected by delivering a sequence of pressure pulses (forming a pressure ripple) to the membrane 33. The speed of a stroke can be adjusted by changing how frequently a supply valve is opened and/or by changing how long it is opened each time it is opened. A pressure pulse involves opening the valve between the actuation chamber and the reservoir for a fixed time and then closing it for the rest of the pulse period. The total length of a pressure pulse is 1/(pulse pumping frequency). In one embodiment, the pulse pumping frequency increases from 2 Hz to 16 Hz as the controller's pumping command increases from 0 to 100%. The minimum frequency of 2 Hz is intended to ensure a minimum flow rate is met when there is water in the system. A maximum frequency of 16 Hz is intended to correspond to the minimum time required for the valve to be at a 50% duty cycle. The pumping algorithm preferably divides a stroke into two periods, the initial pumping period and the end-of-stroke period. During the initial pumping period, the valve open time of the pressure pulse is preferably 166 ms (100% duty cycle at 16 Hz). Thus, with a maximum command from the controller, the valve to the reservoir is always open. The number of pressure pulses in the initial period is increased from one to ten as the pumping command increase from zero to 100%.

Figure 7:
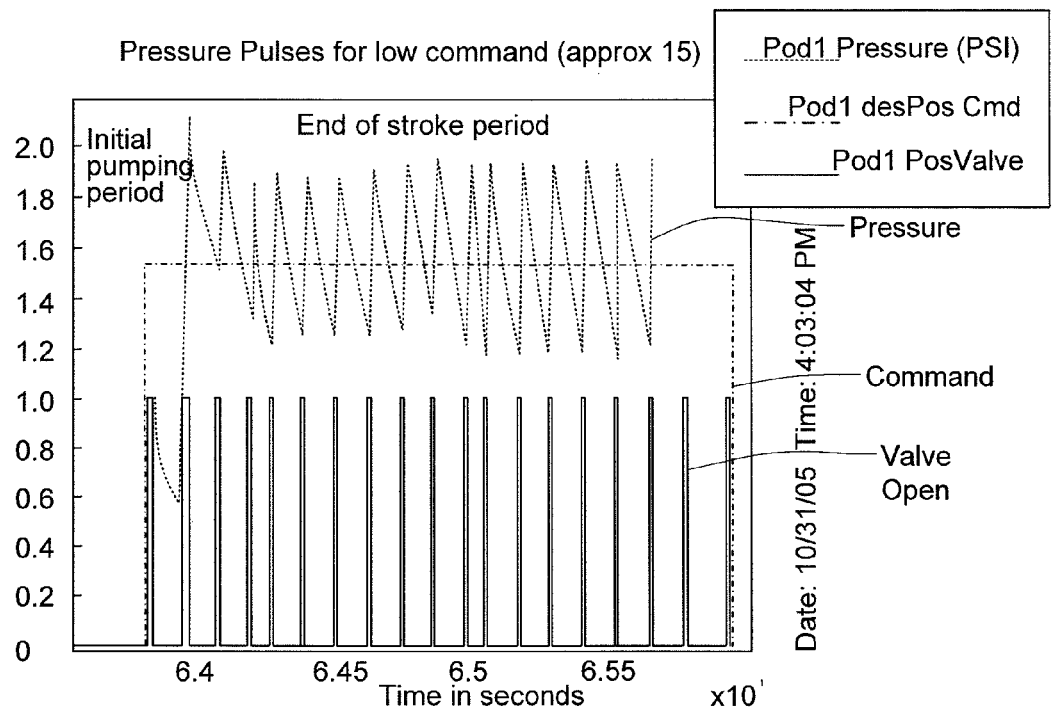
FIGS. 7 and 8 are graphs showing how pressure measurements can be used detect the end of a stroke, in one embodiment.
Figure 8:
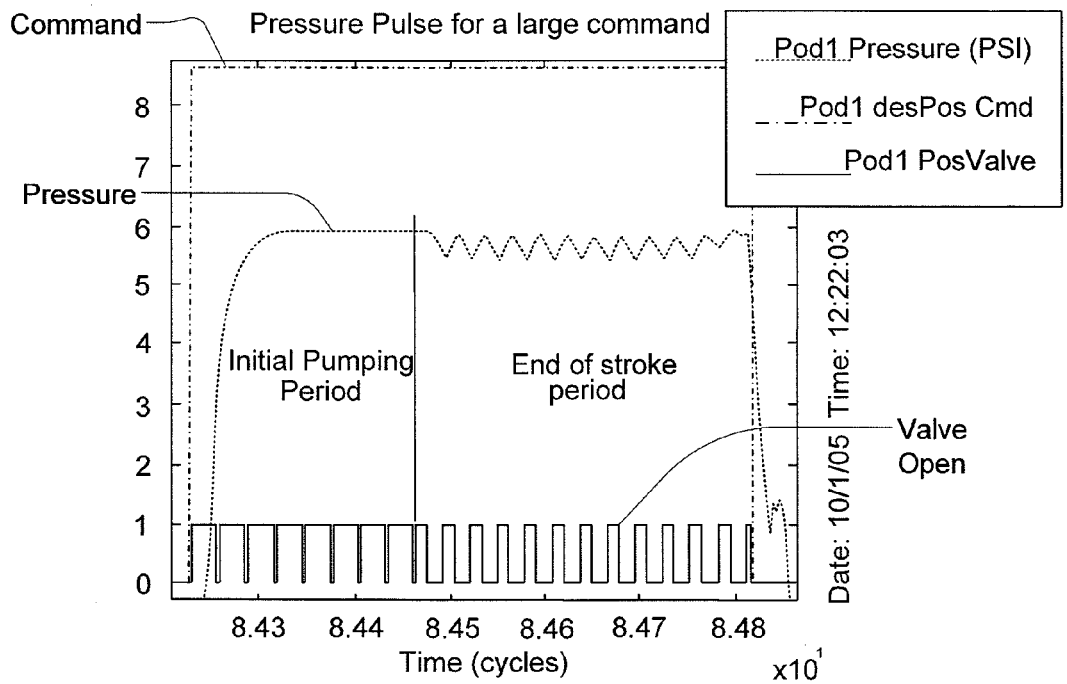

After the initial pumping period, there is a transition to the end-of-stroke pumping period. In this respect, software filters are preferably used to determine when a stroke ends, with at least five pressure pulses used in the end-of-stroke period for the end-of-stroke filters to initialize. The end-of-stroke period ends when the end of stroke is detected. During the end-of-stroke period, the valve open time of the pressure pulse is preferably 83.3 ms (50% duty cycle at 16 Hz). FIGS. 7 and 8 show the pressure pulses during the initial and end-of-stroke periods. FIG. 7 shows pressure pulses for a low-flow command by the controller, and FIG. 8 shows a pressure pulse for a large-flow command by the controller. Note that the on time for a pulse is much longer for higher commands.

The pressure pulses generate a ripple in the measured pressure in the actuation chamber while the membrane is moving. By filtering and isolating this pressure ripple, the end-of-stroke algorithm can detect when the diaphragm has reached the chamber wall and stopped moving. This end-of-stroke information may be used for flow calculations and for sequencing the pump pods for fill and expel strokes.

Figure 9:
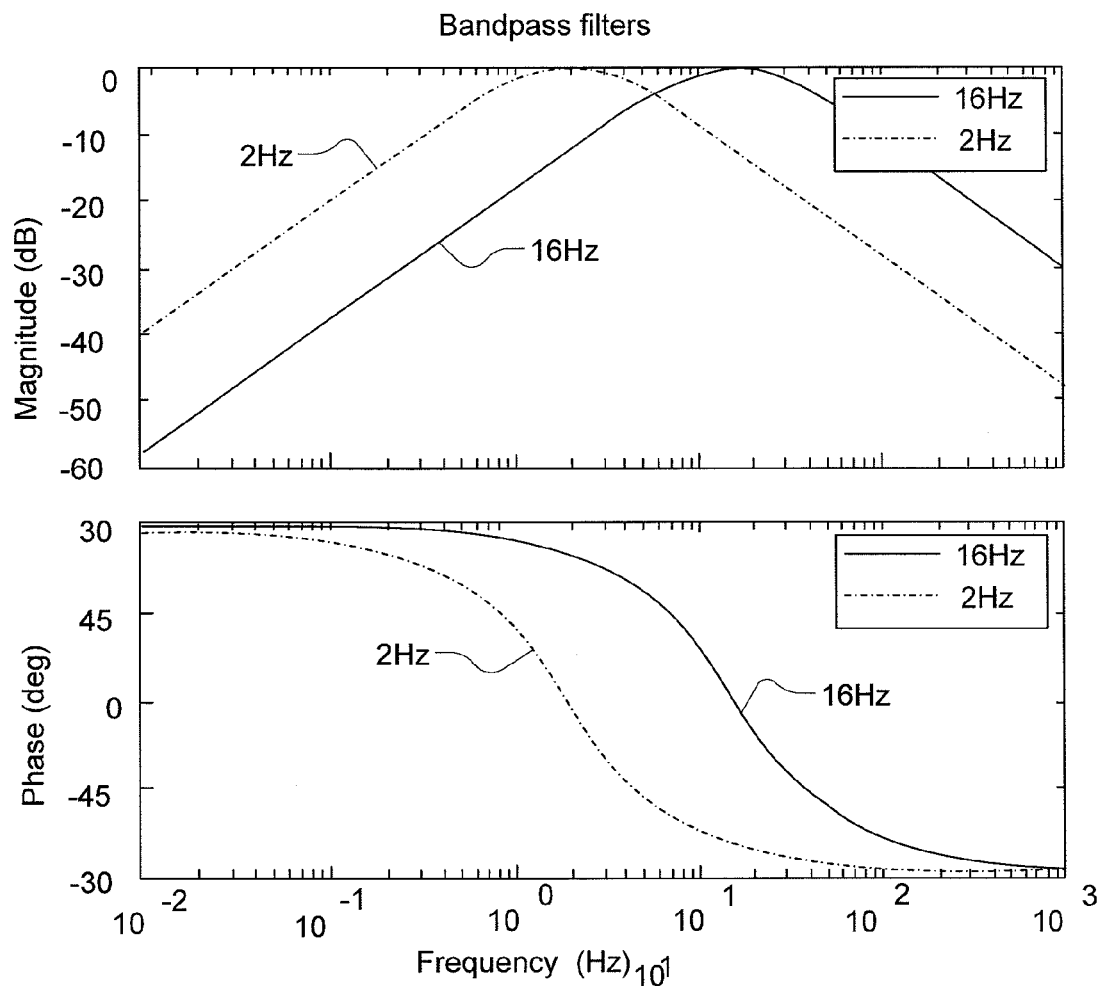
FIGS. 9 and 10 show how the pressure-measurement signals are filtered by the system's controller.

In the first stage of filtering, the pressure signal for each pump pod is passed through a band-pass filter. This filter is used to isolate the pulse-pumping frequency. As discussed above, the pulse-pumping frequency preferably increases from 2 Hz to 16 Hz as the pumping command increases from 0% to 100%. FIG. 9 shows the output of the band-pass filter.

Figure 10:
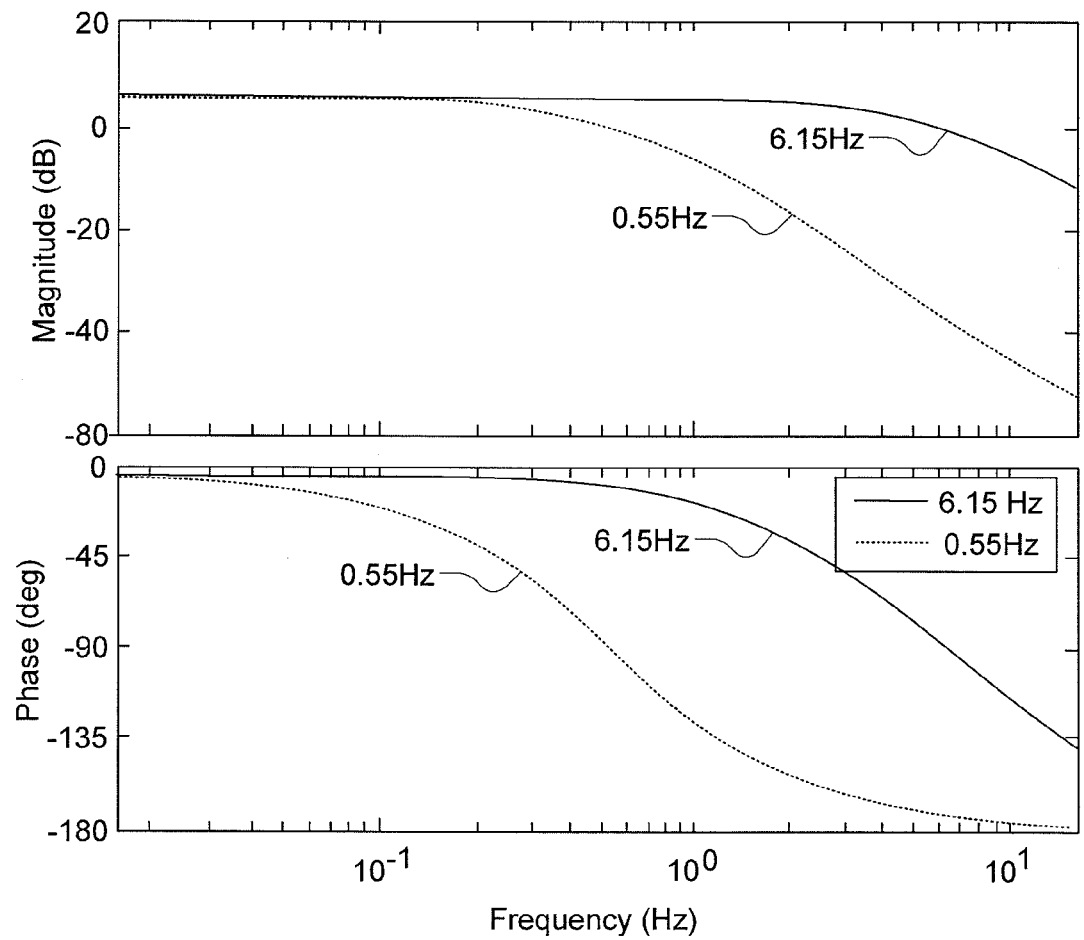

The absolute value of this filtered signal is then passed through a second-order low-pass filter with a damping ratio of one. The corner frequency of this filter is varied based on the pulse pumping frequency. FIG. 10 shows the output of this low-pass filter. The output from the low-pass filter is divided by the absolute value of the supply pressure to normalize the ripple value. This final value of the pressure ripple is then used to detect the end of stroke. Once in the end-of-stroke period, this ripple characteristically drops down to zero when the diaphragm is stopped by the chamber wall.

Figure 11:
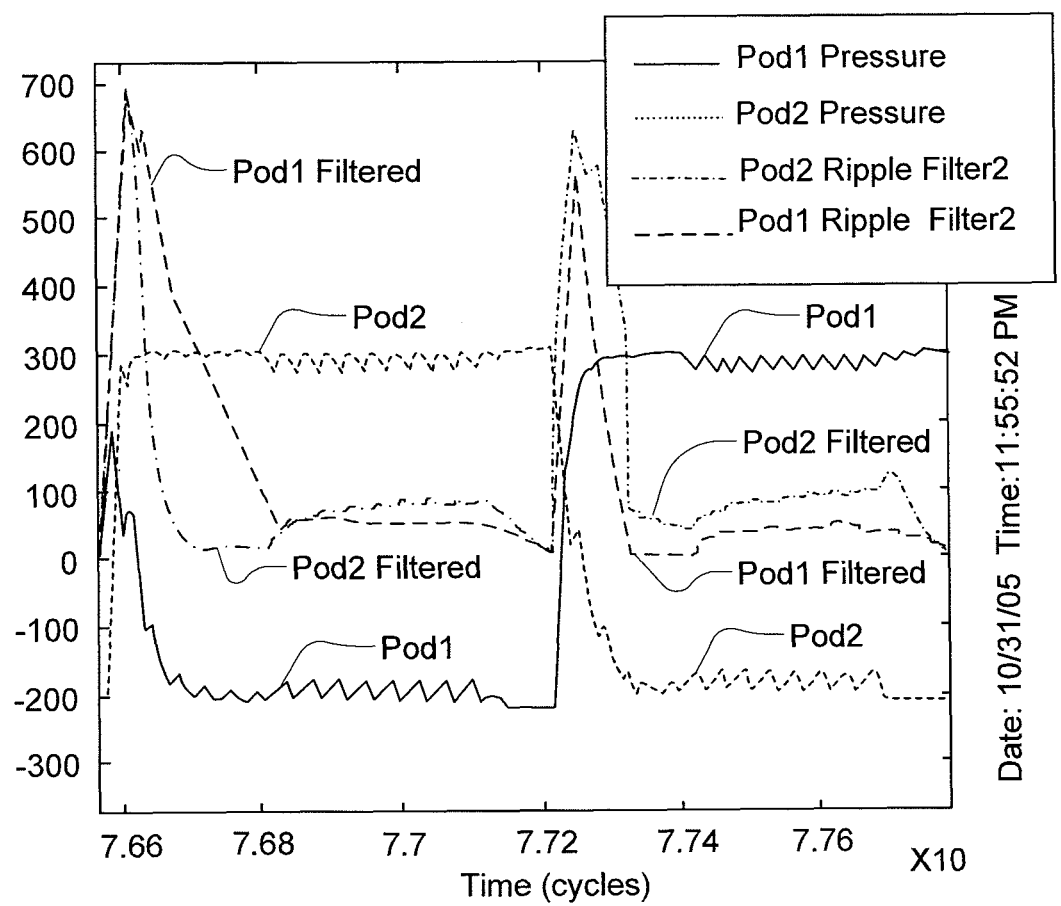
FIG. 11 is a graph showing pressure readings in each of the pump pods in the disposable unit, and the results of filtering these readings.

FIG. 11 is a graph showing pressure measurements in the actuation chambers of each of the pump pods in the disposable unit, and also showing the results of the filtering described above. It should be noted that the unfiltered pressure readings show that the two pump pods are out of phase, with one pump pod expelling liquid while the other is filling with liquid. As can be seen in the plots of filtered readings, these filtered readings drop to zero at the end of each stroke.

At the end of the stroke, the flow rate is calculated for a given pump pod and flow direction by dividing the chamber volume by the time for the stroke to complete. Once the expel stroke has ended, the variables for the stroke are reset, and this process repeats for the fill stroke.

Figure 12:
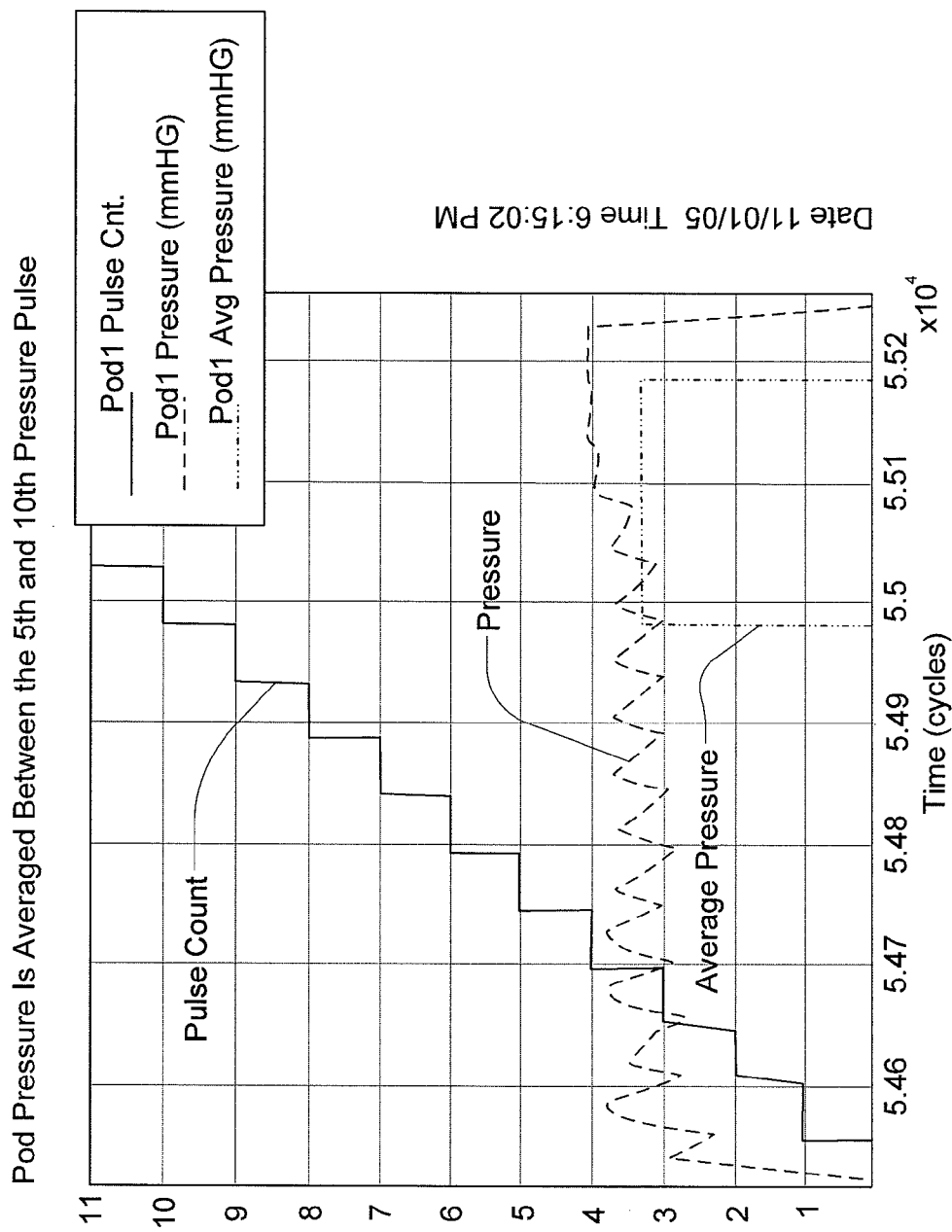
FIG. 12 is a graph showing how pressure measurements are used to determine average pressure.

The pressure ripple causes pressure readings to vary significantly for the duration of the stroke. Thus, an average pressure is calculated and logged. As shown in FIG. 12, the average pressure is preferably computed by integrating pressure between the fifth and tenth pulse. In this embodiment, the fifth and tenth pulses are chosen as the start and end of the average to ignore effects of the pressure when initiating the stroke and when the diaphragm hits the chamber wall.

To check whether any of the pressure transducers (the actuation-chamber-pressure transducer 44, the positive-reservoir-pressure transducer 45 or the negative-reservoir-pressure transducer 46) may be malfunctioning, the controller preferably compares pressure readings at the end of a stroke. Referring to FIG. 4, at the end of an expel stroke, while the positive-supply valve 47 is open, the pressure reading of the actuation-chamber-pressure transducer 44 is compared to the reading of the positive-reservoir-pressure transducer 45. Since at the end of the expel stroke the pressure readings from these two transducers should be the same, any difference in pressure readings from these two transducers indicates a malfunction in one of the two transducers. Similarly, at the end of a fill stroke, while the negative-supply valve 48 is open, the controller 49 preferably compares the pressure reading of the actuation-chamber-pressure transducer 44 to the reading of the negative-reservoir-pressure transducer 46. If the controller detects a significant change in these pressure readings, the controller generates an alarm signal indicating a malfunction in one of the transducers.

The controller can also detect aberrant flow conditions by integrating the pressure readings over time to obtain a measure of the work done in moving the liquid. If the amount of work done goes up or down, the controller preferably generates an alarm signal indicating that something has gone wrong in the line, such as an occlusion, a leak, or a disconnect. The ability to detect a disconnect or a leak may be important, particularly when pumping blood or other life-critical fluids, because of the relatively large flow rates of fluids being pumped. In one embodiment, by integrating the pressure readings and determining the work function, the controller can detect a line disconnect within approximately three seconds.

This calculation can also take into account the head height between the pod pumps and the patient, although this height may be assumed to be constant during a thermal-therapy procedure. This calculation can be represented as $$K_{fluidpath} \times m_{pod} = \int_{stroke} (P_{pod} - P_{height\_diff}) dt$$

where
$K_{fluidpath}$ is the resistance in the fluid path,
$m_{pod}$ is the mass of fluid contained in the pod,
$P_{pod}$ is the pressure in the pump pod, and
$P_{height\_diff}$ is the pressure due to head height between the pod and the patient.

Since both $K_{fluidpath}$ and $m_{pod}$ should be constant during a thermal therapy procedure, any variation in the integrated pressure should indicate a change in resistance in the fluid and/or a change in the amount of mass displaced during a stroke, and thus indicate an aberrant flow condition, such as an occlusion or a disconnect.

In one embodiment, the head height is not monitored during the procedure. The head height is calculated based on the first few pumps of the pod. Those first few pumps set the standard for the head height calculation, based on the following calculation $$P_{pod} = K_{fluidpath} m' + P_{height\_diff}$$

where m' is the mass flow rate.

In particular, since normally the flow rate is low in the first few strokes of the pod, m' may be assumed to be zero and the pressure in the pod equal to the head pressure; $P_{pod} = P_{height\_diff}$. Based on this calculation, the head height is presumed to be constant.

In one embodiment, the controller looks for a change in the integrated pressure between consecutive strokes or a change (with a smaller tolerance) over three strokes of the low-pass filtered value of the integrated pressure. If either of these changes is excessive, an error is declared and pumping is stopped until a medical technician intervenes. This detection algorithm is not run during priming due to the large variations in the integrated pressure signal that occur when there is a mixture of air and liquid in the pods.

Another method of detecting occlusions at low flow rates may be run in tandem with the pod-pressure-integration method. In this method, the controller looks for multiple consecutive short strokes of the exact same length. If such strokes are detected, the pod pump is probably not completing strokes due to an occlusion or a pneumatic problem. In one embodiment, if more than six short strokes occur on a given pod pump, an error signal is generated. During priming, this detection method is not used because fast, short strokes are common when the chambers are filled with air.

If the end of a stroke does not occur within a predetermined number of pressure pulses (e.g., 100 pressure pulses as discussed above in connection with FIGS. 7-12), the controller preferably generates an error signal. Excessive time to complete a stroke may indicate a pneumatic leak. Such a check can be run during priming as well as during the procedure.

2.4. Fluid Flow Management

Generally speaking, a single pump pod operates in a pulsatile fashion, first drawing in fluid and then pumping out fluid. Pulsatile operation may be necessary, desirable, or inherent in certain applications (e.g., extracorporeal blood treatment in which blood is drawn from a patient and returned to the patient through a single needle is inherently pulsatile, since blood generally cannot be drawn from the patient and pumped back into the patient at the same time through the single needle).

Figure 74A:
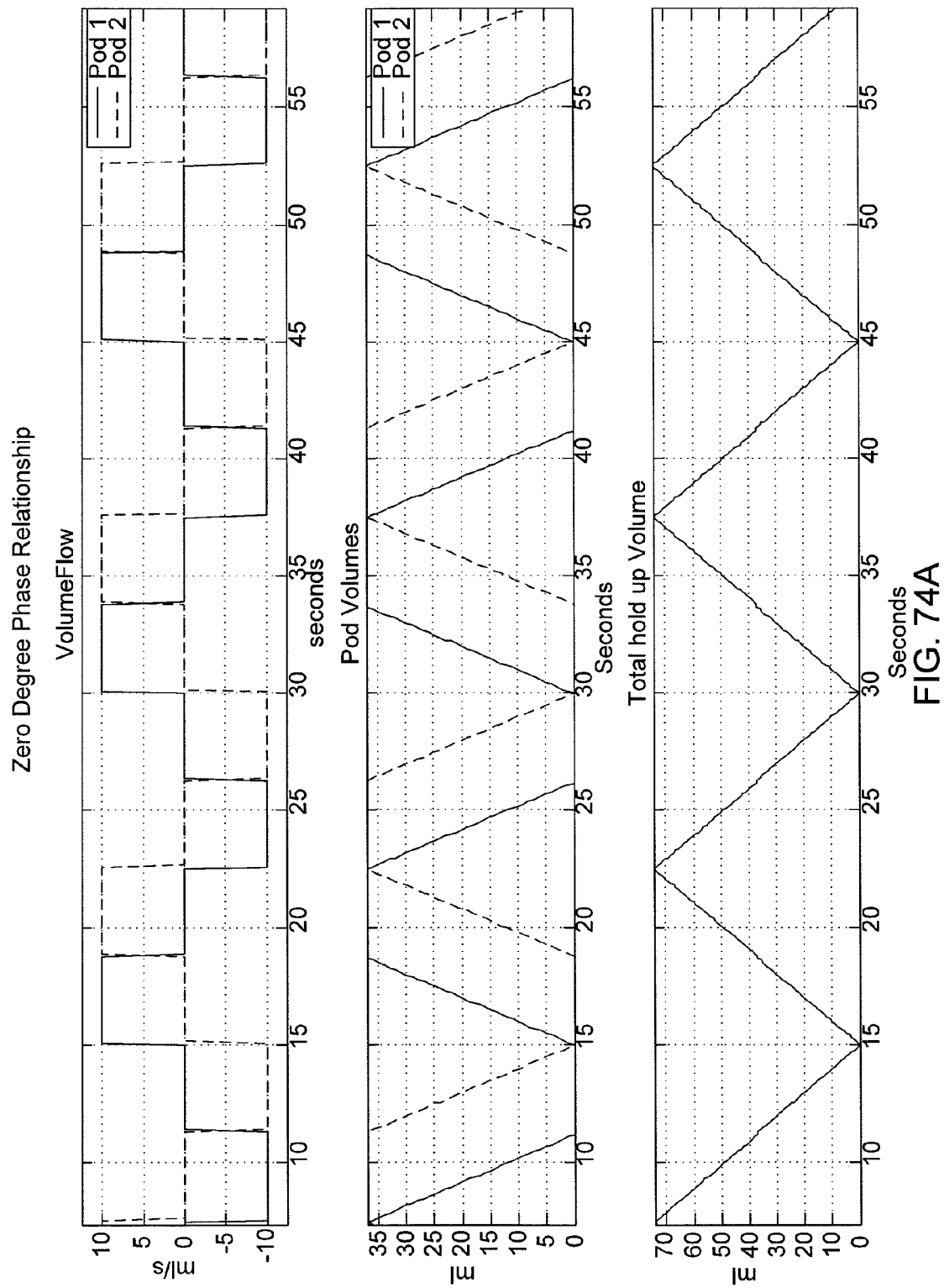
FIGS. 74A-74C show plots for volume flow, pod volumes, and total hold up flow for two pump pods operating in a zero degree phase relationship, a 180 degree phase relationship, and a 90 degree phase relationship, respectively, in accordance with exemplary embodiments of the present invention
Figure 74B:
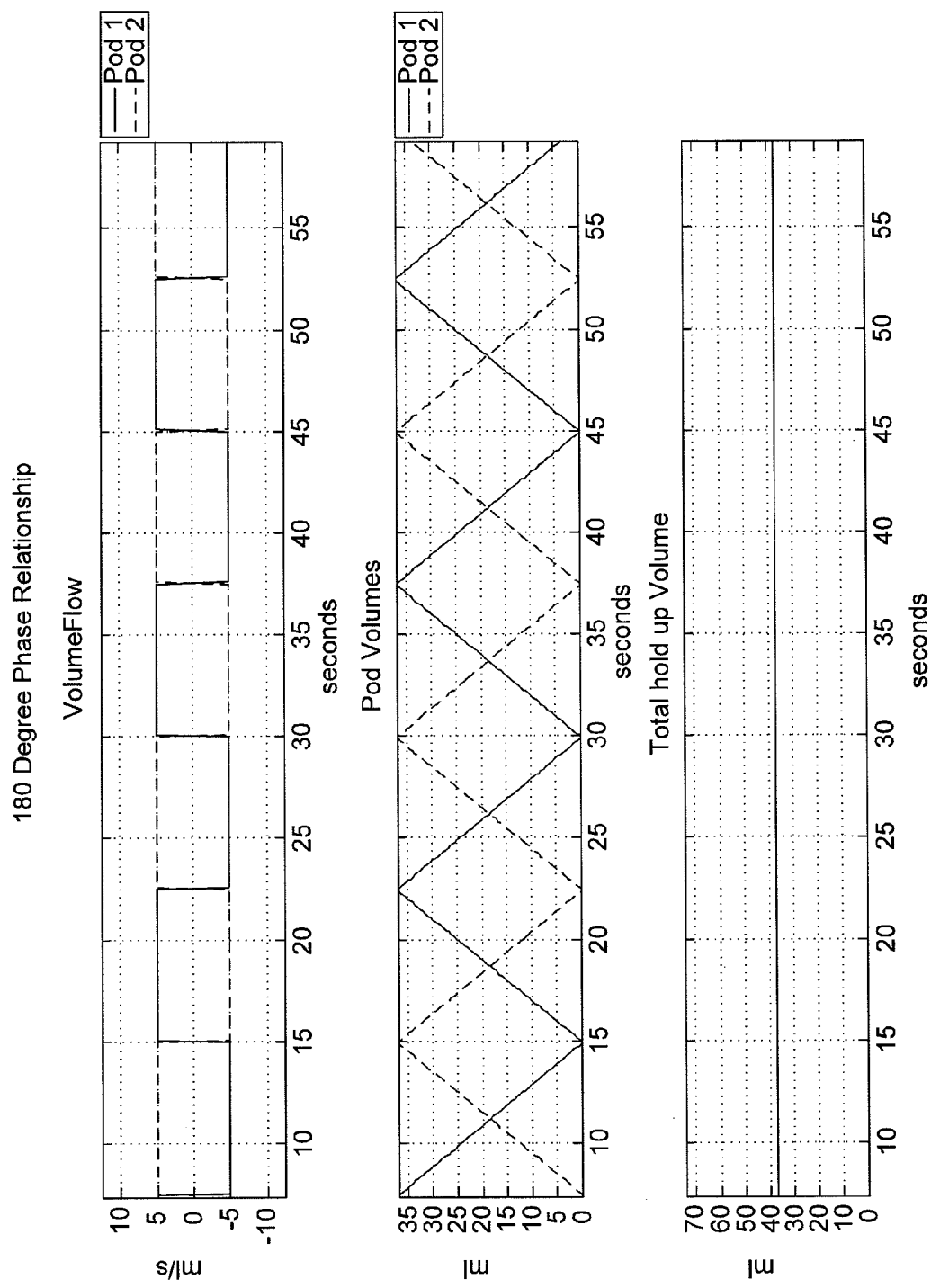
Figure 74C:
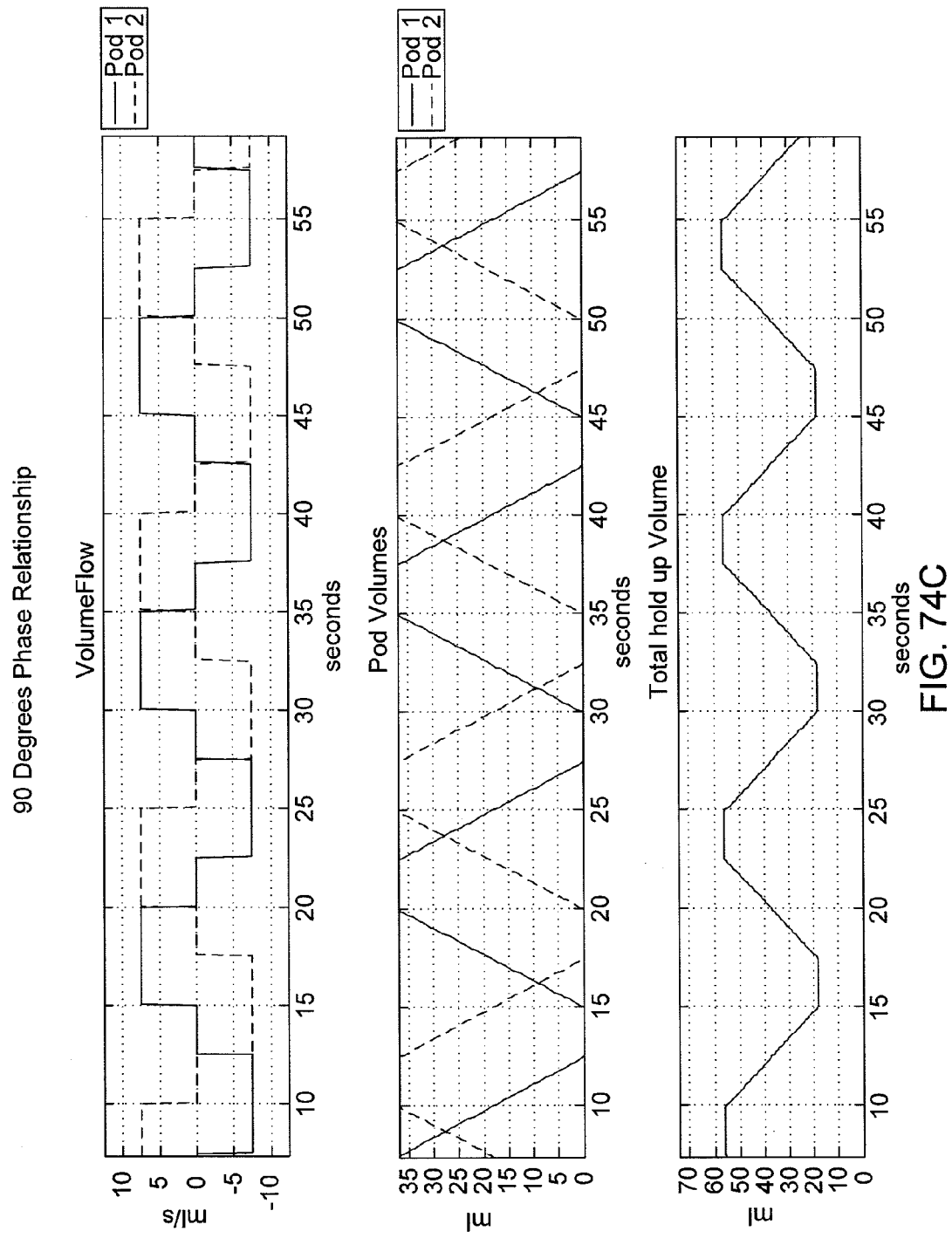

In a dual pump configuration, the two pump pods may be operated from a zero degree phase relationship (i.e., both pumping chambers act in the same direction) to a 180 degree phase relationship (i.e., the pumping chambers act in opposite directions). A zero degree phase relationship can be used to produce a substantially pulsatile fluid flow, similar to a single pump pod. A 180 degree phase relationship can be used to produce a substantially continuous fluid flow both toward the pumps and from the pumps. A 90 degree phase relationship can be used to produce a substantially sinusoidal fluid flow. FIGS. 74A-74C show plots for volume flow, pod volumes, and total hold up flow for a zero degree phase relationship, a 180 degree phase relationship, and a 90 degree phase relationship, respectively.

In some applications, it may be necessary or desirable to provide substantially continuous fluid flow to the pump pod(s) and/or from the pump pod(s). As discussed above, substantially continuous fluid flow may be provided using two pump pods operating with a 180 degree phase relationship. For one or more pump pods operating in a pulsatile mode (e.g., a single pump pod or two pump pods operating in a zero degree phase relationship), one way to produce a more continuous fluid flow output is to fill the pump pod(s) as quickly as possible and then pump out the fluid over an extended period of time (e.g., the desired deliver time could be set to be a total desired stroke time minus the time that the fill stroke took).

Even when operating two pump pods in a 180 degree phase relationship, it is possible for there to be discontinuous fluid flow under some conditions, particularly when the input impedance is significantly different than the output impedance. For example, in extracorporeal blood treatment applications, input impedance may be higher than output impedance due to such things as needle size (e.g., the needle used to draw blood from the patient may be smaller than the needle used to return blood to the patient), blood viscosity (e.g., the patient may have very viscous blood that is thinned as part of the treatment), or poor patient access (e.g., poor patient circulation may limit the rate at which blood can be drawn). Such impedance differences can result in different pump pod fill and delivery times, particularly if the system cannot be balanced by applying more pressure to one pump pod than the other pump pod (in theory, it should be possible to ensure a precise 180 degree phase relationship if there were no limit on the amount of pneumatic pressure that could be applied to the pump pods, but there are typically both physical limits—the maximum pressures in the two reservoirs—and practical limits to the amount of pressure that can be applied). Therefore, in some situations, the stroke of one pump pod might finish before the corresponding stroke of the other pump pod, in which case it may be necessary to delay the former pump pod while the latter pump pod completes its stroke, resulting in a pause in the fluid flow produced by the former pump pod. One possible solution is to limit the flow rate to the slowest of the fill and deliver strokes. Although this would result in slower blood delivery flow rates, the flow rate would still be known and would be continuous.

2.5. Alternative Embodiment Using Variable-Restriction Pneumatic Valves

As noted above, the positive-supply valve 47 and the negative-supply valve 48 in the pneumatic actuation system 40 of FIG. 4 may be variable-restriction valves, as opposed to binary on-off valves. By using variable valves, the pressure applied to the actuation chamber 42 and the membrane 33 can be more easily controlled to be just a fraction of the pressure in reservoirs 51, 52, instead of applying the full reservoir pressure to the membrane. This facilitates use of the same reservoir or set of reservoirs for pump pods having different operating parameters, such as pump volume, pump stroke size, or pump actuation pressure. Of course, the reservoir pressure generally needs to be greater than the desired pressures to be applied to various pump pod's membranes, but one pump pod may be operated at, say, half of the reservoir pressure, and another pump pod may be actuated with the same reservoir but at, say, a quarter of the reservoir pressure. Thus, even though different pump pods may be designed to operate at different pressures, these pump pods may all share the same reservoir or set of reservoirs but still be actuated at different pressures, through the use of variable valves. The pressures used in a pump pod may be changed to address conditions that may arise or change during pumping. For example, if flow through the system's tubing becomes constricted because the tubes get twisted, one or both of the positive or negative pressures used in the pump pod may be increased in order to compensate for the increased restriction.

Figure 28:
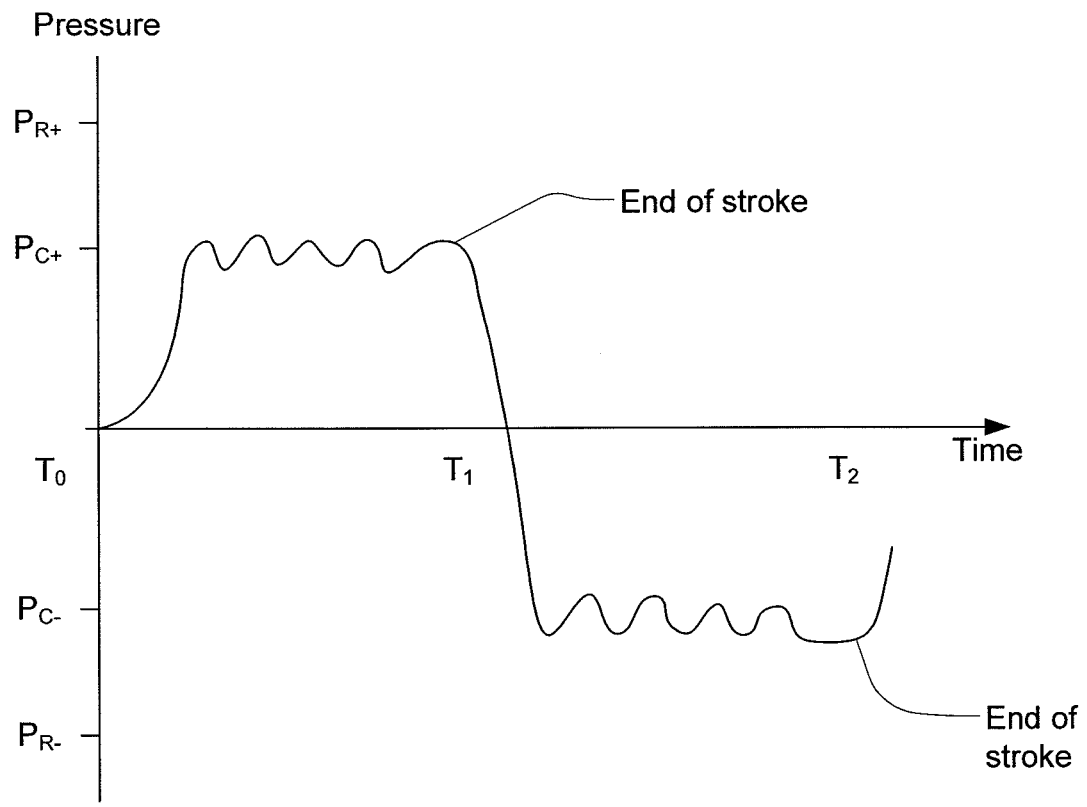
FIG. 28 is a graph showing how pressures applied to a pod pump may be controlled in order to facilitate end-of-stroke detection, in accordance with an exemplary embodiment of the present invention.

FIG. 28 is a graph showing how pressures applied to a pod pump may be controlled using variable valves. The vertical axis represents pressure with $P_{R+}$ and $P_{R-}$ representing respectively the pressures in the positive and negative reservoirs (items 51 and 52 in FIG. 4), and $P_{C+}$ and $P_{C-}$ representing respectively the positive and negative control pressures acting on the pump pod's membrane. As can be seen in FIG. 28, from time $T_0$ to about time $T_1$, a positive pressure is applied to the actuation chamber (so as to force fluid out of the pumping chamber). By repeatedly reducing and increasing the flow restriction caused by the positive variable valve (item 47 in FIG. 4), the pressure being applied to the actuation chamber can be held at about the desired positive control pressure, $P_{C+}$. The pressure varies, in a sinusoidal manner, around the desired control pressure. An actuation-chamber pressure transducer (item 44 in FIG. 4) in communication with the actuation chamber measures the pressure in the actuation chamber and passes the pressure-measurement information to the controller (item 49 in FIG. 4), which in turn controls the variable valve so as to cause the actuation chamber's pressure to vary around the desired control pressure, $P_{C+}$. If there are no fault conditions, the membrane is pushed against a rigid wall of the pumping chamber, thereby ending the stroke. The controller determines that the end of stroke has been reached when the pressure measured in the actuation chamber no longer drops off even though the restriction created by the variable valve is reduced. In FIG. 28, the end of the expelling stroke occurs around time $T_1$. When the end of stroke is sensed, the controller causes the variable valve to close completely so that the actuation chamber's pressure does not increase much beyond the desired control pressure, $P_{C+}$.

After the positive variable valve is closed, the negative variable valve (item 48 in FIG. 4) is partially opened to allow the negative pressure reservoir to draw gas from the actuation chamber, and thus draw fluid into the pumping chamber. As can be seen in FIG. 28, from a time shortly after $T_1$ to about time $T_2$, a negative pressure is applied to the actuation chamber). As with the expelling (positive pressure), stroke described above, repeatedly reducing and increasing the flow restriction caused by the negative variable valve can cause the pressure being applied to the actuation chamber can be held at about the desired negative control pressure, $P_{C-}$ (which is weaker than the pressure in the negative pressure reservoir). The pressure varies, in a sinusoidal manner, around the desired control pressure. The actuation-chamber pressure transducer passes pressure-measurement information to the controller, which in turn controls the variable valve so as to cause the actuation chamber's pressure to vary around the desired control pressure, $P_{C-}$. If there are no fault conditions, the membrane is pulled against a rigid wall of the actuation chamber, thereby ending the draw (negative pressure) stroke.

As described above, the controller determines that the end of stroke has been reached when the partial vacuum measured in the actuation chamber no longer drops off even though the restriction created by the variable valve is reduced. In FIG. 28, the end of the draw stroke occurs around time $T_2$. When the end of stroke is sensed, the controller causes the variable valve to close completely so that the actuation chamber's vacuum does not increase much beyond the desired negative control pressure, $P_{C-}$. Once the draw stroke has ended, the positive variable valve can be partially opened to begin a new expelling stroke with positive pressure.

Thus, two variable-orifice valves may be used to throttle the flow from the positive-pressure source and into the negative-pressure. The pressure in the actuation chamber is monitored and a controller uses this pressure measurement to determine the appropriate commands to both valves to achieve the desired pressure in the actuation chamber. Two advantages of this arrangement are that the filling and delivering pressure may be precisely controlled to achieve a desired flow rate while respecting pressure limits, and that the pressure may be varied with a small sinusoidal signature command. This signature may be monitored to determine when the pump reaches the end of a stroke.

Another advantage of using variable valves in this way, instead of binary valves, is that by only partially opening and closing the variable valves the valves are subject to less wear and tear. The repeated "banging" of binary valves all the way opened and all the way closed can reduce the life of the valve.

Figure 73A:
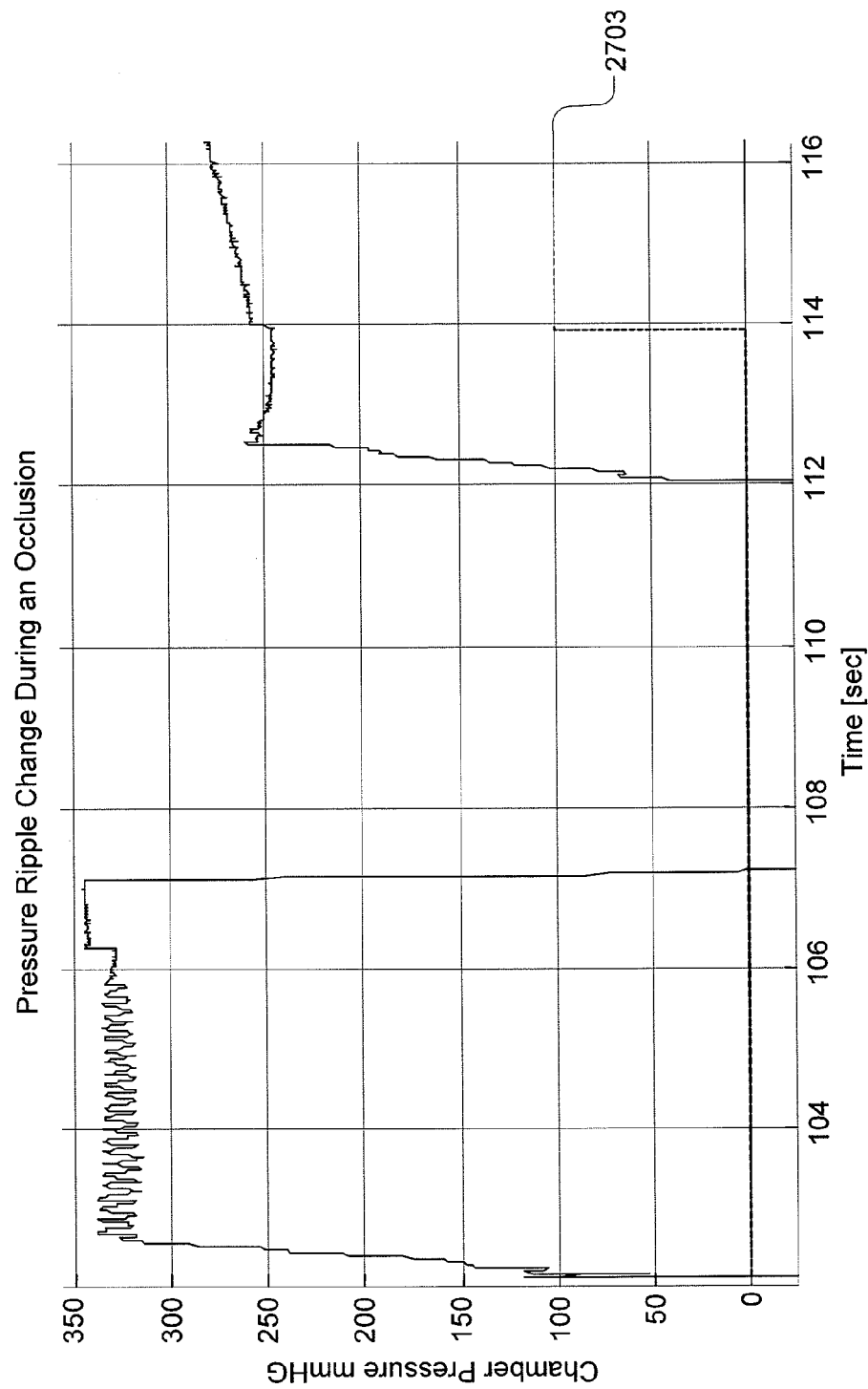
FIGS. 73A-73B are graphical representations of occlusion detection in accordance with an exemplary embodiment of the present invention.
Figure 73B:
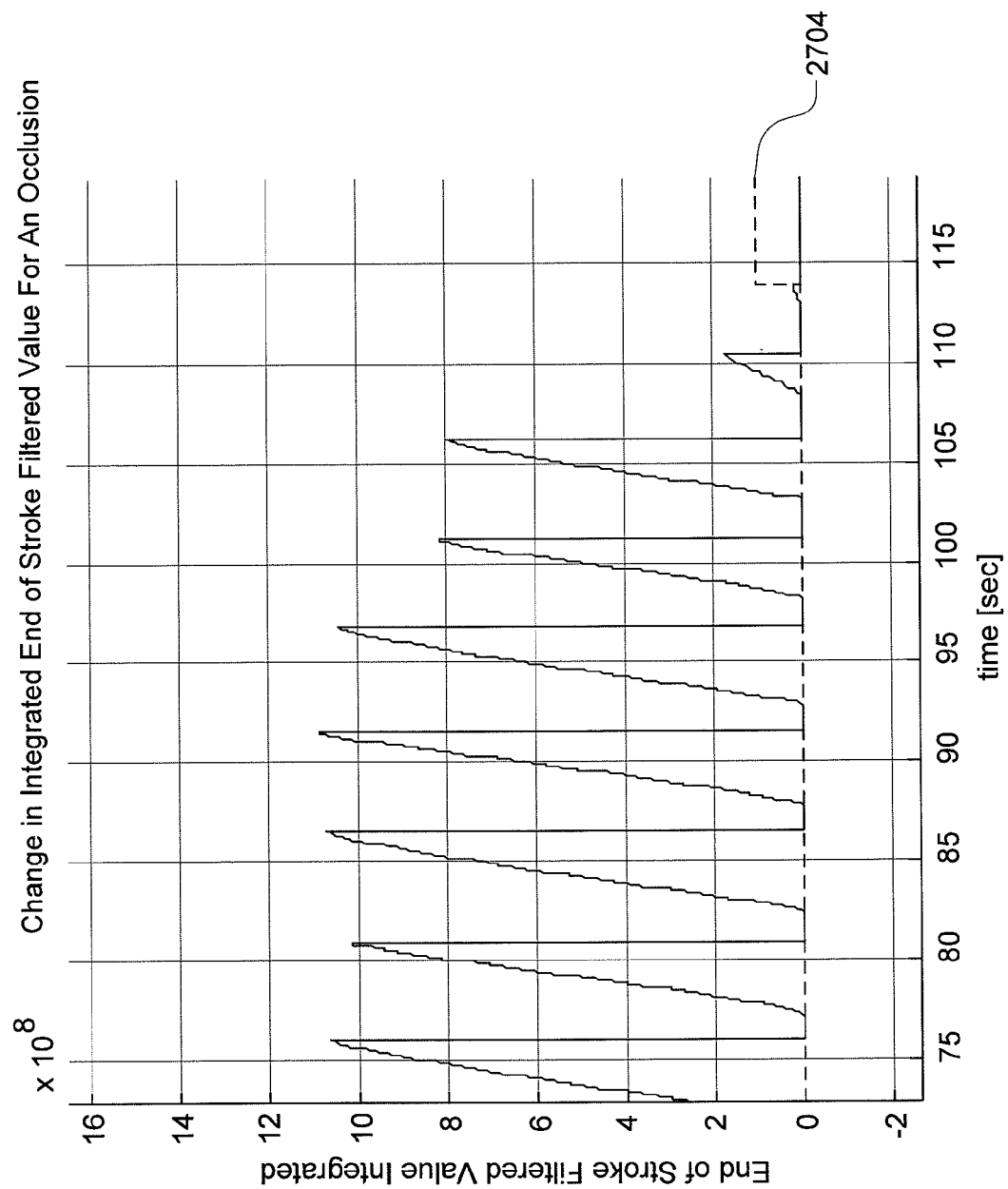

If the end of stroke is detected and the integrated value of the correlation function is very small, this may be an indication that the stroke occluded and did not complete properly. It may be possible to distinguish upstream occlusions from downstream occlusions by looking at whether the occlusion occurred on a fill or a delivery stroke (this may be difficult for occlusions that occur close to the end of a stroke when the diaphragm is near the chamber wall). FIGS. 73A-73B depict occlusion detection (lines 2703 and 2704 represent when occlusion is detected) in accordance with an exemplary embodiment of the present invention.

Under normal operation, the integrated value of the correlation function increases as the stroke progresses. If this value remains small or does not increase, then the stroke is either very short (as in the case of a very low impedance flow or an occlusion) or the actual pressure may not be tracking the desired sinusoidal pressure, e.g., due to a bad valve or pressure signals. Lack of correlation can be detected and used for error handling in these cases.

Under normal circumstances when the flow controller is running, the control loop preferably adjusts the pressure for any changes in flow rate. If the impedance in the circuit increases dramatically and the pressure limits are saturated before the flow has a chance to reach the target rate, the flow controller generally will not be capable of adjusting the pressures higher to reach the desired flow rate. These situations may arise if a line is partially occluded (e.g., a blockage, such as a blood clot in a blood pumping embodiment) has formed in the circuit. Pressure saturation when the flow has not reached the target flow rate can be detected and used in error handling.

If there are problems with the valves or the pneumatics, such as a leaking fluid valve or a noisy pressure signal, ripple may continue on the stroke indefinitely and the end of stroke algorithm may not see enough of a change in the pressure ripple to detect end of stroke. For this reason a safety check is preferably added to detect if the time to complete a stroke is excessive. This information can be used for error handling.

2.6. Exemplary Applications for Pump Pods

Reciprocating positive-displacement pumps and related control systems of the types described above may be used in a wide variety of fluid pumping applications, and are particularly well-suited for (although not limited to) use in applications that involve artificial or extracorporeal blood pumping such as, for example, hyperthermic or hypothermic blood treatments, hemodialysis and other blood processing and filtering treatments (e.g., plasmapheresis and apheresis), cardiac bypass and other assisted blood circulation treatments (e.g., ventricular assist), cardioplegia (as part of cardiac bypass or otherwise), lung bypass or artificial lung and other applications involving extracorporeal blood oxygenation, and chemotherapy and other drug treatments (e.g., regional hyperthermic chemotherapy), to name but a few. For example, in certain embodiments, reciprocating positive-displacement pumps and related control systems of the types described above may be used in a heat-exchanger system that can be used to heat or cool a fluid such as blood. Exemplary heat-exchanger systems are described below.

3. EXEMPLARY HEAT-EXCHANGER SYSTEMS

Embodiments of the present invention relate generally to heat-exchanger systems that can be used to heat or cool a fluid such as blood. A blood heating system may be particularly useful for whole-body hyperthermic treatments (e.g., to raise the body temperature to combat hypothermia or to combat certain diseases, such as Hepatitis C and possibly some types of cancer, HIV/AIDS, rheumatoid arthritis and psoriasis) or for regional hyperthermic chemotherapy treatments. Exemplary heat-exchanger systems are described below, one in the context of the pumping and heating of blood as part of whole-body hyperthermic treatment, and the other in the context of regional hyperthermic chemotherapy treatment. Of course, it should be noted that such a heat-exchanger systems may be used in other applications for heating and/or cooling fluid. Furthermore, while the exemplary heat-exchanger systems described below incorporate pump pods of the types described above, it should be noted that embodiments are not limited to the use of pump pods. Other types of pumps may be usable in various alternative embodiments.

3.1. Whole-Body Hyperthermic Treatment

As discussed above, a blood heating system may be used for whole-body hyperthermic treatments (e.g., to raise the body temperature to combat hypothermia or to combat Hepatitis C by raising the core body temperature to a sufficient level so as to purge the virus from infected liver cells). Generally speaking, whole-body hyperthermic treatment for Hepatitis C involves raising the core body temperature to approximately 41.6 degrees Celsius (107 degrees Fahrenheit) for an extended period of time. A typical treatment might last three to four hours, including a 30-60 minute warm-up period, 80-120 minute plateau period, and 30-45 minute cool-down period. Core body temperature, and therefore fluid temperature generated by the heat-exchanger system, must be controlled carefully to maintain the patient at the target core temperature with little variation—if the core temperature is too low, then the treatment may not be effective; if the core temperature gets too high, then the patient can be harmed.

Figure 24:
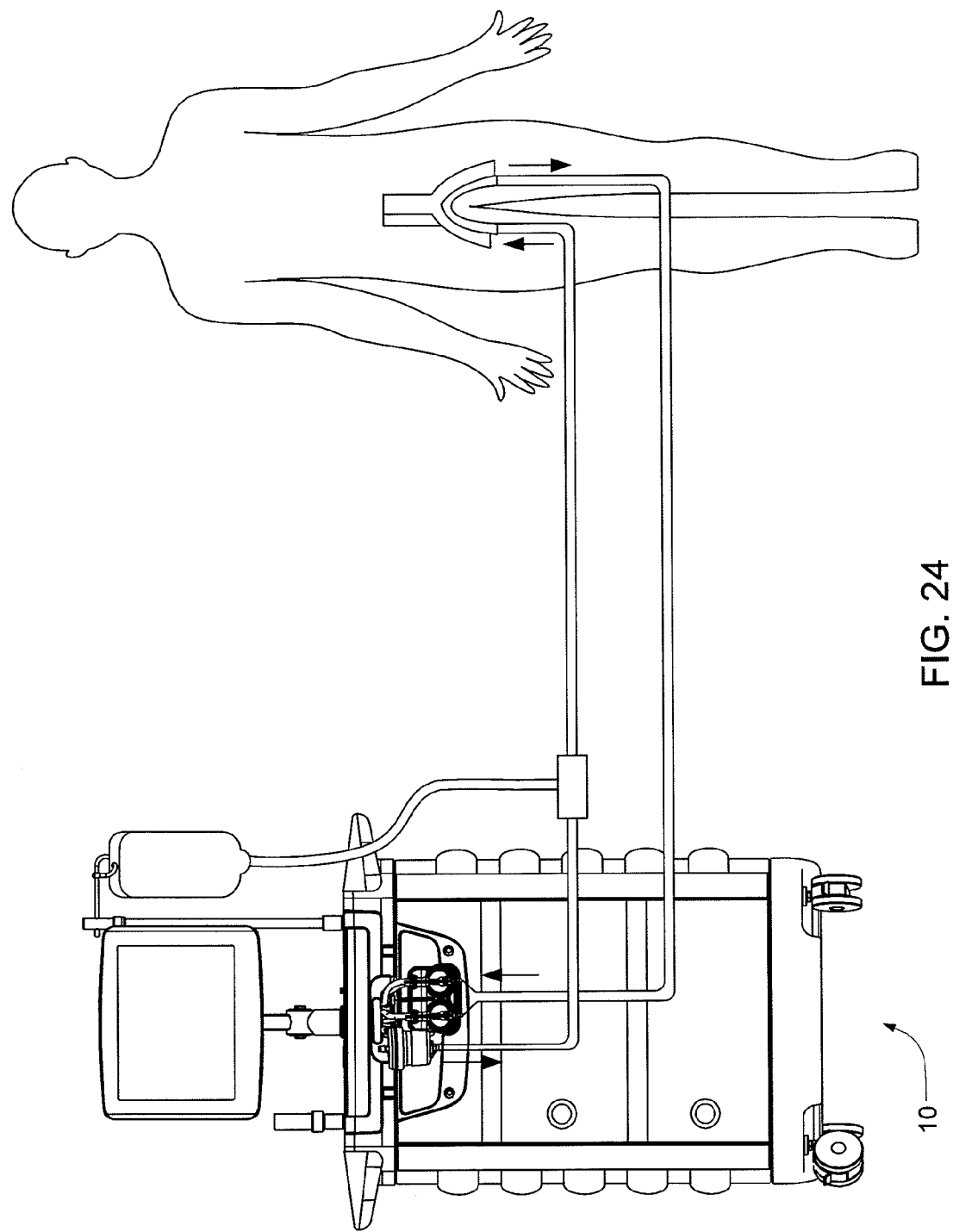
FIG. 24 is a schematic view of a whole-body hyperthermic treatment system in accordance with an exemplary embodiment of the present invention.

FIG. 24 is a schematic view of a whole-body hyperthermic treatment system in accordance with an exemplary embodiment of the present invention. Blood leaves the patient via the 14F left femoral venous cannulae. Within the heat-exchanger system 10, the blood is pumped by two pump pods through a heat exchanger for heat exchange. A control system monitors various parameters (e.g., blood temperature entering and exiting the heater/cooler as well as patient core temperature) and adjusts operation of the pump pods and the heater/cooler accordingly. following the heat exchanger, the blood passes through a particulate and air filter and returns to the patient via the 12F right femoral venous cannulae. During this procedure, the patient is typically supine, intubated, anesthetized, and monitored by a doctor or other professional.

3.1.1. Exemplary Heat Exchanger Systems

FIG. 1 shows a heat-exchanger system 10 in accordance with an exemplary embodiment of the present invention. The heat-exchanger system 10 includes a base unit 11 and a disposable unit 16. As described further below, the disposable unit 16 is installed into the base unit 11 such that a heat-exchanger bag (e.g., a heat-exchanger bag 21 as shown in FIGS. 2 and 48) of the disposable unit 16 rests within a heat exchanger portion of the base unit 11. As blood from a patient circulates through the disposable unit 16, and specifically through the heat-exchanger bag 21, the blood is heated by the heat exchanger and is returned to the patient. During such circulation, the blood remains within the disposable unit 16 and generally does not come into contact with components of the base unit 11. The disposable unit 16 is considered to be "disposable" in that it is generally discarded after a patient treatment, whereas the base unit 11 can be re-used repeatedly by simply installing a new disposable unit 16. In fact, the base unit 11 may include mechanisms to prevent re-use of a disposable unit (e.g., using a bar code, RFID tag, or other identifier associated with the disposable unit).

3.1.2. Exemplary Base Unit

Figure 25:
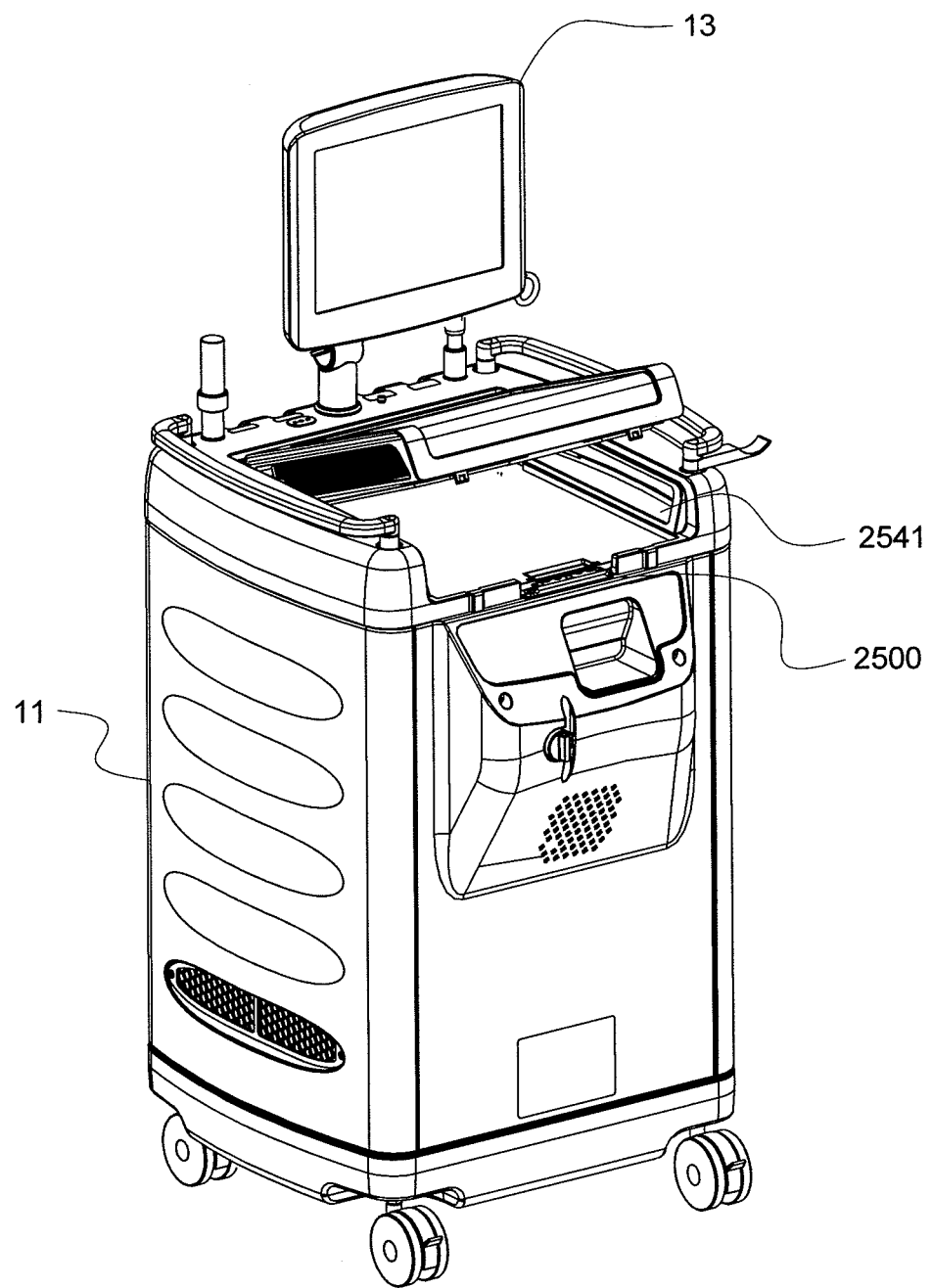
FIG. 25 shows the base unit of FIG. 11, in accordance with an exemplary embodiment of the present invention.
Figure 47A:
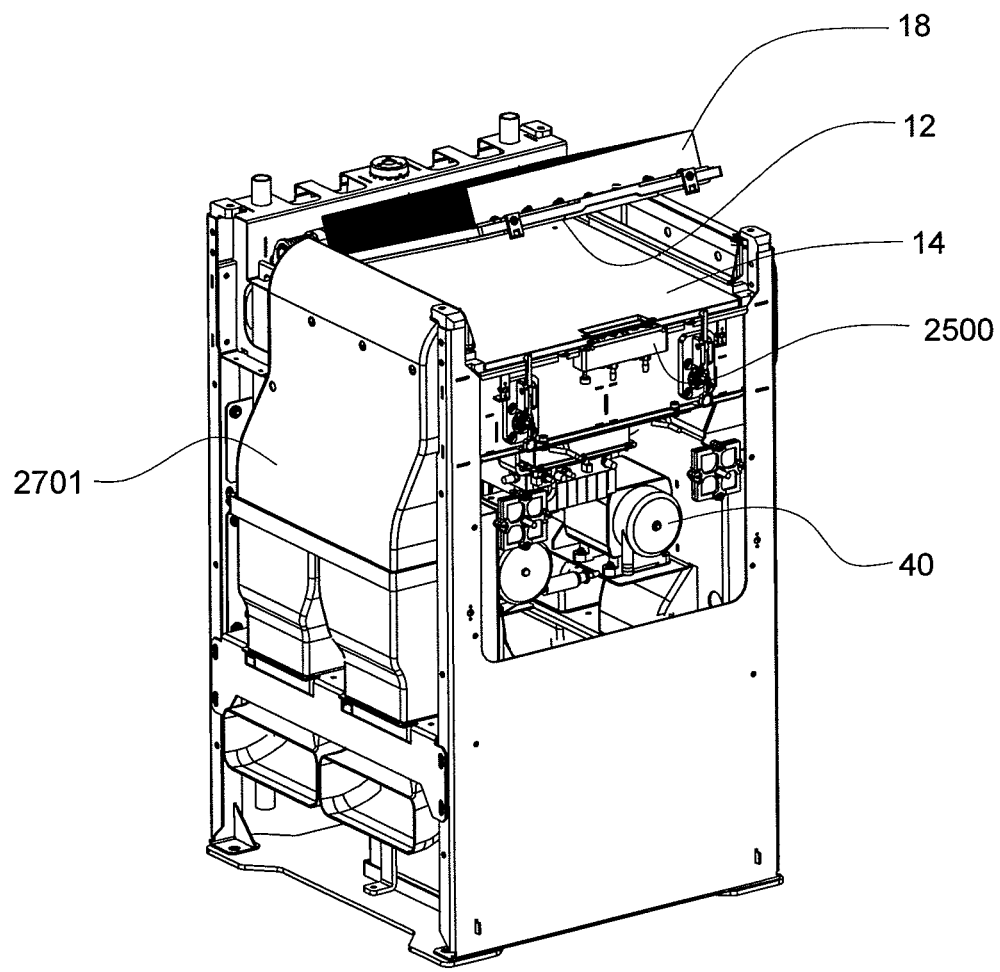
FIG. 47A shows some of the interior components of the base unit of FIGS. 1 and 25, in accordance with an exemplary embodiment of the present invention.
Figure 47B:
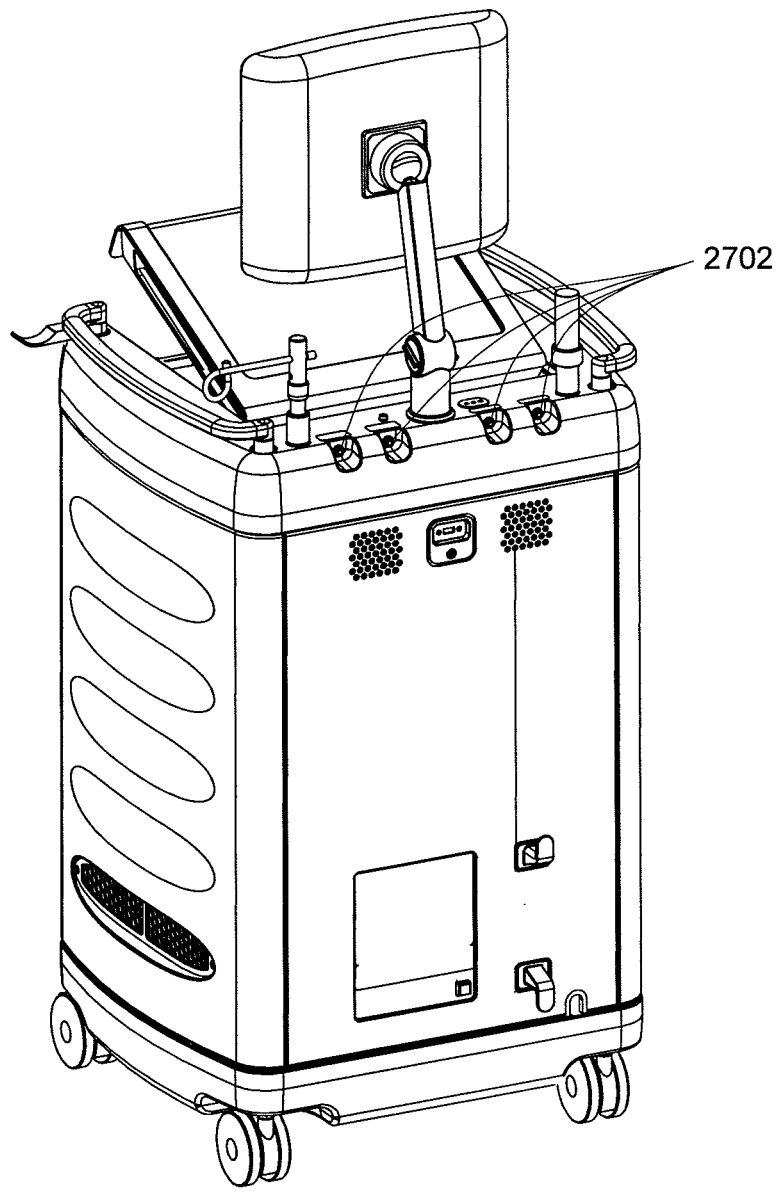
FIG. 47B shows a rear perspective view of the base unit of FIGS. 1 and 25 showing patient interfaces, in accordance with an exemplary embodiment of the present invention.

FIG. 25 shows the base unit 11 in accordance with an exemplary embodiment of the present invention. FIG. 47A shows some of the interior components of the base unit 11 in accordance with an exemplary embodiment of the present invention, while FIG. 47B shows a rear perspective view of the base unit 11. The base unit 11 includes, among other things, a heat exchanger 2541, a pneumatic actuation system 40, a disposables interface 2500 (also referred to as a manifold interface), a patient interface, a controller, a user interface console 13, and a ventilation system 2701. The pneumatic actuation system 40 may be generally of the type shown in FIG. 4, but with separate pneumatic interfaces, valves, and sensors for each of two pump pods. The disposables interface may include two sensors that provide both thermal and electrical connectivity to a disposable unit to allow for monitoring blood temperature both upstream and downstream of the heat exchanger and also to allow for monitoring other parameters, as discussed below. The patient interface may include one or more temperature inputs 2702 for receiving temperature information (specifically patient temperature information) from one or more temperature probes. The user interface console allows the user to control and monitor operation of the system. In an exemplary embodiment, the controller controls operation of the heat exchanger and the pump pods based on, among other things, blood temperature information received from the disposables interface, pressure information received from the pneumatic actuation system, patient temperature information received from the patient interface, and user inputs received from the user interface console.

3.1.3. Exemplary Disposable Unit Configurations

As mentioned above, a disposable unit for a heat-exchanger system typically includes a heat-exchanger bag through which blood flows while passing through the heat exchanger. The heat-exchanger bag may include one or more fluid paths. In one exemplary embodiment described below, a heat-exchanger bag includes a single fluid path connecting two fluid inlets to a common fluid outlet. In another exemplary embodiment described below, a heat-exchanger bag includes a single fluid path having a single inlet and a single outlet. Heat-exchanger bags are typically made of a flexible plastic material, although the heat-exchanger bag may be made from other materials and may include a metallic material or other material to improve thermal conductivity.

FIG. 2 shows relevant components of a disposable unit 16, in accordance with an exemplary embodiment of the present invention. The disposable unit 16 includes, among other things, a heat-exchanger bag 21 (also referred to as a "flow-path bag") with a manifold 130 and a panel 2017 holding (or configured to hold) two pump pods 25a and 25b and a filter/air trap 29. The disposable unit 16 preferably also includes a handle (not shown here, but shown in FIG. 48) that is used to mechanically interconnect the above-referenced components into a cohesive unit that can be readily installed into the base unit 11, which preferably includes a manifold interface (described below) for receiving the manifold 130 and providing pneumatic connections for operating the pumps 25a, 25b. The bag 21 includes a fluid path 150 through which fluid can be pumped. In this embodiment, the manifold 130 is integrated with the heat-exchanger bag 21 and is configured with appropriate tubing connections and supports that are used to interconnect the heat-exchanger bag 21 with the two pump pods 25a and 25b.

In the embodiment shown in FIG. 2, the manifold 130 includes two flow-path inlets 23a and 23b (also referred to as "heat-exchanger bag inlets") in fluid communication with one end of the fluid path 150 and a flow-path outlet 27 (also referred to as a "heat-exchanger bag outlet") in fluid communication with the other end of the fluid path 150. The blood is preferably pumped from the patient and through the heat-exchanger bag 21, in this embodiment by a pair of self-contained pump pods 25a, 25b (referred to individually as a pump pod 25), which are preferably reciprocating positive-displacement pumps of the types described herein. In this embodiment, the manifold 130 includes pneumatic passageways 138a, 138b to facilitate establishment of pneumatic connections respectively to the pump pods 25a, 25b (typically using tubing). It should be noted that embodiments are not limited to the use of two pump pods or, for that matter, to the use of pump pods. The manifold 130 is described more fully below.

Figure 72:
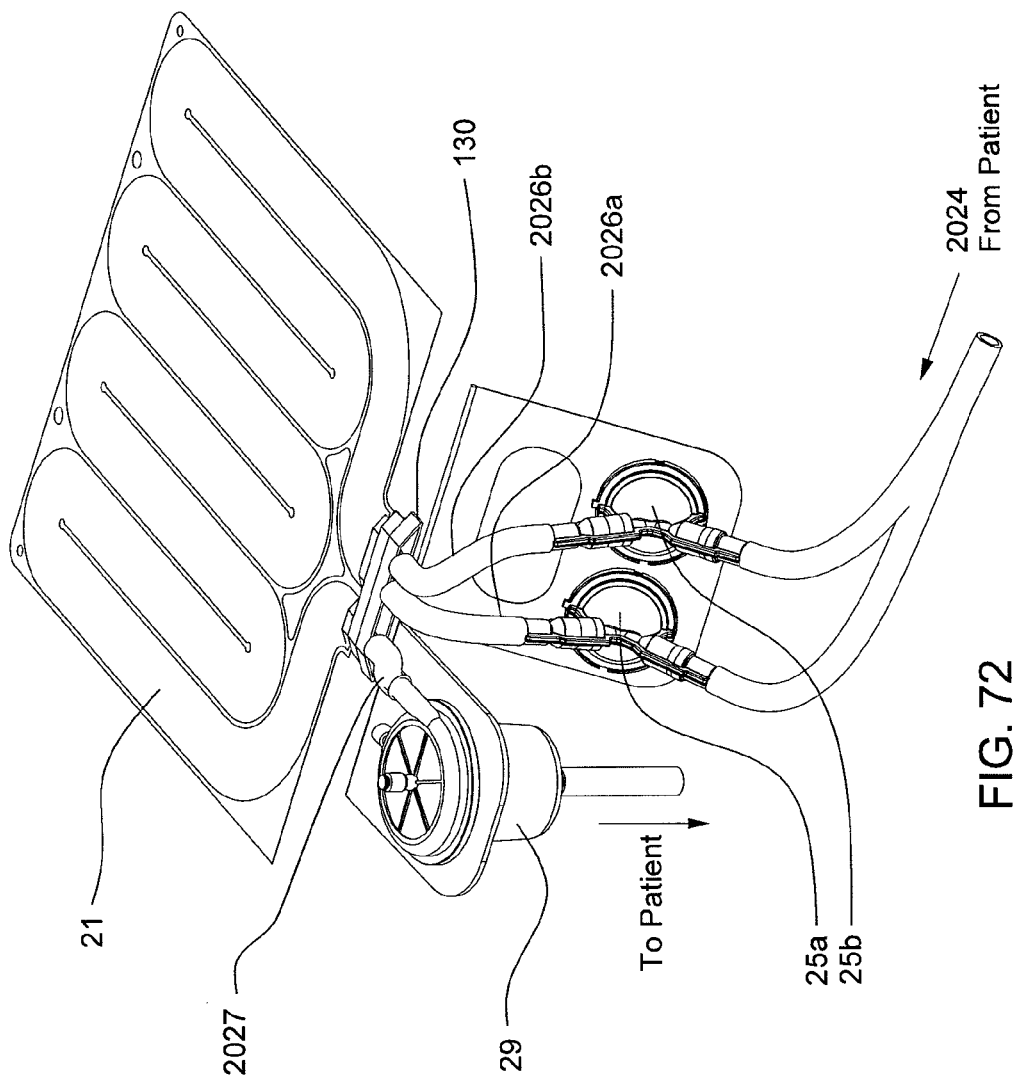
FIG. 72 shows one way in which the various components of the disposable unit of FIG. 2 can be interconnected.

In this embodiment, each pump pod 25 includes an inlet 34 and an outlet 37 (i.e., pump pod 25a has an inlet 34a and an outlet 37a, while pump pod 25b has an inlet 34b and an outlet 37b). The various components may be interconnected in at least two configurations. In a first configuration shown in FIGS. 48 and 72, the pump pods 25a, 25b may be coupled upstream of the heat-exchanger bag 21 such that the pump inlets 34a, 34b are coupled to receive blood directly from the patient (e.g., through a "Y" connector 2024), the pump outlets 37a, 37b are connected respectively to the heat-exchanger-bag inlets 23a, 23b by tubes 2026a, 2026b, and the filter/air trap 29 is connected to the heat-exchanger-bag outlet 27 by tube 2027. In this way, the pump pods 25a, 25b are operable to urge blood through the heat-exchanger bag 21, from which the blood exits through the flow-path outlet 27 and then passes through the filter/air trap 29 before returning to the patient. In a second configuration (not shown), the pump pods 25a, 25b may be coupled downstream of the heat-exchanger bag 21 such that blood from the patient enters the heat-exchanger-bag inlets 23a, 23b (e.g., through a "Y" connector, not shown), the pump inlets 34a, 34b are coupled to the flow-path outlet 27 (e.g., through a "Y" connector, not shown), and the pump outlets 37a, 37b are coupled (e.g., through a "Y" connector, not shown) to return blood to the patient via the filter/air trap 29. In this way, the pump pods 25a, 25b draw blood through the heat-exchanger bag 21 and pump the blood through the filter/air trap 29 to the patient. It should be noted, in an alternate embodiment, the heat-exchanger bag 21 could include separate outlets, which could facilitate its coupling with the pump pods in some situations. In the embodiments shown in FIGS. 2 and 48, the filter/air trap 29 is preferably provided with a purge port to allow air to escape from the filter. FIG. 48 shows a data key slot 2542 in which a data key can be placed, for example, during manufacturing.

Figure 81:
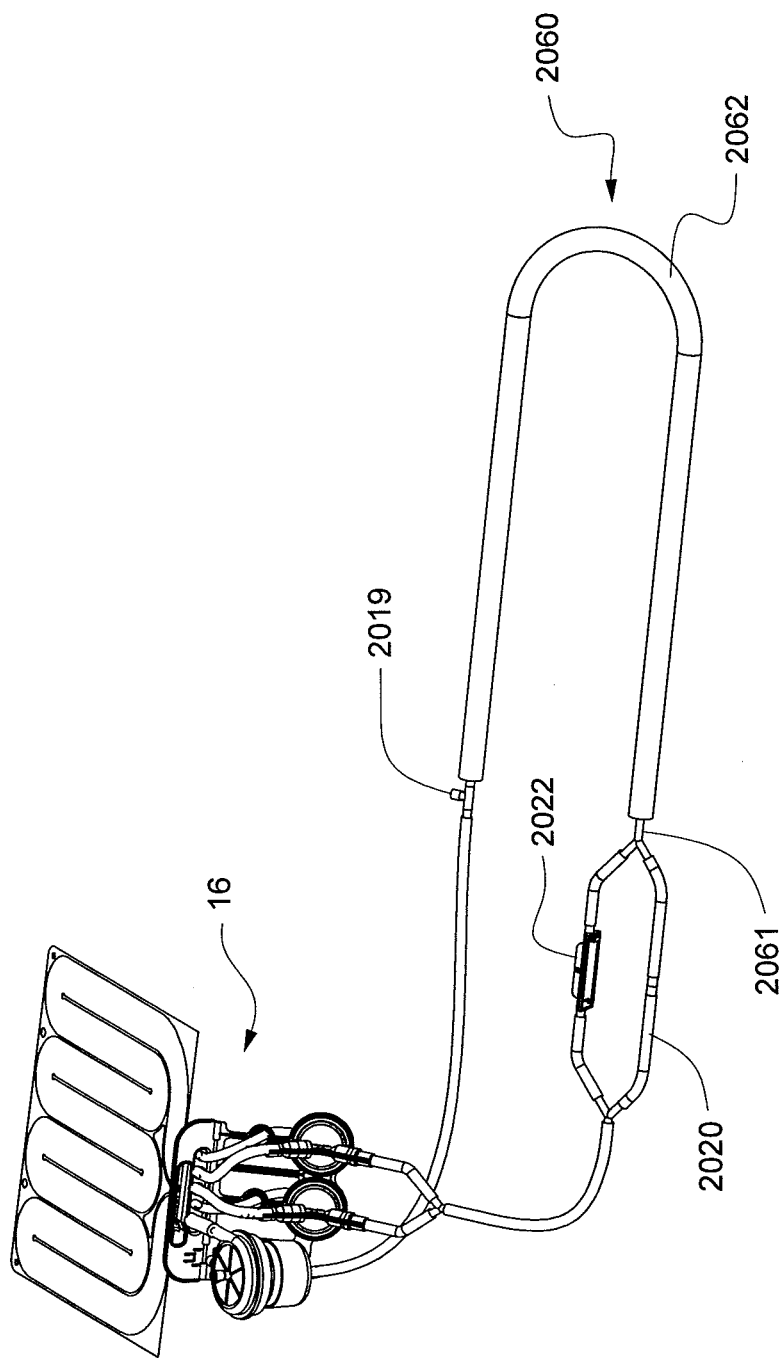
FIG. 81 shows a variation of the disposable unit of FIG. 48 including a patient connection circuit having a sterile protective covering, in accordance with an exemplary embodiment of the present invention.

FIG. 81 shows a variation of the disposable unit 16 of FIG. 48 including a patient connection circuit 2060 having a sterile protective covering 2062, in accordance with an exemplary embodiment of the present invention. Specifically, a configuration of tubing 2061 is connected between the pump pod inlets and the filter outlet to form a complete circuit. In this embodiment, the tubing 2061 includes an air purge/sample port 2019 and a blood monitoring interface optionally including shunt sensor connections 2020 and/or disposable H/S cuvette 2022. In order to effectuate connections to the patient, the surgeon or other technician typically cuts through the tubing 2061 at or about the distal portion of the tubing (in this embodiment, the U-shaped portion toward which the arrow for reference numeral 2060 points, which may be referred to as the "circus maximus") in order to create two tube ends. The surgeon or technician can then connect appropriate needles to the two tube end for insertion into the patient.

Figure 82:
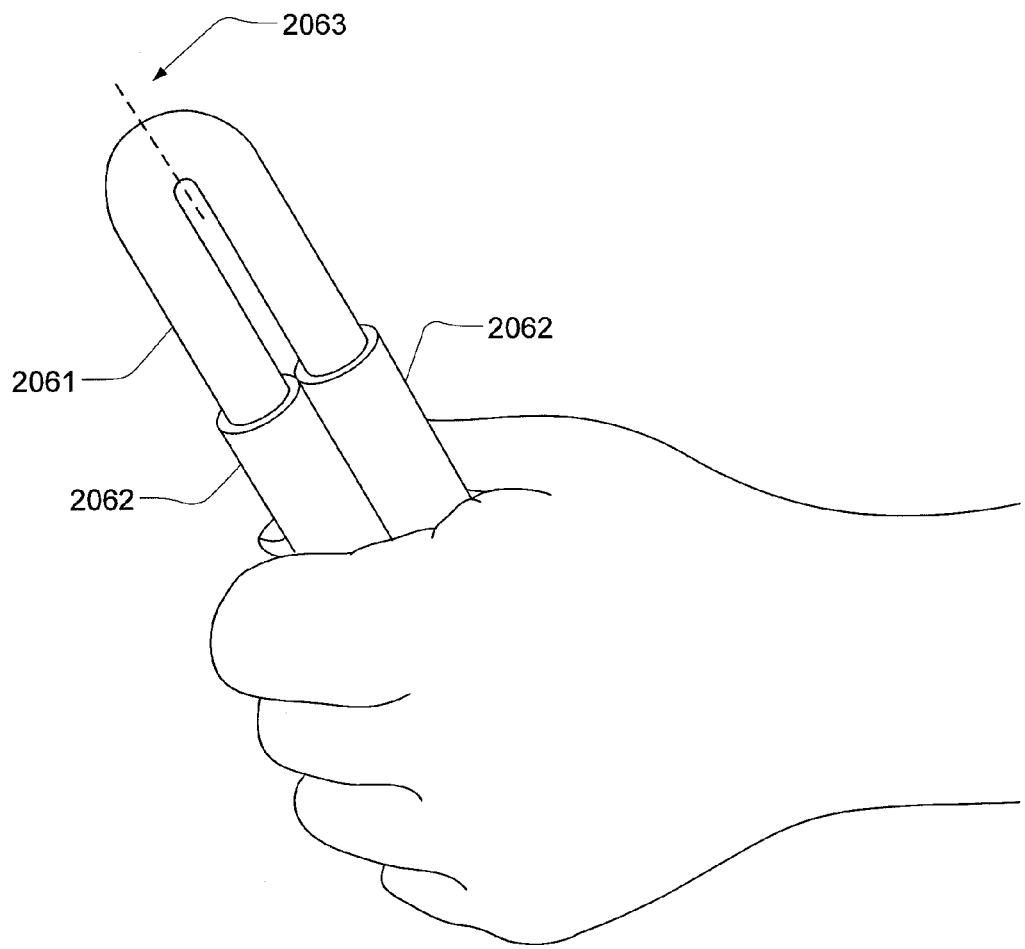
FIG. 82 shows a representation of the patient connection circuit from FIG. 81 with a portion of tubing exposed through the sterile protective covering, in accordance with an exemplary embodiment of the present invention.

In this embodiment, the distal portion is sterilized and covered with a thin plastic protective material 2062 in order to maintain sterility. Prior to cutting through the tubing 2061, a portion of the tubing 2061 in the sterile field is exposed, for example, by pulling on the protective material 2062 in opposite directions until it separates. FIG. 82 shows a representation of the patient connection circuit from FIG. 81 with a portion of tubing 2061 exposed through the sterile protective covering 2062, in accordance with an exemplary embodiment of the present invention. Once the section of tubing 2061 has been exposed, a cut can be made at location 2063.

Figure 83:
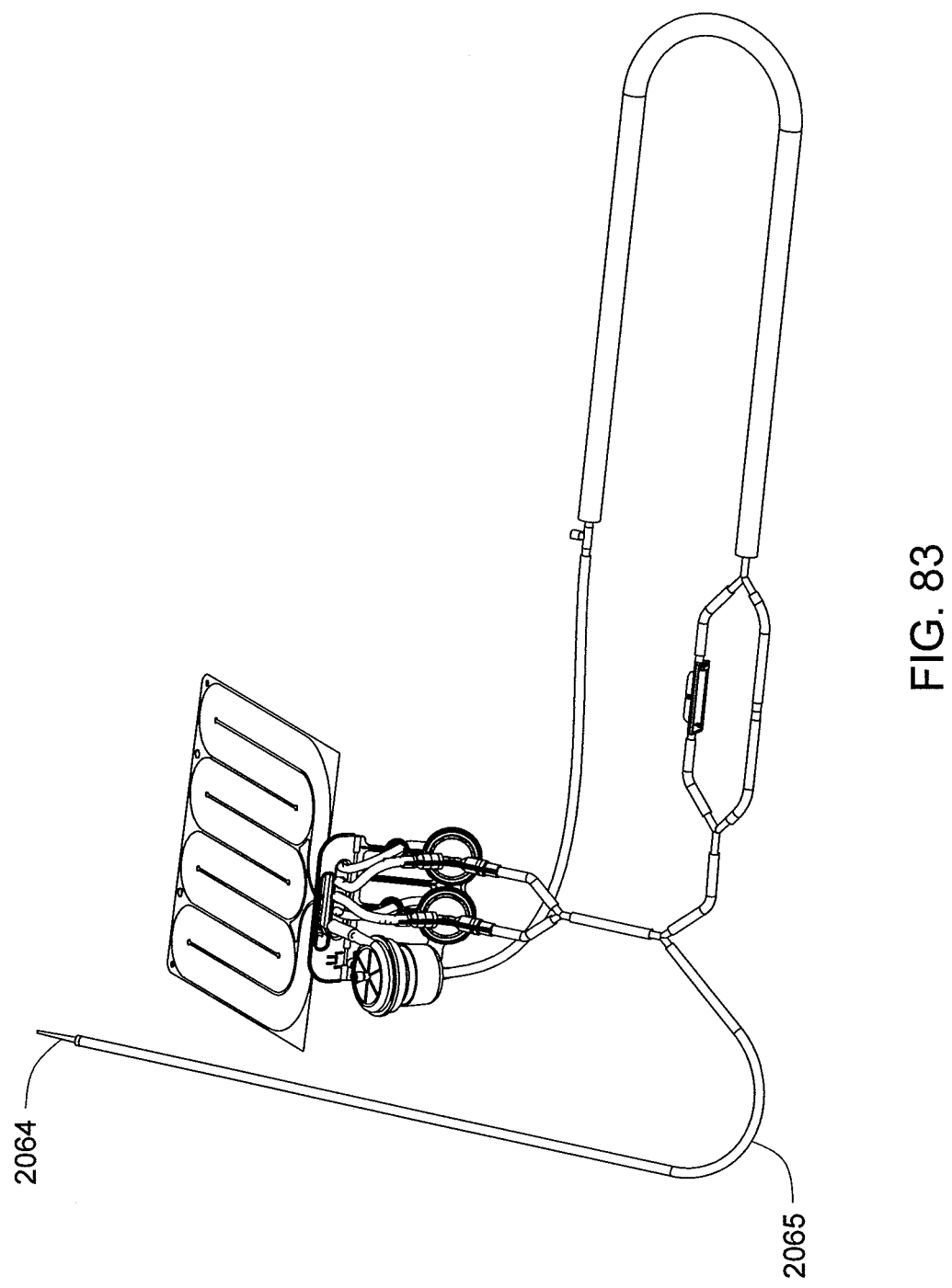
FIG. 83 shows a variation of the disposable unit of FIG. 81 including an additional fluid delivery line, in accordance with an exemplary embodiment of the present invention.

FIG. 83 shows a variation of the disposable unit of FIG. 81 including an additional fluid delivery line 2065, in accordance with an exemplary embodiment of the present invention. The fluid delivery line 2065 is in fluid communication with the pump pod inlets to that fluid from the fluid delivery line 2065 (e.g., IV fluids) can be incorporated into the patient blood and circulated through the heat exchanger and into the patient. In this embodiment, the fluid delivery line 2065 is configured with a connector 2064 (e.g., a needle for introduction into an IV bag) in order to facilitate connection with a fluid source.

Figure 15:
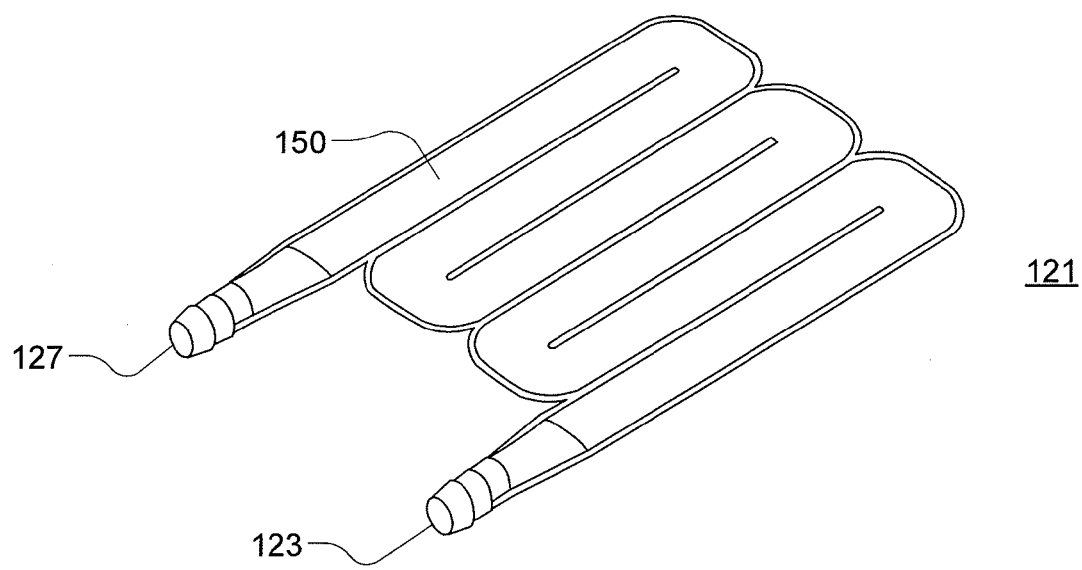
FIGS. 15, 16 and 17 show respectively top perspective, end perspective and top plan views of the disposable unit's heat-exchanger bag used in the heat exchanger shown in FIG. 14.
Figure 16:
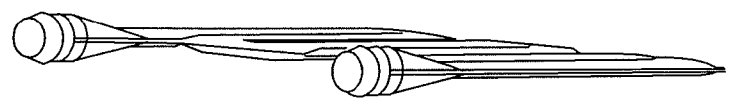
Figure 17:
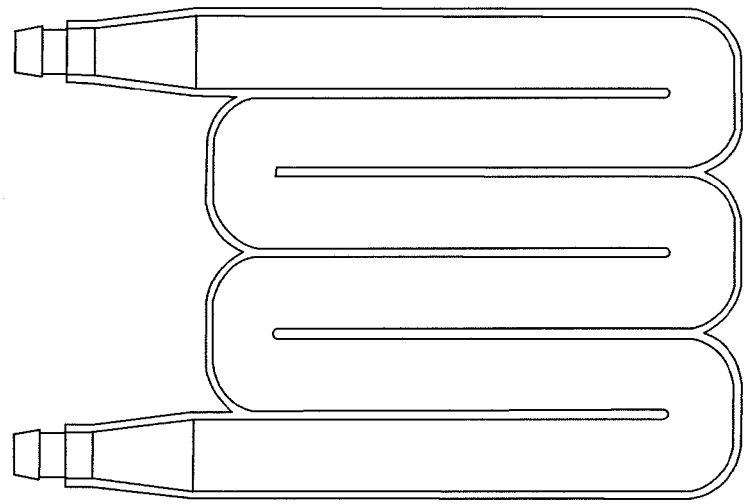

FIGS. 15, 16 and 17 show respectively top perspective, end perspective, and top plan views of an alternative heat-exchanger bag 121 in accordance with another embodiment of the present invention. In this embodiment, the bag 121 has a single inlet 123, a single outlet 127, and a flow path 150 extending between the inlet 121 and the outlet 123. The inlet 123 and the outlet 127 of this bag 121 are spaced away from each other, whereas in the bag 21 of FIGS. 2 and 48, the inlet 23a, 23b and outlet 27 are adjacent each other. Having the inlet and outlet adjacent each other (like the bags shown in FIGS. 2 and 48) generally makes the disposable unit less bulky to handle. The bag 121 may be formed from two sheets of plastic or other appropriate material that are welded at the seams to produce the flow path 150.

It should be noted that alternative embodiments may employ other pump pod configurations as part of the disposable unit 16. For example, various alternative embodiments could employ the pump pod assembly 2004 shown in FIGS.

5A and 5B, the pump cassette 2015 shown in FIGS. 22A and 22B, or the dual-housing arrangement 2016 shown in FIG. 23. With regard to pump pod assembly 2004, the common inlet 54 may be coupled to receive blood from the patient and the common outlet 57 may be coupled to provide blood to the heat-exchanger bag 21, or the common inlet 54 may be coupled to receive heated blood from the heat-exchanger bag 21 and the common outlet 57 may be coupled to provide blood to the filter/air trap 29. Similarly, with regard to pump cassette 2015, the common inlet 2005 may be coupled to receive blood from the patient and the common outlet 2006 may be coupled to provide blood to the heat-exchanger bag 21, or the common inlet 2005 may be coupled to receive heated blood from the heat-exchanger bag 21 and the common outlet 2006 may be coupled to provide blood to the filter/air trap 29.

It should be noted that various components of the disposable unit 16 may be provided separately and/or in various assemblies and sub-assemblies, and therefore the word "unit" is not intended to require that the disposables be provided as a complete system or kit. Thus, for example, the pump pods (or pump pod assemblies/cassettes) could be provided separately from the rest of the disposable unit 16. Among other things, providing the pump pods separately could allow pump pods of different volumes to be easily integrated, without requiring separate versions of the main disposable unit for different pump volumes. Furthermore, the disposable unit 16 could be provided with some tubing connections already in place, e.g., with the pump outlets 37*a*, 37*b* already coupled to the heat-exchanger-bag inlets 23*a*, 23*b* and/or with the pump inlets 34*a*, 34*b* already coupled to a "Y" connector and/or with the flow-path outlet 27 already coupled to the filter/air trap 29.

In typical embodiments, the same controller 49 preferably controls both pump pods (items 25*a* and 25*b* of FIGS. 2 and 48) of the disposable unit 16, and preferably (although not necessarily) causes the two pump pods to pump out of phase (i.e., one pumping chamber is emptying while the other is filling) during normal blood-pumping operation in order to provide for more continuous flow to/from the patient and through the heater. Some ways in which the controller 49 may monitor and control the pumps, heaters, and other components are discussed above as well as further below.

3.1.4. Exemplary Heat Exchanger Components

Figure 13A:
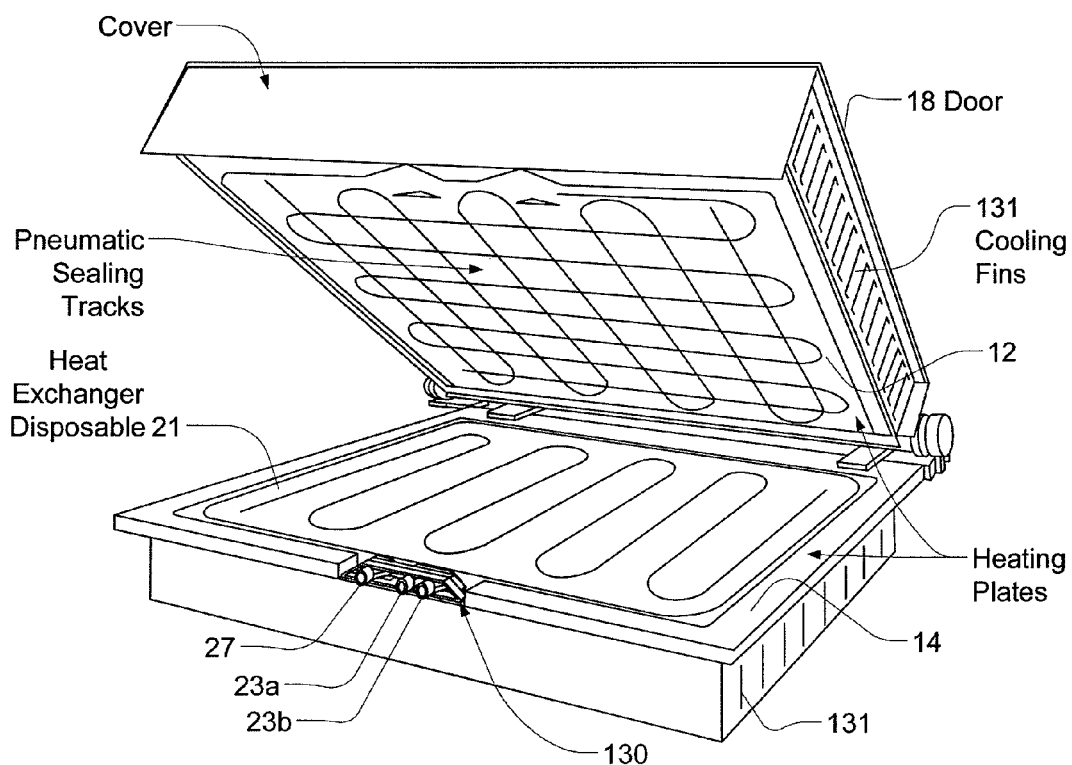
FIG. 13A is a perspective view of the components from the system of FIG. 1 used for transferring heating to the blood.

FIG. 13A shows greater detail of the heat exchanger 2541 shown in FIG. 25. In this embodiment, an upper heating plate 12 is mounted in a door 18 located at the top of the base unit. A lower heating plate 14 is located in the base unit 11 under the door 18. The heat-exchanger bag 21, which is part of the disposable unit 16, is placed on top of the lower heating plate 14, such that when the door 18 is closed, the bag 21 rests between the two heating plates 12, 14. This arrangement generally permits more heat to be transferred to the blood more quickly than a single-plate arrangement would, although alternative embodiments may use a single plate either above or below the heat-exchanger bag 21 and/or may use other types of heating elements. The door 18 and/or the upper plate 12 may include pneumatic sealing tracks to evacuate air from the heat exchanger or produce a better coupling between the upper plate 12 and the bag 21 (e.g., by producing a vacuum that pulls the upper surface of the bag 21 into contact with the upper plate 12.

Figure 14:
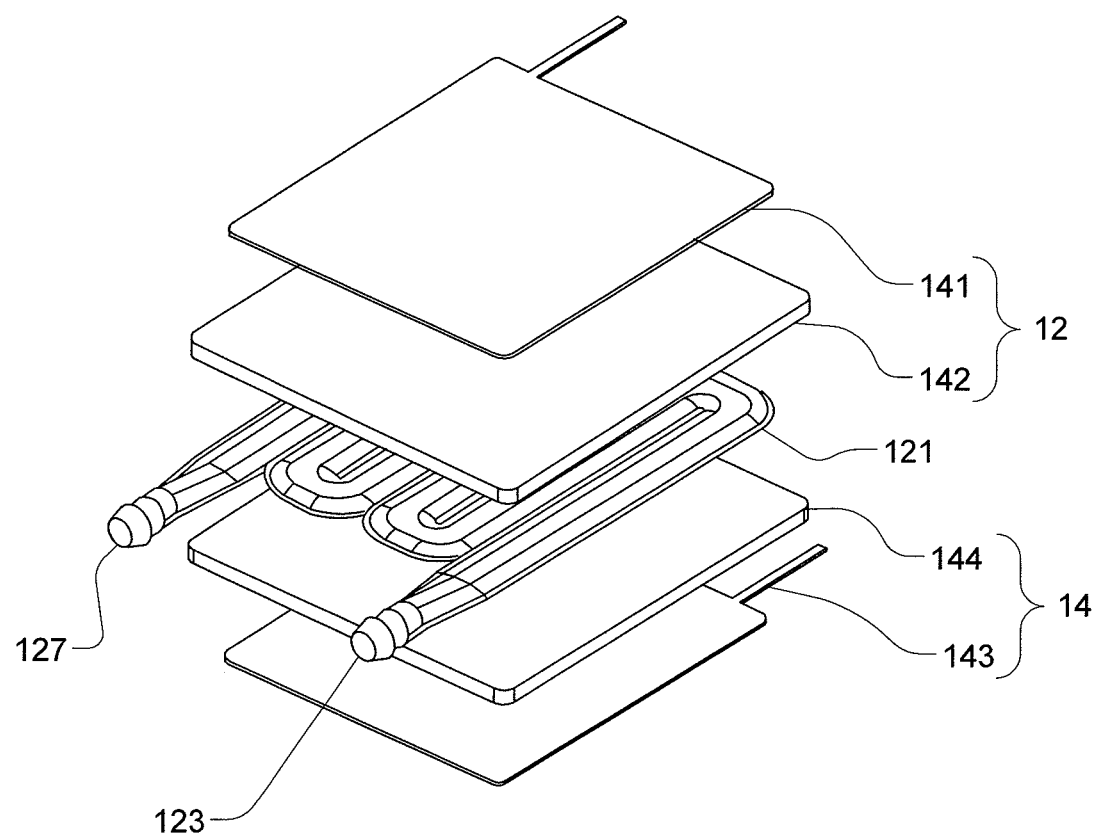
FIG. 14 is an exploded view showing the basic components of a heat exchanger in an alternative embodiment.
Figure 18:
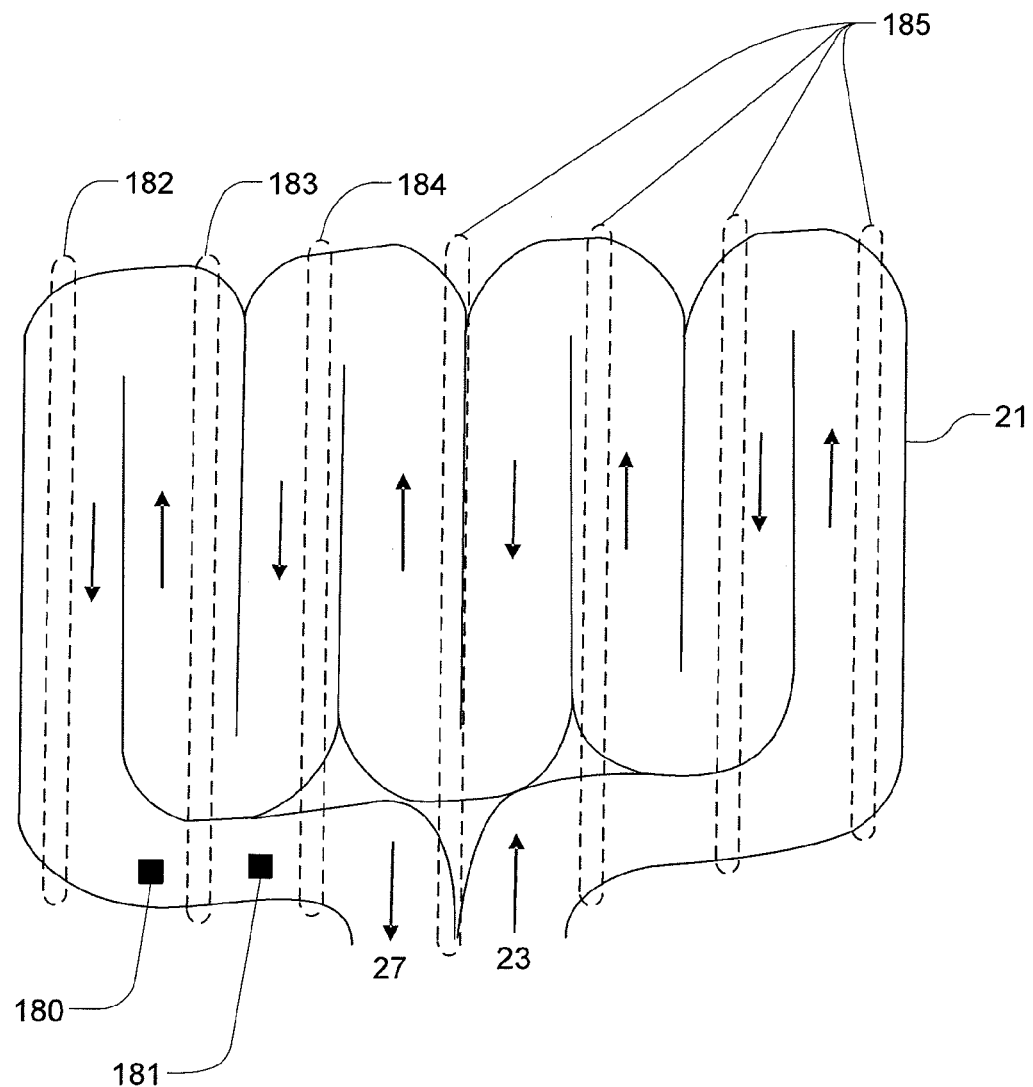
FIG. 18 shows a preferred placement of temperature transducers in a heat exchanger.

Each of the heating plates 12, 14 may include a single heating element or multiple heating elements. The heating elements are typically (although not necessarily) electric heating elements. FIG. 14 shows an exploded view of one exemplary heating element configuration in which the upper heating plate 12 includes a single heater element 141 and a platen 142 and the lower heating plate 14 includes a single heater element 143 and a platen 144. FIG. 18 shows an alternative heating element configuration in each of the heating plates 12, 14 includes seven heating elements 182, 183, 184, 185. In practice, electricity passing through the heating elements heats the heating elements, which in turn heat the platens, which in turn conduct heat to the blood passing through the heat-exchanger bag. It should be noted that heating elements can be used without platens, although the platens tend to provide a more even distribution of heat. In the embodiment shown in FIG. 18, if one or even several of the heating elements fails, the heat exchanger should still be able to perform at least some blood heating, since the platens generally can still be heated with fewer than all the heating elements working and still impart heat to the blood passing through the heat-exchanger bag.

In order to improve thermal coupling between the heating plates 12, 14 and the heat-exchanger bag, the door 18 may produce a substantially air-tight seal when closed. Furthermore, air may be evacuated from around the heat-exchanger bag to achieve better thermal coupling between the bag and the plates. In this regard, a compressor (not shown) that may be used to produce the positive and/or negative pressures for the reservoirs 51, 52 may be used to evacuate air from around the heat-exchanger bag. Cooling fins 131 or other elements may be provided to draw away excess heat.

The temperature inside the heat exchanger may be monitored to ensure that the blood does not get so heated as to cause damage to the blood. In the embodiment shown in FIG. 18, each heating plate is provided with two temperature sensors 180, 181 located near the outlet 27 at points near where the blood should be at its hottest. Since the inlet 23 is near the outlet 27 (in this figure), the blood flowing through the outlet may be a little cooler than further upstream, because the cooler blood flowing into the inlet can cool the warmer blood passing through the outlet nearby. Three of the heating elements 182, 183, 184 are located towards the end of the flow path in the heat-exchanger bag 21. Each temperature sensor 180, 181 may be located between heating elements and near the outlet 27, and the temperature sensors 180, 181 are preferably spaced some distance apart with at least one heating element located between them (in this embodiment, heating element 183). Thus, as shown in FIG. 18, one sensor 181 is located between the last two heating elements 183, 184 that the flow path crosses before the blood exits the outlet 27. The other sensor 180 is located upstream of both of these two heating elements 183, 184 and between two heating elements 182, 183. If the two temperature sensors 180, 181 are working properly and if the heat exchanger is working properly, the two temperature sensors should have readings within a certain number of degrees of each other (although they would not typically have the exact same temperature reading). The controller preferably receives temperature information from the two temperature sensors 180, 181 and may generate an alarm, discontinue operation, reduce power to the heating elements, and/or take other action if either (or both) of the temperature sensors indicates an unsafe temperature or if the difference in temperature readings measured by the two sensors exceeds a predetermined limit. The maximum temperature of the plates should not be allowed to exceed the maximum allowable blood temperature, because otherwise, if the flow of blood were to stop or slow, the blood could be over-heated.

In certain embodiments, one or both of the heating plates 12, 14 may be translatable in a vertical direction when the door is closed, e.g., to facilitate evacuation of air from the heat-exchanger bag 21 during priming or to squeeze residual blood out of the heat-exchanger bag 21 and back into the patient at the end of the blood-heating procedure. The plates may additionally or alternatively be tiltable so that the bag may be tilted, e.g., in order to assist in removing air bubbles from the bag during priming or to assist with returning blood to the patient. Such vertical translation and/or tilting could be performed manually or could be performed automatically, for example, under control of the controller 49.

Thus, at the end of the blood-heating procedure, the membranes in the pump pods 25a, 25b may be urged against the pumping-chamber wall so as to minimize the volume of the pumping chambers and expel as much blood as possible back toward the patient. Furthermore, in embodiments that include vertically translatable and/or tiltable plates, the heat-exchanger bag 21 may be squeezed and/or tilted to direct as much blood as possible back toward the patient.

3.1.5. Exemplary Manifold and Manifold Interface

Figure 49A:
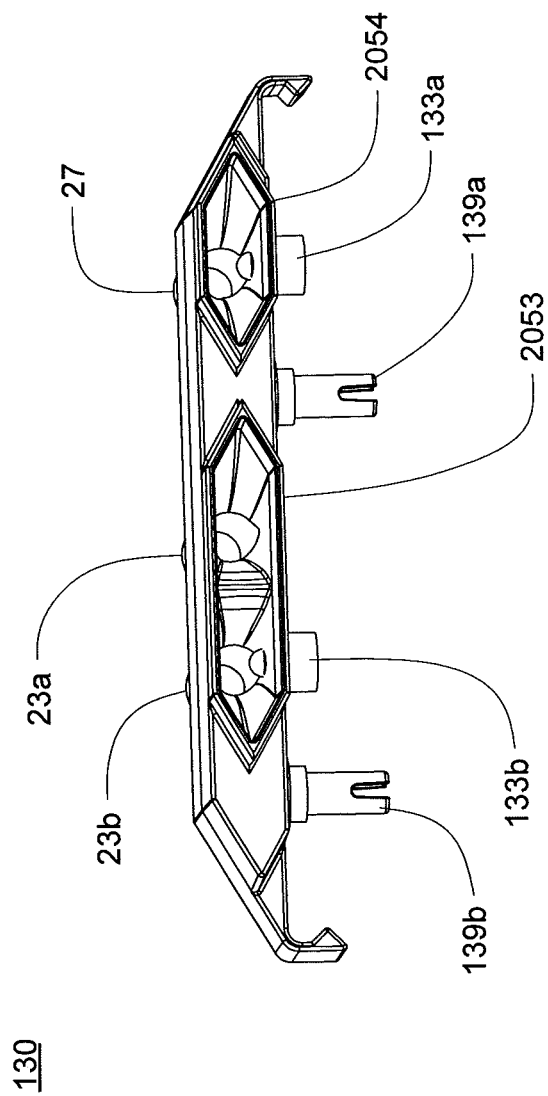
FIGS. 49A and 49B respectively show a perspective backside view and a perspective bottom view of the manifold from FIG. 2, in accordance with an exemplary embodiment of the present invention.
Figure 49B:
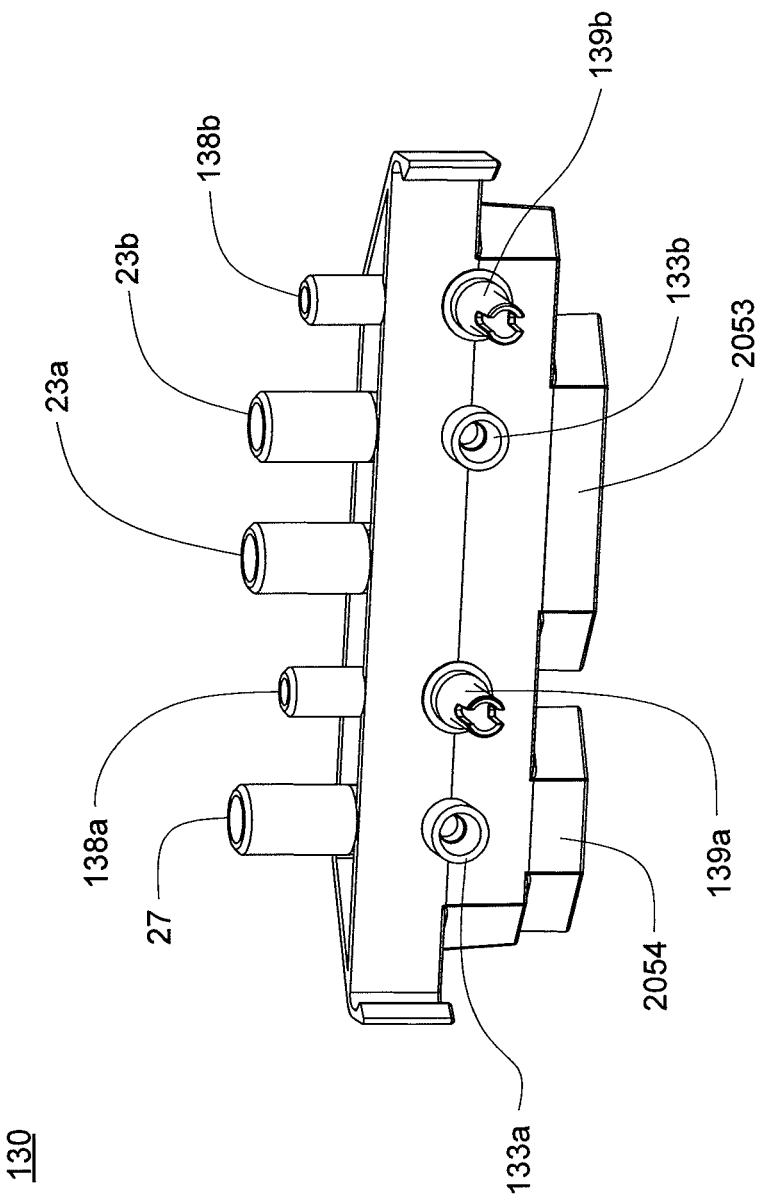

FIGS. 49A and 49B respectively show a perspective back-side view and a perspective bottom view of the manifold 130 from FIG. 2, in accordance with an exemplary embodiment of the present invention. FIG. 49A shows bag inlet and outlet connectors 2053, 2054 for connection at the inlet and outlet openings of the fluid channel 150 of the bag 21. The bag inlet connector 2053 is in fluid communication with the inlets 23a, 23b, while the bag outlet connector 2054 is in fluid communication with the outlet 27. The thermowells 133a and 133b are shown in the outlet fluid path and the inlet fluid path, respectively. The pneumatic interfaces 139a, 139b that are used to provide pneumatic pressure from the base unit 11 to the pneumatic ports 138a, 138b are shown.

Figure 13B:
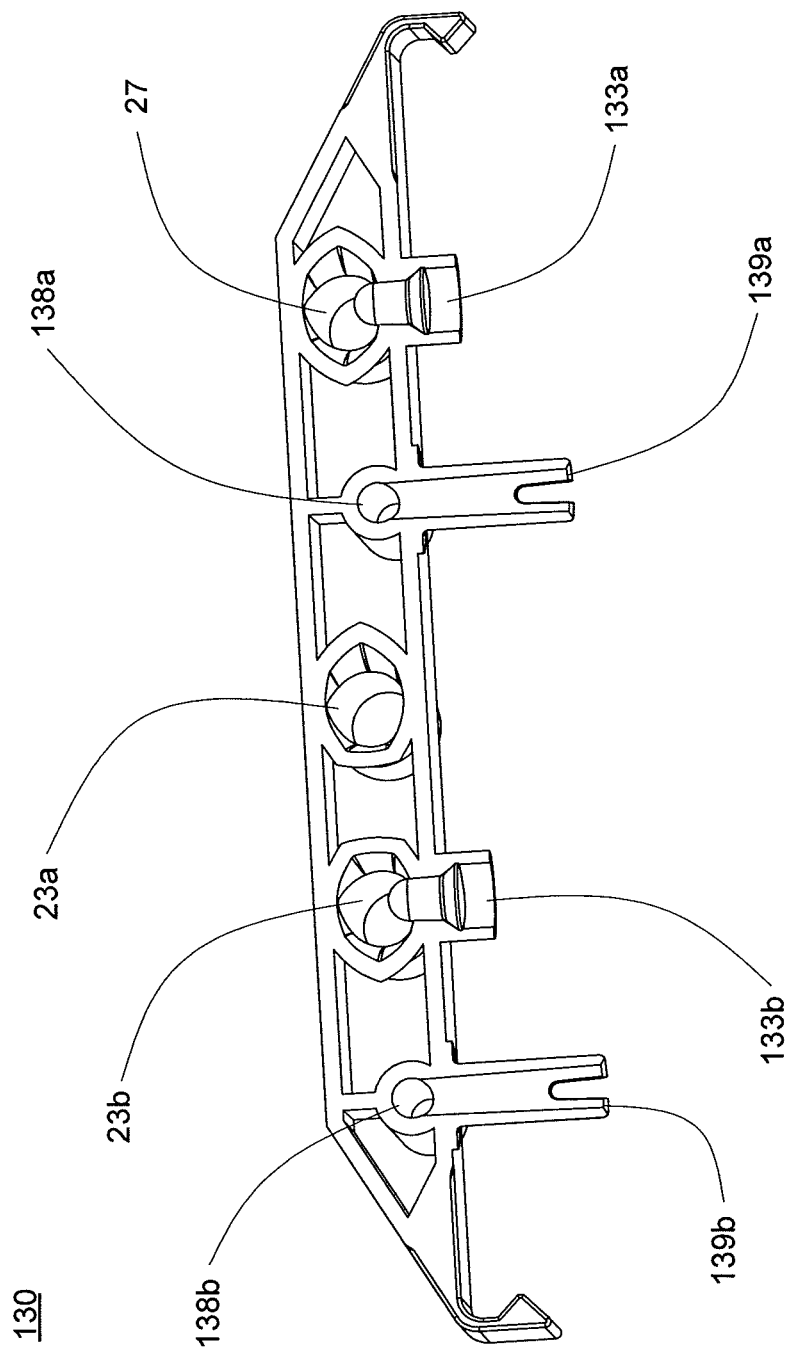
FIG. 13B is a perspective, back-side cross-sectional view of the manifold of FIGS. 2 and 49, in accordance with an exemplary embodiment of the present invention.
Figure 13C:
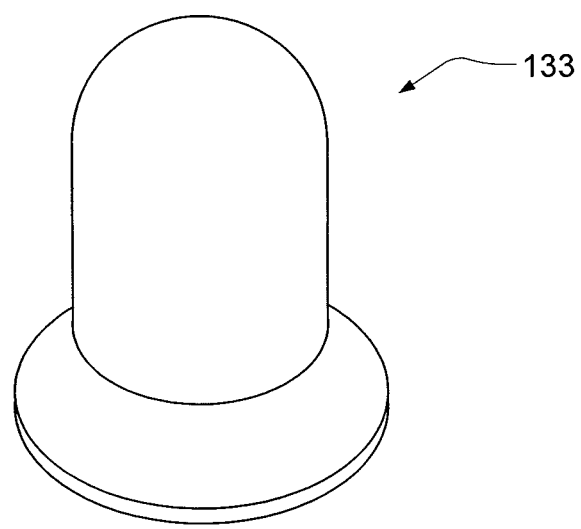
FIG. 13C shows a thermowell that may be used in the manifold of FIGS. 2, 49, and 13B in the heat-exchanger figure of FIG. 1, in accordance with an exemplary embodiment of the present invention.

FIG. 13B shows a perspective back-side cross-sectional view of the manifold 130 of FIGS. 2, 49A, and 49B, in accordance with an exemplary embodiment of the present invention. In this embodiment, the manifold 130 includes an inlet thermowell 133a located in a bag inlet 23a and an outlet thermowell 133b located in a bag outlet 27. The thermowells 133a, 133b interface with corresponding probes in a manifold interface of the base unit 11 (discussed below) when the disposable unit 16 is installed in the base unit 11. FIG. 13C shows a close-up view of an exemplary thermowell.

The thermowells 133a, 133b provide for both thermal and electrical interconnections between the base unit 11 and the disposable unit 16. Among other things, such thermal and electrical interconnections allow the controller 49 to monitor blood temperature as the blood enters and exits the heat-exchanger bag 21 and also allow the controller 49 to take other measurements (e.g., to detect the presence of blood or air in the heat-exchanger bag 21 and to perform leak detection) as discussed below. In this embodiment, each of the thermowells 133a, 133b is coupled so as to have a portion residing directly in the fluid path (i.e., in contact with the blood) so as to permit better transmission of blood temperature from the disposable unit 16 to the base unit 11. In lieu of, or in addition to, the thermowells, the disposable unit 16 may include other temperature probes/sensors and interfaces by which the controller 49 can monitor blood temperature as the blood enters and exits the heat-exchanger bag 21.

While the exemplary embodiment shown in FIGS. 13B, 49A, and 49B include thermal wells for transmitting thermal information to the base unit 11 and optionally for use in conductivity sensing, it should be noted that other types of sensor components may be additionally or alternatively used. For example, rather than using a thermal well, a sensor component that sends temperature measurements or signals to the base unit 11 may be used. Various types and configurations of sensors are described below.

Additionally, the manifold 130 includes various tube supports to holds tubes extending from the pumps (items 25a, 25b in FIG. 2) and the heat-exchanger bag (item 21 in FIG. 13A). These tubes include the tubes leading from the outlets (items 37a, 37b in FIG. 2) of the pumps into the inlets 23a, 23b of the heat-exchanger bag. The outlet 27 of the heat-exchanger bag is also held by the tube support. In a preferred embodiment, the tube support 130 also holds tubes leading to the pneumatic ports (item 38 of FIG. 3) of the pumps and provides the interface between pumps' pneumatic ports and base unit's pneumatic actuation system (item 40 of FIG. 4). The tubes from the pneumatic ports pass into the pneumatic passageways 138a, 138b in the tube support 130; the pneumatic passageways 138a, 138b are respectively in fluid communication with the pneumatic interfaces 139a, 139b. The pneumatic interfaces 139a, 139b connect to receptacles in the base unit, and the receptacles in turn provide fluid communication with pneumatic actuation systems for each of the pumps. This arrangement allows the disposable unit's interface to the base unit to be manufactured more easily and eases the installation of the disposable unit in the base unit. Instead of manufacturing the pumps so that the pneumatic ports are properly positioned with respect to each other for installation into the base unit, the more compact tube support 130 holds the pneumatic interfaces 139a, 139b in the proper position; the smaller size and simpler structure of the tube support 130 makes it easier to manufacture the pneumatic interfaces 139a, 139b with the desired tolerances for installation into the base unit 11. The disposable unit 16 may also include a data key or other feature for interfacing with the base unit 11 in order to provide relevant information to the base unit 11 (e.g., disposable unit serial number and prior usage information) and/or store information provided by the base unit 11 (e.g., usage information).

A similar arrangement may be used with disposable cassettes that include pneumatically actuated pumps and/or valves. As discussed above, if the number of pneumatically actuated pumps and/or valves in a cassette is large enough, the cassette containing these pumps and valves can become so large—and the pressures involved can become so great—that it may become difficult to properly seal and position all of the pumps and valves. This difficulty may be alleviated by placing the valves and pumps in a main cassette, from which connecting tubes lead from pneumatic ports, so that pneumatic communication is provided between valves and pumps in the main cassette and a smaller, secondary tube-support cassette, which is provided with a pneumatic interface for each of the tubes, as shown in FIG. 23. In this way, the proper positioning and sealing of all the pneumatic interfaces can be accomplished more easily with the smaller tube-support cassette than it would be if the pneumatic actuation needed to be applied to the larger main cassette directly. Additionally, or alternatively, valves in the main cassette may be ganged to together in some embodiments, so that several valves may be actuated simultaneously through a single pneumatic interface on the tube-support cassette and through a single connecting tube between the pneumatic interface and the valves.

Figure 26:
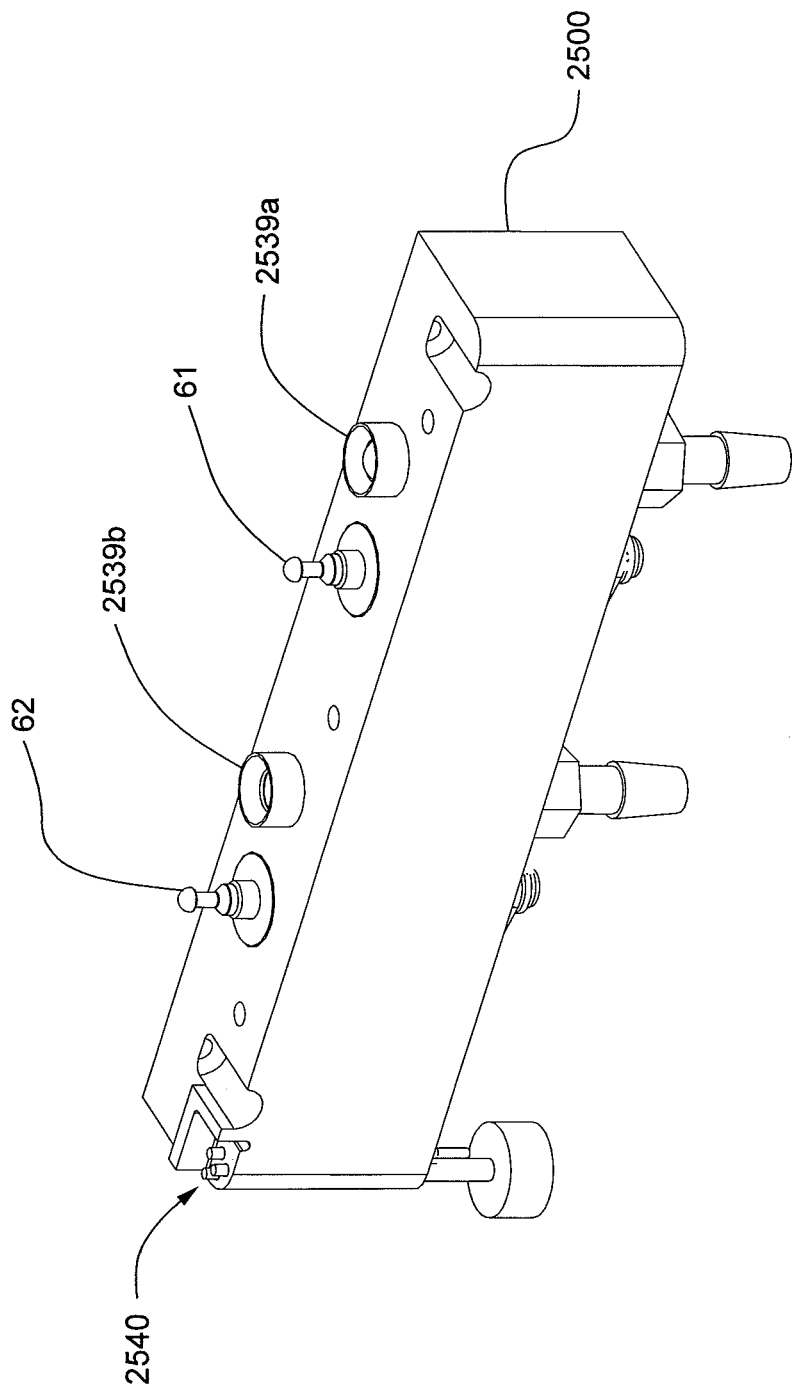
FIG. 26 shows a close-up view of the manifold interface of FIG. 25, in accordance with an exemplary embodiment of the present invention.

FIG. 26 shows a close-up view of the manifold interface 2500 shown in FIG. 25. The manifold interface 2500 includes, among other things, probes 61, 62 and pneumatic ports 2539a, 2539b. With reference again to FIG. 13B, it can be seen that the manifold 130 can be installed in the manifold interface 2500 such that the probes 61, 62 interface respectively with the thermowells 133a, 133b and the pneumatic ports 2539a, 2539b interface respectively with the pneumatic interfaces 139a, 139b. The manifold interface 2500 also includes a data key interface 2540 for interfacing with a corresponding data key in the disposable unit. The data key interface 2540 preferably provides a bi-directional communication interface through which the controller 49 can read information from the disposable unit (e.g., serial/model number, expiration date, and prior usage information) and write information to the disposable unit (e.g., usage information). In an exemplary embodiment, the controller 49 may prevent the start of a treatment if the data key is not present or if the disposable unit is unusable, for example, because it includes an unacceptable serial/model number, is past a pre-configured expiration date, or has already been used. The controller 49 may terminate a treatment if the data key is removed. In lieu of a data key interface 2540, the base unit 11 or manifold interface 2500 may include other types of interfaces for reading information from the disposable unit and/or writing information to the disposable unit (e.g., RFID, bar code reader, smart key interface).

It should be noted that one or more pumps (e.g., pump pods) may be integral with a manifold such as the manifold 130 and placed in a base unit as a single cartridge. The assembly could include pneumatic connections from the pneumatic ports (which are connected to the base unit) directly to the pump actuation chambers so that no external tubing would be needed to make the pneumatic connections to the pump pods. The assembly could additionally or alternatively include fluidic connections (e.g., from the pump outlets to the interface with the heat-exchanger bag) so that no external tubing would be needed between the pump outlets and the manifold or bag.

3.1.6. Exemplary Blood Heating Schematic

Figure 6:
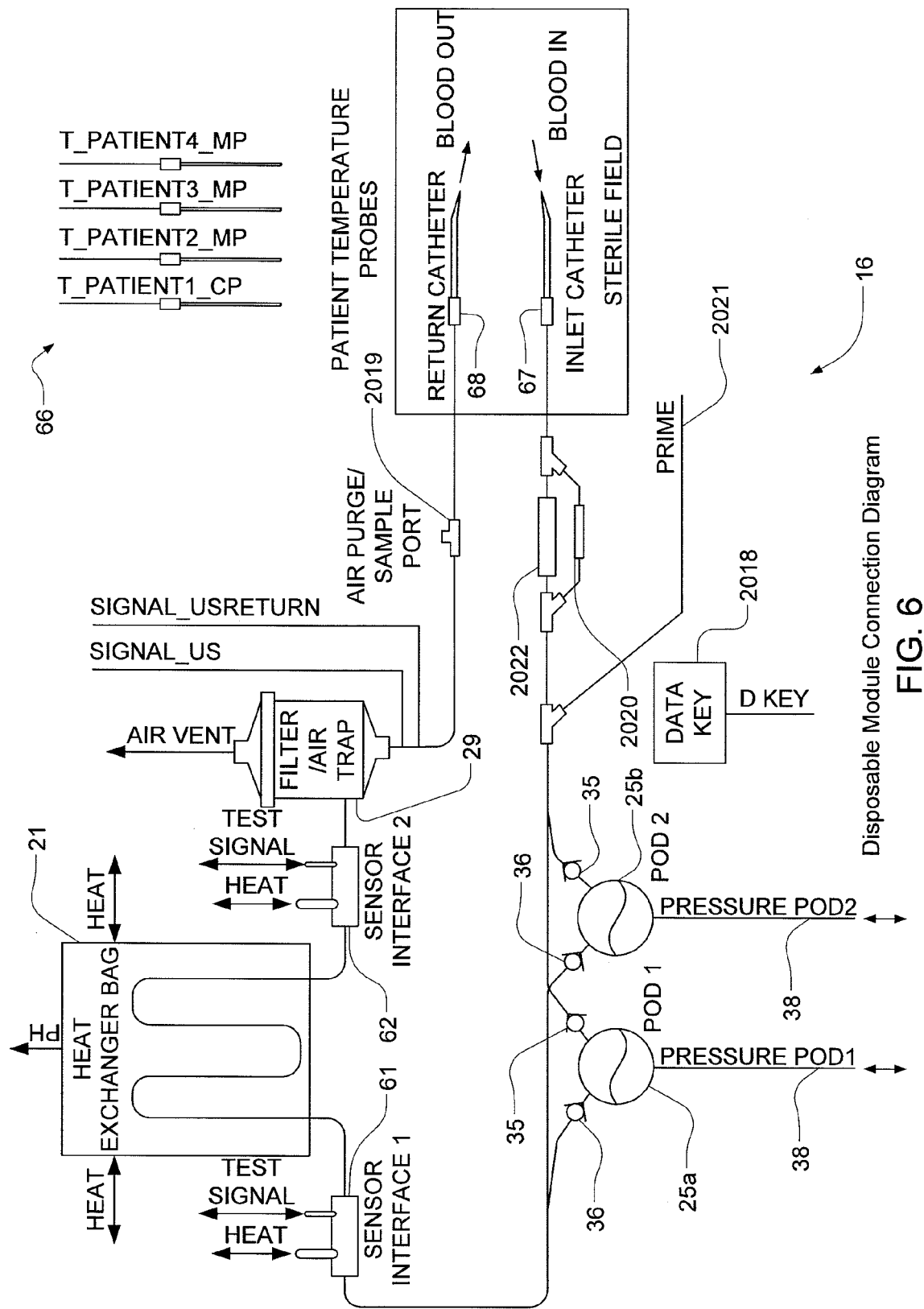
FIG. 6 is a schematic of an embodiment of the extracorporeal blood heating system.

FIG. 6 is a schematic of the disposable unit 16 connections in accordance with an exemplary embodiment of the present invention. After the disposable unit 16 is primed, an inlet catheter 67 and an outlet catheter 68 are inserted into a vein or veins of a patient. Several patient-temperature probes 66 are disposed in or on the patient; these probes 66 provide patient-temperature information to the controller in order to monitor possible overheating of the patient.

The action of the pump pods 25a, 25b—which are acted on by the base unit's pneumatic actuation system (under control of the controller 49) through pneumatic ports 38—draws the blood from the inlet catheter 67 into the disposable unit's tubing. The pump pods' inlet and outlet check valves 35, 36 ensure that the blood travels in the correct direction through the disposable unit's tubing (i.e., in a clockwise direction in the schematic shown in FIG. 6). After exiting the pump pods 25a, 25b, the blood is pumped to the heat-exchanger bag 21, which is preferably installed between two heating plates in the base unit. Before the blood enters the heating area, the temperature is measured via a bag-inlet temperature sensor 61, which communicates inlet temperature information to the controller 49. After being heated, the blood's temperature is again measured via a bag-outlet temperature sensor 62, which also provides temperature information to the controller 49. The heated blood then flows through the air trap/filter 29 and then to the patient through the return catheter 68.

The controller preferably uses a closed-loop control scheme based on, among other things, patient temperature information (e.g., received through the patient interface 2704), blood temperature information (e.g., received via the thermal wells in the manifold 130 and the corresponding sensors in the manifold interface 2500), and pump status information (e.g., reservoir pressure, actuation chamber pressure, end-of-stroke detection, volumetric measurements, air detection, occlusion detection, leak detection) to attain/maintain patient body temperature and ensure that blood is not overheated locally (e.g., even if the patient body temperature is at a safe level, it may be possible for the blood to overheat in the heat-exchanger component, for example, if the heat exchanger malfunctions or blood is not pumped at a sufficient rate). Furthermore, the controller typically receives multiple patient temperature inputs. The controller may adjust the heat exchanger and/or pump operation dynamically based on patient temperature information and blood temperature information.

The bag-inlet temperature sensor 61 and the bag-outlet temperature sensor 62 may be mounted permanently in the base unit 11 adjacent where the inlet and outlet of the bags are located. In order to improve thermal conductivity between the blood flowing within the bag and the temperature sensors located outside of the bag—and thereby improve the accuracy of the temperature readings—the bag may be provided with metal thermowells which extend into the flowpath of the blood at the bag's inlet and outlet. When the bag is placed between the heating plates, the thermowells can accommodate and receive the temperature sensors 61, 62 extending from the base unit 11. As discussed below, the metal thermowells can also be used as electrical conductors and thus be used to detect leaks or air in the bag 21.

In the system shown in FIG. 6, a prime line 2021 may be provided to supply a priming fluid (e.g., water) to the pod pumps. An air purge/sample port 2019 may also be provided to facilitate air purging and also to allow for sampling of the blood being returned to the patient. A blood monitoring interface may also be provided, for example, including shunt sensor connections (mating luer locks) 2020 and disposable H/S cuvette 2022 for a CDI™ Blood Parameter Monitoring System 500 blood gas monitor sold by Terumo Cardiovascular Systems, Corp.

In various alternative embodiments, the controller 49 may detect abnormal conditions in the system based on several factors including: (i) the difference in the bag-inlet and bag-outlet temperatures measured respectively by the bag-inlet and bag-outlet sensors 61, 62, (ii) the volumetric flow rate of blood through the disposable unit 16, and (iii) the power being provided to the base unit's heating plates. If each the pump pod 25a, 25b expels the same, known volume of blood during each expel stroke, the volumetric flow rate can be measured by simply measuring the rate of expel strokes, and multiplying that rate by volume expelled per stroke. (The flow rate can be determined in this way as long as full pump strokes are being performed. As discussed above, the controller in a preferred embodiment monitors whether full strokes are being performed by dithering the valving mechanism and analyzing the pressure information from the actuation-chamber-pressure transducers.) The product of three factors—the measured flow rate, the measured increase in blood temperature, and the specific heat of the blood—should be proportional to the power going into the heating plates. If this proportion varies significantly during a procedure, the controller preferably generates an alarm signal, which may be used to cause an indication to a medical technician monitoring the procedure or which may be used directly to stop the procedure.

Preferably, the controller generates two estimates based on a given set of temperature and flow-rate measurements, with one estimate based on all the uncertainties biased one way and the other estimate based on all the uncertainties biased the other way. The electrical power being consumed by the heating plates should always be below one estimate and above the other estimate; if the power measurement falls outside of this range, the controller will preferably generate the alarm signal.

It should be noted that the system may include other types of sensors and systems. For example, the system could provide anticoagulant to the patient, particularly to allow for extended treatments. The system could provide additional fluid to the patient, and may include a hydration sensor to detect dehydration of the patient, particularly due to the hyperthermic treatment. The system could also include a hemolysis sensor to monitor for excessive amounts of hemolysis. Some of this sensing may involve conductivity sensing using the thermal wells/sensors or other mechanisms.

3.1.7. Leak and Air Detection

In certain embodiments, detection of leaks in the heat-exchanger bag 21 may be accomplished by measuring the electrical conductivity between one or both of the thermowells 133*a*, 133*b* and one or both of the upper and lower heating plates 12, 14. As discussed above, the base unit 11 includes sensors 61, 62 that interface with the thermowells 133*a*, 133*b* for providing electrical connectivity between the base unit 11 and the disposable unit 16. The base unit 11 typically also includes electrical probes connected to each of the heating plates 12, 14, which should also be electrically conductive. If there is a leak, the electrical conductivity between the thermowells and the heating plates should increase substantially (because the fluid passing through the leak is generally a much better conductor of electricity than the bag material). Normally, the resistance between the electrical probe contacting the thermowell and each of the electrical probes on the heating plates should be quite high, because the plastic material from which the bag is made is a relatively good insulator. However, if there is a leak, the liquid (e.g., the blood) passing through the leak in the bag provides a very good conductor of electricity, so the resistance drops significantly when there is a leak. Thus, the controller, which is in communication with these electrical probes, measures the conductivity between the probes and generates an alarm signal when the conductivity increases by a certain amount.

Similarly, the metal thermowells can also be used to detect air in the flow path in the bag. If there is air in the bag, the resistance between the thermowells and the plates will increase, because air is a poor conductor of electricity. Thus, if the controller detects a decrease in the electrical conductivity between the plates and the thermowells, and if the decrease is more than a certain amount, the controller will preferably generate an error signal and will preferably cause the procedure to stop.

Additionally or alternatively, the system could include other types of sensors to detect leaks, e.g., a carbon dioxide sensor for detecting blood leakage. A carbon dioxide sensor would typically be placed in an appropriate location, such as proximate to the fluidic paths through which blood passes, perhaps within a partially or fully enclosed space (e.g., within the heat exchanger with the door closed). The carbon dioxide detector could be included in the base unit or otherwise in communication with the base unit controller.

3.1.8. Patient Temperature Monitoring

In a blood-heating procedure, the temperature of the patient must be closely monitored in order to prevent the patient from overheating beyond a safe limit. In certain embodiments, at least two separate temperature probes are located in the patient, e.g., one in the abdomen—either in the bladder or the rectum, in contact with the bladder wall or the rectal wall—and the other through the nasal passage, in contact with back wall of the nasal passage (patient temperature can be monitored using a single probe or more than two probes and can be monitored from other locations or methods, e.g., by monitoring air expired by the patient). If both sensors are properly positioned, the temperature readings of the two probes should be within a certain range. If the temperature readings from the two probes differ from each other too much, the controller may generate an alarm signal and/or abort the procedure. During the preparation for the blood-heating procedure, as the probes are being inserted into the patient, the readings of the two probes may be compared with each other and also compared normal patient temperature readings; when the two probes fall within a pre-set range of each other and within a range of normal patient temperature readings, the medical personnel positioning the probes will be able to tell when they have properly positioned the probes.

Figure 19:
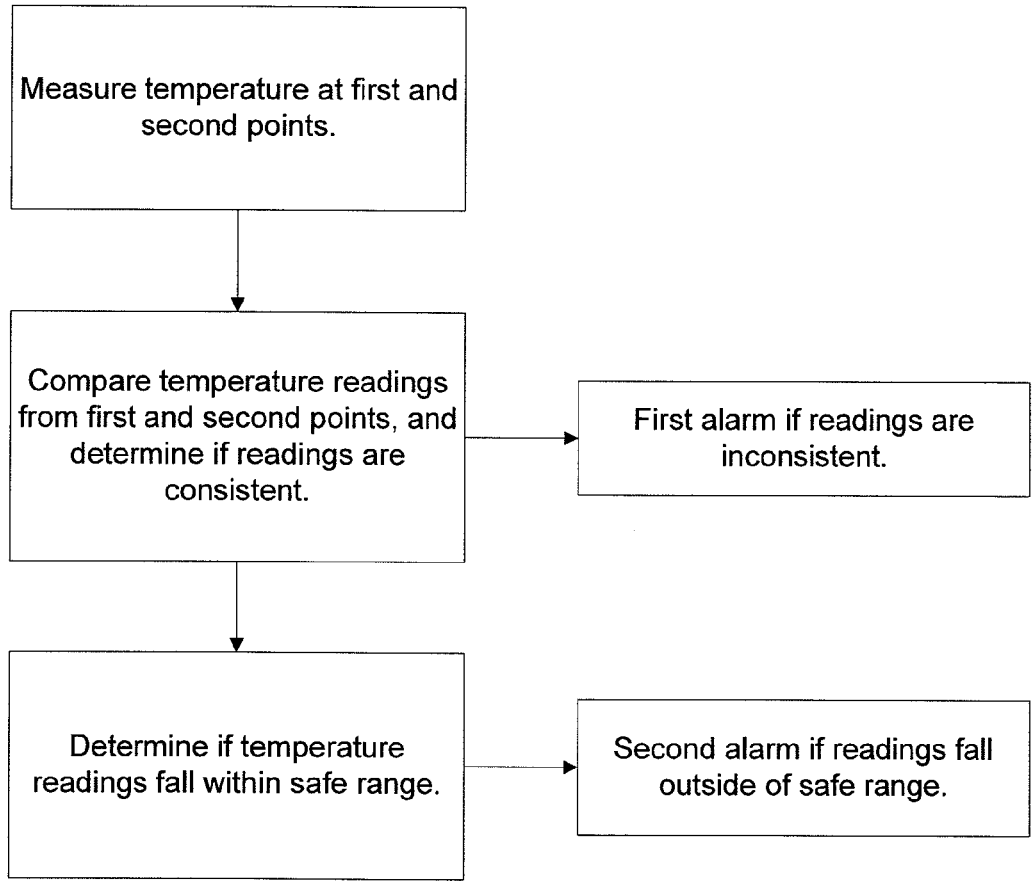
FIG. 19 is a flow chart showing a method for checking a patient's temperature.

During the blood-heating procedure, the method shown in FIG. 19 is preferably followed in order to ensure that the patient does not get dangerously overheated. In step 90, temperature readings from the abdominal and nasal probes are taken. In step 91, the readings are compared with each other; if the readings fall outside of a pre-set range, an alarm signal is generated indicating a fault in the temperature readings. In step 92, the controller monitors the temperature readings from one of the two probes and compares those readings to a pre-set upper limit; if a reading is above this pre-set upper limit, an alarm signal is generated indicating the patient is getting too overheated.

As discussed above, the controller of the heat-exchanger system may monitor patient body temperature using at least two temperature probes. In actuality, the controller really only needs temperature readings from a single temperature probe; the second temperature probe essentially provides a control against which readings from the first temperature probe can be compared. In certain embodiments, then, a single temperature probe may be used to provide patient temperature readings to the controller. In such embodiments, an operator could independently monitor a second temperature probe and manually abort the procedure if the two temperature readings do not match sufficiently.

3.1.9. User Interface

Figure 27:
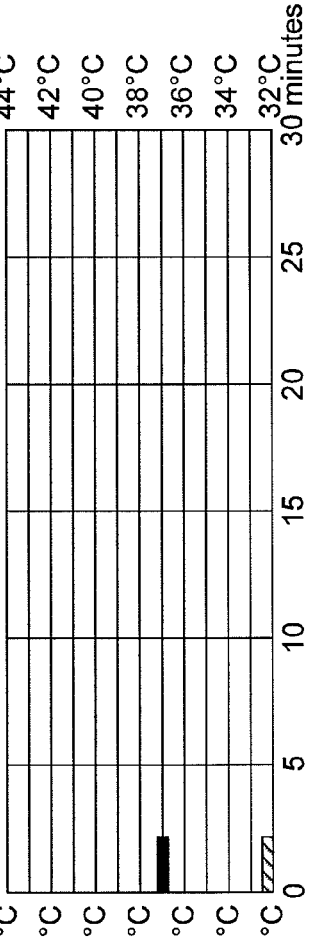
FIG. 27 shows an exemplary user interface screen in accordance with an exemplary embodiment of the present invention.

FIG. 27 shows an exemplary user interface screen in accordance with an exemplary embodiment of the present invention. The right-hand side of the screen includes various therapy controls including (from top to bottom) indicators for the various therapy phases (i.e., system idle, pre-check, prime, warm-up, plateau, cool-down, and end-therapy) for displaying the current phase of treatment (in this example, "warm-up" is highlighted, indicating that the therapy is currently in the warm-up phase), a phase progress indicator for showing, e.g., the time remaining or time elapsed in the current phase, and four control buttons through which the operator can control the therapy (e.g., pause treatment, stop treatment, start or re-start treatment, and step to the next phase). It should be noted that these four control buttons prevent an operator from stepping backward to a previous stage. The left-hand side of the screen allows the operator to tab through screens providing patient information, status information, temperature graphs, flow graphs, and logs.

3.1.10 Alternative Heat-Exchanger Embodiments

In the embodiments described above, fluid is heated or cooled by running the fluid through a heat-exchanger bag that is placed between two plates of a heat exchanger. Of course, the present invention is in no way limited to the use of a heat-exchanger bag or plates. In alternative embodiments, heat-exchanger bags may be used with other types of heat exchangers (e.g., a heat-exchanger bag could be rolled up and placed in a tubular chamber or could be placed in other types of heat exchangers, such as an oven, refrigerator, water bath, or radiator). Additionally or alternatively, other types of fluid conduits (e.g., a length of tubing and/or a radiator) may be used with one or more plates. The heat exchanger may include heating and/or cooling capabilities. In fact, the heat-exchanger could include both heating and cooling capabilities so that the heat-exchanger system could be used for both heating and cooling applications, either as part of the same treatment (e.g., so that blood could be heated for hyperthermic treatment and quickly returned to normal temperature following treatment) or as part of separate treatments (e.g., the base unit could be used to provide hyperthermic treatment to one patient and later to provide hypothermic treatment to another patient).

In one particular alternative embodiment, the disposable unit includes, or is configured to use, a length of tubing as the heat-exchanger component. The length of tubing is preferably thin-walled lay-flat tubing, although other types of tubing may be used. The tubing is placed in the radiator, which may be part of the disposable (e.g., the radiator may be attached to the manifold so that the entire unit can be placed in a base unit), part of the base unit (e.g., the radiator may be integral or attached to one of the heat-exchanger plates), or a separate component that may be disposable or reusable. In any case, the radiator preferably includes a channel for receiving the length of tubing.

Figure 75:
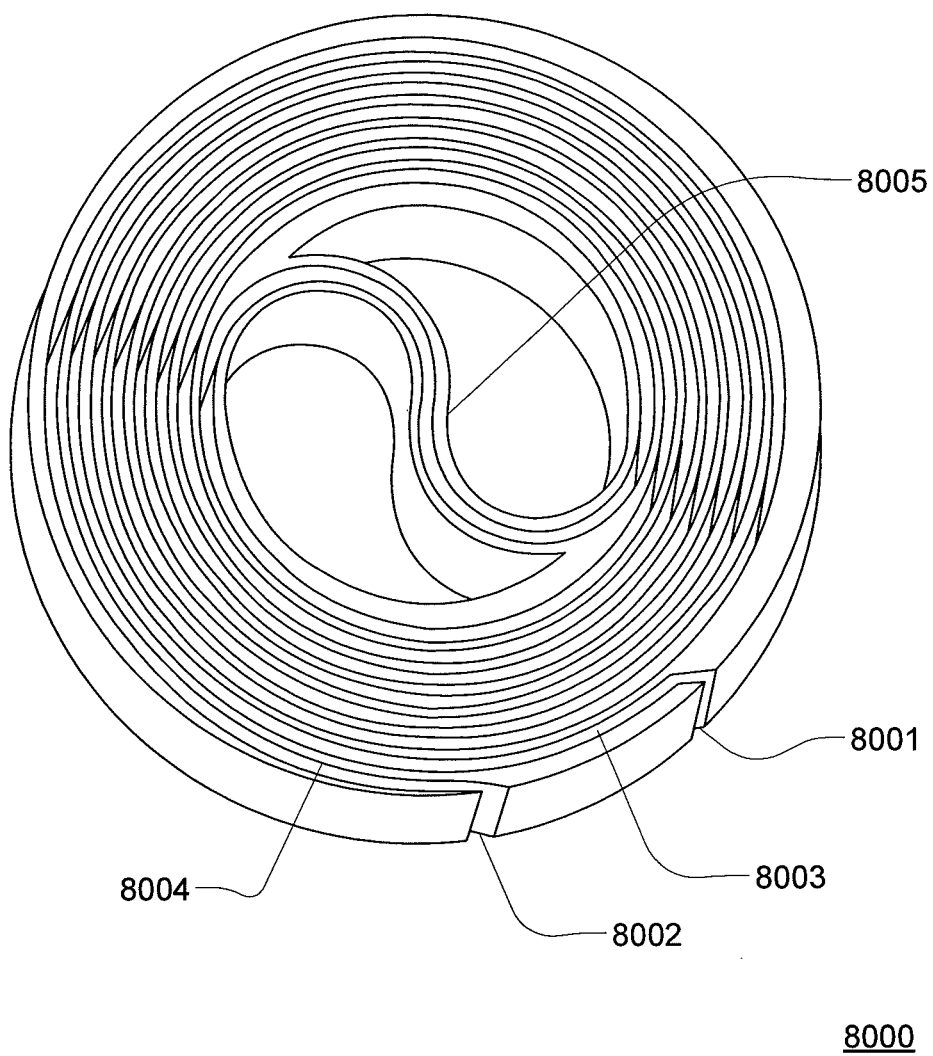
FIG. 75 shows a radiator for use with a length of tubing, in accordance with an exemplary embodiment of the present invention.
Figure 76:
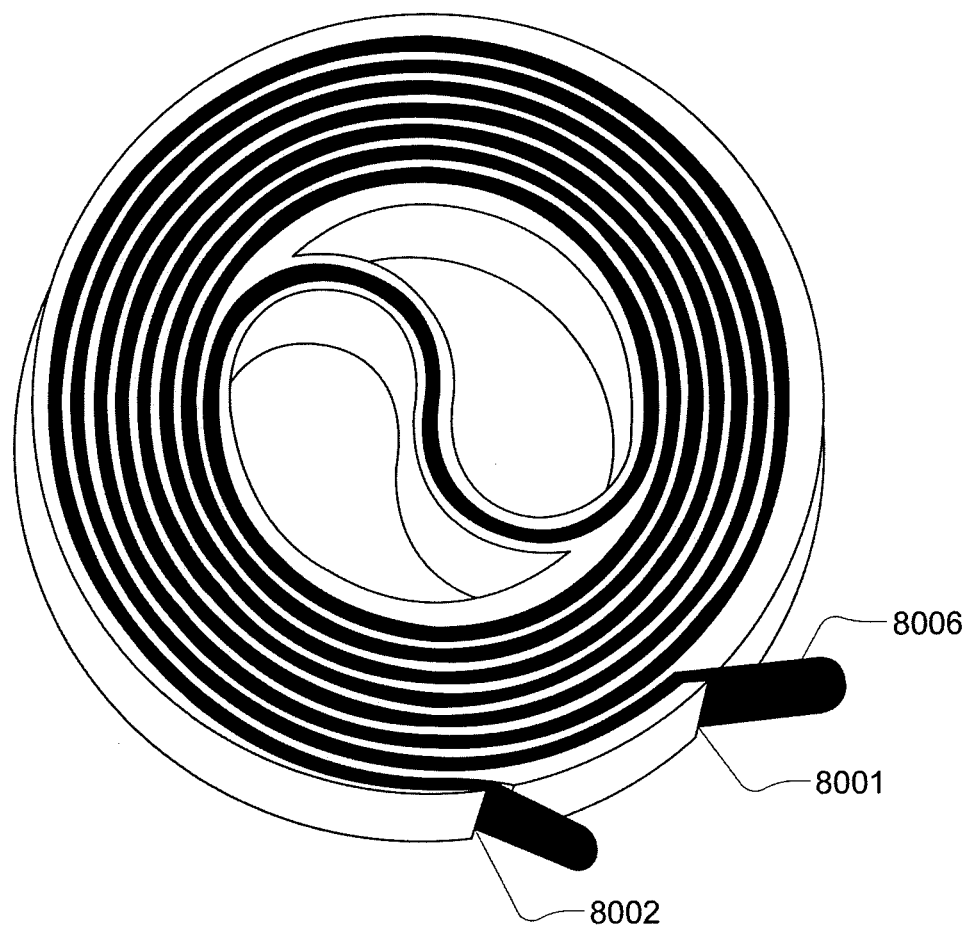
FIG. 76 shows a length of flexible tubing install in the radiator of FIG. 75 in accordance with an exemplary embodiment of the present invention.

FIG. 75 shows a radiator 8000 in accordance with an exemplary embodiment of the present invention. The radiator 8000 has a contiguous channel from a first opening 8001 to a second opening 8002. The channel is configured to receive a length of tubing 8006 (e.g., thin-walled lay-flat tubing) such that one end of the tubing will protrude from the opening 8001 and the other end of the tubing will protrude from the opening 8002, as shown in FIG. 76. The tubing may be placed in the radiator by the user (particularly if the radiator is part of the base unit or is a separate, reusable component) or may be provided already installed in the radiator (particularly if the radiator is part of the disposable unit). The radiator is generally made of a thermally conductive material, such as a thermally conductive plastic or metal. In an exemplary embodiment, the radiator 8000 may be approximately six inches in diameter and approximately two inches in height.

In this embodiment, the channel includes inner and outer concentric loops (8003 and 8004, respectively) that are connected via a serpentine section 8005. Among other things, this configuration allows both of the openings 8001, 8002 to be accessible along the outer edge of the radiator. Assuming the opening 8001 (leading to the inner loop 8003) represents the fluid inlet point and the opening 8002 (leading to the outer loop 8004) represents the fluid outlet point, then the fluid will flow through the tubing in the inner loop 8003 in a clockwise direction and will flow through the tubing in the outer loop 8004 in a counter-clockwise direction (using the orientation shown in FIG. 76). The serpentine section 8005 connects the two loops and reverses the flow direction. It should be noted that the inner and outer loops 8003, 8004 and the serpentine section 8005 are configured to avoid sharp or abrupt fluid direction changes and therefore avoid imparting excessive shear forces or turbulence on the fluid. It should also be noted that the arrangement of tubing (and particularly lay-flat tubing, which expands when carrying pressurized fluid) and radiator should provide for efficient heat exchange because of the close coupling of the tubing with the radiator and because of the large surface areas involved.

Figure 77:
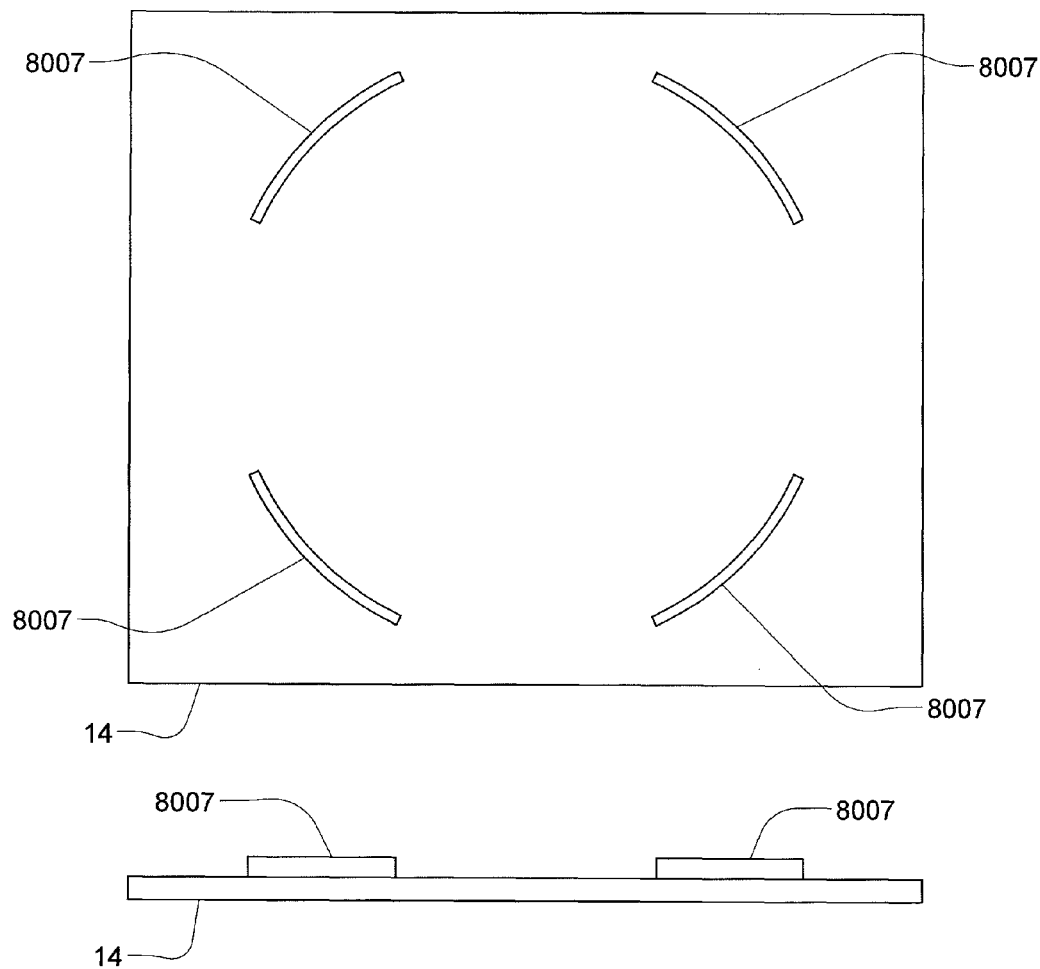
FIG. 77 shows a heat exchanger plate having guides for receiving the radiator of FIG. 75, in accordance with an exemplary embodiment of the present invention.
Figure 78:
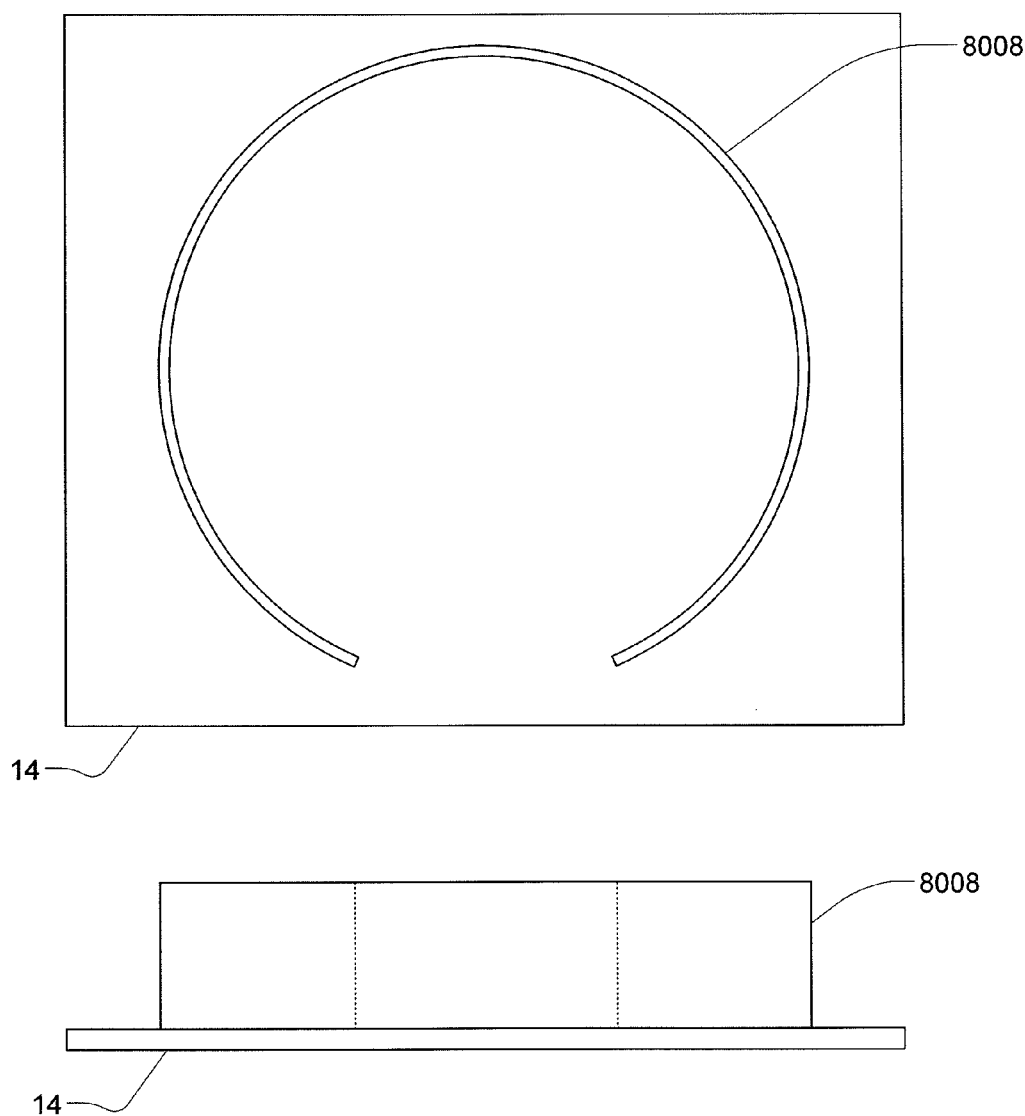
FIG. 78 shows a heat exchanger plate having a cylindrical wall for receiving the radiator of FIG. 75, in accordance with an exemplary embodiment of the present invention.
Figure 79:
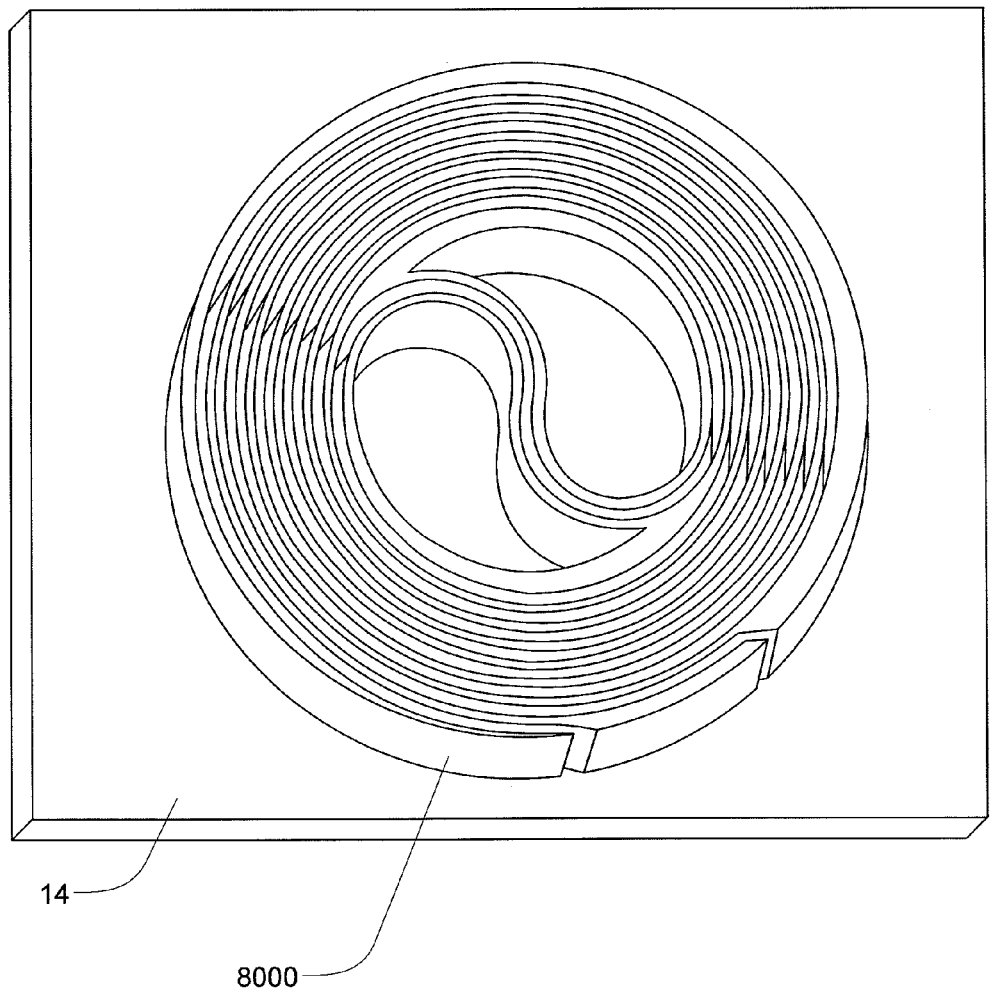
FIG. 79 shows a heat exchanger plate having an integral radiator of the type shown in FIG. 75, in accordance with an exemplary embodiment of the present invention.

As discussed above, the radiator 8000 could be provided as part of the disposable unit or as a separate component, and in such cases the radiator 8000 would generally be placed into an appropriately configured heat exchanger of the base unit. For example, the radiator 8000 could be placed between two plates of a heat exchanger (similar to the way the heat-exchanger bag is placed between two plates in various embodiments described above), in which case the heat exchanger may be configured to accommodate the radiator 8000, such as, for example, by having the two plates farther apart and/or using a special door hinge to allow the upper plate to lie flat against the top of the radiator. The bottom plate could include guides (e.g., guides 8007 as shown in FIG. 77 in both top view and front view) or a cylindrical wall (e.g., cylindrical wall 8008 as shown in FIG. 78 in both top view and front view) to facilitate placement of the radiator into the heat exchanger. Also as discussed above, the radiator could be part of the base unit. For example, the radiator 8000 could be integral to the bottom plate 14, as shown in FIG. 79.

Figure 80:
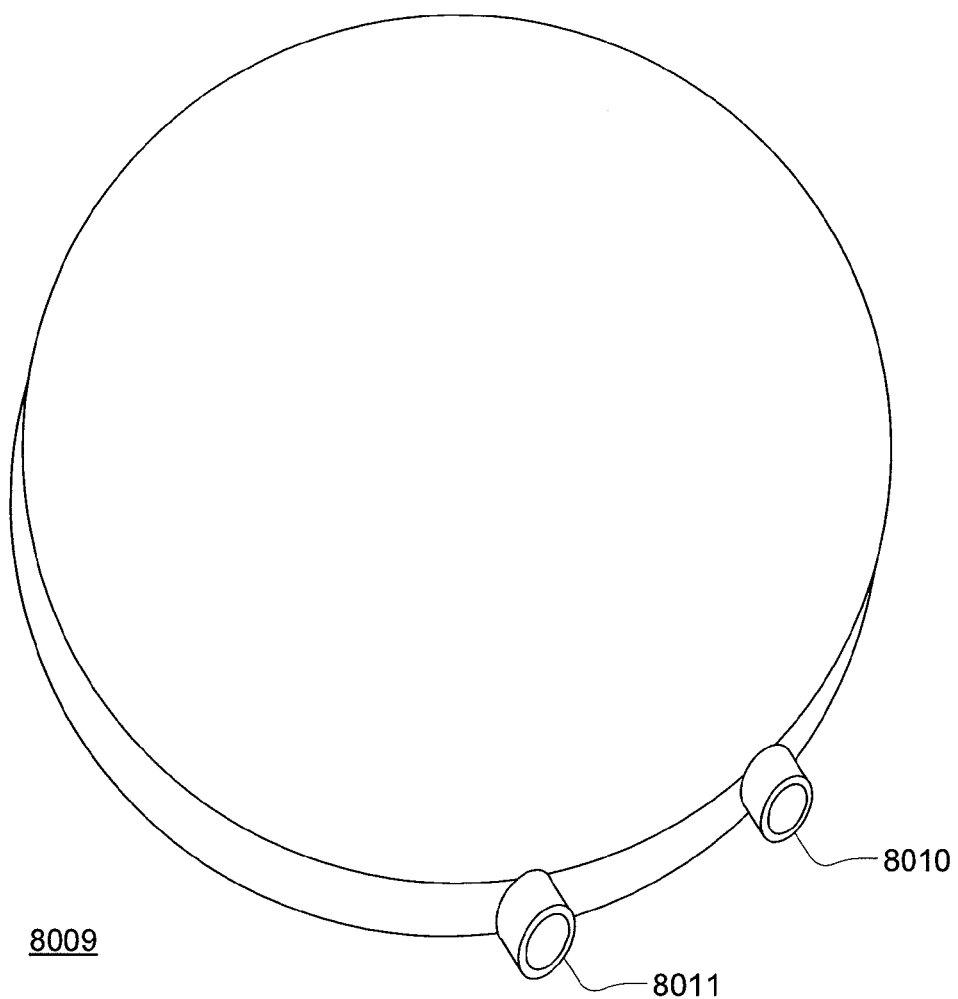
FIG. 80 shows an enclosed radiator having fluid inlet and outlet ports, in accordance with an alternate embodiment of the present invention.

Alternatively, certain types of radiators may be used without separate tubing, such that fluid is carried directly in the channel of the radiator. Such radiators would typically be disposable, although they could be reusable, for example, after being rinsed and disinfected. FIG. 80 shows an enclosed radiator 8009, similar to the radiator 8000 described above, and including two ports 8010, 8011 for accommodating fluid connections such as tubing connections to a manifold or directly to one or more pumps. As with the radiator 8000 described above, the radiator 8009 could be part of the base unit, part of the disposable unit, or a separate component.

It should be noted that these embodiments are exemplary and are not intended to represent all of the types of heat-exchanger components that can be used in heat-exchanger systems of the types described herein.

3.2. Regional Hyperthermic Chemotherapy Treatment

Figure 45:
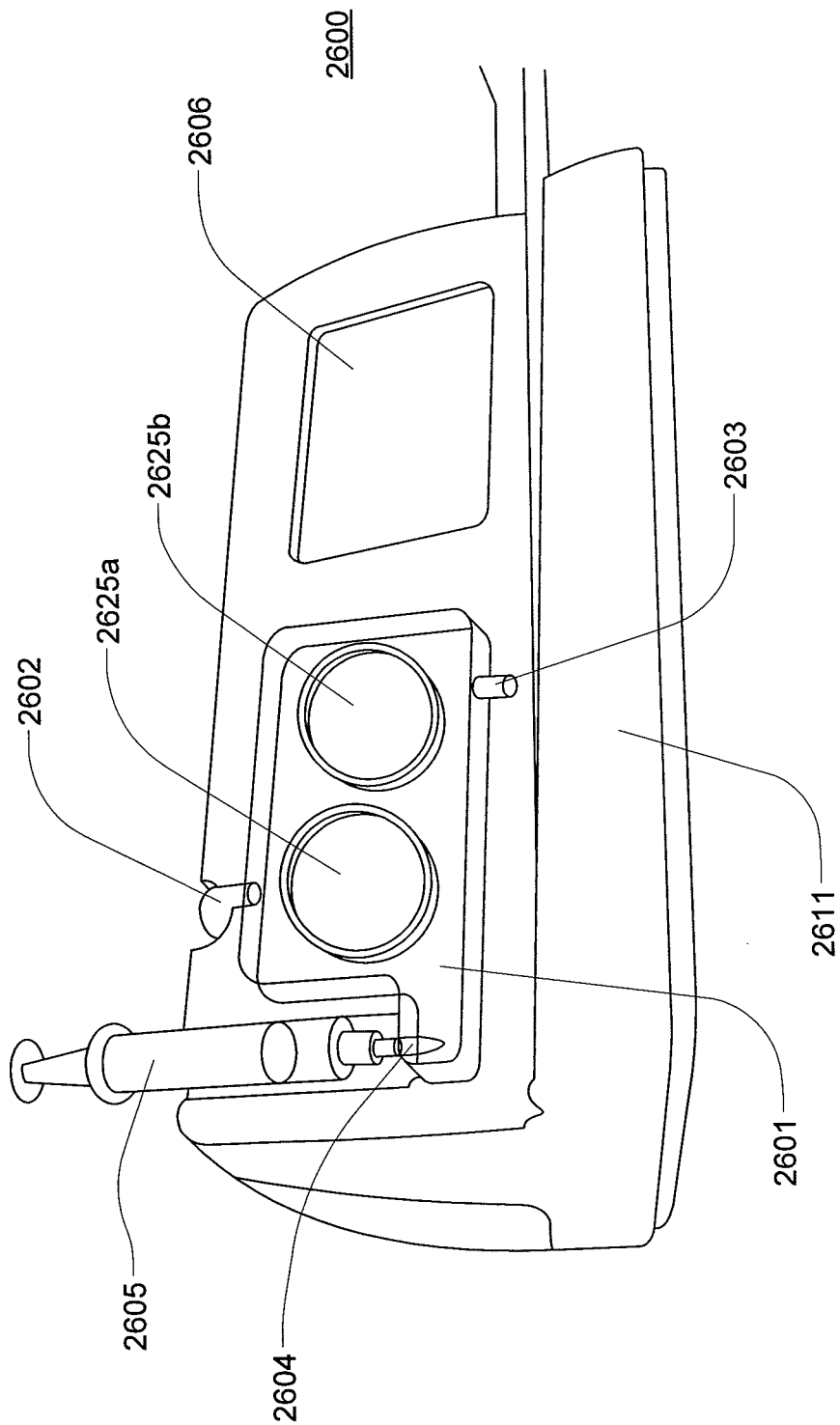
FIG. 45 shows a representation of a regional hyperthermic chemotherapy treatment system in accordance with an exemplary embodiment of the present invention.

FIG. 45 shows a representation of a regional hyperthermic chemotherapy treatment system 2600 in accordance with an exemplary embodiment of the present invention. The system 2600 is essentially a smaller version of a heat-exchanger system of the types described above in that it includes a base unit 2611 and a disposable unit 2601. Similar to the systems described above, the base unit 2611 includes a heat exchanger, a pneumatic control system, a controller, and a built-in user interface screen 2606. The disposable 2601 (e.g., a cassette) includes two pump pods 2625a and 2625b, a single inlet 2602, a single outlet 2603, and a drug delivery interface 2604 (in this example, a syringe interface, although other types of interfaces, such as a luer port or a spike, may be included in alternative embodiments).

An exemplary embodiment of the system 2600 is designed to circulate approximately 1-2 liters per minute with added medication delivery, and also provide for draining. The system 2600 may be used for regional or localized therapies, such as, for example, filling a body cavity (e.g., upon removal of a tumor) with a chemotherapy solution at elevated temperature for some period of time, and then draining the cavity. The system 2600 may also be used to locally circulate bodily fluid (e.g., blood) with added medication, e.g., tourniquet a section of the body (e.g., a single lung) and circulate fluid.

In a typical application, the pump inlet 2602 may be in fluid communication with a fluid source (typically a separate reservoir, although fluid could be drawn directly from the patient), and the pump outlet 2603 may be in fluid communication with the patient for delivering fluid from the fluid source to the patient. A fluid source reservoir or a separate receptacle may coupled so as to receive fluid drained from the patient. Thus, for example, a reservoir may be used to provide source fluid and a separate receptacle may be used to receive the drained fluid or the same reservoir (which could be the patient) may be used both to provide the source fluid and receive the drained fluid. The pump can be any fluid pump, including but not limited to, a pod pump of the types described herein, or any other type of diaphragm or other fluid pump. As fluid is pumped to the patient, medications or other fluids (e.g., one or more chemotherapy drugs) may be introduced into the fluid through the drug delivery interface 2604, for example, using an automatic syringe or any other automated or manual drug delivery device.

During such pumping, the temperature of the fluid is controlled and is maintained at a predetermined temperature (e.g., about 37° C., or body temperature) during the entire process. The temperature control can be accomplished by use of a temperature sensor in conjunction with a heater. In certain embodiments, the temperatures sensor may be any of the types described herein. The temperature sensor can be located anywhere in the fluid path, and in the preferred embodiment, is anywhere in the fluid path outside of the patient. The fluid may be heated using any method including, but not limited to, induction heating or surface heating. The fluid may be heated in the reservoir or somewhere else along the fluid path.

In one exemplary embodiment, the patient inlet may be located in the patient's peritoneum. The fluid and drug may be pumped into the patient until either a threshold fluid pressure has been reached or until a threshold fluid volume has been pumped into the patient, signifying completion of a fill stage. The fluid is typically allowed to remain in the patient for a certain amount of time, after which it is typically drained from the patient (e.g., by actuating a variable impedance on the patient outlet side). Fill/drain cycles may be repeated a predetermined number of times based on the patient's therapy needs.

In another exemplary embodiment, a portion of the patient (e.g., a patient's limb) may be isolated, e.g., using a tourniquet or pressure cuff. Bodily fluid (e.g., blood) mixed with medication or other fluid may be circulated through the isolated area in a manner similar to that described above. The fluid temperature may be maintained using an in-line heater.

Figure 84:
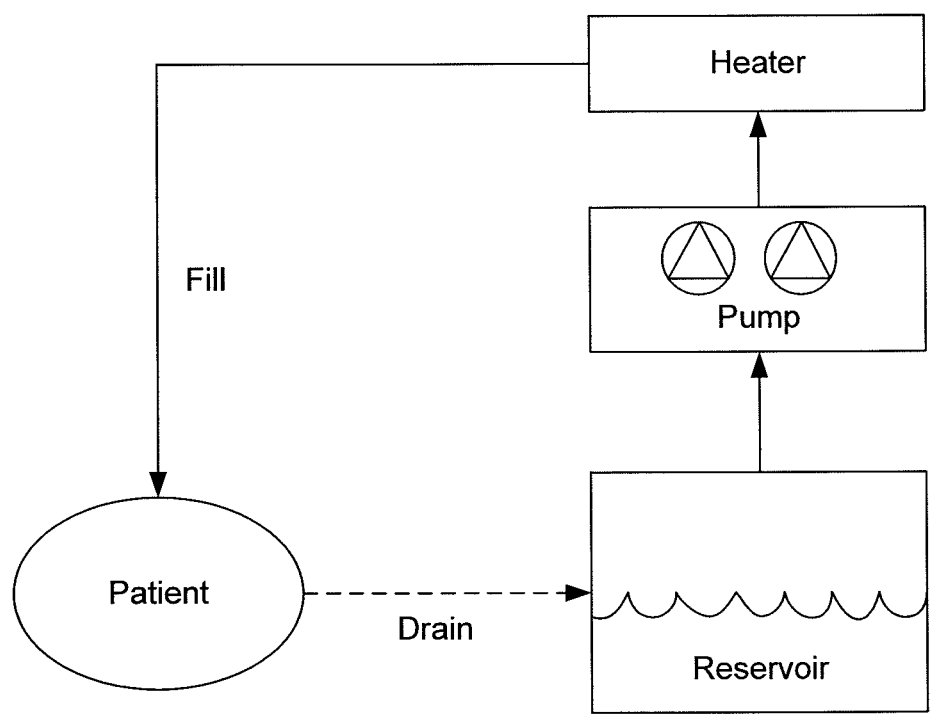
FIG. 84 shows a fluid circuit that may be used for providing regional hyperthermic chemotherapy treatment, in accordance with an exemplary embodiment of the present invention.

FIG. 84 shows a fluid circuit that may be used for providing regional hyperthermic chemotherapy treatment, in accordance with an exemplary embodiment of the present invention. A reservoir holds fluid to be delivered to the patient. In this example, the fluid is pumped through a heater and into the patient. In alternative embodiments, the fluid may be heated in the reservoir and the in-line heater may be omitted. In some embodiments, the fluid in the reservoir may include medication, while in other embodiments, fluid may be added via the pump or by other means (e.g., a separate inlet into the fluid path. Fluid from the patient may be drained back to the reservoir or to some other receptacle (or simply discarded). The volume of fluid pumped and/or drained may be monitored in the reservoir, e.g., using a capacitive level probe or other sensor.

Figure 85:
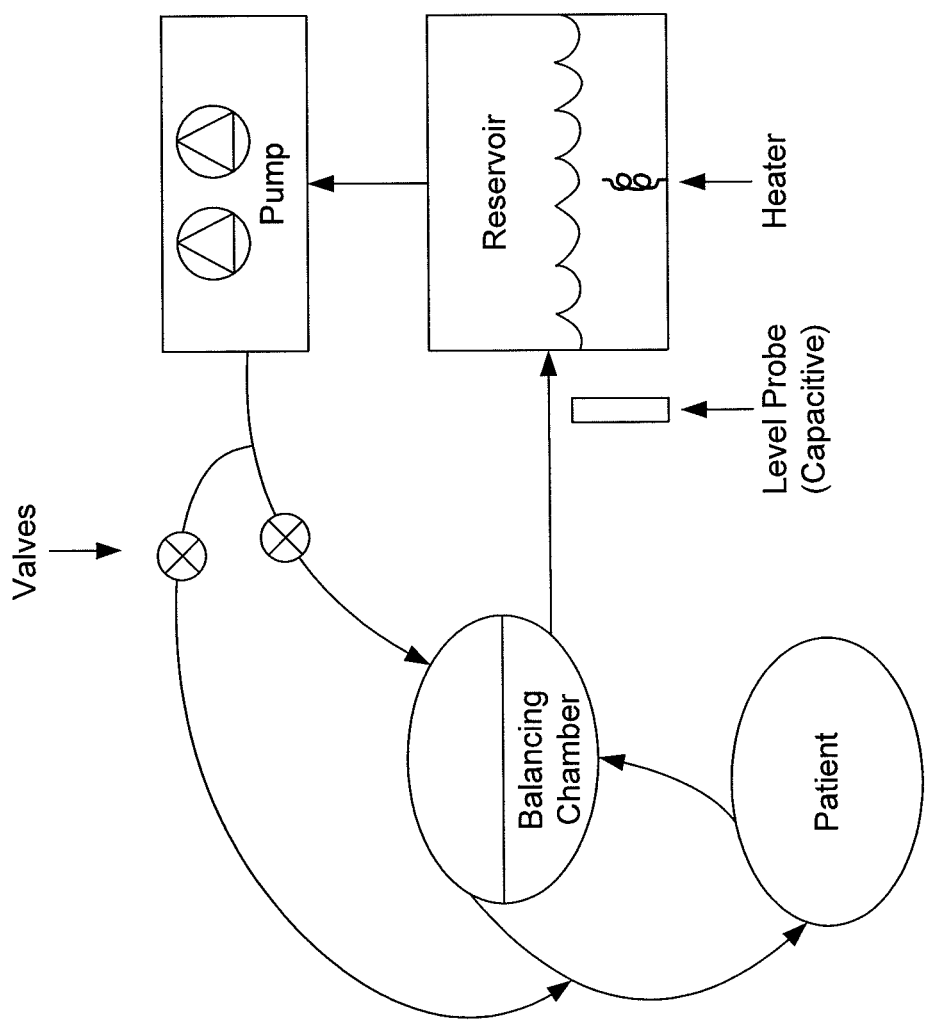
FIG. 85 shows another fluid circuit including a balancing chamber that may be used for providing regional hyperthermic chemotherapy treatment, in accordance with an exemplary embodiment of the present invention.

FIG. 85 shows another fluid circuit including a balancing chamber that may be used for providing regional hyperthermic chemotherapy treatment, in accordance with an exemplary embodiment of the present invention. In this example, fluid is heated in the reservoir, and the volume of fluid in the reservoir is monitored using a capacitive level probe. Fluid is typically pumped to the patient through the top balancing chamber by appropriate control the valves, although fluid may be pumped directly to the patient (i.e., bypassing the balancing chamber) by appropriate control of the valves. Fluid drained from the patient flows through the bottom balancing chamber back to the reservoir. The balancing chambers help to maintain a constant volume of fluid into and out of the patient.

Figure 86:
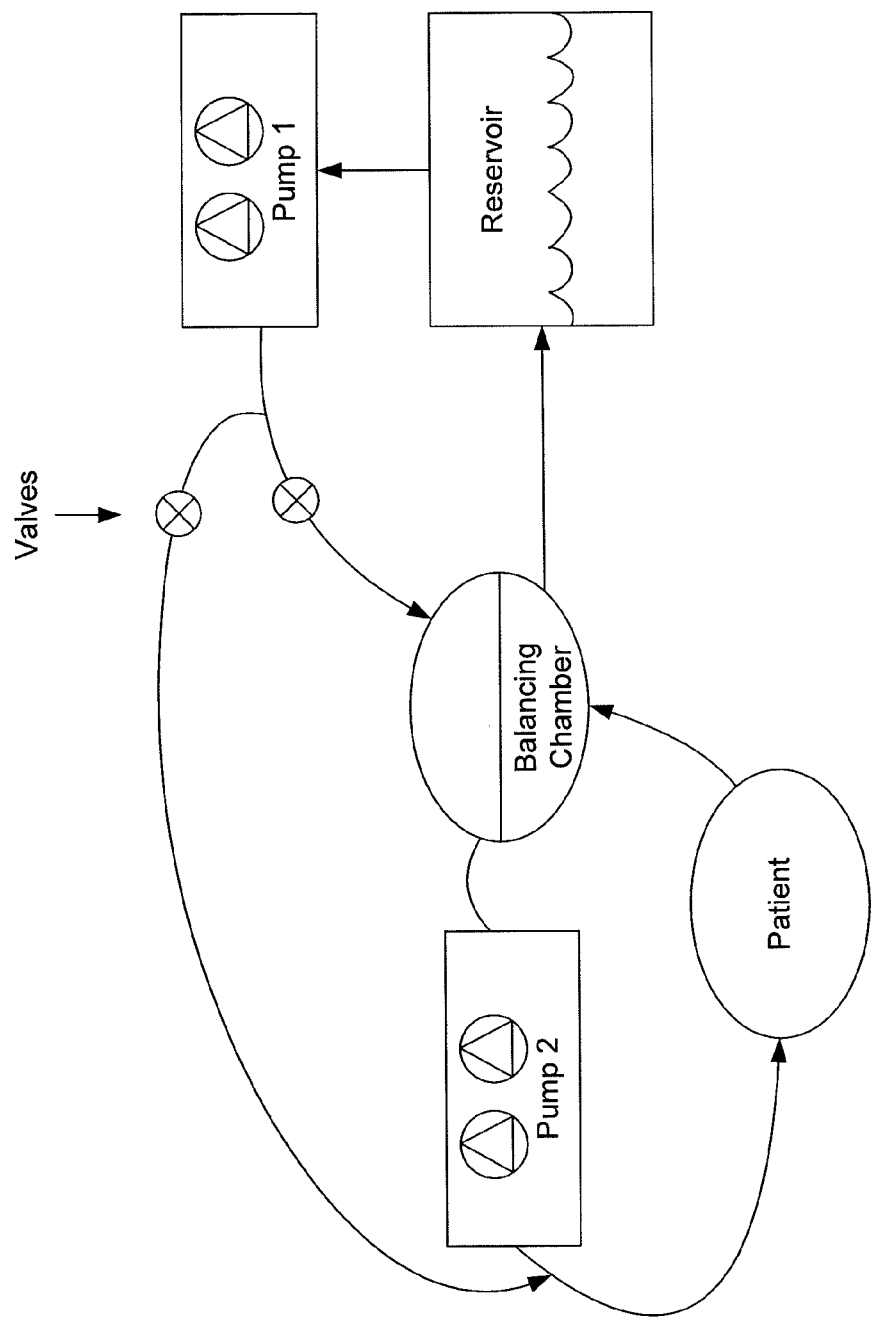
FIG. 86 shows another fluid circuit including a balancing chamber and a second pump that may be used for providing regional hyperthermic chemotherapy treatment, in accordance with an exemplary embodiment of the present invention.

FIG. 86 shows another fluid circuit including a balancing chamber and a second pump that may be used for providing regional hyperthermic chemotherapy treatment, in accordance with an exemplary embodiment of the present invention. In this example, the second pump is used to pump fluid from the top balancing chamber to the patient, which also helps to drain fluid from the patient to the bottom balancing chamber. As in previous embodiments, the fluid may be heated in the reservoir or in the fluid path.

Figure 87:
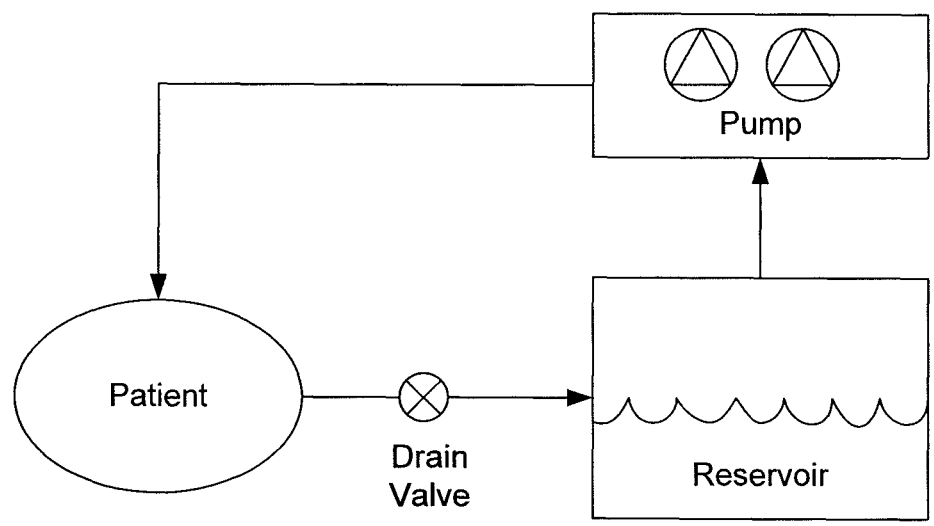
FIG. 87 shows a fluid circuit including a drain valve that may be used for providing regional hyperthermic chemotherapy treatment, in accordance with an exemplary embodiment of the present invention.

FIG. 87 shows a fluid circuit including a drain valve that may be used for providing regional hyperthermic chemotherapy treatment, in accordance with an exemplary embodiment of the present invention. In this example, the drain valve may be controlled to control the amount of fluid entering and leaving the patient. For example, with the valve closed, fluid may be pumped into the patient, e.g., to fill up a cavity of the patient. The drain valve may be partially or fully opened to drain the fluid from the patient or to allow for fluid circulation through the patient.

4. THERMAL/CONDUCTIVITY SENSORS

Various embodiments of thermal and/or conductivity sensors are described. Such thermal/conductivity sensors can be used in a wide variety of applications and are by no means limited to thermal/conductivity measurements of fluids or to thermal/conductivity measurements in the context of heat-exchanger systems.

4.1. Thermal Wells

In one exemplary embodiment, a thermal well is used to accommodate a temperature sensing probe. The thermal well comes into direct contact with a subject media (e.g., a liquid such as blood) and the sensing probe does not. Based on heat transfer dictated in large part by the thermodynamic properties of the thermal well and sensing probe construction, the sensing probe can determine the properties of the subject media without coming into direct contact with the subject media. The accuracy and efficiency of the sensor apparatus arrangement depends on many factors including, but not limited to: construction material and geometry of both the probe and the thermal well.

Figure 50A:
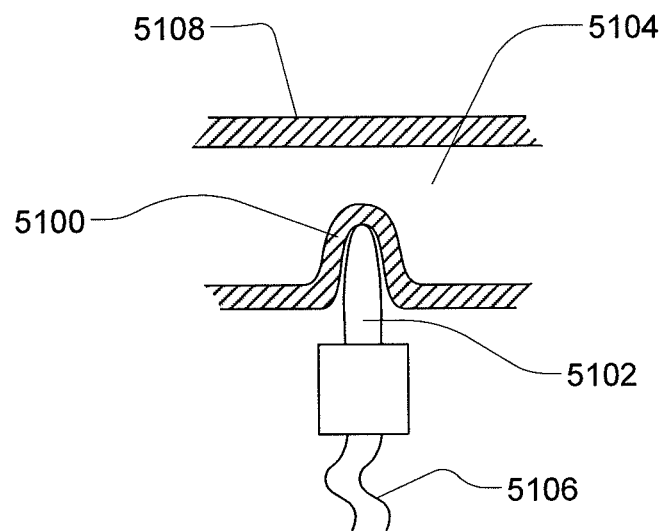
FIGS. 50A and 50B are embodiments of the sensing apparatus where the thermal well is a continuous part of the fluid line.
Figure 50B:
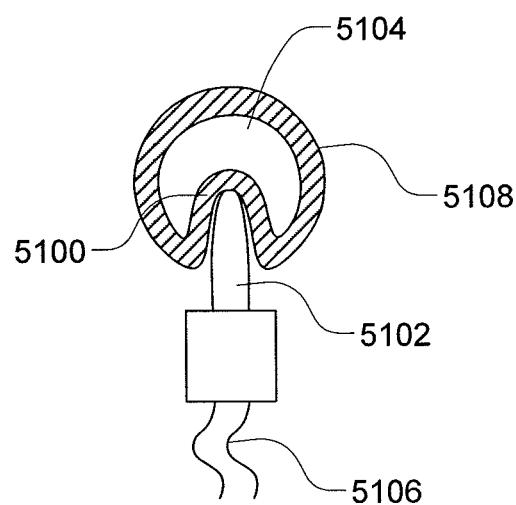

Referring now to FIGS. 50A and 50B, two embodiments of the sensor apparatus which includes the thermal well 5100 and the sensing probe 5102, are shown in relation to a fluid line 5108. In these embodiments, the thermal well 5100 is integrated into the fluid line 5108. However, in other embodiment, some described below, the thermal well 5100 is not completely integrated into the fluid line 5108, i.e., the thermal well 5100 can be made from different materials as compared with the fluid line 5108. In alternate embodiments, the thermal well 5100 is not integrated into any fluid line but can be integrated into anything or nothing at all. For example, in some embodiments, the thermal well 5100 can be integrated into a container, chamber, machine, protective sleeve, fluid pump, pump cassette, disposable unit, manifold, or other assembly, sub-assembly, or component. For purposes of the description, an exemplary embodiment is described for illustrative purposes. The exemplary embodiment includes the embodiment where the thermal well 5100 is in a fluid line. However, the sensor apparatus and the thermal well can be used outside of a fluid line.

Referring now to FIG. 50A, a side view showing a thermal well 5100 formed in a fluid line 5108 which provides the space 5104 for subject media to flow through, and a sensing probe 5102 is shown. Data from the sensing probe is transmitted using at least one lead 5106. An end view of FIG. 50A is shown in FIG. 50B.

In this embodiment, the thermal well 5100 is one piece with the fluid line 5108. The total area of the thermal well 5100 can vary. By varying the geometry of the thermal well 5100, the variables, including, but not limited to, the thermal conductivity characteristic of the thermal well 5100 and thus, the heat transfer between the thermal well 5100 and the sensing probe 5102 will vary. As described in more detail below, the material construction of the thermal well 5100 is another variable in the sensor apparatus.

In some embodiments, the fluid line 5108 is made from a material having a desired thermal conductivity. This material may vary depending on the purpose. The material can be anything including, but not limited to, any plastic, ceramic, metals or alloys of metals or combinations thereof.

Figure 51A:
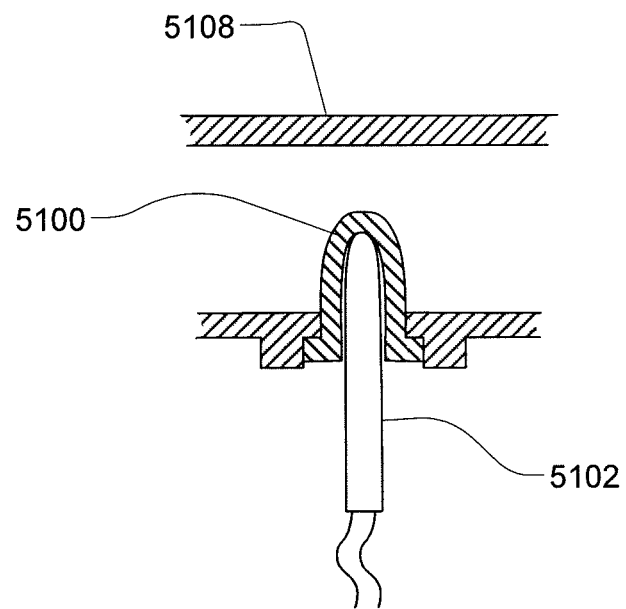
FIGS. 51A and 51B are embodiments of the sensing apparatus where the thermal well is a separate part from the fluid line.
Figure 51B:
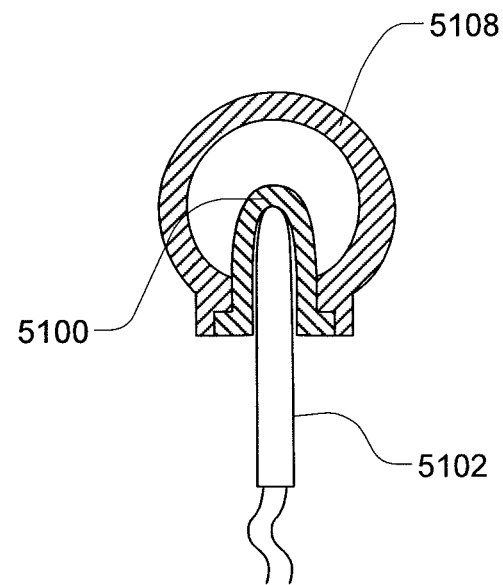

Referring now to FIGS. 51A and 51B, in these embodiments, the fluid line 5108 and the thermal well 5100 are separate parts. In some embodiments, the fluid line 5108 and the thermal well 5100 are made form different materials.

FIGS. 50A-50B and FIGS. 51A-51B show relatively simple embodiments of the sensor apparatus. Thus, for these embodiments, the sensing apparatus includes a thermal well 5100 and a sensing probe 5102 where the thermal well either is integrated as one continuous part with the fluid line 5108 or is a separate part from the fluid line 5108. However, many embodiments of the sensor apparatus are contemplated. Much of the various embodiments include variations on the materials and the geometries of the thermal well 5100 and/or the sensing probe 5102. These variations are dictated by multiple variables related to the intended use for the sensor apparatus. Thus, the subject media and the constraints of the desired sensor, for example, the accuracy, time for results and the fluid flow and subject media characteristics are but a sampling of the various constraints that dictate the embodiment used. In most instances, each of the variables will affect at least one part of the embodiment of the sensor apparatus.

Thus, multiple variables affect the various embodiments of the sensor apparatus, these variables include but are not limited to: 1) geometry of the thermal well; 2) material composition of the thermal well; 3) material composition of the sensing probe; 4) desired flow rate of the subject media; 5) length and width of the thermal well; 6) desired accuracy of the sensing probe; 7) wall thicknesses; 8) length and width of the sensing probe; 9) cost of manufacture; 10) subject media composition and characteristics including tolerance for turbulence; 11) geometry of sensing probe; and 12) desired speed of readings.

In the foregoing, various embodiments of the sensor apparatus are described. The description is intended to provide information on the affect the variables have on the sensor apparatus embodiment design. However, these are but exemplary embodiments. Many additional embodiments are contemplated and can be easily designed based on the intended use of the sensor apparatus. Thus, by changing one or more of the above mentioned partial list of variables, the embodiment of the sensor apparatus may vary.

Figure 52A:
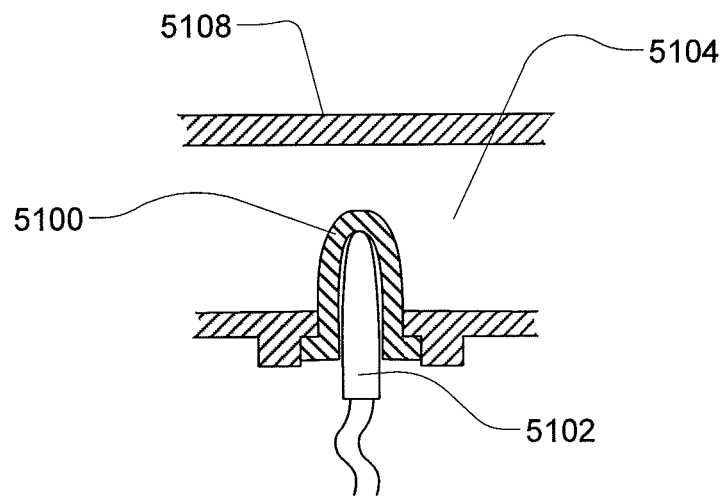
FIGS. 52A and 52B are embodiments of the sensing apparatus showing various lengths and widths of the thermal well.
Figure 52B:
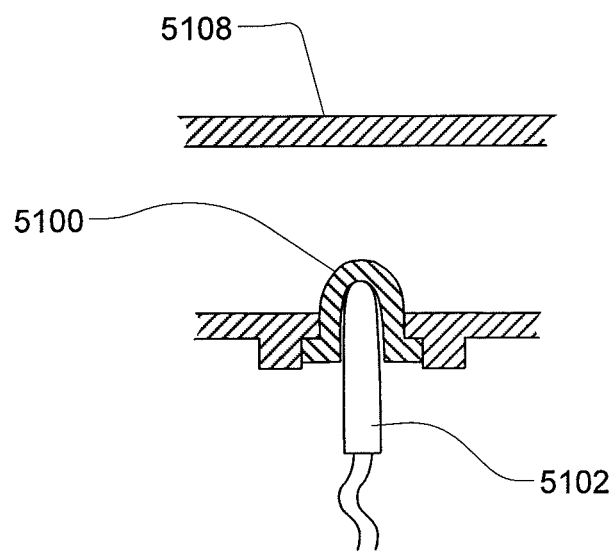

Referring now to FIGS. 52A and 52B, two embodiments of the thermal well 5100 are shown as different parts from the fluid line 5108. These embodiments show two geometries of the thermal well 5100. In FIG. 52A, the geometry includes a longer thermal well 5100. In FIG. 52B, the thermal well 5100 geometry is shorter. The length and width of the thermal well 5100 produce varying properties and accuracies of the thermal conductivity between the thermal well 5100 and the sensing probe 5102. Depending on the use of the sensor apparatus, the thermal well 5100 geometry is one variable.

Referring now to FIG. 52A, the longer thermal well 5100 generally provides a greater isolation between the subject media temperature in the fluid line 5104 and the ambient temperature. Although the longer thermal well 5100 geometry shown in FIG. 52A may be more accurate, the embodiment shown in FIG. 52B may be accurate enough for the purpose at hand. Thus, the length and width of the thermal well 5100 can be any length and width having the desired or tolerable accuracy characteristics. It should be understood that two extremes of length are shown in these embodiments; however, any length is contemplated. The description herein is meant to explain some of the effects of the variables.

Still referring to FIGS. 52A and 52B, the longer thermal well 5100 shown in FIG. 52A may impact the fluid flow of the subject media in the fluid line 5108 to a greater degree than the embodiment shown in FIG. 52B. It should be understood that the length of the thermal well 5100 may also impact the turbulence of the fluid flow. Thus, the length and width of the thermal well 5100 may be changed to have greater or lesser impact on the fluid flow and turbulence of the fluid, while mitigating the other variables.

The shape of the thermal well 5100 is also a variable. Any shape desired is contemplated. However, the shape of the thermal well 5100, as with the other variables, is determined in part based on the intended use of the sensor apparatus. For purposes of description, an exemplary embodiment is described herein. However, the shape in the exemplary embodiment is not meant to be limiting.

Figure 53:
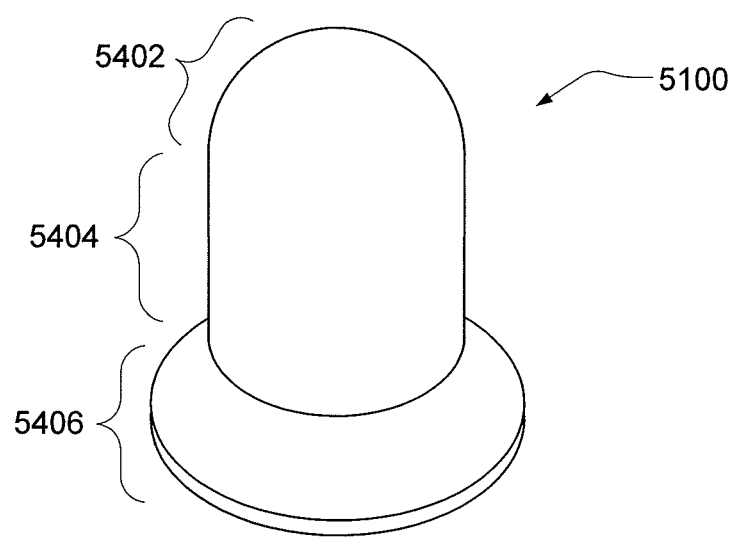
FIG. 53 is a pictorial view of a thermal well according to one embodiment of the sensing apparatus.

Referring now FIG. 53 for purposes of description, the thermal well 5100 has been divided into 3 zones. The top zone 5402 communicates with the sensing probe (not shown); the middle zone 5404 provides the desired length of the thermal well 5100. As described above, the length may dictate the level of protrusion into the fluid path. The length is dictated in part by the desired performance characteristics as discussed above. The middle zone 5404 also isolates the top zone 5402 from the ambient. The middle zone 5404 may also serve to locate, fasten or seal the thermal well 5100 into the fluid line (shown as 5108 in FIGS. 50A-50B).

The bottom zone 5406, which in some embodiments may not be necessary (see FIG. 56K) thus, in these embodiments, the middle zone 5404 and the bottom zone 5406 may be a single zone. However, in the exemplary embodiment, the bottom zone 5406 is shaped to aid in press fitting the thermal well into an area in the fluid line and may locate and/or fasten the thermal well 5100 into the fluid line 5108. In other embodiments, zone 5406 may be formed to facilitate various joining methods (see FIGS. 56A-56J, 56L-56S)

Figure 54:
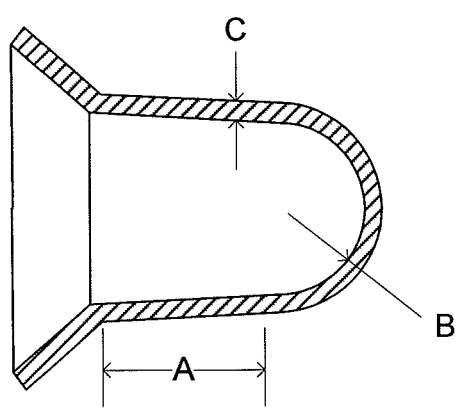
FIG. 54 is a cross sectional view of an exemplary embodiment of the thermal well.

Referring now to FIG. 54 a cross section of the exemplary embodiment of the thermal well 5100 is shown. The dimensions of the exemplary embodiment of the thermal well 5100 include a length A of approximately 0.113 inches (with a range from 0-0.379 inches), a radius B of approximately 0.066 inches and a wall thickness C ranging from approximately 0.003-0.009 inches. These dimensions are given for purposes of an exemplary embodiment only. Depending on the variables and the intended use of the sensing apparatus, the thermal well 5100 dimensions may vary, and the various embodiments are not necessarily proportional.

In some embodiments, the wall thickness can be variable, i.e., the wall thickness varies in different locations of the thermal well. Although these embodiments are shown with variable thicknesses in various locations, this is for description purposes only. Various embodiments of the thermal well may incorporate varying wall thickness in response to variables, these varying wall thicknesses can be "mixed and matched" depending on the desired properties of the sensing apparatus. Thus, for example, in some embodiments, a thinner zone 5404 may be used with thinner zone 5406 and vice-versa. Or, any other combination of "thinner" and "thicker" may be used. Also, the terms used to describe the wall thicknesses are relative. Any thickness desired is contemplated. The figures shown are therefore for descriptive purposes and represent two embodiments where many more are contemplated.

Figure 55A:
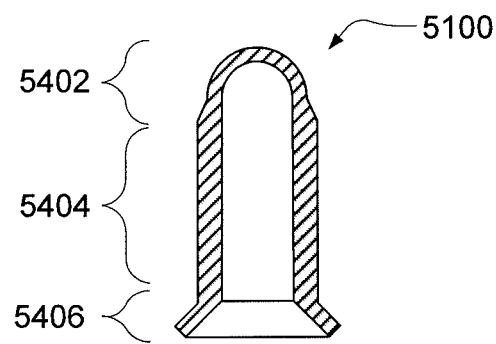
FIGS. 55A and 55B show section views of embodiments of thermal wells having variable wall thickness.
Figure 55B:
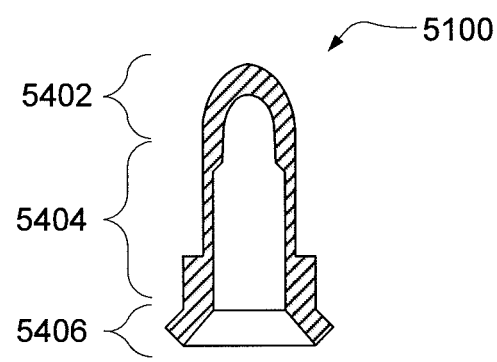

Referring now to FIGS. 55A and 55B, zone 5402 can be thicker or thinner as desired. The thinner zone 5402, amongst other variables, generally provides for a faster sensing time while a thicker zone may be useful for harsh environments or where sensor damping is desired. Zone 5404 may be thicker, amongst other variables, for greater strength or thinner for, amongst other variables, greater isolation from ambient. Zone 5406 can be thinner or thicker depending on the fastening method used.

Figure 56A:
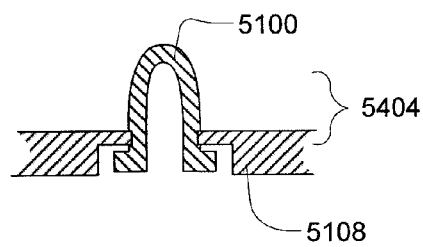
FIGS. 56A-56S are sectional views of various embodiments of the thermal well embedded in a fluid line.
Figure 56B:
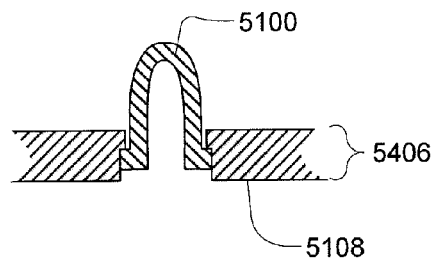
Figure 56C:
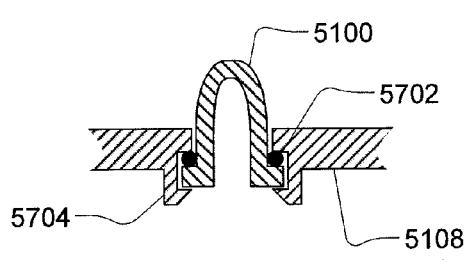
Figure 56D:
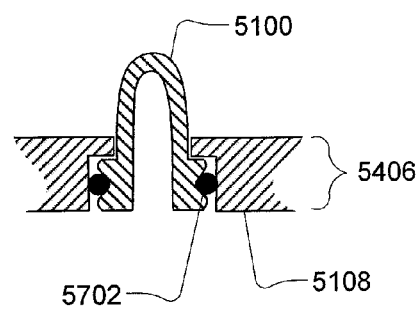
Figure 56E:
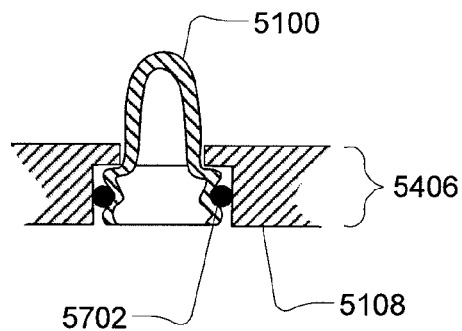

The thermal well 5100, in practice, can be embedded into a fluid line 5108, as a separate part from the fluid line 5108. This is shown and described above with respect to FIGS. 51A-51B. Various embodiments may be used for embedding the thermal well 5100 into the fluid line 5108. Although the preferred embodiments are described here, any method or process for embedding a thermal well 5100 into a fluid line 5108 can be used. Referring now to FIGS. 56A-56S, various configurations for embedding the thermal well 5100 into the fluid line 5108 are shown. For these embodiments, the thermal well 5100 can be made from any materials, including but not limited to, plastic, metal, ceramic or a combination thereof. The material may depend in some part on the compatibility with the intended subject media. The fluid line 5108, in these embodiments, may be made from plastic, metal, or any other material that is compatible with the subject media.

Referring first to FIG. 56A, the thermal well 5100 is shown press fit into the fluid line 5108 using the zone 5404 (shown in FIG. 53). In FIG. 56B, the thermal well 5100 is shown press fit into the fluid line 5108 using the zone 5406. Referring now to FIG. 56C, the thermal well 5100 is shown retained in the fluid line 5108 with flexible tabs 5704, an O-ring is also provided. Referring now to FIG. 56D, the thermal well 5100 is shown inserted into the fluid line 5108 with an O-ring 5702. The thermal well 5100 is also shown as an alternate embodiment, where the thermal well 5100 zone 5406 includes an O-ring groove. The O-ring groove can be cut, formed, spun, cast or injection molded into the thermal well, or formed into the thermal well 5100 by any other method. FIG. 56E shows a similar embodiment to that shown in FIG. 56D, however, the O-ring groove is formed in zone 5406 rather than cut, molded or cast as shown in FIG. 56D.

Figure 56F:
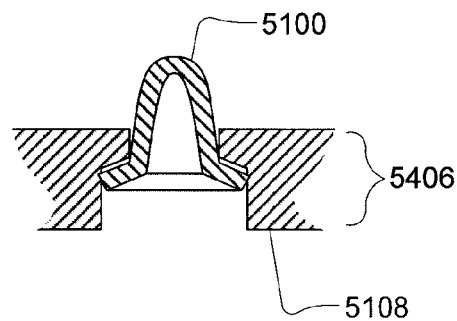
Figure 56G:
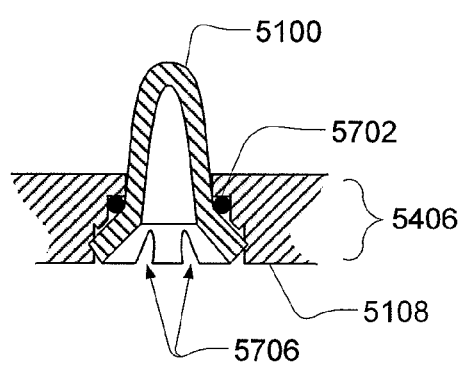

Referring now to FIG. 56F, the thermal well 5100 is shown press fit into the fluid line 5108, zone 5406 includes flexibility allowing the edge of zone 5406 to deform the material of the fluid line 5108. Referring now to FIG. 56G, the thermal well 5100 includes cuts 5706 on the zone 5406 providing flexibility of the zone 5406 for assembly with the fluid line 5108. An O-ring 5702 is also provided. Although two cuts are shown, a greater number or less cuts are used in alternate embodiments.

Figure 56H:
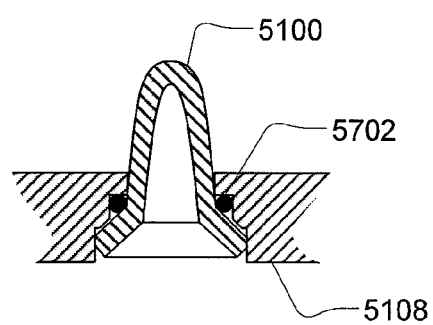
Figure 56I:
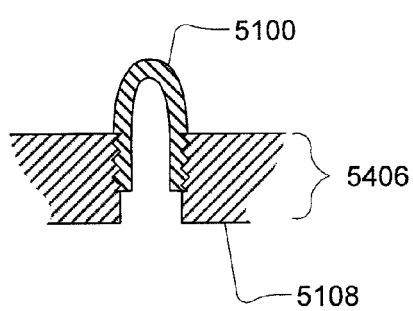

Referring now to FIG. 56H, the embodiment shown in FIG. 56F is shown with the addition of an O-ring 5702. Referring to FIG. 56I, the thermal well 5100 is shown insert molded in the fluid line 5108. Zone 5406 is formed to facilitate or enable assembly by insert molding.

Figure 56J:
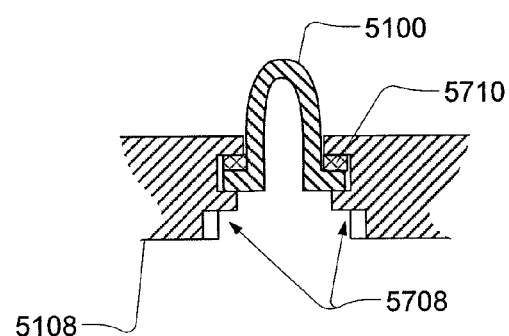

FIG. 56J shows an embodiment where the thermal well 5100 is heat staked 5708 to retain the thermal well 5100 in the fluid line 5108. In some embodiments of FIG. 56J, an O-ring 5710 is also included. In this embodiment, the O-ring 5710 has a rectangular cross section. However, in alternate embodiments, the O-ring may have a round or X-shaped cross section. Likewise, in the various embodiments described herein having an O-ring, the O-ring in those embodiments can have a round, rectangular or X-shaped cross section, or any cross sectional shape desired.

Figure 56K:
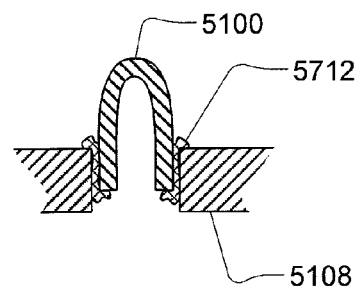

Referring now to FIG. 56K, the thermal well 5100 is retained in the fluid line 5108 by adhesive 5712. The adhesive can be any adhesive, but in one embodiment, the adhesive is a UV curing adhesive. In alternate embodiments, the adhesive may be any adhesive that is compatible with the subject media. In this embodiment, the thermal well 5100 is shown without a zone 5406.

Figure 56L:
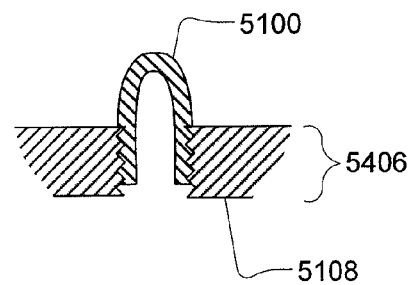

Referring now to FIG. 56L, thermal well 5100 is shown ultrasonically welded in the fluid line 5108. The zone 5406 is fabricated to enable joining by ultrasonic welding.

Referring now to FIG. 56M, a thermal well 5100 is shown insert molded in the fluid line 5108. Zone 5406 is a flange for the plastic in the fluid line 5108 to flow around. In the embodiment shown, the flange is flat, however, in other embodiments; the flange may be bell shaped or otherwise.

Referring now to FIG. 56N, the thermal well 5100 is shown retained in the fluid line 5108 by a retaining plate 5714 and a fastener 5716. O-ring 5702 is also shown.

Referring now to FIGS. 56O-56P, an end view is shown of a thermal well 5100 that is retained in a fluid line 5108 by a retaining ring 5718 (FIG. 56O) or in an alternate embodiment, a clip 5720 (FIG. 56P). O-ring 5702 is also shown.

Figure 56Q:
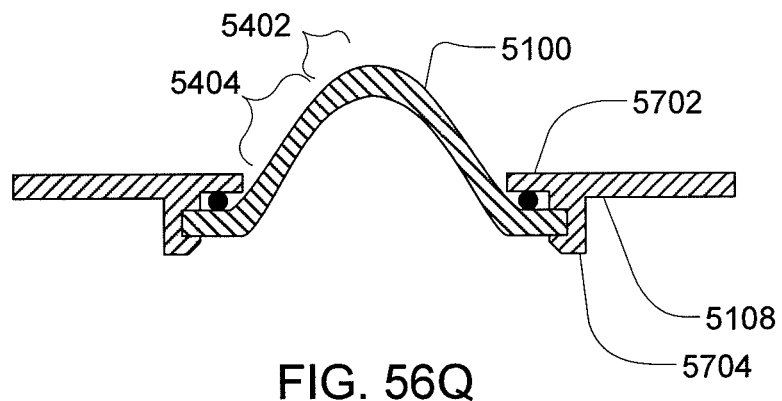

Referring now to FIG. 56Q, the embodiment of FIG. 56C is shown with an alternate embodiment of the thermal well 5100. In this embodiment of the thermal well 5100 the referred to as zone 5404 in FIG. 53 includes a taper that may allow for easier alignment with a sensing probe, better isolation of zone 5402 from the ambient and better flow characteristics in the fluid path. The thermal well 5100 is shown retained in the fluid line 5108 using flexible tabs 5704. An O-ring is also provided.

Figure 56R:
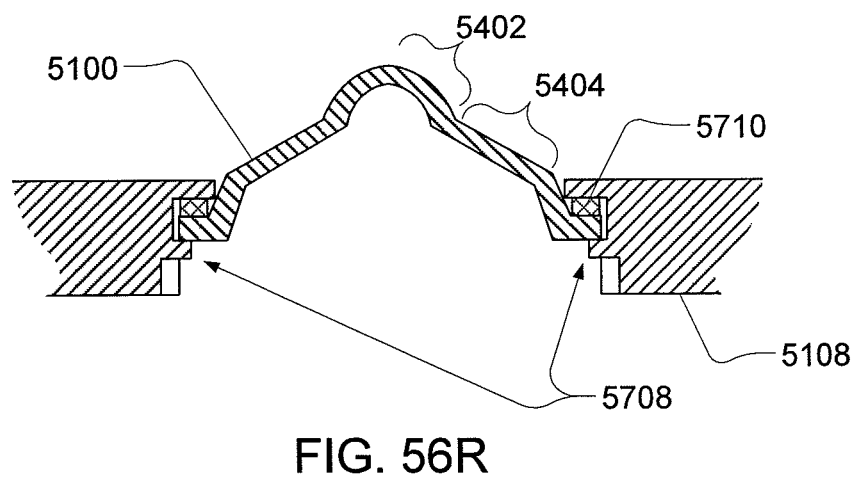
Figure 56S:
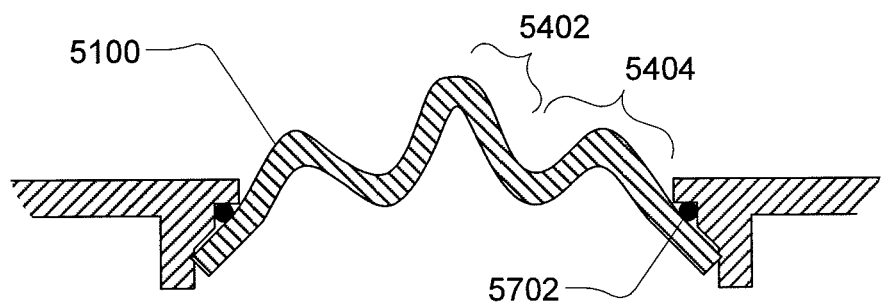

FIG. 56R shows the embodiment of FIG. 56J with an alternate embodiment of the thermal well 5100. The thermal well 5100 shown in this embodiment has a taper in zone 5404 that may allow for easier alignment with a sensing probe, may allow better isolation of zone 5402 from the ambient and may allow better flow characteristics in the fluid path. Zone 5402 provides a hemispherical contact for effective thermal coupling with a thermal probe. The thermal well 5100 is heat staked 5708 to retain the thermal well 5100 in the fluid line 5108. In some embodiments of FIG. 56R, an O-ring 5710 is also included. In this embodiment, the O-ring 5710 has a rectangular cross section. However, in alternate embodiments, the O-ring can have a round or X-shaped cross section.

Referring now to FIG. 56S, the embodiment of FIG. 56H is shown with an alternate embodiment of the thermal well 5100. FIG. 56S is shown with the addition of an O-ring 5702. In this embodiment of the thermal well 5100 zone 5404 (as shown in FIG. 53) has convolutions that may allow better isolation of zone 5402 from the ambient. While several geometries have been shown for zone 5404, many others could be shown to achieve desired performance characteristics.

4.2. Sensing Probes

Figure 57:
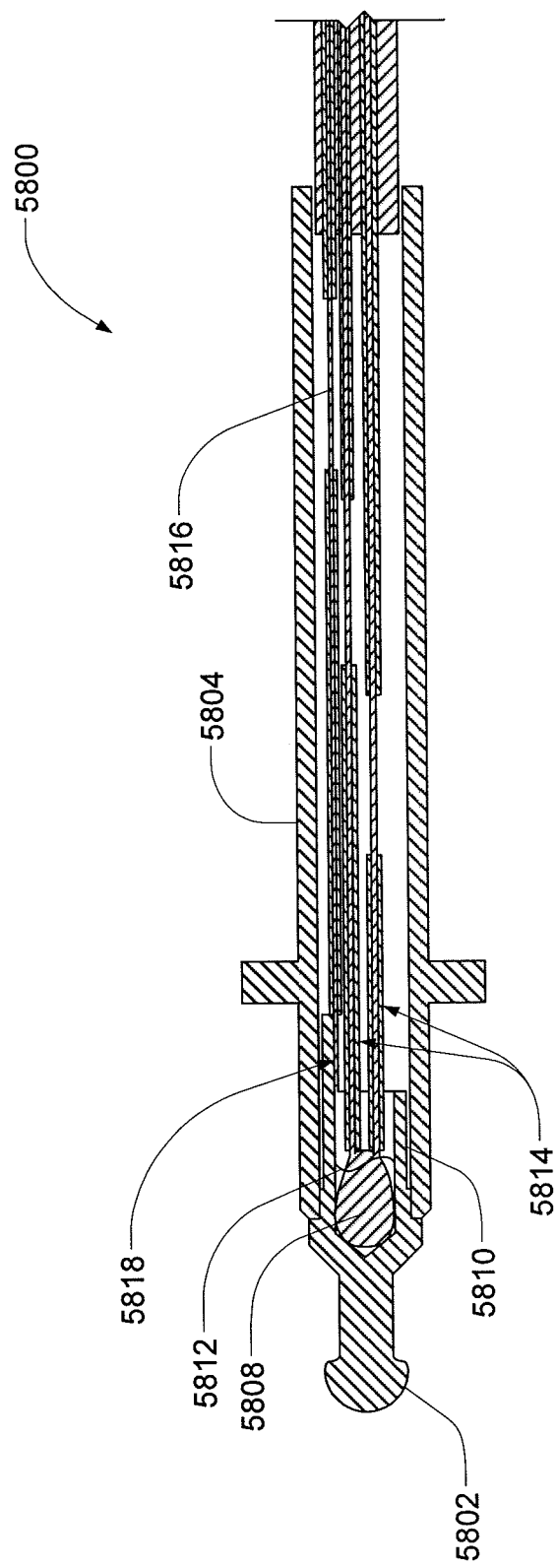
FIG. 57 is a section side view of one embodiment of the sensing probe.

Referring now to FIG. 57, a sectional view of an exemplary embodiment of the sensing probe 5800 is shown. The housing 5804 is a hollow structure that attaches to the tip 5802. The tip is made of a highly thermally conductive material. The housing 5804, in the exemplary embodiment, is made from a thermally insulative material. In some embodiments, the housing is made of a thermally and electrically insulative material. In the exemplary embodiment, the housing 5804 is made of plastic which is a thermally insulative and electrically insulative material. The tip 5802 either contacts the subject media directly, or else is mated with a thermal well.

In the exemplary embodiment, the tip 5802 is attached to the housing 5804 using a urethane resin or another thermal insulator in between (area 5807) the tip 5802 and the housing

5804. Urethane resin additionally adds structural support. In alternate embodiments, other fabrication and joining methods can be used to join the tip 5802 to the housing 5804.

The tip 5802 of the sensing probe 5800 is made of a thermally conductive material. The better thermally conductive materials, for example, copper, silver and steel, can be used, however, depending on the desired use for the sensing probe and the subject media; the materials may be selected to be durable and compatible for the intended use. Additionally, factors such as cost and ease of manufacture may dictate a different material selection. In one exemplary embodiment, the tip 5802 is made from copper. In other embodiments, the material can be an alloy of copper or silver, or either solid or an alloy of any thermally conductive material or element, including but not limited to metals and ceramics. However, in the exemplary embodiments, the tip 5802 is made from metal.

In the exemplary embodiment, the tip 5802 is shaped to couple thermally with a thermal well as described in the exemplary embodiment of the thermal well above. In the exemplary embodiment as well as in other embodiments, the tip 5802 may be shaped to insulate the thermal sensor 5808 from the ambient. In the exemplary embodiment, the tip 5802 is made from metal.

In alternate embodiments a non-electrically conductive material is used for the tip. These embodiments may be preferred for use where it is necessary to electrically insulate the thermal well from the probe. In another alternate embodiment, the tip 5802 may be made from any thermally conductive ceramic.

In the exemplary embodiment, the thermal sensor 5808 is located in the housing and is attached to the interior of the tip 5802 with a thermally conductive epoxy 5812. In the exemplary embodiment, the epoxy used is THERMALBOND, however, in other embodiments; any thermal grade epoxy can be used. However, in alternate embodiments, a thermal grease may be used. In alternate embodiments, an epoxy or grease is not used.

The thermal sensor 5808, in the exemplary embodiment, is a thermistor. The thermistor generally is a highly accurate embodiment. However in alternate embodiments, the thermal sensor 5808 can be a thermocouple or any other temperature sensing device. The choice of thermal sensor 5808 may again relate to the intended use of the sensing apparatus.

Figure 58:
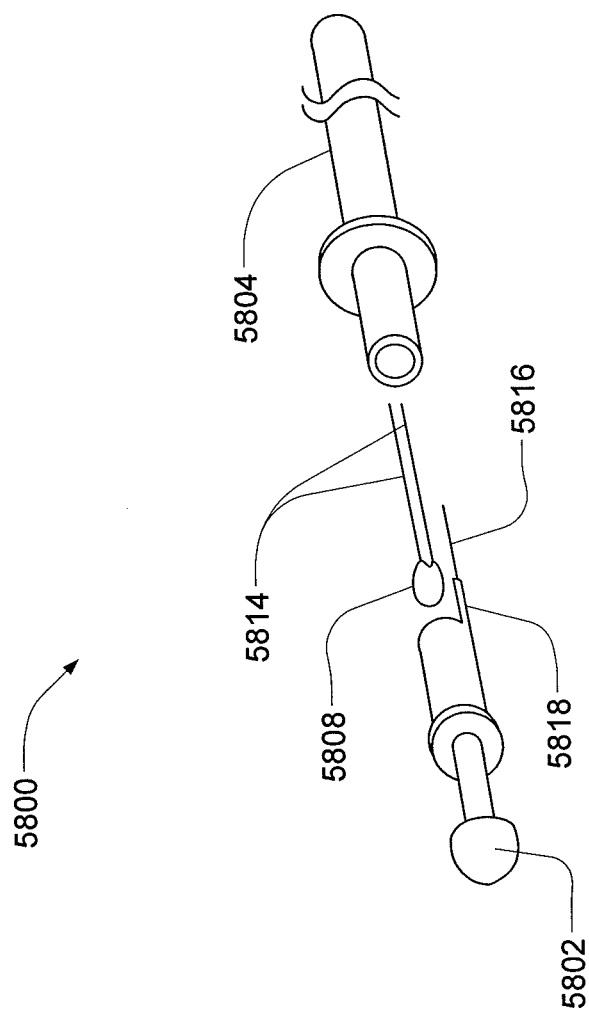
FIG. 58 is an exploded view of the embodiment shown in FIG. 8.

Leads 5814 from the thermal sensor 5808 exit the back of the housing 5804. These leads 5814 attach to other equipment used for calculations. In the exemplary embodiment, a third lead 5816 from the tip 5802 is also included. This third lead 5816 is attached to the tip on a tab 5818. The third lead 5816 is attached to the tip 5802 because in this embodiment, the tip 5802 is metal and the housing is plastic. In alternate embodiments, the housing 5804 is metal, thus the third lead 5816 may be attached to the housing 5804. Thus, the tip 5802, in the exemplary embodiment, includes a tab 5818 for attachment to a lead. However, in alternate embodiments, and perhaps depending on the intended use of the sensing apparatus, the third lead 5816 may not be included. Also, in alternate embodiments where a third lead is not desired, the tip 5802 may not include the tab 5818. Referring now to FIG. 58, an exploded view of the sensing probe 5800 is shown.

Figure 59:
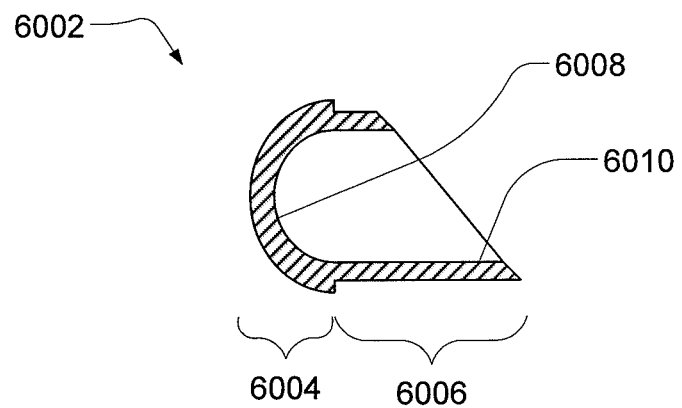
FIG. 59 is a sectional view of an alternate embodiment of the tip of the sensing probe.

Referring now to FIG. 59 an alternate embodiment of the exemplary embodiment is shown. In this embodiment, the tip 6002 of the sensing probe is shown. The tip 6002 includes a zone 6004 that will contact either a subject media to be tested or a thermal well. A zone 6006 attaches to the sensor probe housing (not shown). An interior area 6008 accommodates the thermal sensor (not shown). In this embodiment, the tip 6002 is made from stainless steel. However, in other embodiments, the tip 6002 can be made from any thermally conductive material, including but not limited to: metals (including copper, silver, steel and stainless steel), ceramics or plastics.

Figure 60A:
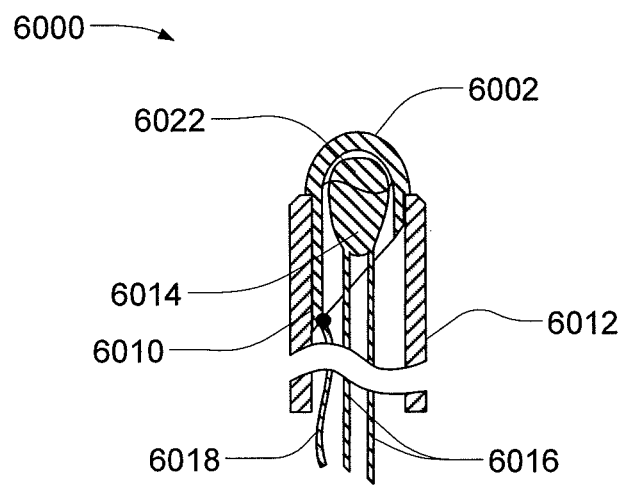
FIG. 60A is an alternate embodiment of the sensing probe.
Figure 60B:
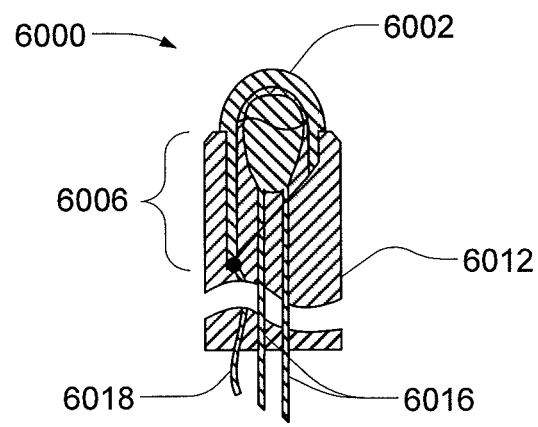
FIG. 60B is an alternate embodiment of the sensing probe.

In the exemplary embodiment, zone 6006 includes a tab 6010. A third lead (as described with respect to FIG. 57, 5816) attaches from the tab 6010. Referring next to FIGS. 60A and 60B, the sensing probe 6000 is shown including the tip 6002 and the housing 6012. In one embodiment, the housing 6012 is made from any thermally insulative material, including but not limited to, plastic. In one embodiment, the housing 6012 is press fit to the tip 6002, glued or attached by any other method. In one embodiment, the thermal sensor 6014 is thermally coupled to the tip 6002 with thermal grade epoxy or, in alternate embodiments, thermal grease 6022. Two leads 6016 from the thermal sensor 6014 extend to the distal end of the housing. In some embodiments, a third lead 6018 is attached to the tip 6002 from the tab 6010. As discussed above, in some embodiments where the third lead is not desired, the tip 6002 does not include a tab 6010.

Referring now to FIG. 60B, an alternate embodiment of the sensing probe 6000 is shown. In this embodiment, the housing 6012 is a plastic molded over zone 6006 of the tip 6002 and the leads 6016, and in some embodiments, a third lead 6018.

Figure 61:
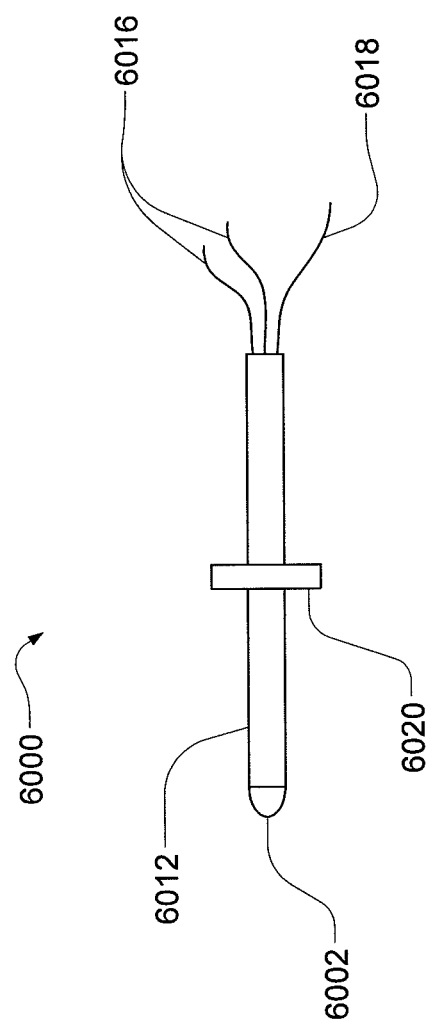
FIG. 61 is a side view of an alternate embodiment of the sensing probe.

Referring now to FIG. 61, a full side view of one embodiment of the sensing probe 6000 shown in FIGS. 59-60B is shown. The sensing probe 6000 includes a housing 6012, a tip 6002 and the leads 6016, 6018. Flange 6020 is shown. In some embodiment, flange 6020 is used to mount and/or attachment to equipment.

Figure 62A:
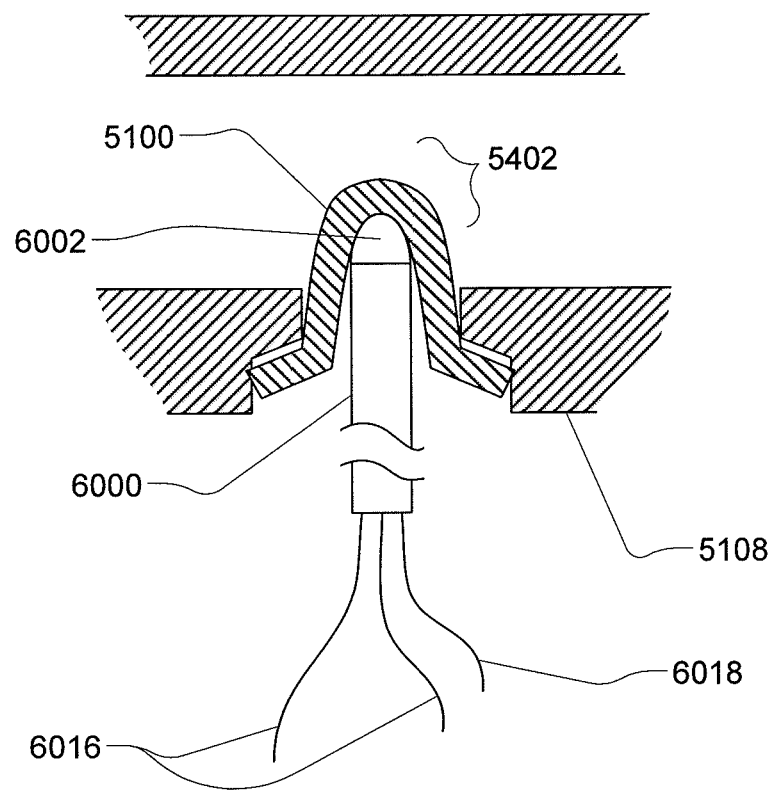
FIG. 62A is a section view of a sensing probe coupled to a thermal well.
Figure 62B:
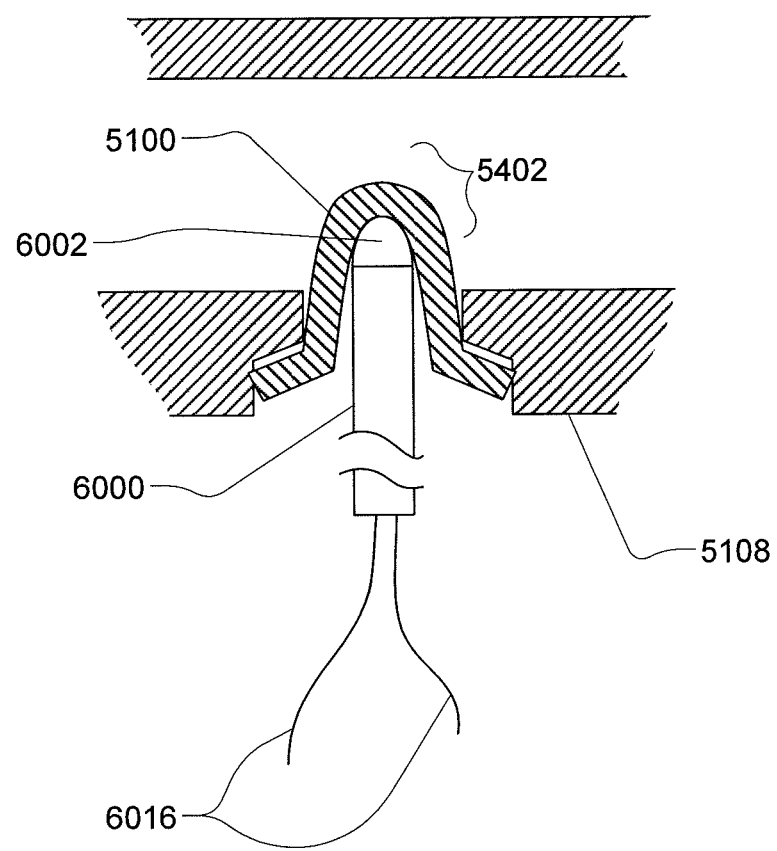
FIG. 62B is an alternate embodiment of the sensing probe shown in FIG. 13A.

Referring now to FIG. 62A, the sensing probe 6000 shown in FIGS. 59-61, is shown coupled to a thermal well 5100 which is fastened into a fluid line 5108. In the embodiment as shown, two leads 6016 are shown at the distal end of the sensing probe 6000. And, in some embodiments, a third lead 6018 is also incorporated into the sensing probe 6000. FIG. 62B shows an alternate embodiment where the sensing probe 6000 includes two leads 6016 but does not include the third lead 6018.

Referring now to both FIGS. 62A and 62B, the tip 6002 of the sensing probe 6000 is in direct contact with the thermal well 5100. Referring back to FIG. 53 and still referring to FIGS. 62A and 62B the thermal well 5100 includes a zone 5402. The thermal well 5100 is hollow, and the inner part of zone 5402 is formed such that it will be in mating contact with the sensing probe tip 6002. As shown in this embodiment, the thermal well 5100 is designed to have a mating geometry with the sensing probe 6000. Thus, the geometry of the thermal well 5100 may depend on the geometry of the tip 6002 of the sensing probe 6000 and vice-versa. In some embodiments, it may be desirable that the sensing probe 6000 does not have a tight fit or a perfect mate with the thermal well 5100.

Figure 63A:
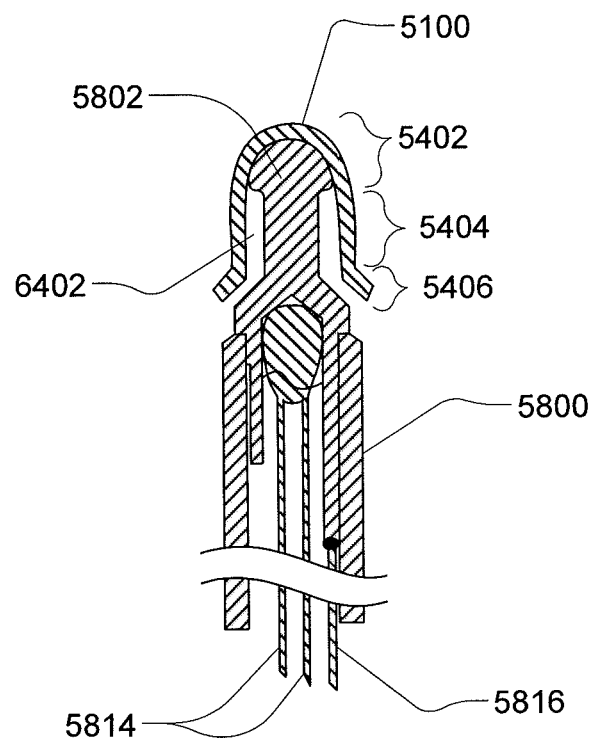
FIG. 63A is a section view of a sensing probe as shown in FIG. 8 coupled to a thermal well.
Figure 63B:
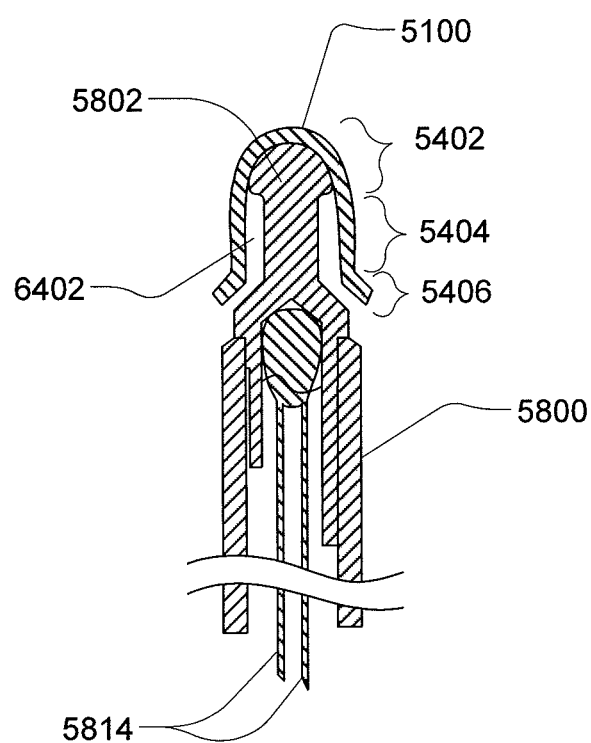
FIG. 63B is an alternate embodiment of the sensing probe shown in FIG. 14A.

Referring now to FIG. 63A, one embodiment of the sensing probe 5800 (as shown in FIG. 57) is shown coupled to a thermal well 5100 which is fastened into a fluid line 5108. In the embodiment as shown, two leads 5814 are shown at the distal end of the sensing probe 5800. In some embodiments, a third lead 5816 is also incorporated into the sensing probe 5800. FIG. 63B shows an alternate embodiment where the sensing probe 5800 includes two leads 5814 but does not include the third lead 5816.

Referring now to both FIGS. 63A and 63B, the tip 5802 of the sensing probe 5800 is in direct contact with the thermal well 5100. Referring back to FIG. 53 and still referring to FIGS. 63A and 63B, the thermal well 5100 includes a zone 5402. The thermal well 5100 is hollow, and the inner part of zone 5402 is formed such that it will be in mating contact with the sensing probe tip 5802. As shown in this embodiment, the thermal well 5100 is designed to have a mating geometry with the sensing probe 5800. Thus, the geometry of the thermal well 5100 depends on the geometry of the tip 5802 of the sensing probe 5800 and vice-versa.

4.3. Sensor Apparatus

Figure 64:
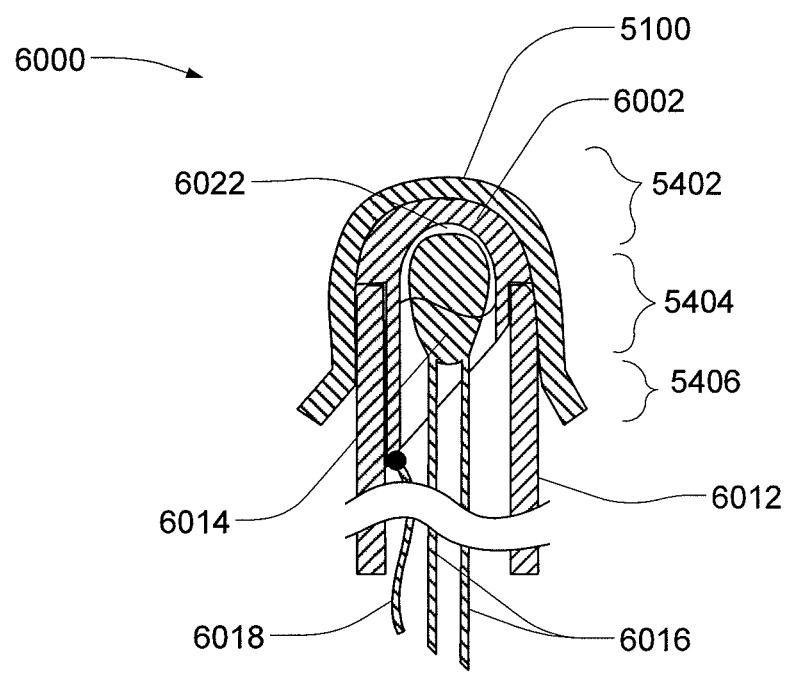
FIG. 64 is a sectional view of one exemplary embodiment of the sensor apparatus.

For purposes of description of the sensor apparatus, the sensor apparatus is described with respect to exemplary embodiments. The exemplary embodiments are shown in FIGS. 62A, 62B, and FIG. 64, with alternate exemplary embodiments in 63A and 63B. In alternate embodiments of the sensor apparatus, the sensing probe can be used outside of the thermal well. However, the sensor apparatus has already been described herein alone. Thus, the description that follows describes one embodiment of the exemplary embodiment of the sensor apparatus which includes, for this purpose, a sensing probe and a thermal well.

Referring now to FIG. 64, in an exemplary embodiment, the sensing probe 6000 shown in FIG. 62A and the thermal well 5100 are shown coupled and outside of a fluid line. As described above, the thermal well 5100 can be in a fluid line, a protective sleeve, any disposable, machine, chamber, cassette or container. However, for purposes of this description of the exemplary embodiment, the thermal well 5100 is taken to be anywhere where it is used to determine thermal and/or conductive properties (FIG. 62A) of a subject media.

A subject media is in contact with the outside of zone 5402 of the thermal well 5100. Thermal energy is transferred from the subject media to the thermal well 5100 and further transferred to the tip 6002 of the sensing probe 6000. Thermal energy is then conducted to the thermal sensor 6014. The thermal sensor 6014 communicates via leads 6016 with equipment that can determine the temperature of the subject media based on feedback of the thermal sensor 6014. In embodiments where conductivity sensing is also desired, lead 6018 communicates with equipment that can determine the conductivity of the subject media. With respect to determining the conductivity of the subject media, in addition to the lead 6018, a second electrical lead/contact (not shown) would also be used. The second lead could be a second sensor apparatus as shown in FIG. 64, or, alternatively, a second probe that is not necessarily the same as the sensor apparatus shown in FIG. 64, but rather, any probe or apparatus capable of sensing capacitance of the subject media, including, an electrical contact.

Heat transfer from the tip 6002 to the thermal sensor 6014 may be improved by the use of a thermal epoxy or thermal grease 6022.

Referring now to FIGS. 63A and 63B, in the alternate exemplary embodiment, whilst the sensing probe 5800 is coupled to the thermal well 5100, the tip 5802, having the geometry shown, forms an air gap 6402 between the inner zones 5404 and 5406 of the thermal well 5100 and the tip 5802. The air gap 6402 provides an insulative barrier so that only the top of the sensing tip of 5802 is in communication with the top zone 5402 of the thermal well 5100.

The sensing probe 5800 and thermal well 5100 are shown coupled and outside of a fluid line. As described above, the thermal well 5100 can be in a fluid line, a protective sleeve, disposable unit, machine, non-disposable unit, chamber, cassette or container. However, for purposes of this description of the exemplary embodiment, the thermal well 5100 is taken to be anywhere where it is used to determine thermal and/or conductive properties (FIG. 63A) of a subject media.

A subject media is in contact with the outside of zone 5402 of the thermal well 5100. Thermal energy is transferred from the subject media to the thermal well 5100 and further transferred to the tip 5802 of the sensing probe 5800. Thermal energy is then conducted to the thermal sensor 5808. The thermal sensor 5808 communicates via leads 5814 with equipment that can determine the temperature of the subject media based on feedback of the thermal sensor 5808. In embodiments where conductivity sensing is also desired, lead 5816 communicates with equipment that can determine the conductivity of the subject media. With respect to determining the conductivity of the subject media, in addition to the lead 5816, a second electrical lead (not shown) would also be used. The second lead could be a second sensor apparatus as shown in FIG. 63A, or, alternatively, a second probe that is not necessarily the same as the sensor apparatus shown in FIG. 63A, but rather, any probe or apparatus capable of sensing capacitance of the subject media, including, an electrical contact.

Heat transfer from the tip 5802 to the thermal sensor 5808 can be improved by the use of a thermal epoxy or thermal grease 5812.

Figure 65:
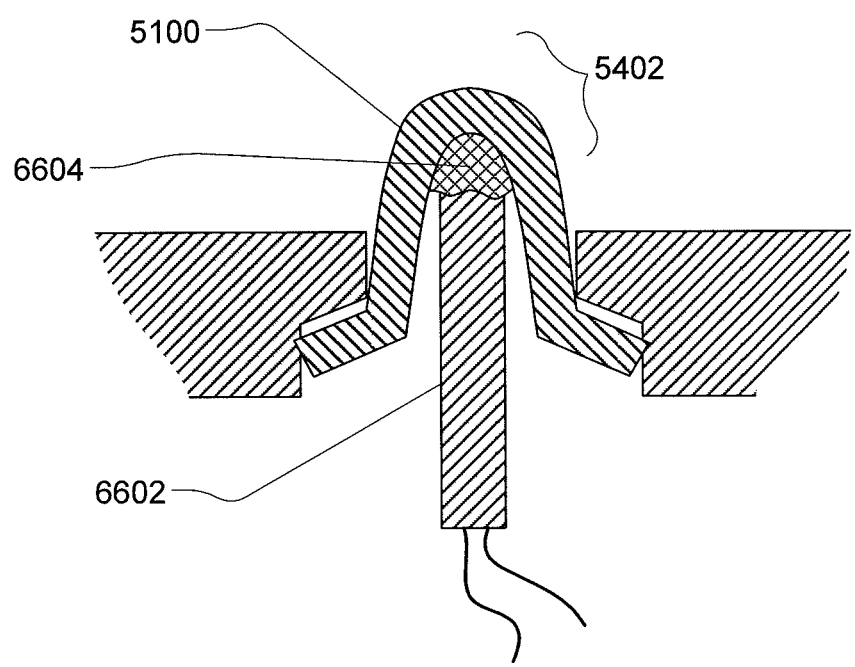
FIG. 65 shows an alternate embodiment of a sensing probe coupled to a thermal well.

Referring now to FIG. 65, an alternate embodiment showing a sensing probe 6602 coupled to a thermal well 5100 is shown. For purposes of this description, any embodiment of the sensing probe 6602 and any embodiment of the thermal well 5100 can be used. In this embodiment, to increase the thermal coupling between the tip of the sensing probe 6602 and the thermal well 5100, thermal grease 6604 is present at the interface of the tip of the sensing probe 6602 and the inner zone 5402 of the thermal well 5100. In one embodiment, the amount of thermal grease 6604 is a volume sufficient to only be present in zone 5402. However, in alternate embodiments, larger or smaller volumes of thermal grease can be used.

4.4. Sensor Apparatus Systems

Figure 66:
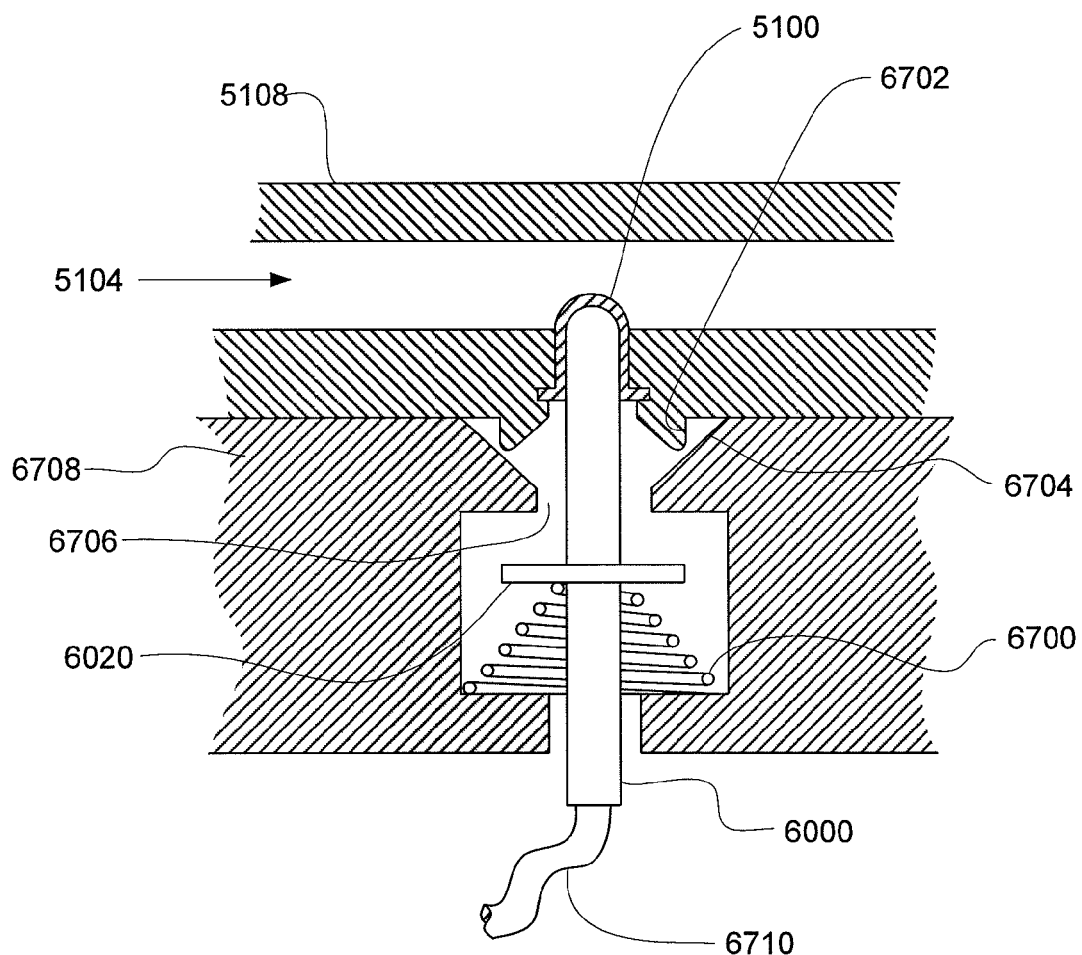
FIG. 66 is a section view of one embodiment of a sensing probe coupled to a thermal well and suspended by a spring.

Referring now to FIG. 66, a sensor apparatus system is shown. In the system, the sensor apparatus is shown in a device containing a fluid line 5108. The sensor apparatus includes the sensing probe 6000 and the thermal well 5100. In this embodiment, the thermal well 5100 and fluid line 5108 is a disposable portion and the sensing probe 6000 is a reusable portion. Also in the reusable portion is a spring 6700. The spring 6700 and sensing probe 6000 are located in a housing 6708. The housing 6708 can be in any machine, container, device or otherwise. The spring 6700 can be a conical, a coil spring, wave spring, or urethane spring.

In this embodiment, the thermal well 5100 and the sensing probe 6000 may include alignment features 6702, 6704 that aid in the thermal well 5100 and sensing probe 6000 being aligned. The correct orientation of the thermal well 5100 and the sensing probe 6000 may aid in the mating of the thermal well 5100 and the sensing probe 6000 to occur. The configuration of the space 6706 provides the sensing probe 6000 with space for lateral movement. This allows the sensing probe 6000 to, if necessary; move laterally in order to align with the thermal well 5100 for mating.

The sensing probe 6000 is suspended by a spring 6700 supported by the flange 6020. The spring 6700 allow vertical movement of the sensing probe 6000 when the thermal well 5100 mates with the sensing probe 6000. The spring 6700 aids in establishing full contact of the sensing probe 6000 and the thermal well 5100. The fluid line 5108 can be in any machine, container, device or otherwise. The fluid line 5108 contains a fluid path 5104. A subject media flows through the fluid path 5104 and the thermal well 5100, located in the fluid line 5108 such that the thermal well 5100 has ample contact with the fluid path 5104 and can sense the temperature properties and, in some embodiments, the conductive properties of the subject media. The location of the thermal well 5100 in the fluid path 5104, as described in more detail above, may be related to the desired accuracy, the subject media and other considerations.

The spring 6700 and sensing probe 6000 assembly, together with the space 6706 in the housing 6708 may aid in alignment for the mating of the sensing probe 6000 and the thermal well 5100. The mating provides the thermal contact so that the thermal well 5100 and the sensing probe 6000 are thermally coupled.

A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 67:
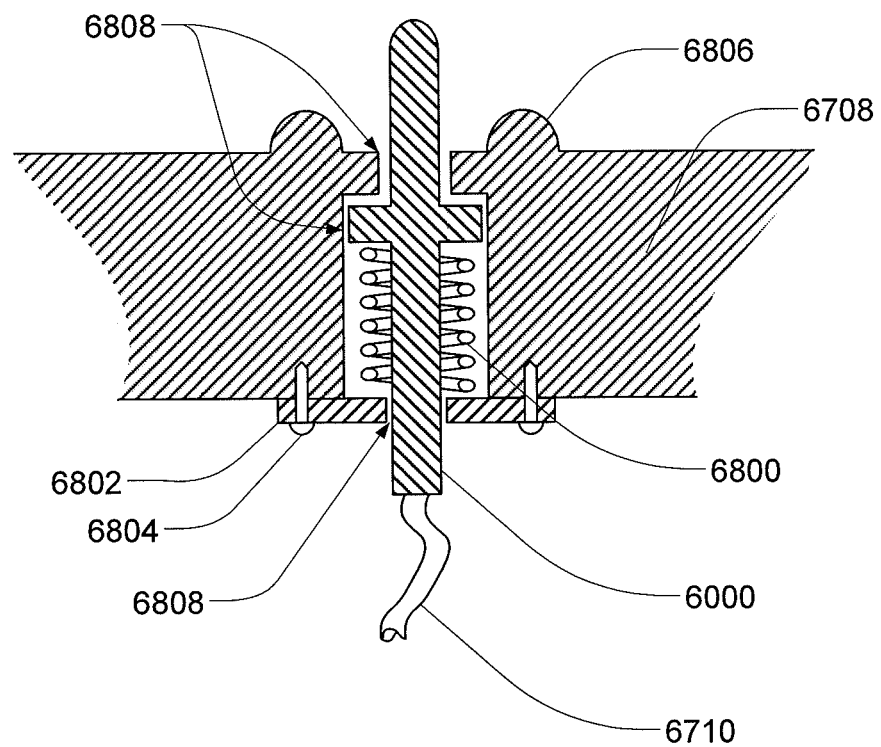
FIG. 67 is a section view of one embodiment of a sensing probe in a housing.

Referring now to FIG. 67, an alternate embodiment of the system shown in FIG. 66 is shown. In this embodiment, the sensing probe 6000 is suspended by a coil spring 6800. A retaining plate 6802 captures the coil spring 6800 to retain the spring 6800 and sensing probe 6000. In one embodiment, the retaining plate 6802 is attached to the housing 6708 using screws. However, in alternate embodiments, the retaining plate 6802 is attached to the housing 6708 using any fastening method including but not limited to: adhesive, flexible tabs, press fit, and ultrasonic welding. Aligning features 6806 on the housing 6708 aid in alignment of the sensing probe 6000 to a thermal well (not shown). Lateral movement of the sensing probe 6000 is provided for by clearance in areas 6808 in the housing 6708. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 68:
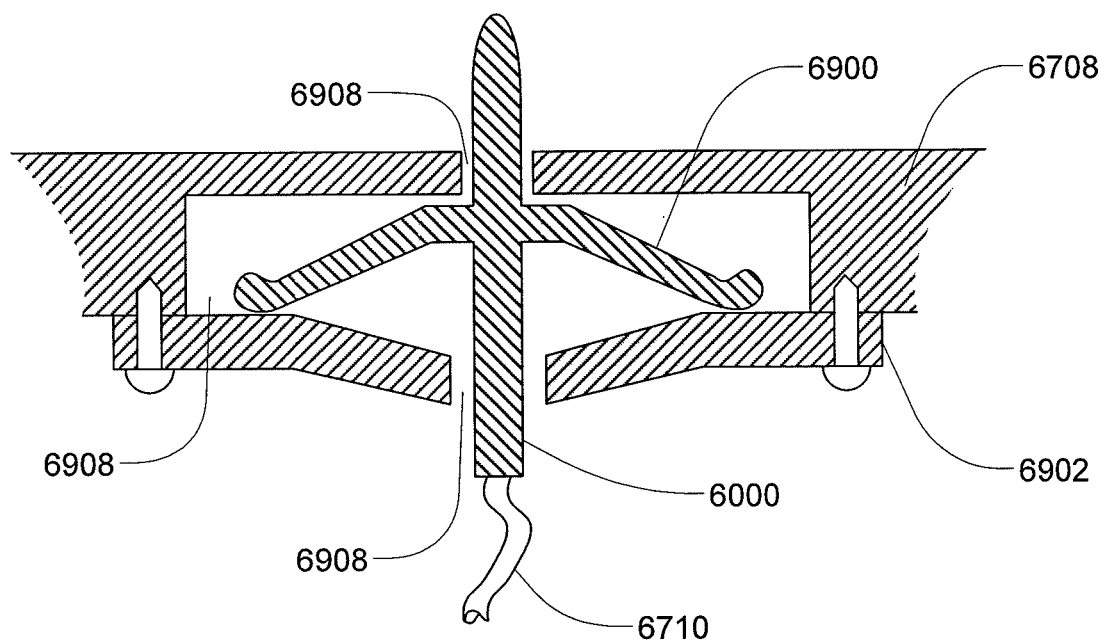
FIG. 68 is a section view of one embodiment of a sensing probe in a housing.

Referring now to FIG. 68, a sensing probe 6000 is shown in a housing 6708. In these embodiments, an alternate embodiment of a spring, a flexible member 6900, is integrated with the sensing probe 6000 to allow vertical movement of the sensing probe 6000 within the housing 6708. A retaining plate 6902 captures the flexible member 6900 to retain the flexible member 6900 and sensing probe 6000. In one embodiment, the retaining plate 6902 is attached to the housing 6708 using screws. However, in alternate embodiments, the retaining plate 6902 is attached to the housing 6708 using any fastening method including but not limited to: adhesive, flexible tabs, press fit, and ultrasonic welding. Lateral movement of the sensing probe 6000 is provided for by clearance in areas 6908 in the housing 6708. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 69:
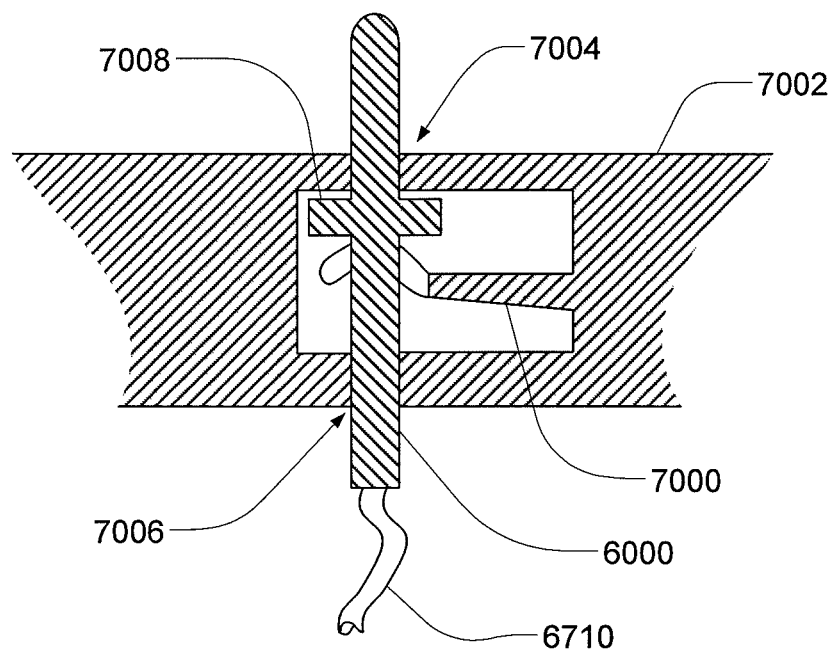
FIG. 69 is a section view of one embodiment of a sensing probe in a housing.

Referring now to FIG. 69, an alternate embodiment of a sensing probe 6000 in a housing 7002 is shown. In this embodiment, flexible member 7000 is attached or part of the housing 7002, provides for vertical movement of the sensing probe 6000. In this embodiment, the openings 7004, 7006 in housing 7002 are sized such that the sensing probe 6000 experiences limited lateral movement. Flexible member 7000 acts on the flange 7008 on the sensing probe 6000. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

The flange, as shown and described with respect to FIGS. 61, 66, 69, can be located in any area desired on the sensing probe 6000. In other embodiments, the sensing probe may be aligned and positioned by other housing configurations. Thus, the embodiments of the housing shown herein are only some embodiments of housings in which the sensor apparatus can be used. The sensor apparatus generally depends on being located amply with respect to the subject media. The configurations that accomplish this can vary depending on the subject media and the intended use of the sensing apparatus. Further, in some embodiments where the thermal well is not used, but rather, the sensing probe is used only, the housing configurations may vary as well.

The sensing apparatus, in some embodiments, is used to sense conductivity. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Figure 70:
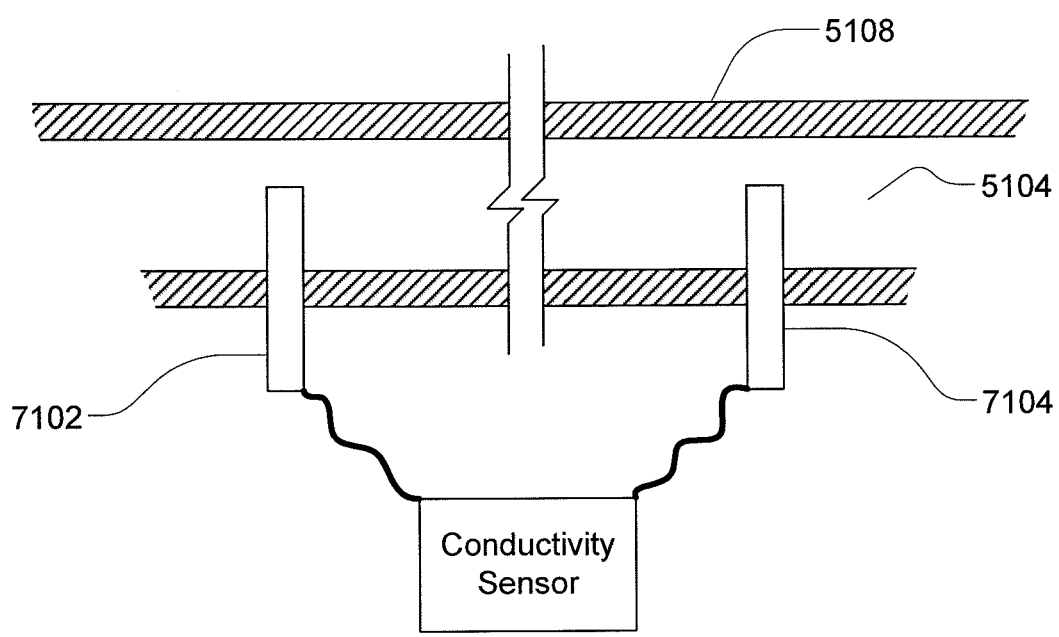
FIG. 70 is a side view of a fluid line including two sensors.

Referring now to FIG. 70, for conductivity sensing, at least two sensors 7102, 7104 are located in an area containing the subject media. In the embodiment shown, the area containing the subject media is a fluid path 5104 inside a fluid line 5108. The conductivity sensors 7102, 7104 can be one of the various embodiments of sensing probes as described above, or one of the embodiments of the sensor apparatus embodiments (including the thermal well) as described above. However, in other embodiments, only one of the sensors is one of the embodiments of the sensor apparatus or one of the embodiments of the sensing probe, and the second sensor is any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

Figure 71:
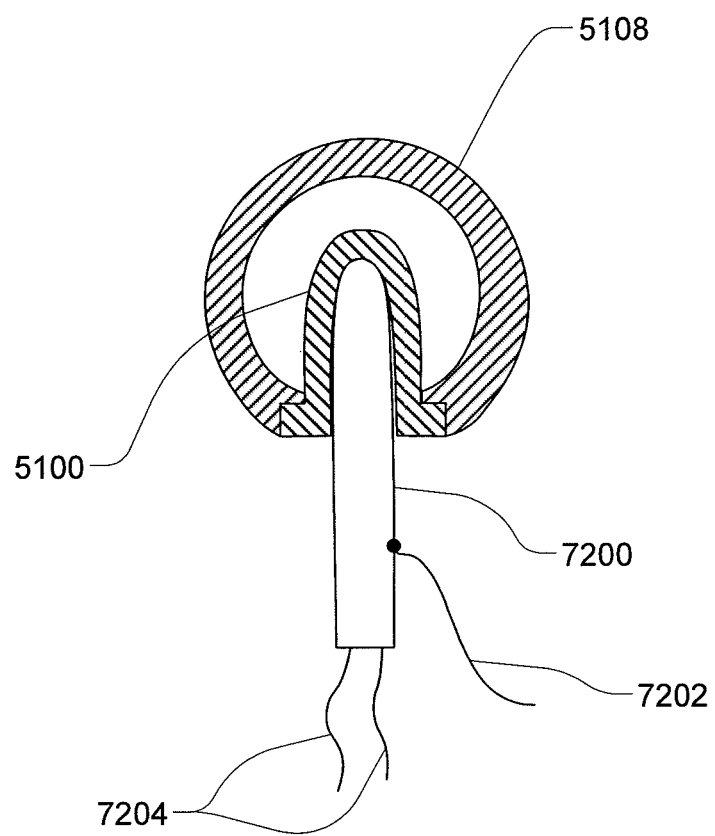
FIG. 71 is a section view of a fluid line with a sensor apparatus.

Referring now to FIG. 71, an alternate embodiment of a sensor apparatus including a sensing probe 7200 and a thermal well 5100 is shown in a fluid line 5108. In this embodiment, the sensing probe 7200 is constructed of a metal housing. The thermal well 5100 is also constructed of metal. The thermal well 5100 and the sensing probe 7200 can be made from the same metal or a different metal. The metal, in the preferred embodiment, is a conductive metal, which may include stainless steel, steel, copper and silver. A lead 7202 is attached to the sensing probe 7200 housing for conductivity sensing. The thermal sensing leads 7204 are attached to a thermal sensor located inside the sensing probe 7200 housing. In this embodiment, therefore, the third lead 7202 (or the lead for conductivity sensing) can be attached anywhere on the sensing probe 7200 because the sensing probe 7200 is constructed of metal. In the previously described embodiments, where the sensing probe housing was constructed of plastic, and the sensing tip constructed of metal, the third lead for conductivity sensing was attached to the sensing tip.

A known volume of subject media may be used to determine conductivity. Thus, two sensors may be used and the volume of fluid between the two sensors can be determined. Conductivity sensing is done with the two electrical contacts (as described above), where one or both can be the sensor apparatus. The volume of subject media between the two contacts is known.

Conductivity sensing is done by determining the conductivity from each of the sensors and then determining the difference. If the difference is above a predetermined threshold, indicating an abnormal difference in conductivity between the first and second sensor (the designations "first" and "second" being arbitrary), then it can be inferred that air may be trapped in the subject media and a bubble detection alarm may be generated to indicate a bubble. Thus, if there is a large decrease in conductivity (and likewise, a large increase in resistance) between the first and second sensor, air could be trapped and bubble presence may be detected.

Leaks in a machine, system, device or container may be determined using the conductivity sensing. Where a sensing apparatus is in a machine, device or system, and that sensing apparatus senses conductivity, in one embodiment, a lead from the sensor apparatus (or electrical contacts) to an analyzer or computer machine may be present.

In some embodiments, the analyzer that analyzes the electrical signals between the contacts is connected to the metal of the machine, device, system or container. If the analyzer senses an electrical signal from the machine, then a fluid leak may be inferred.

For the various embodiments described herein, a fluid line can be made of any material including metal and plastic. In most embodiments, the fluid line is compatible with the subject media and has the desired characteristics depending on the configuration of the thermal well in the fluid line. The fluid line can be part of a disposable unit that attaches to the sensor apparatus. In some of these embodiments, the fluid line includes the thermal well. The subject media is located inside the fluid line and the sensing probe provides sensing data regarding the subject media once the sensing probe and thermal well are amply mated.

The fluid line can be a chamber, a hose, a fluid path or other space or conduit for holding a volume of subject media. In some embodiments, the fluid line is a designed to hold fluid having a flow rate. In other embodiments, the space is designed to hold mostly stagnant media or media held in the conduit even if the media has flow.

In some embodiments, the sensor apparatus may be used based on a need to separate the subject media from the sensing probe. However, in other embodiments, the sensing probe is used for temperature and/or conductivity sensing directly with subject media.

In some embodiments, the thermal well may be part of a disposable portion of a device, machine, system or container. Thus, the thermal well may be in direct contact with subject media and may be the only component that is contaminated by same. In these embodiments, the sensing probe may be part of a machine, device, system or container, and be disposable or non-disposable.

5. CONCLUSION

Various types and configurations of pump pods, heat-exchanger systems, and thermal/conductivity sensors are described above. It should be noted that a wide variety of embodiments can be produced from various combinations of components. For example, certain heat-exchanger systems may be configured without pump pods or thermal/conductivity sensors, may be configured with pump pods but not thermal/conductivity sensors, or may be configured with thermal/conductivity sensors but not pump pods. Pump pods can be used in a wide variety of applications and are by no means limited to use in heat-exchanger systems or for pumping of bodily fluids or medical fluids. Thermal/conductivity sensors can be used in a wide variety of applications and are by no means limited to thermal/conductivity measurements of fluids or to thermal/conductivity measurements in the context of heat-exchanger systems.

Various embodiments are described above with reference to pneumatic actuation systems, specifically for operating pod pumps. It should be noted, however, that pod pumps can be operated using other types of control fluids, such as, for example, hydraulic fluids, in which case the actuation system would typically include an appropriate control fluid delivery system for delivering control fluid under positive and/or negative pressures. Thus, for example, a heat-exchanger system could include a hydraulic actuation system rather than a pneumatic actuation system, in which case pressurized hydraulic fluid could be stored in one or more reservoirs or be provided using other pressurizing means (e.g., a hydraulic fluid pump).

Although the above discussion discloses various exemplary embodiments of the invention, it should be apparent that those skilled in the art can make various modifications that will achieve some of the advantages of the invention without departing from the true scope of the invention.

We claim:

1. A method for using a controller to control a fluidly actuated pumping cassette, the method comprising:
    opening an inlet valve on the cassette to fluidly connect a source of the liquid with at least one reciprocating positive-displacement pump on the cassette, each pump comprising:
        a curved rigid chamber wall;
        a flexible membrane attached to the rigid chamber wall, the flexible membrane and rigid chamber wall defining a pumping chamber;
        a rigid limit structure for limiting movement of the membrane and limiting the maximum volume of the pumping chamber, the flexible membrane and the rigid limit structure defining an actuation chamber connected via a fluidic control port in the rigid limit structure to a fluid source under positive or negative pressure; and
        a pressure transducer configured to measure a pressure in the pumping chamber or the actuation chamber to provide pressure information to the controller;
    introducing a quantity of the liquid into the pumping chamber through the inlet valve;
    closing the inlet valve and fluidly isolating the pumping chamber;
    applying a known pressure to the actuation chamber;
    measuring a rate of pressure change in the pumping chamber or the actuation chamber;
    comparing the measured rate of pressure change with the controller to a pre-determined range of values; and
    determining that air is present in the pumping chamber if the measured rate of pressure change differs from the pre-determined range of values.

2. A method according to claim 1, wherein the rigid chamber wall is hemispheroid.

3. A method according to claim 2, wherein the rigid limit structure is hemispheroid, such that the pumping chamber is spheroid when the membrane is urged against the rigid limit structure and the actuation chamber is spheroid when the membrane is urged against the rigid chamber wall.

4. A method according to claim 1, wherein the at least one reciprocating positive-displacement pump comprises a pair of reciprocating positive-displacement pumps.

5. A method according to claim 4, wherein the pair of pumps are operated out of phase so as to produce a substantially continuous liquid flow.

6. A method according to claim 1, wherein the at least one pump is fluidly connected to a disposable conduit having an inlet and an outlet, and wherein the method further comprises:
    placing the disposable conduit in proximity with a heat exchanger; and
    pumping the liquid through the disposable conduit so as to heat or cool the liquid.

7. A method according to claim 6, wherein the disposable conduit includes at least one of a heat-exchanger bag, a length of tubing, and a radiator.

8. A method according to claim 1, wherein the source is a patient and the liquid is a bodily fluid.

9. A method according to claim 8, further comprising:
monitoring the patient's temperature; and
controlling the operation of at least one of (a) the at least one pump and (b) the heat exchanger in order to maintain the temperature of the liquid within a predetermined range.

10. A method according to claim 1, wherein the actuation chamber is fluidly connected to a pneumatic actuation system for providing either a positive or a negative pressure to the actuation chamber of each pump.

11. A method according to claim 10, wherein the pneumatic actuation system includes:
a gas reservoir containing a gas at either a positive or a negative pressure, and
a valving mechanism for controlling the flow of gas between the gas reservoir and the actuation chamber of each pump.

12. A method according to claim 11, wherein the controller receives pressure information from at least one actuation-chamber pressure transducer and controls the valving mechanism.

13. A method according to claim 12, wherein the pneumatic actuation system further comprises a reservoir pressure transducer for measuring the pressure of the gas in the reservoir, and wherein the controller receives pressure information from the reservoir pressure transducer.

14. A method according to claim 13, wherein the controller compares pressure information from the actuation-chamber pressure transducer with pressure information from the reservoir pressure transducer to determine whether at least one pressure transducer is malfunctioning.

15. A method according to claim 1, wherein a pneumatic actuation system provides positive pressure alternating with negative pressure to the actuation chamber of each pump.

16. A method according to claim 15, wherein the pneumatic actuation system comprises:
a positive-pressure gas reservoir;
a negative-pressure gas reservoir; and
a valving mechanism for controlling the flow of gas between the gas reservoirs and the actuation chamber of each pump.

17. A method according to claim 16, wherein the pneumatic actuation system further comprises:
at least one actuation-chamber pressure transducer for measuring the pressure of the actuation chamber of each pump, and wherein
the controller receives pressure information from the at least one actuation-chamber pressure transducer and controls the valving mechanism.

18. A method according to claim 17, wherein the controller controls the valving mechanism to cause the flexible membrane of each pump to move toward the rigid chamber wall in a pump stroke beginning or move toward the rigid limit structure in a pump stroke end, and
wherein the controller determines the amount of fluid flow through each pump based on a number of pump strokes.

19. A method according to claim 18, wherein the controller integrates pressure information received from an actuation-chamber pressure transducer during a pump stroke to detect an aberrant flow condition.

20. A method according to claim 1, wherein the inlet valve prevents flow out of the pumping chamber through an inlet of the at least one pump and an outlet valve prevents flow into the pumping chamber through an outlet of the at least one pump.

21. A method according to claim 20, wherein the controller controls opening or closing of the inlet valve and the outlet valve.

22. A method according to claim 1, wherein the inlet valve and the outlet valve each comprises a flexible valve membrane capable of occluding liquid flow in the valve, and an actuation housing with actuation port to transmit fluid under positive or negative pressure to the flexible valve membrane.

23. A method according to claim 1, wherein the fluid source is a pneumatic source.

24. A method according to claim 1, wherein the predetermined range of values comprises a predetermined rate of change in measured pressure in response to the application of the known pressure to the actuation chamber.

25. A fluidly activated liquid pumping system comprising:
a controller; and
a disposable cassette comprising:
(a) at least one reciprocating positive-displacement pump, each pump comprising:
(i) a curved rigid chamber wall;
(ii) a flexible membrane attached to the rigid chamber wall, the flexible membrane and rigid chamber wall defining a pumping chamber;
(iii) a rigid limit structure for limiting movement of the membrane and limiting the maximum volume of the pumping chamber, the flexible membrane and the rigid limit structure defining an actuation chamber;
(iv) a port in the rigid limit structure fluidly connecting the actuation chamber to a fluid source supplying fluid at a positive or negative pressure to actuate the flexible membrane; and
(v) a pressure transducer configured to measure a fluid pressure in the pumping chamber or the actuation chamber and to provide pressure information to the controller;
(b) an inlet valve configured to be controllable by the controller for directing liquid into the pumping chamber through an inlet in the rigid chamber wall; and
(c) an outlet valve configured to be controllable by the controller for directing liquid out of the pumping chamber through an outlet in the rigid chamber wall; wherein
the controller is configured to detect the presence of air in the pumping chamber by controlling the application of a known fluid pressure to the actuation chamber via the port, by commanding the inlet valve and the outlet valve to a closed position, and by monitoring a rate of change of pressure measured by the pressure transducer.

26. A method according to claim 25, wherein the pressure transducer is in fluid communication with the actuation chamber.

27. A fluidly activated liquid pumping system according to claim 25, wherein each rigid chamber wall is hemispheroid.

28. A fluidly activated liquid pumping system according to claim 25, wherein the inlet valve prevents flow out of the pumping chamber through the inlet and the outlet valve prevents flow into the pumping chamber through the outlet.

29. A fluidly activated liquid pumping system according to claim 25, wherein the outlet in the rigid chamber wall is connected to a fluid conduit comprising a heat-exchanger bag or a radiator, the fluid conduit having an inlet in fluid communication with the outlet of the at least one pump for pumping liquid into the fluid conduit for heating or cooling.

30. A fluidly activated liquid pumping system according to claim 29, further comprising:
a filter in fluid communication with an outlet of the fluid conduit for filtering heated or cooled fluid flowing out of the fluid conduit.

31. A fluidly activated liquid pumping system according to claim 29, further comprising:
a manifold including:
at least one inlet port for providing fluidic connection to an inlet of the fluid conduit; and
an outlet port for providing fluidic connection to an outlet of the fluid conduit.

32. A fluidly activated liquid pumping system according to claim 31, wherein the manifold further includes at least one sensor component, each sensor component disposed in a port and capable of transmitting thermal information regarding fluid passing through the port.

33. A fluidly activated liquid pumping system according to claim 32, wherein each sensor component includes a thermal well.

34. A disposable cassette according to claim 25, wherein the inlet valve and the outlet valve each comprises a flexible valve membrane capable of occluding liquid flow in the valve, and an actuation housing with actuation port to transmit fluid under positive or negative to actuate the flexible valve membrane.

35. A fluidly activated liquid pumping system according to claim 25, wherein the fluid source is a pneumatic source.

36. A method according to claim 1, wherein the pressure transducer is in fluid communication with the actuation chamber.

\* \* \* \* \*